United States Patent
Hatamian

(10) Patent No.: US 11,307,164 B2
(45) Date of Patent: Apr. 19, 2022

(54) LATERAL FLOW ASSAY WITH CONTROLLED CONJUGATE TIME AND CONTROLLED FLOW TIME

(71) Applicant: 2Pi-Sigma Corp., Newport Beach, CA (US)

(72) Inventor: Mehdi Hatamian, Mission Viejo, CA (US)

(73) Assignee: 2Pi-Sigma Corp., Newport Beach, CA (US)

( * ) Notice: Subject to any disclaimer, the term of this patent is extended or adjusted under 35 U.S.C. 154(b) by 0 days.

(21) Appl. No.: 17/332,989

(22) Filed: May 27, 2021

(65) Prior Publication Data

US 2021/0285910 A1   Sep. 16, 2021

Related U.S. Application Data

(63) Continuation-in-part of application No. 17/129,902, filed on Dec. 21, 2020, now Pat. No. 11,022,578, (Continued)

(51) Int. Cl.
| | |
|---|---|
| *G01N 27/327* | (2006.01) |
| *B01L 3/00* | (2006.01) |
| *G01N 33/53* | (2006.01) |

(52) U.S. Cl.
CPC ......... *G01N 27/3275* (2013.01); *B01L 3/502* (2013.01); *G01N 33/53* (2013.01); *B01L 2200/026* (2013.01)

(58) Field of Classification Search
CPC .... G01N 27/3275; G01N 33/53; B01L 3/502; B01L 2200/026
(Continued)

(56) References Cited

U.S. PATENT DOCUMENTS

| 4,943,522 A | 7/1990 | Eisinger et al. |
| 5,766,961 A | 6/1998 | Pawlak et al. |
(Continued)

FOREIGN PATENT DOCUMENTS

| WO | WO-2004008146 A2 * | 1/2004 | ............ B07C 5/344 |
| WO | WO-2013130995 A1 * | 9/2013 | ........... G01N 33/558 |
| WO | WO-2016059258 A1 * | 4/2016 | ....... G01N 33/54366 |

OTHER PUBLICATIONS

U.S. Appl. No. 17/165,955, filed Feb. 3, 2021, Hatamian, Mehdi, Non-published commonly owned U.S. Appl. No. 17/,165,955.
(Continued)

*Primary Examiner* — Benjamin R Whatley
*Assistant Examiner* — Jacqueline Brazin
(74) *Attorney, Agent, or Firm* — Makoui Law, PC; Ali Makoui

(57) ABSTRACT

A lateral flow assay device comprising a conjugate pad for receiving a quantity of fluid, and a membrane comprising a test line for determining whether the fluid comprises a target analyte. The device includes an actuator connected to a moving element comprising a shaft or a wheel. A first magnet is connected to the backing of the membrane. Second and third magnets are connected to the moving element. The actuator moves the moving element between first and second positions. In the first position, the opposite poles of the first and second magnets attract each other and maintain a gap between the membrane and the conjugate pad separate. In the second position, the similar poles of the first and third magnets repel each other and close the gap between membrane and the conjugate pad, allowing the fluid to flow from the conjugate pad into the membrane and the test line.

36 Claims, 48 Drawing Sheets

Related U.S. Application Data which is a continuation-in-part of application No. 16/986,175, filed on Aug. 5, 2020, now Pat. No. 10,914,704, which is a continuation of application No. 16/698,788, filed on Nov. 27, 2019, now Pat. No. 10,739,297.

(60) Provisional application No. 62/772,525, filed on Nov. 28, 2018.

(58) Field of Classification Search
USPC .................................................... 205/777.5
See application file for complete search history.

(56) References Cited

U.S. PATENT DOCUMENTS

| | | |
|---|---|---|
| 6,553,390 B1 | 4/2003 | Chandler |
| 10,739,297 B2 | 8/2020 | Hatamian |
| 10,914,704 B2 | 2/2021 | Hatamian |
| 11,022,578 B2 | 6/2021 | Hatamian |
| 2004/0110167 A1 | 6/2004 | Gerdes et al. |
| 2006/0172435 A1 | 8/2006 | Cho et al. |
| 2008/0145843 A1* | 6/2008 | Song ............... G01N 33/558 435/6.16 |
| 2008/0188009 A1 | 8/2008 | Ford et al. |
| 2009/0180929 A1* | 7/2009 | Petruno ............ G01N 33/558 422/400 |
| 2011/0053289 A1 | 3/2011 | Lowe et al. |
| 2015/0219658 A1 | 8/2015 | Scheefers et al. |
| 2016/0011183 A1 | 1/2016 | Egan et al. |
| 2016/0025639 A1 | 1/2016 | Jakubowicz |
| 2016/0038936 A1 | 2/2016 | Ding et al. |
| 2016/0282343 A1 | 9/2016 | Jeyendran et al. |
| 2016/0303558 A1 | 10/2016 | Lehane |
| 2016/0340714 A1* | 11/2016 | Siciliano ............. C12Q 1/6804 |
| 2018/0217145 A1 | 8/2018 | Skraba et al. |

OTHER PUBLICATIONS

Portions of prosecution history of U.S. Appl. No. 16/698,788, filed Jul. 13, 2020, Hatamian, Mehdi, Portions of prosecution history of commonly owned U.S. Appl. No. 16/698,788, listed as item #4 above, including actions and/or responses/amendments (29 pages).
Portions of prosecution history of U.S. Appl. No. 16/986,175, filed Jan. 20, 2021, Hatamian, Mehdi, Portions of prosecution history of commonly owned U.S. Appl. No. 16/986,175, listed as item #5 above, including actions and/or responses/amendments (34 pages).
Portions of prosecution history of U.S. Appl. No. 17/129,902, filed May 12, 2021, Hatamian, Mehdi, Portions of prosecution history of commonly owned U.S. Appl. No. 17/129,902, listed as item #6 above, including actions and/or responses/amendments (23 pages).
PCT/US2019/063785, filed Nov. 27, 2019, 2PI-SIGMA CORP., Commonly owned International Patent Application PCT/US2019/063785.
International Search Report and Written Opinion of PCT/US2019/063785, dated Feb. 4, 2020, 2PI-SIGMA CORP., International Search Report and Written Opinion of commonly owned International Patent Application PCT/US2019/063785.

\* cited by examiner

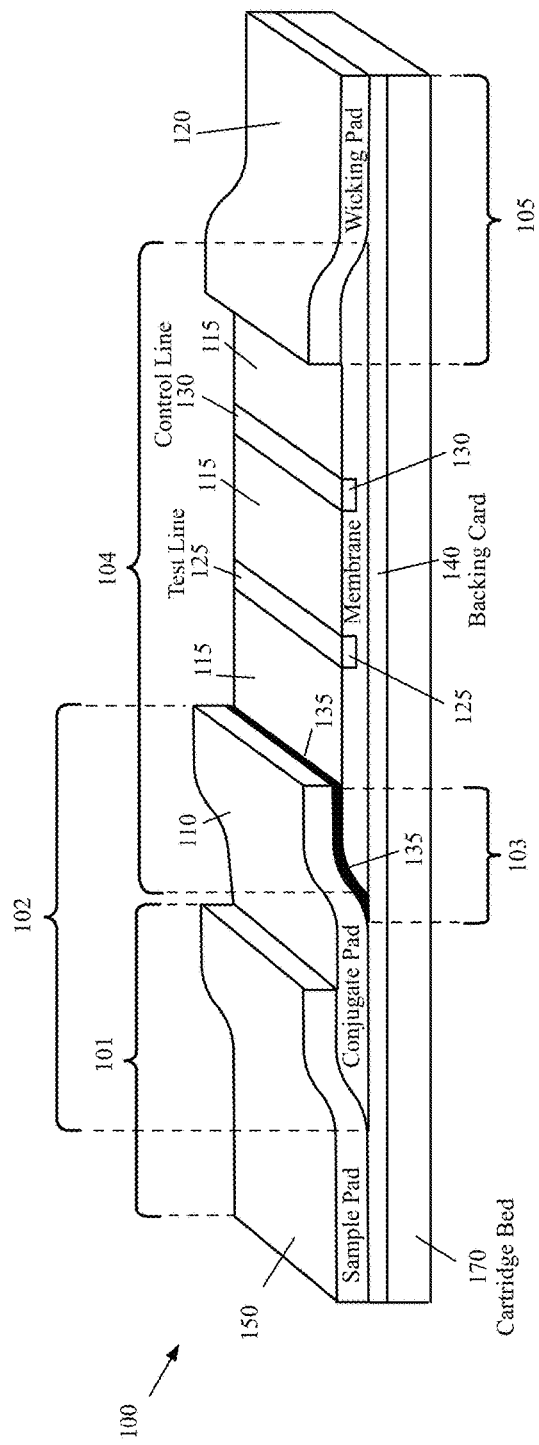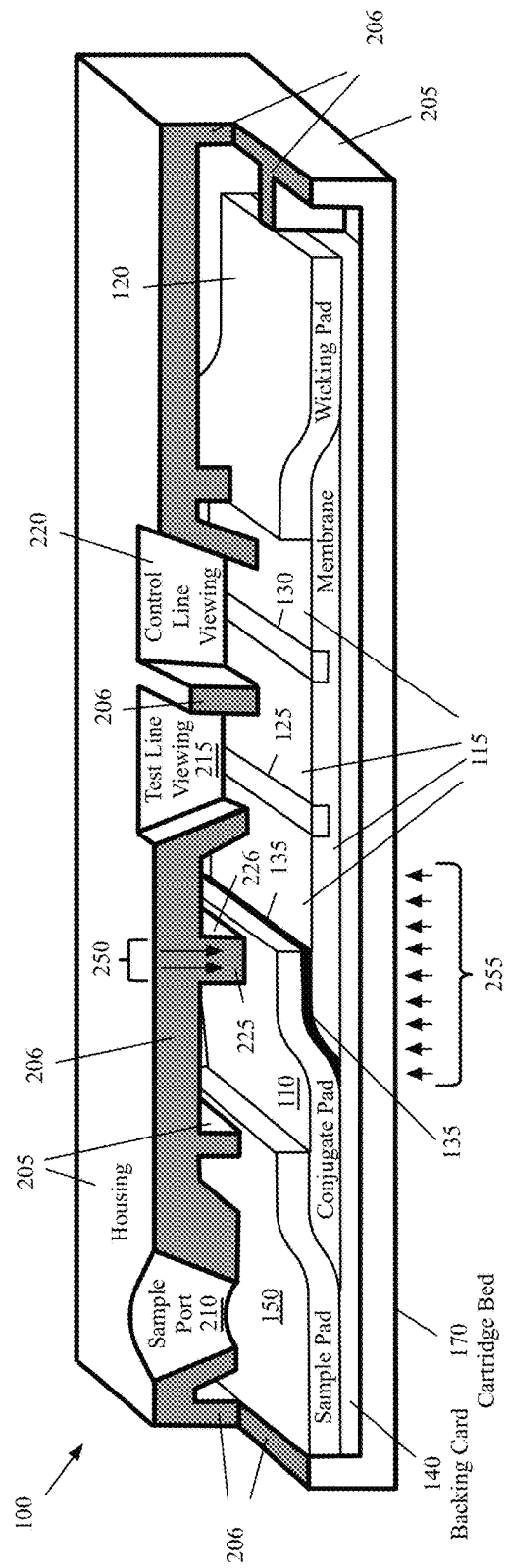

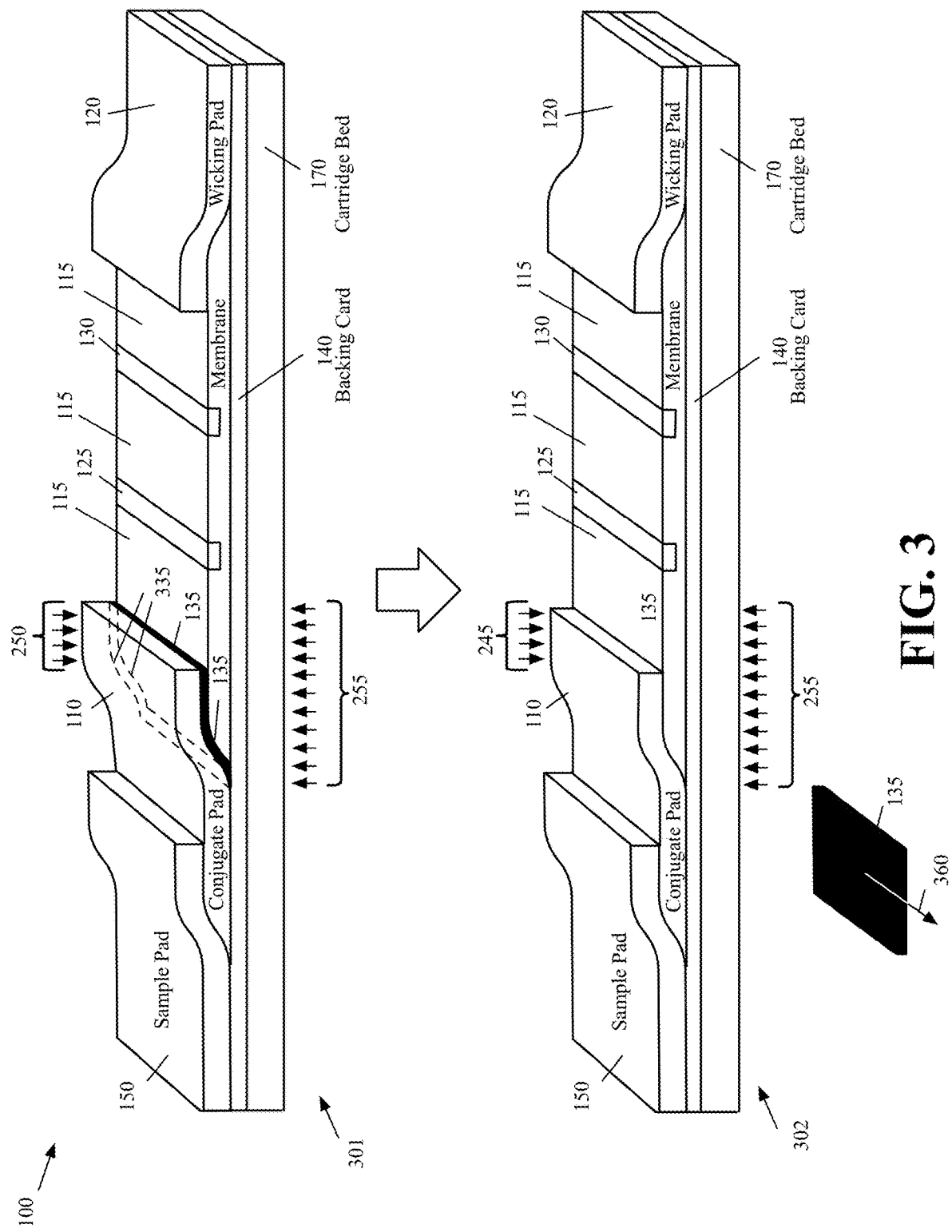

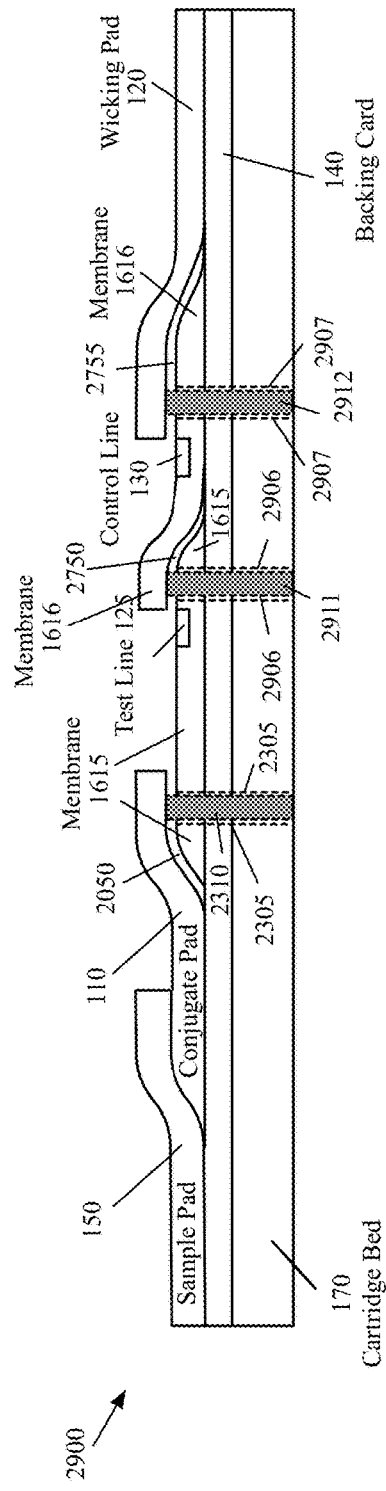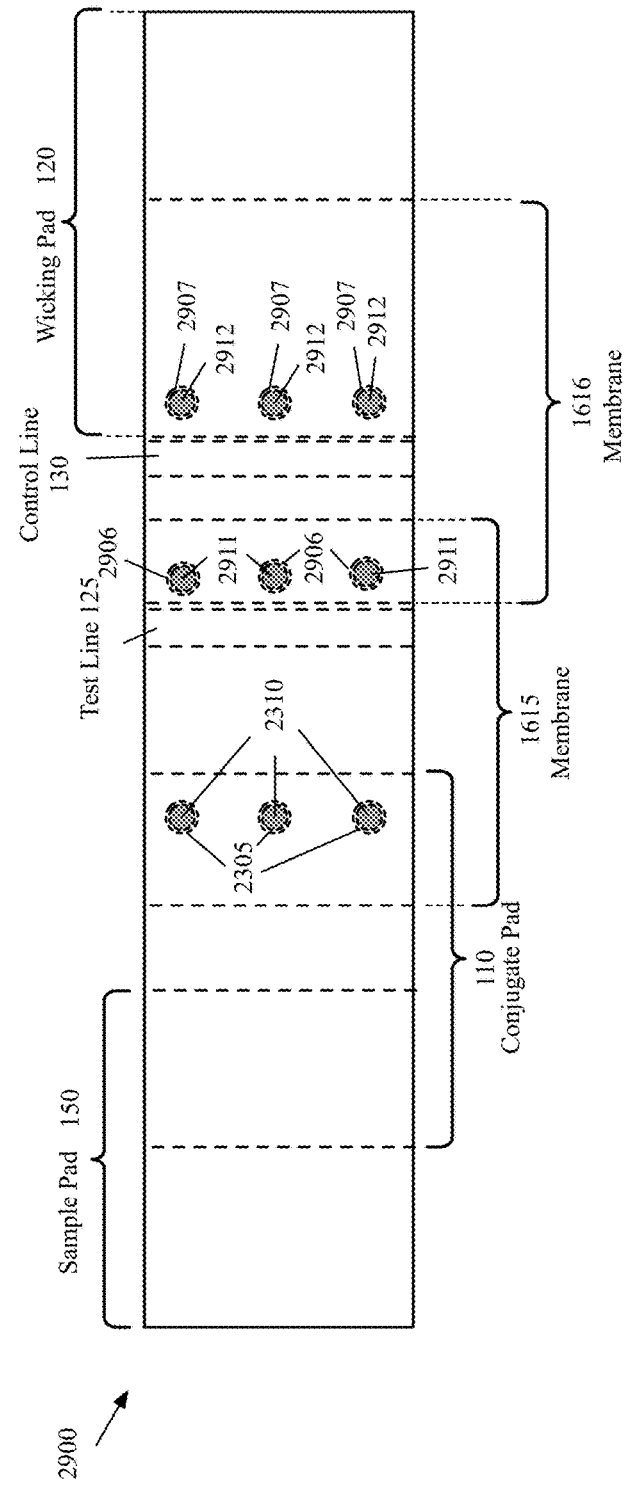
FIG. 29
FIG. 30

LATERAL FLOW ASSAY WITH CONTROLLED CONJUGATE TIME AND CONTROLLED FLOW TIME

CLAIM OF BENEFIT TO PRIOR APPLICATIONS

This application is a continuation-in-part of U.S. patent application Ser. No. 17/129,902, filed on Dec. 21, 2020, published as U.S. Patent Publication 2021/0109055. U.S. patent application Ser. No. 17/129,902 is a continuation-in-part of U.S. patent application Ser. No. 16/986,175, filed on Aug. 5, 2020, issued as U.S. Pat. No. 10,914,704. U.S. patent application Ser. No. 16/986,175 is a continuation of U.S. patent application Ser. No. 16/698,788, filed on Nov. 27, 2019, issued as U.S. Pat. No. 10,739,297. U.S. patent application Ser. No. 16/698,788 claims the benefit of U.S. Provisional Patent Application Ser. No. 62/772,525, filed on Nov. 28, 2018. The contents of U.S. patent application Ser. No. 17/129,902, published as U.S. Patent Publication 2021/0109055; U.S. patent application Ser. No. 16/986,175 issued as U.S. Pat. No. 10,914,704; U.S. patent application Ser. No. 16/698,788, issued as U.S. Pat. No. 10,739,297; and Provisional Patent Application 62/772,525 are hereby incorporated by reference.

BACKGROUND

Lateral flow assays (LFAs) are devices that are used to detect the presence (or absence) of a target analyte in a sample fluid without the need for specialized equipment. The lateral flow assays are widely used for medical diagnostics for point of care testing, home testing, or laboratory use.

A lateral flow assay typically includes a series of capillary pads for transporting fluid. A sandwich assay format may be used for detecting analytes that have at least two binding sites to bind to an antibody. A sample pad is used to receive a quantity of fluid (referred to as the sample fluid) and transport the sample fluid to an adjacent conjugate pad. The conjugate pad contains a solubilized antibody labeled with a detector such as colloidal gold nanoparticles. The antibody is specific to a certain analyte which is the target of interest in the sample fluid. As the sample fluid flows through the conjugate pad, the analyte (if any) in the sample fluid binds with the labeled antibody on the conjugate pad and forms an immunocomplex.

The immunocomplex then flows from the conjugate pad into an adjacent membrane (or membrane pad). The membrane has a test area, or test line, that contains an immobilized unlabeled antibody. As the immunocomplex moves over the test area, the immunocomplex binds with the immobilized antibody on the test area, resulting in a colored test line. When the sample fluid does not include the target analyte, no immunocomplex is formed on the conjugate pad and no immunocomplex binds with the immobilized antibody on the test area. As a result, the test line does not change color.

A lateral flow assay may also include a control line in the membrane. In a sandwich assay format, the control line may contain an immobilized antibody that binds to the free antibodies labeled with the detector resulting in a colored control line, which confirms that the test has operated correctly regardless of whether or not the target analyte has been present in the sample.

A competitive assay format may be used for detecting analytes that cannot simultaneously bind to two antibodies. The sample pad and the conjugate pad in a competitive assay format are similar to the sample pad and the conjugate pad in the sandwich assay format. In the competitive assay format, the test line contains immobilized analyte molecules. If the sample liquid does not contain the analyte, the labeled antibody flows from the conjugate pad into the test line and binds to the analyte at the test line, resulting in a colored test line that indicates the lack of the target analyte in the sample liquid. If, on the other hand, the target analyte is present in the sample liquid, the analyte binds to the labeled antibodies on the conjugate pad and prevents the labeled antibody to bind to the analyte at the test line, resulting in the lack of color on the test line. In a competitive assay format, the control line may contain an immobilized analyte that binds to the free antibodies labeled with the detector resulting in a colored control line, which confirms that the test has operated correctly regardless of whether or not the target analyte has been present in the sample.

BRIEF DESCRIPTION OF THE DRAWINGS

The various embodiments of the present lateral flow assay with controlled conjugate time and controlled flow time now will be discussed in detail with an emphasis on highlighting the advantageous features. These embodiments depict the novel and non-obvious lateral flow assay with controlled conjugate time and controlled flow time shown in the accompanying drawings, which are for illustrative purposes only. These drawings include the following figures, in which like numerals indicate like parts:

FIG. 1 is an upper front perspective view of one example embodiment of a portion of a lateral flow assay device, according to various aspects of the present disclosure;

FIG. 2 is an upper front perspective view of one example embodiment of a portion of a lateral flow assay device showing a cross section of the lateral flow assay device's housing, according to various aspects of the present disclosure;

FIG. 3 is an upper front perspective view of one example embodiment of a portion of a lateral flow assay device showing the removal of the barrier, according to various aspects of the present disclosure;

Figure 10:
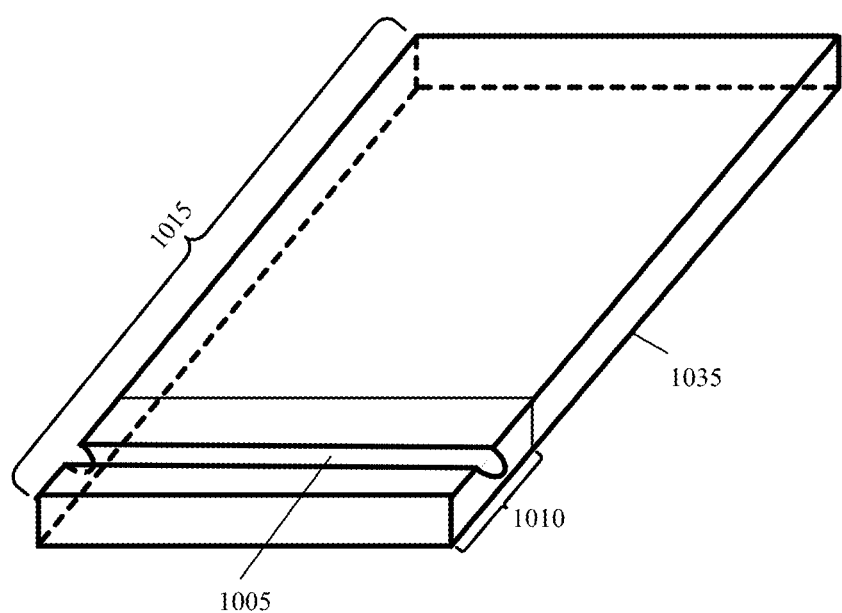
Figure 11:
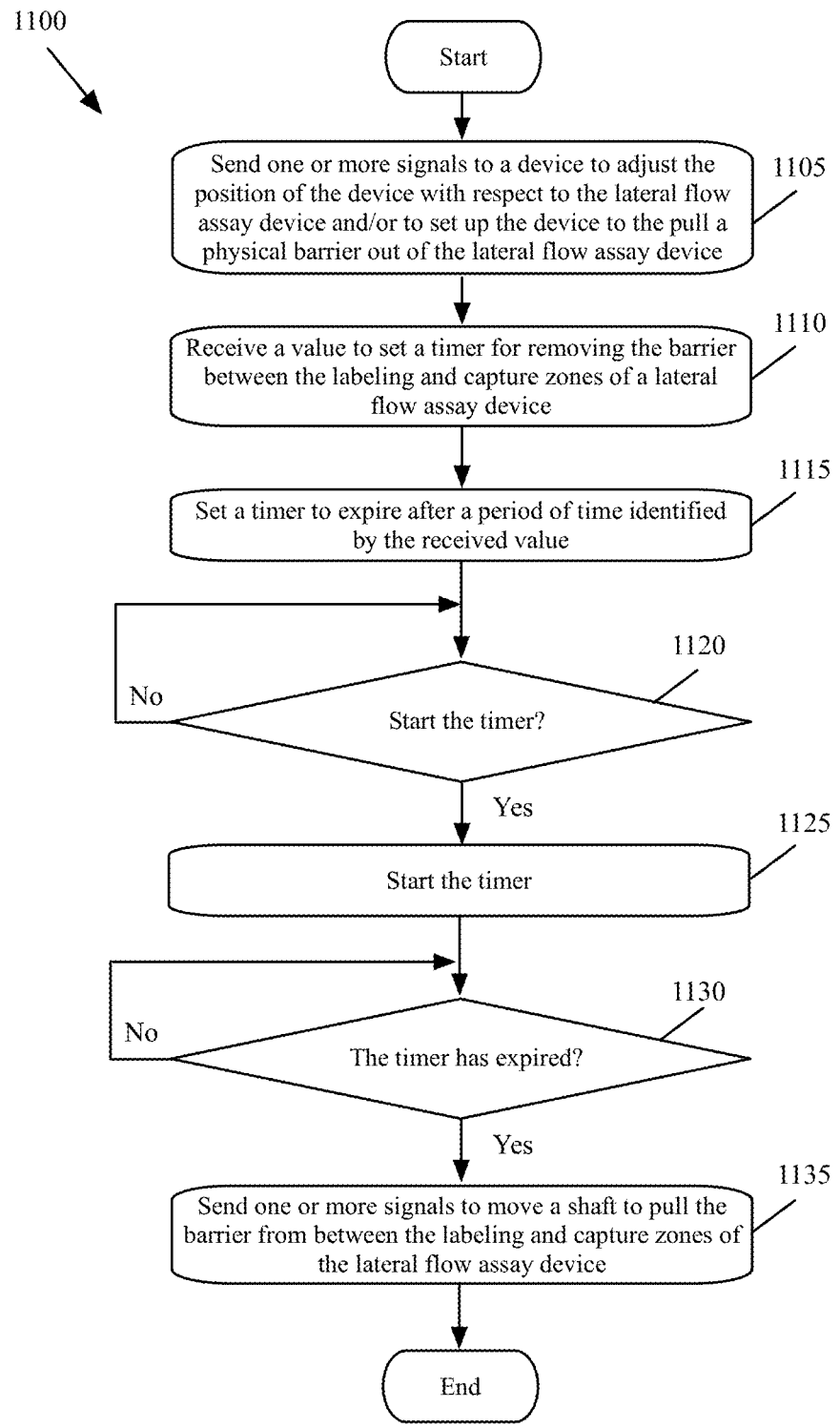
Figure 12:
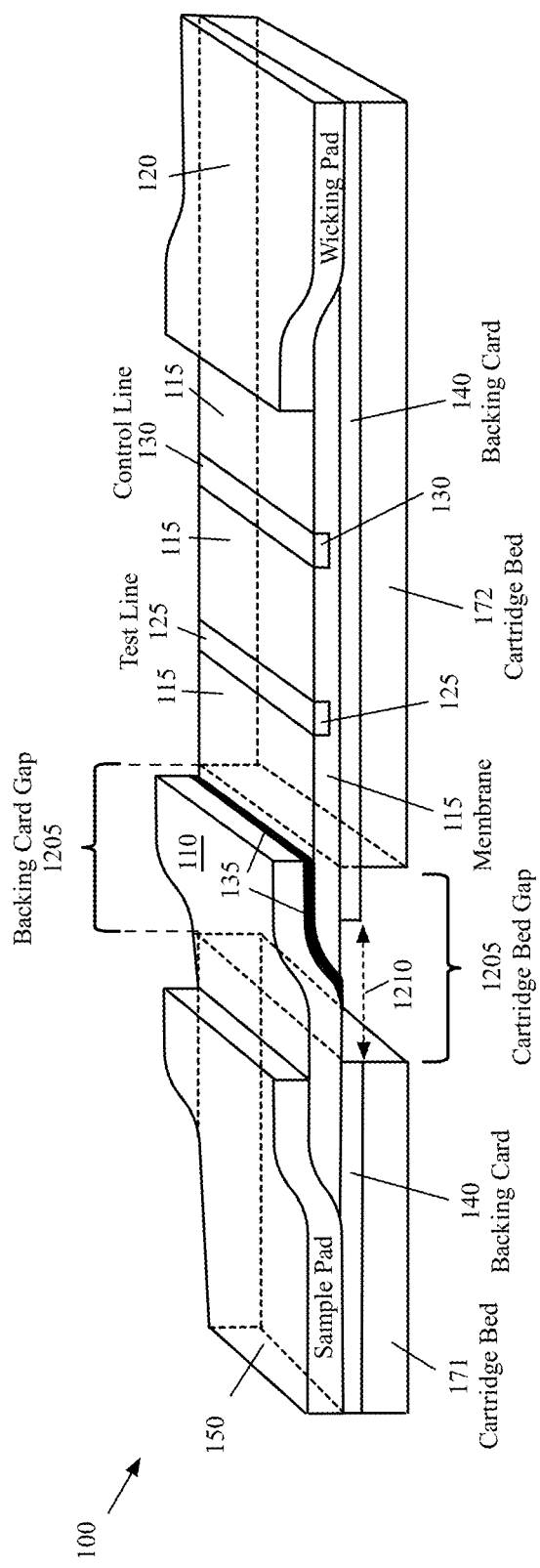
Figure 13:
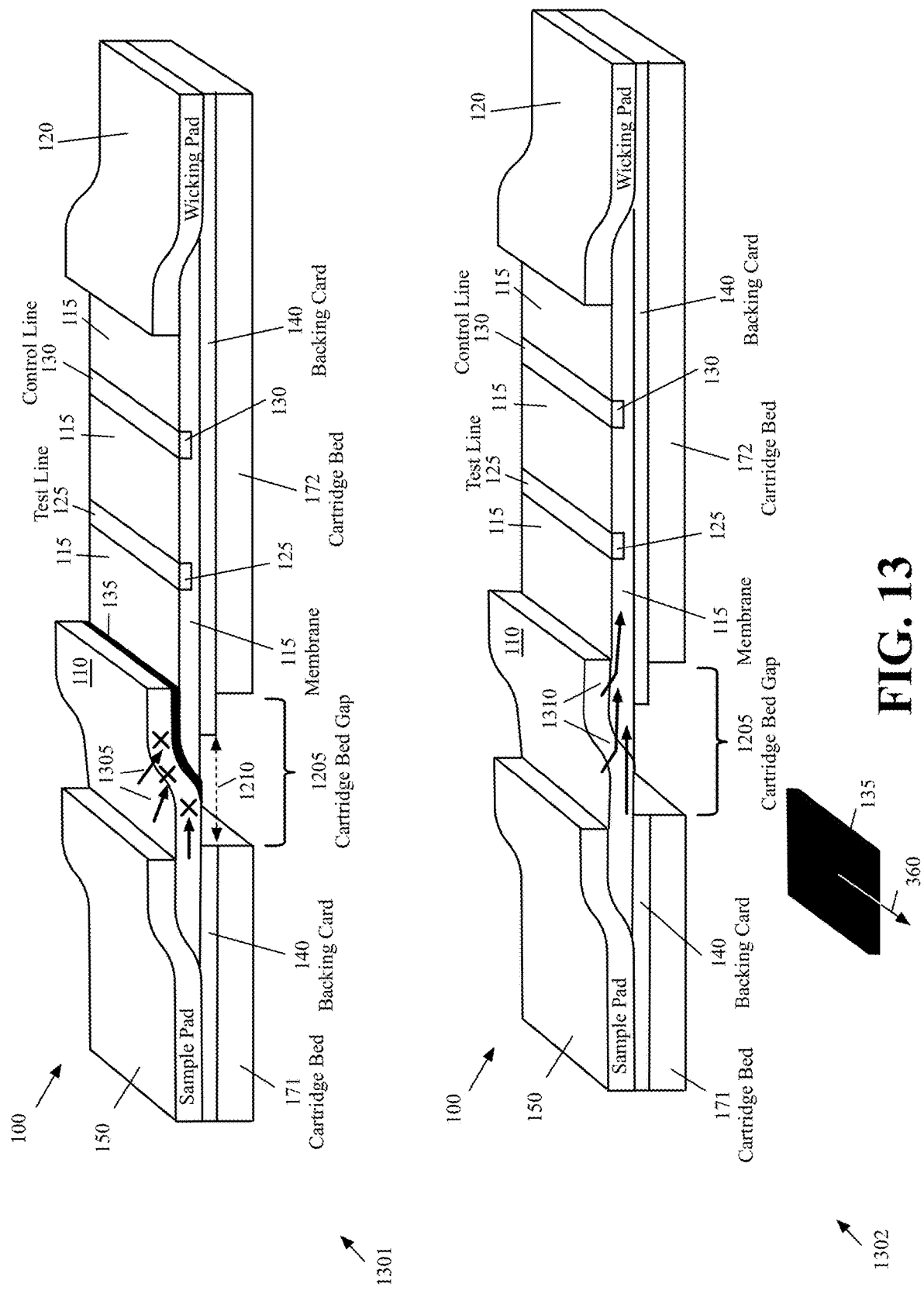
Figure 14:
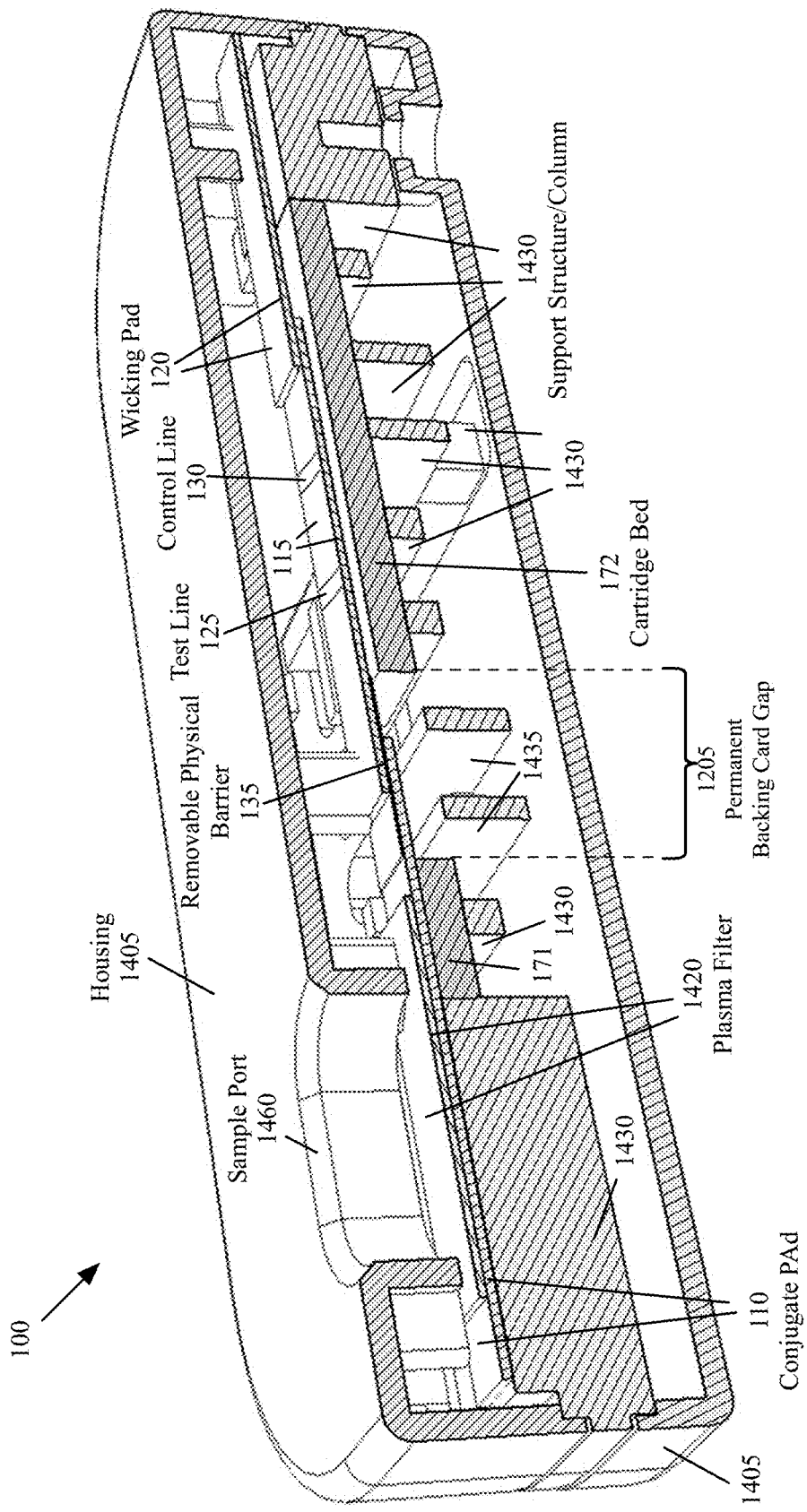
Figure 15:
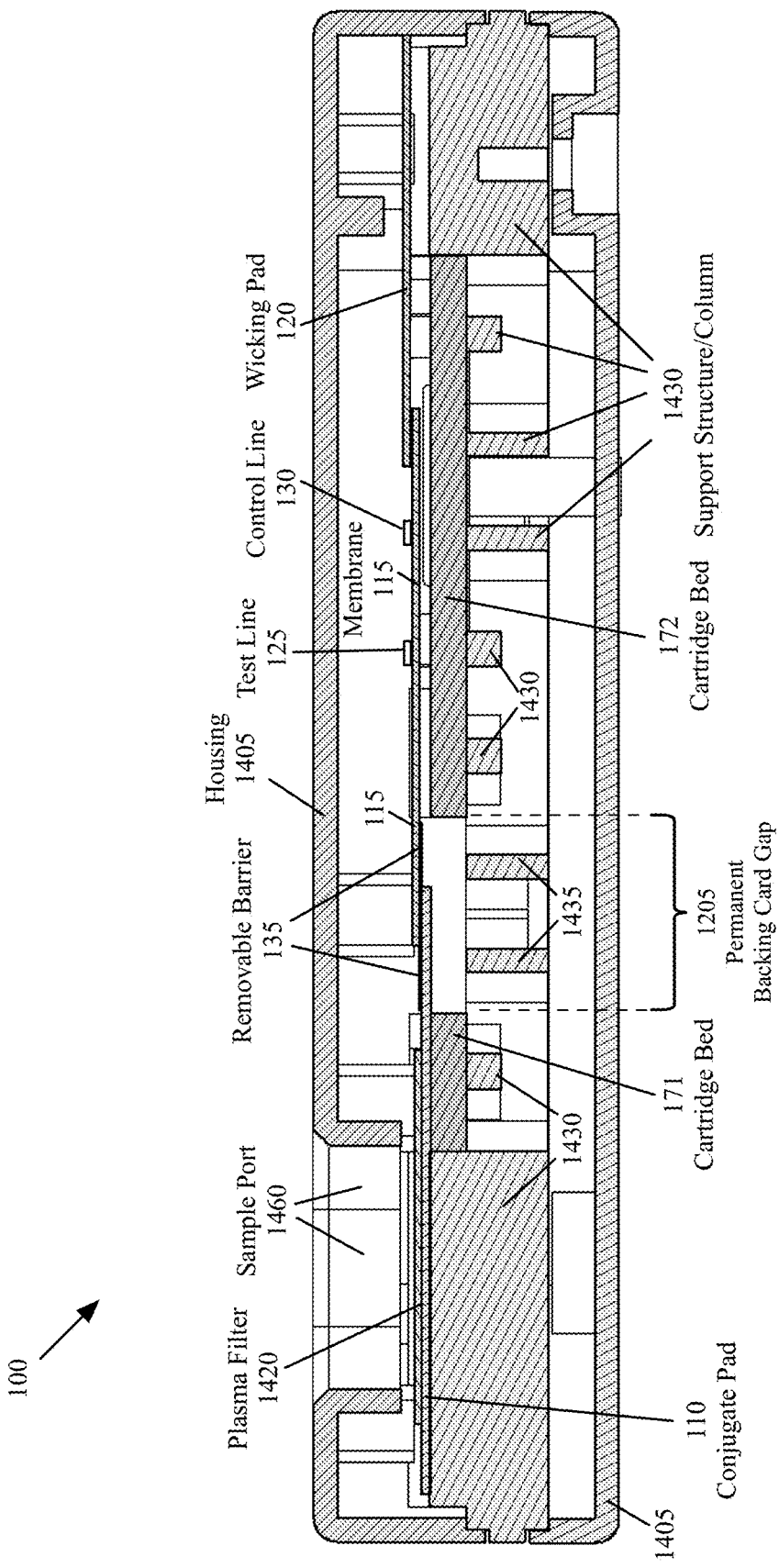
Figure 16:
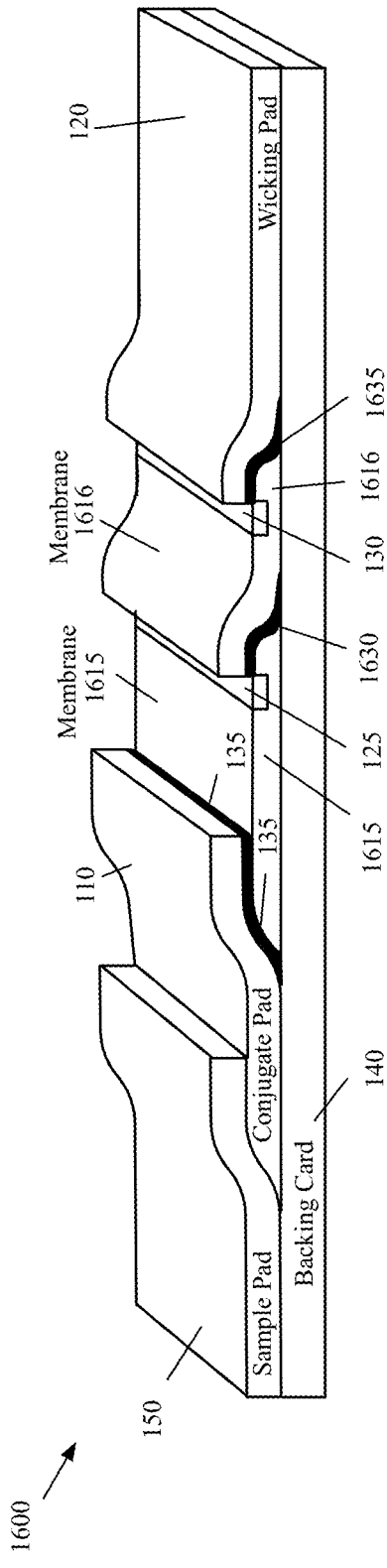
Figure 17:
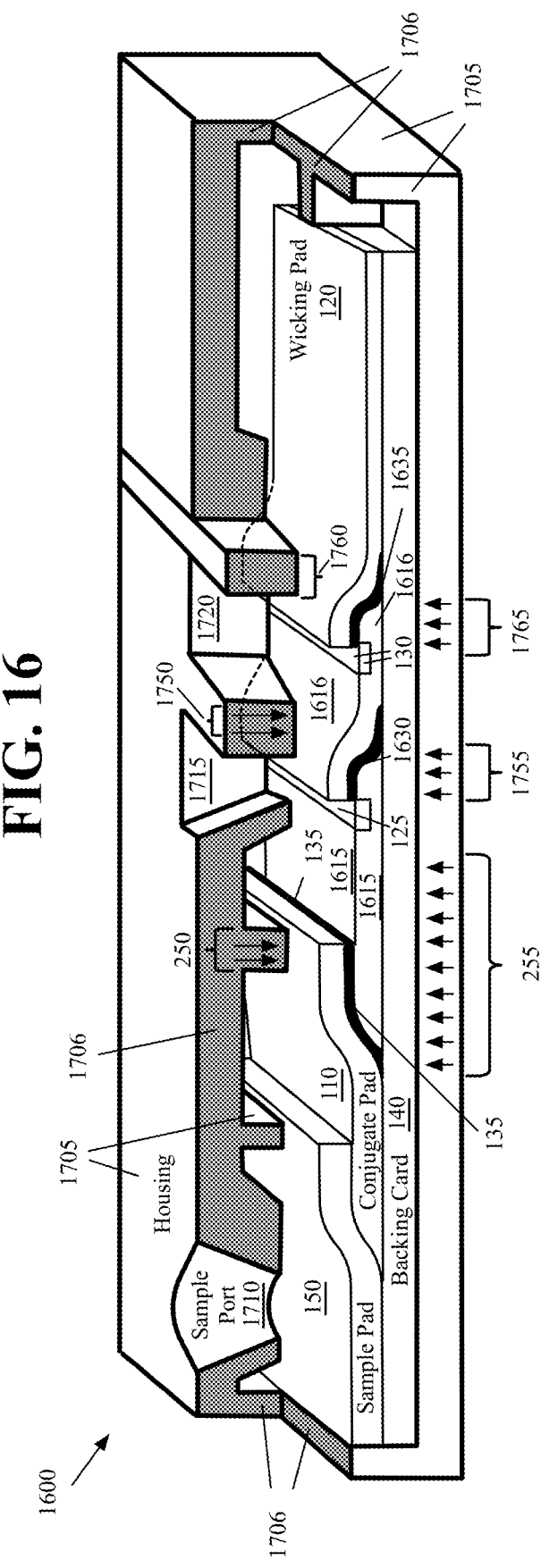
Figure 18:
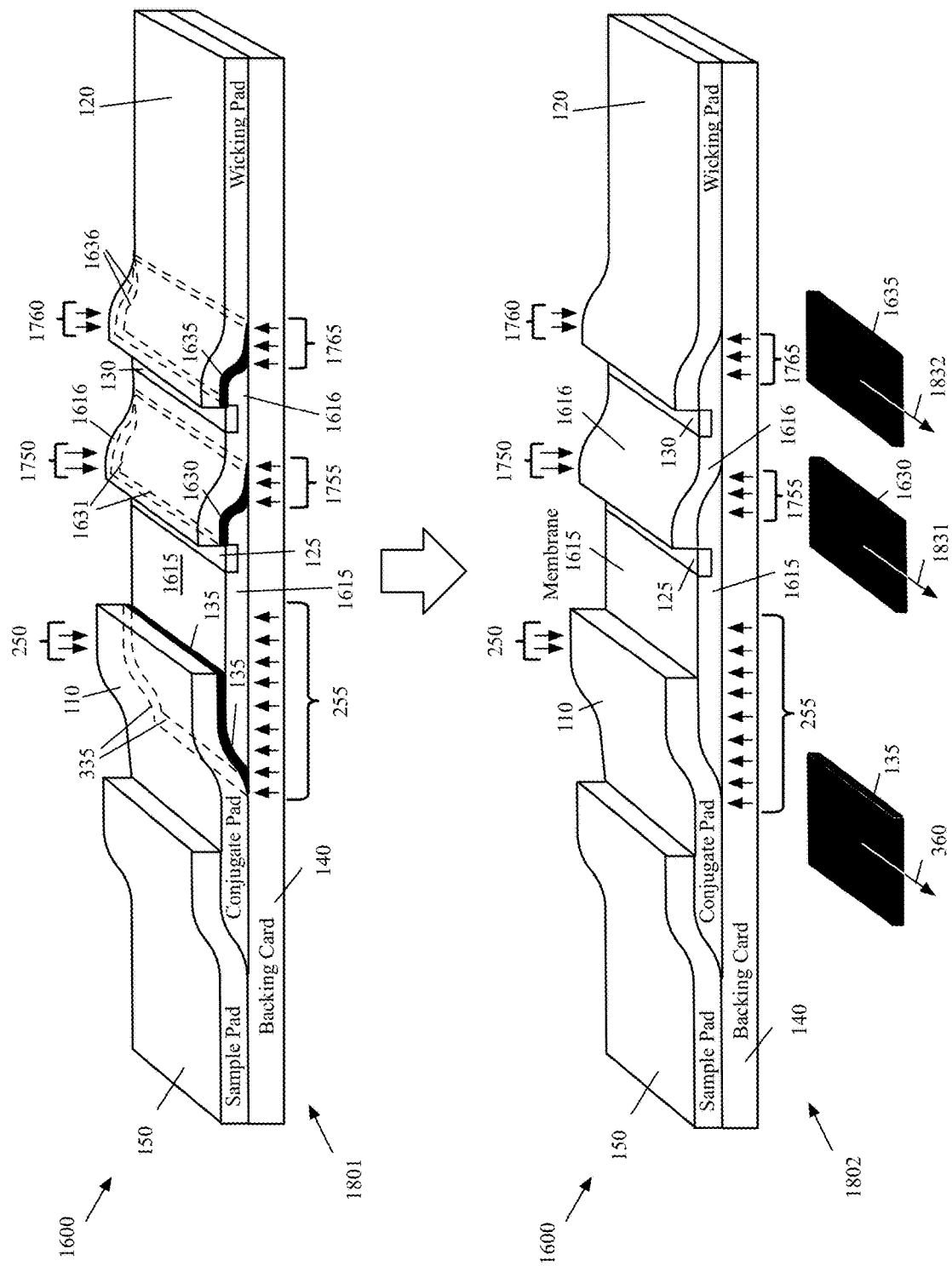
Figure 19:
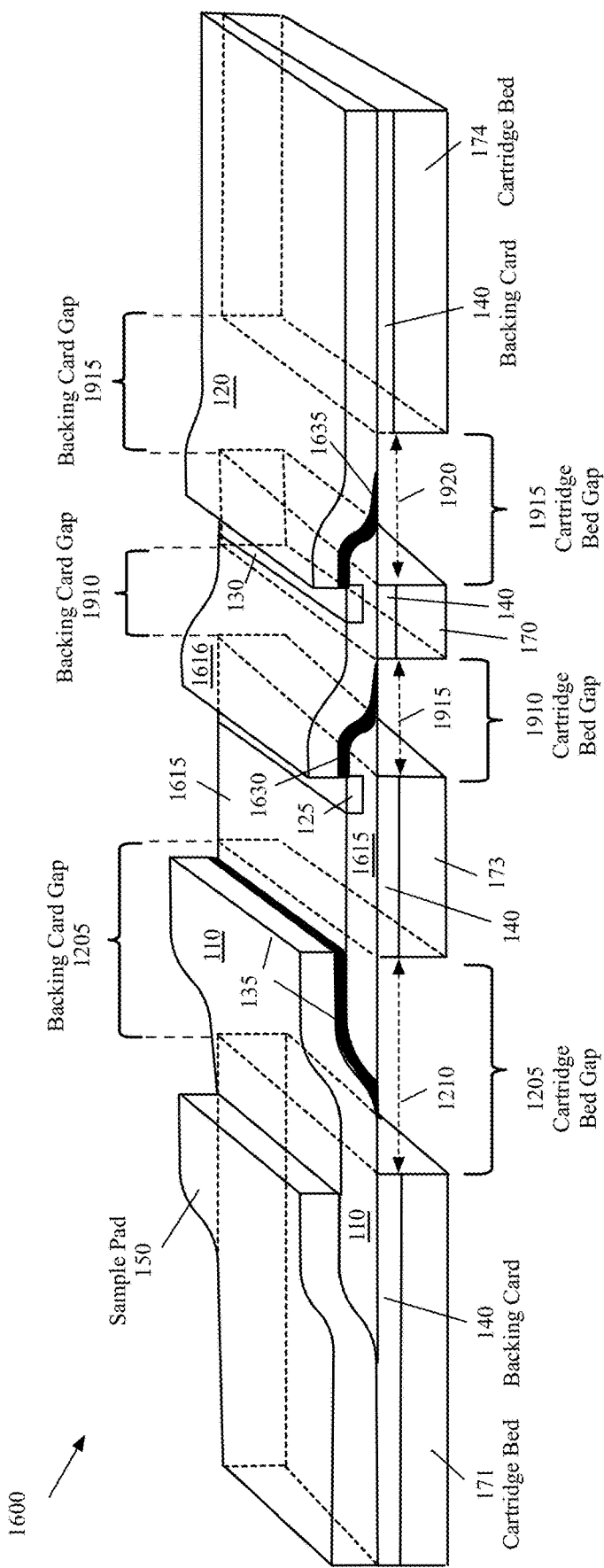
Figure 20:
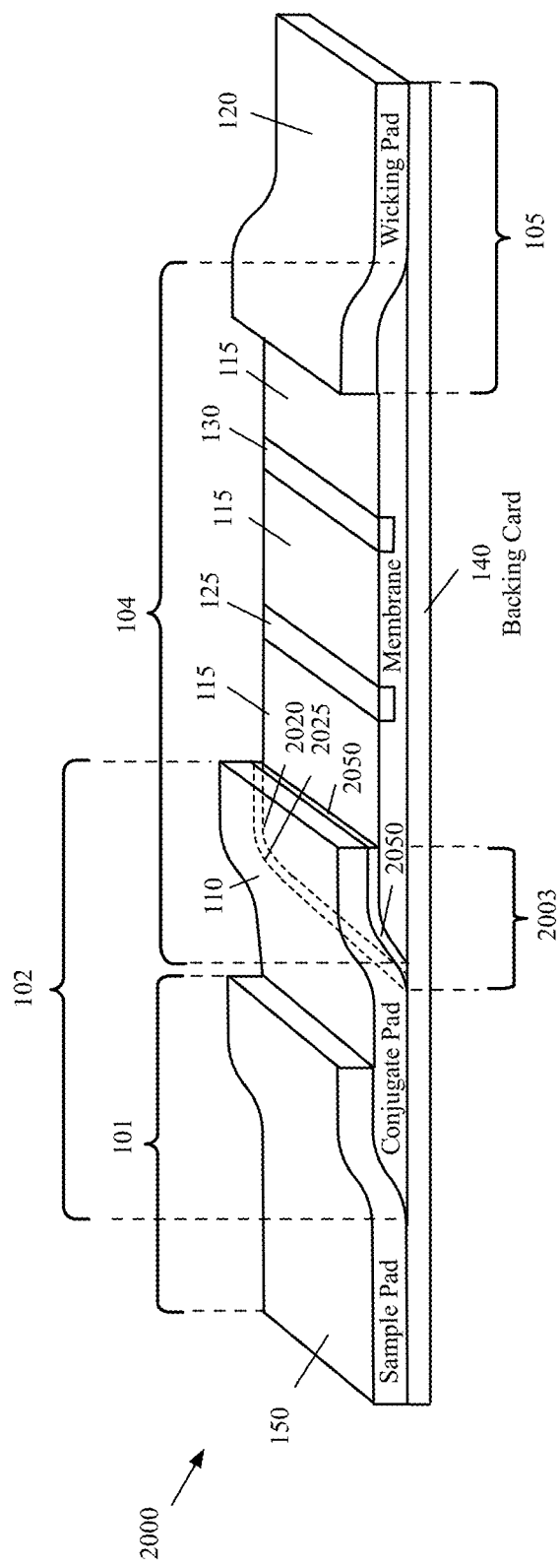
Figure 21:
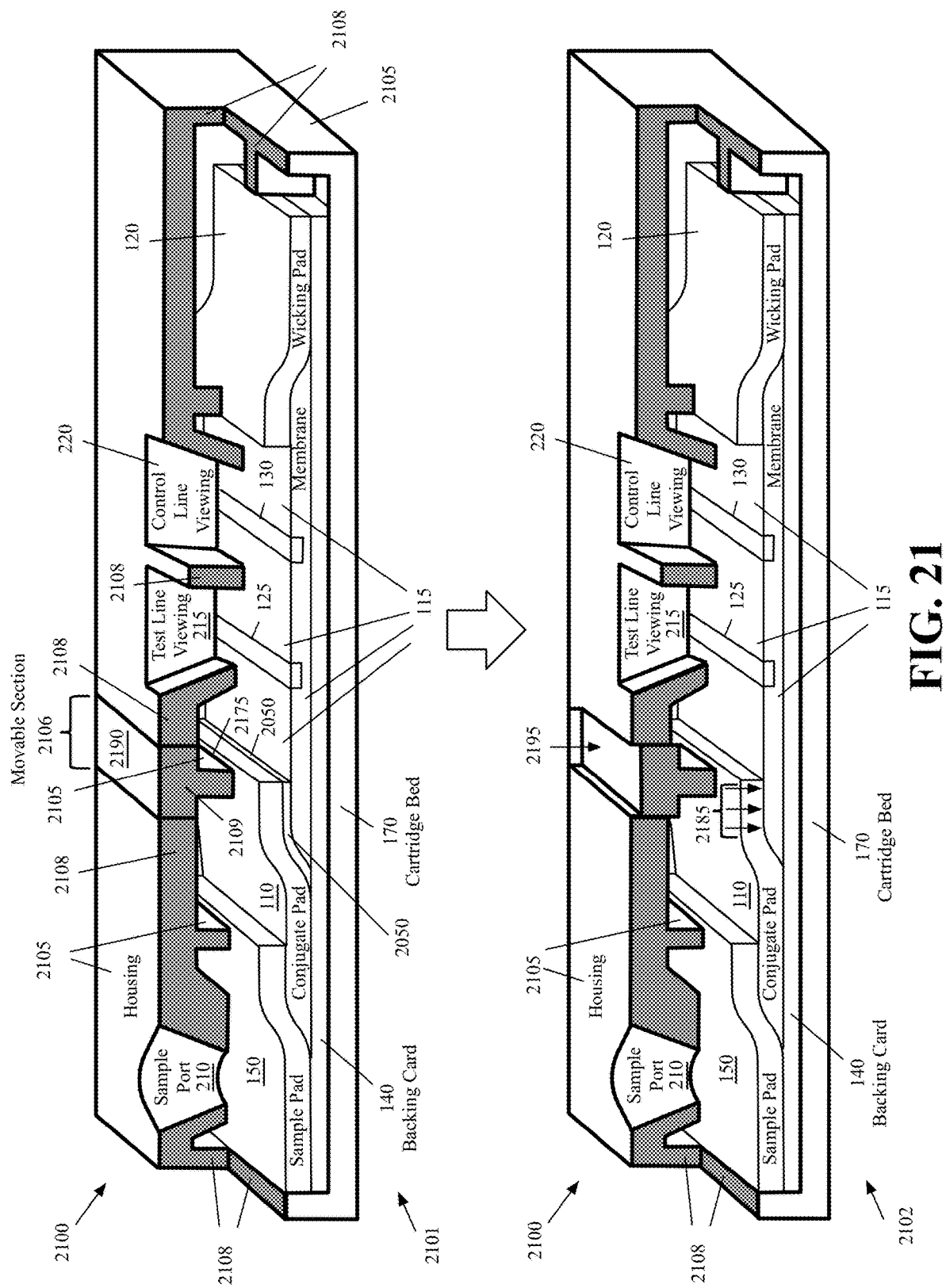
Figure 22:
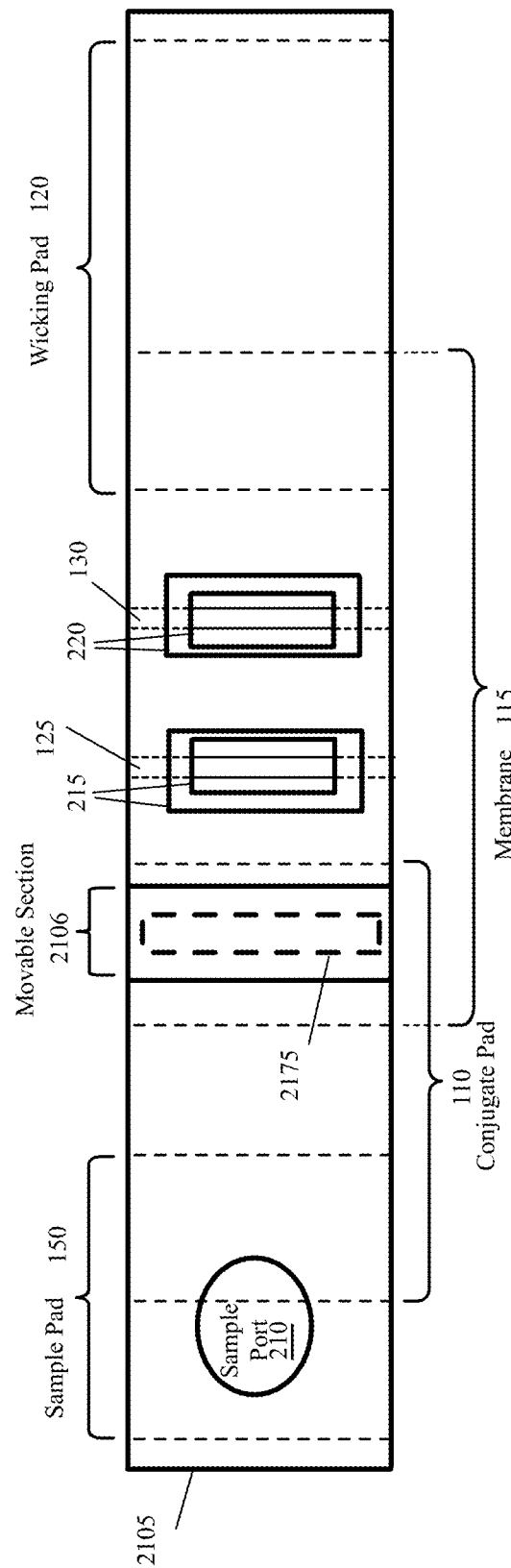
Figure 23:
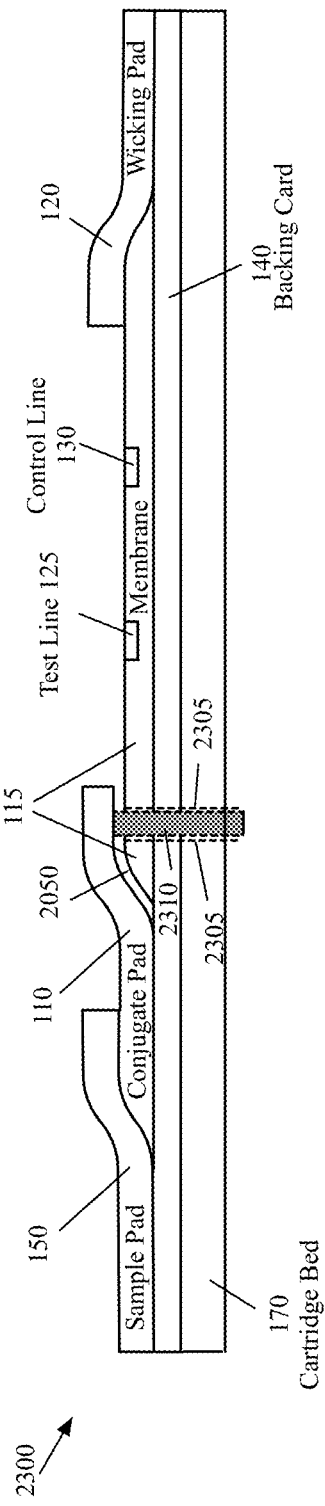
Figure 24:
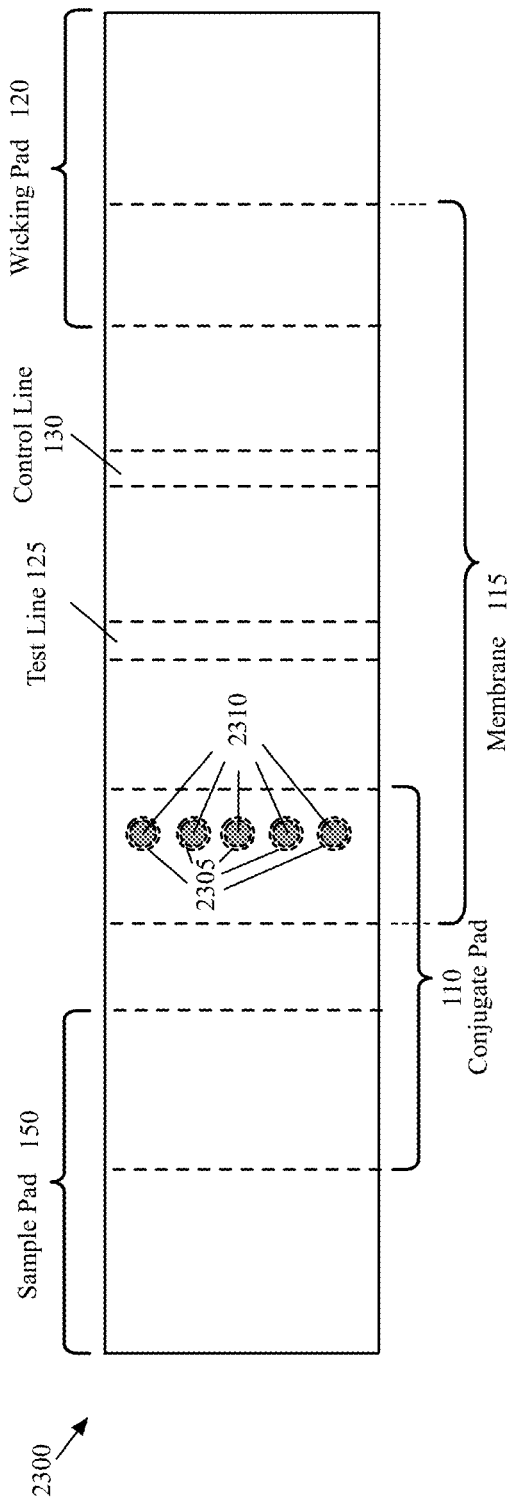
Figure 25:
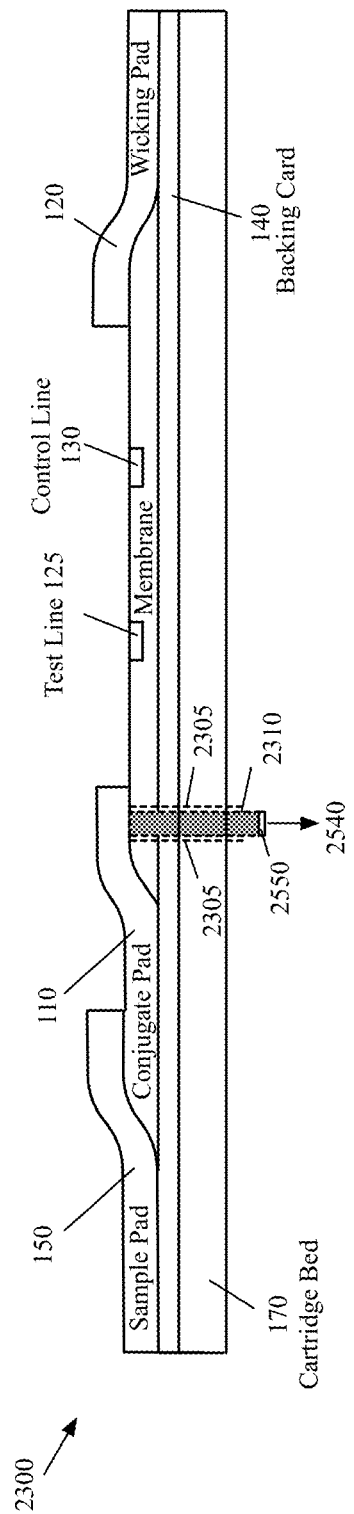
Figure 26:
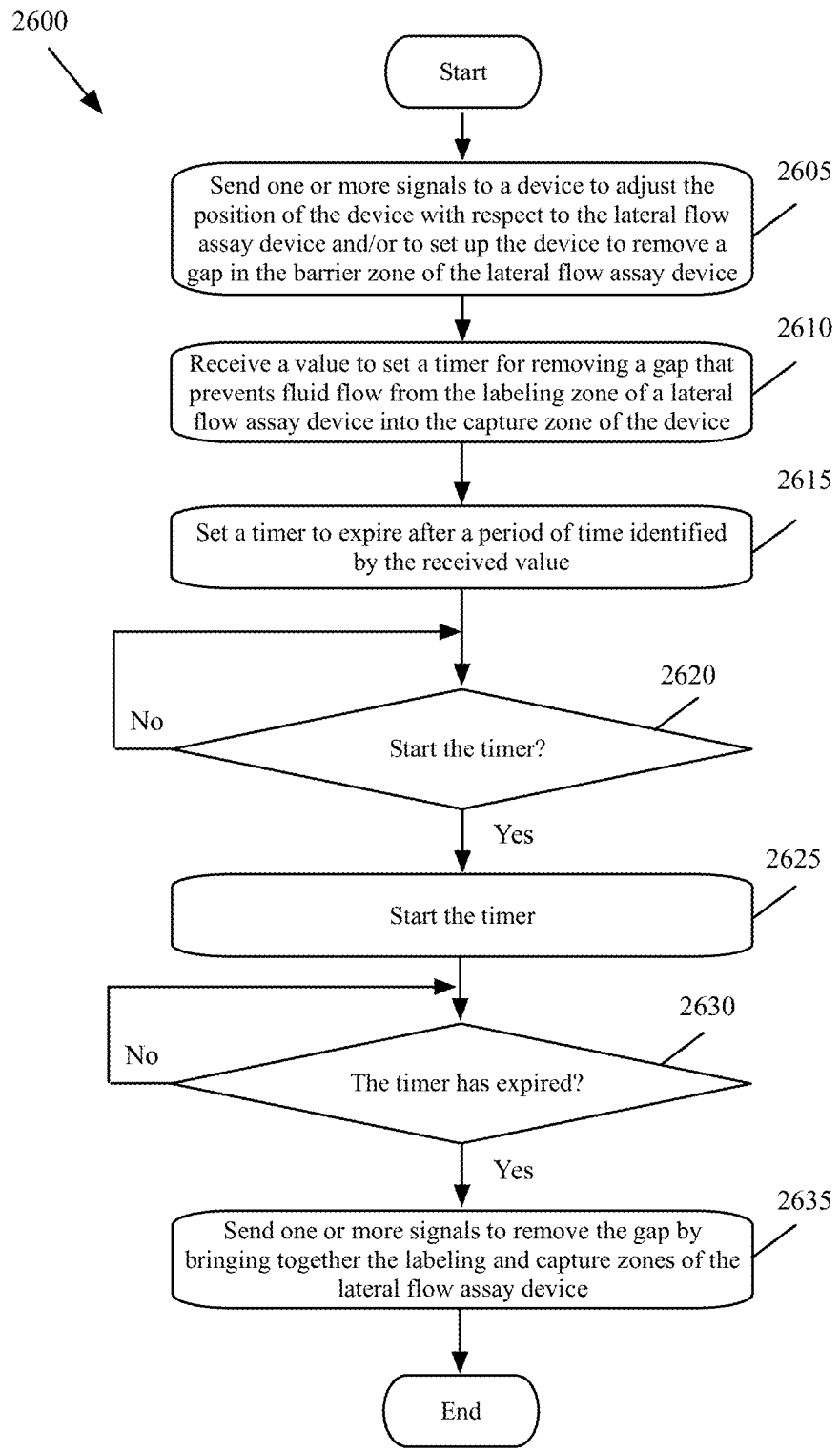
Figure 27:
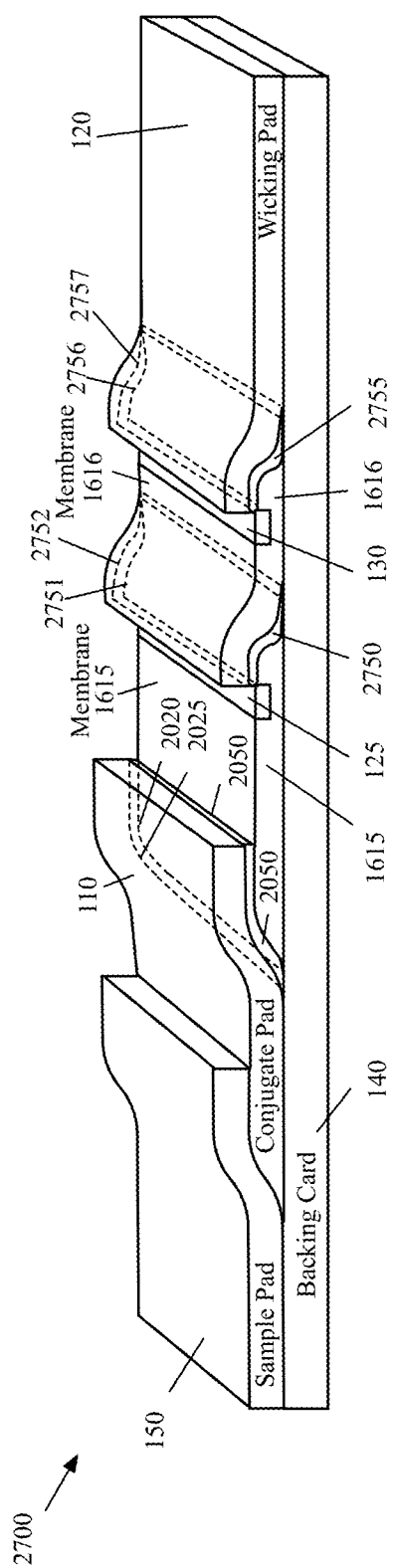
Figure 28:
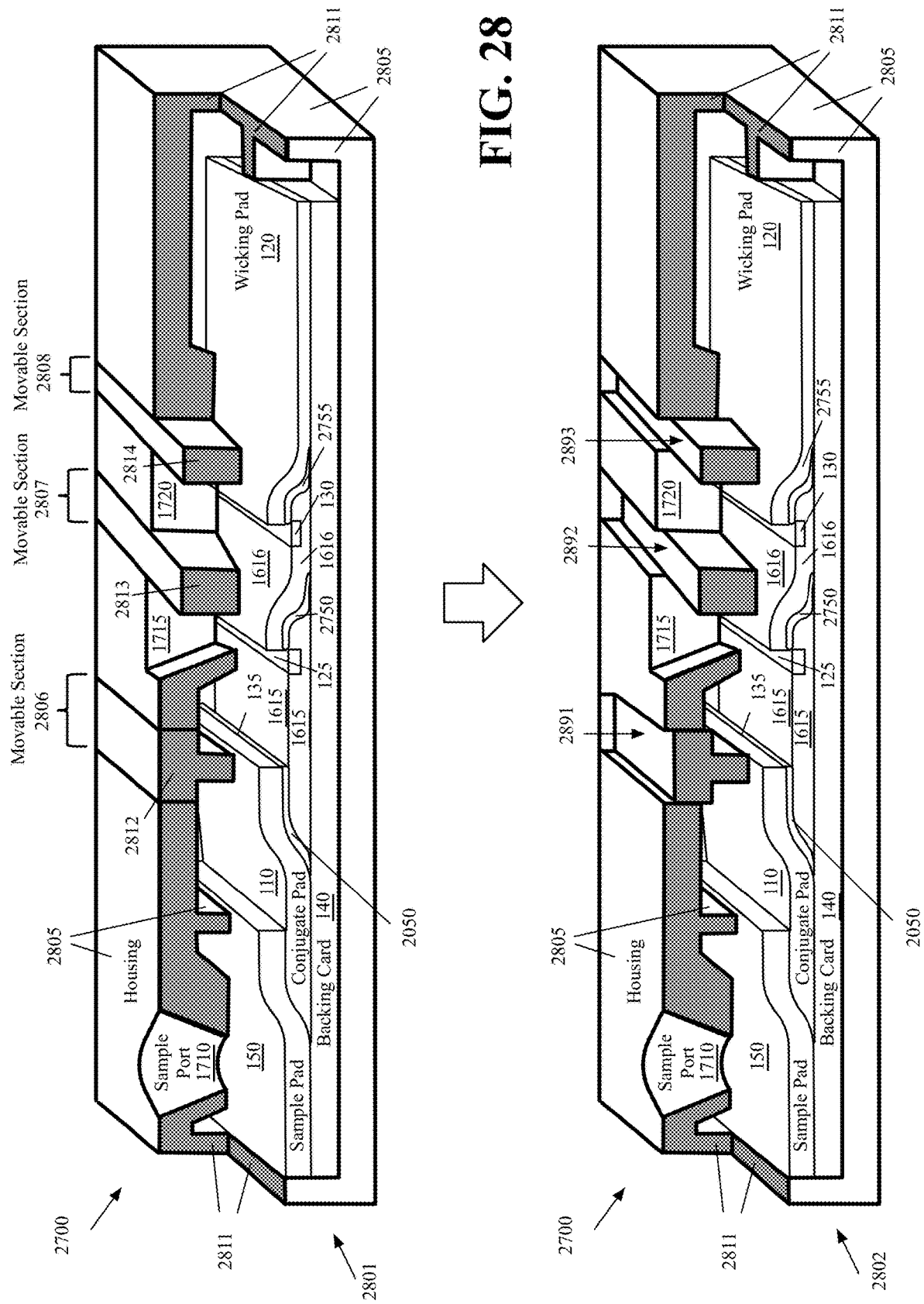
Figure 31:
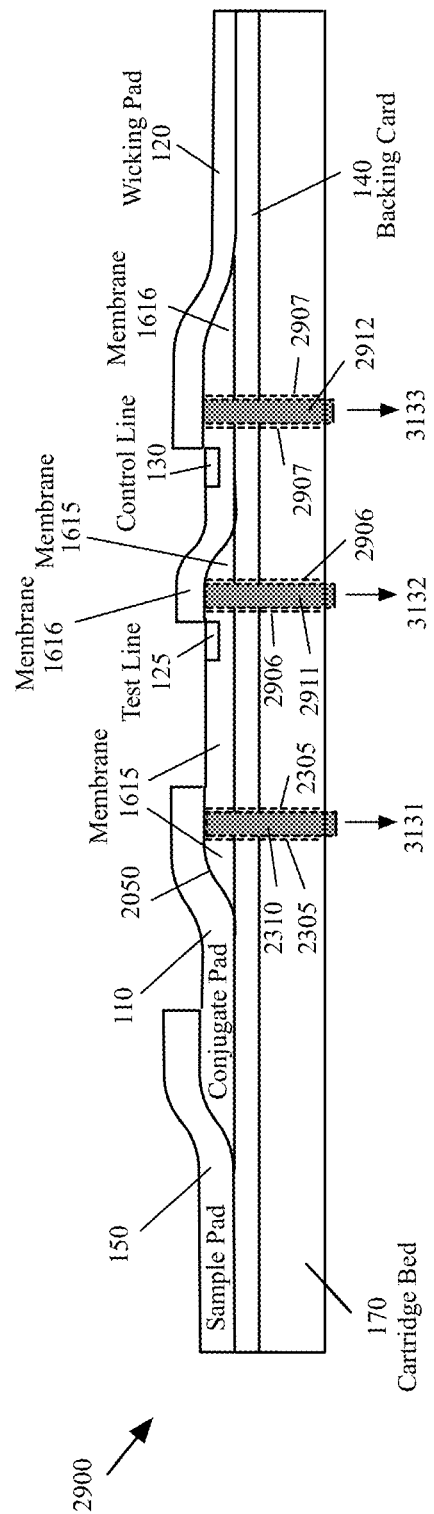
Figure 32:
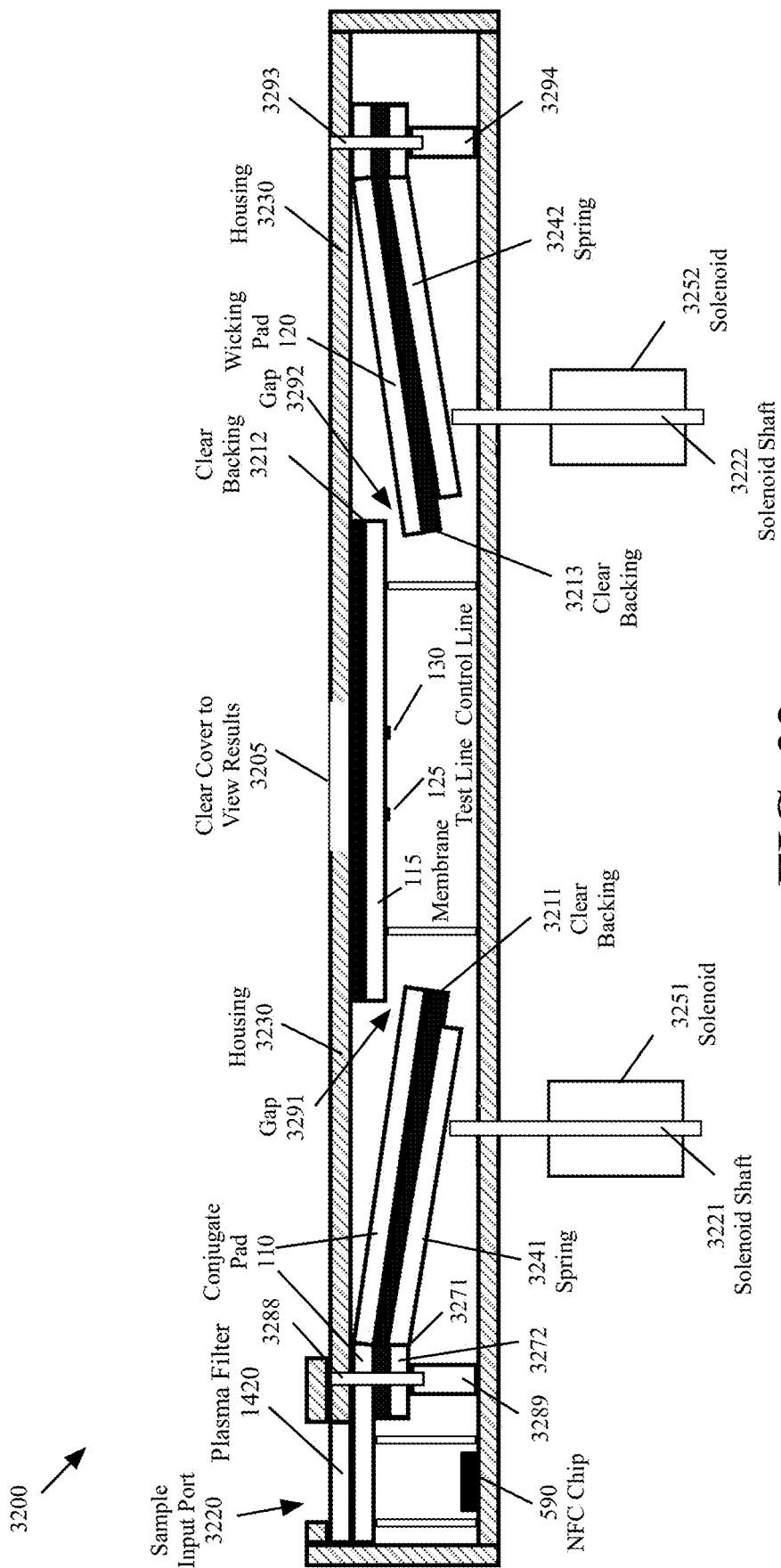
Figure 33:
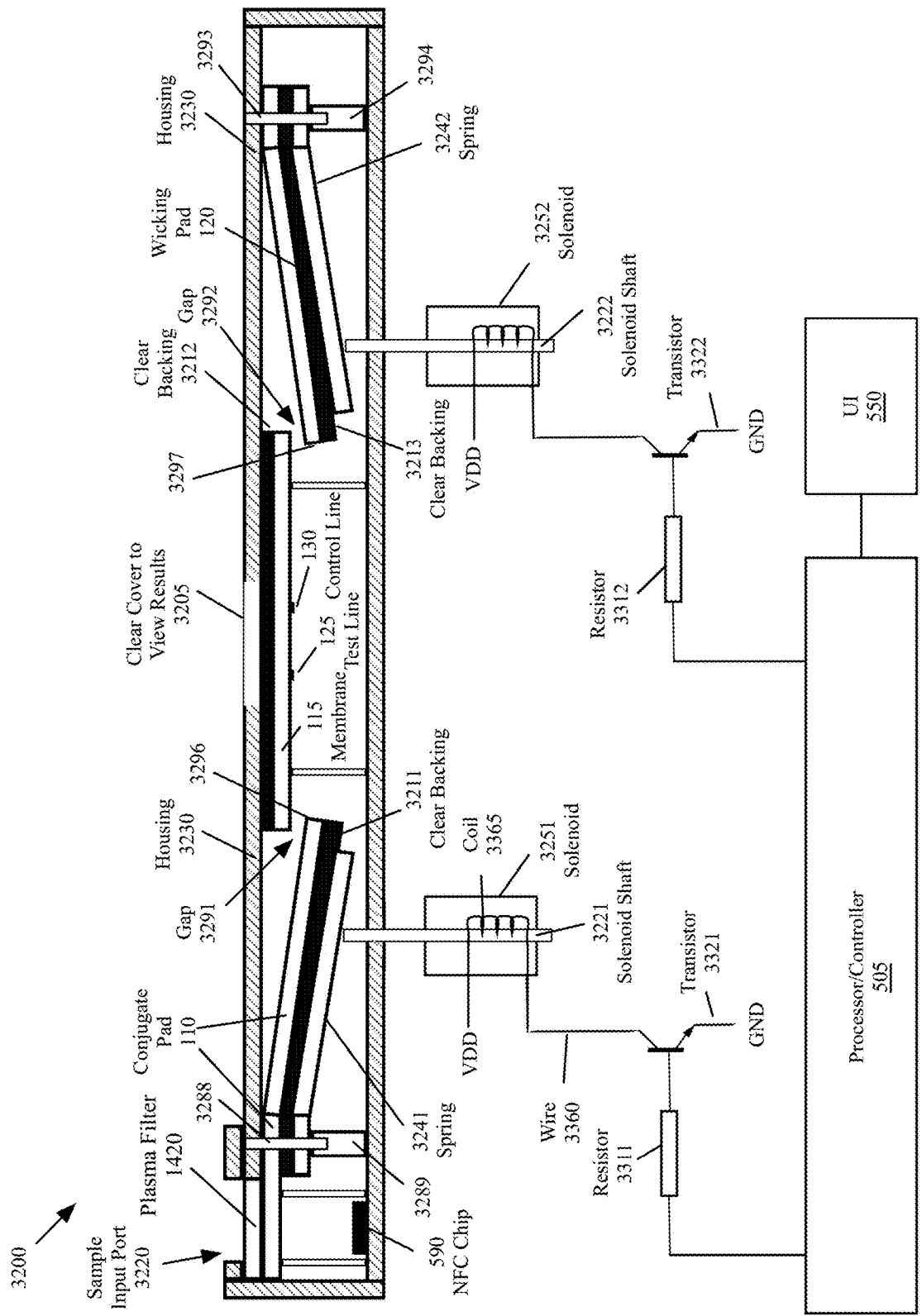
Figure 34:
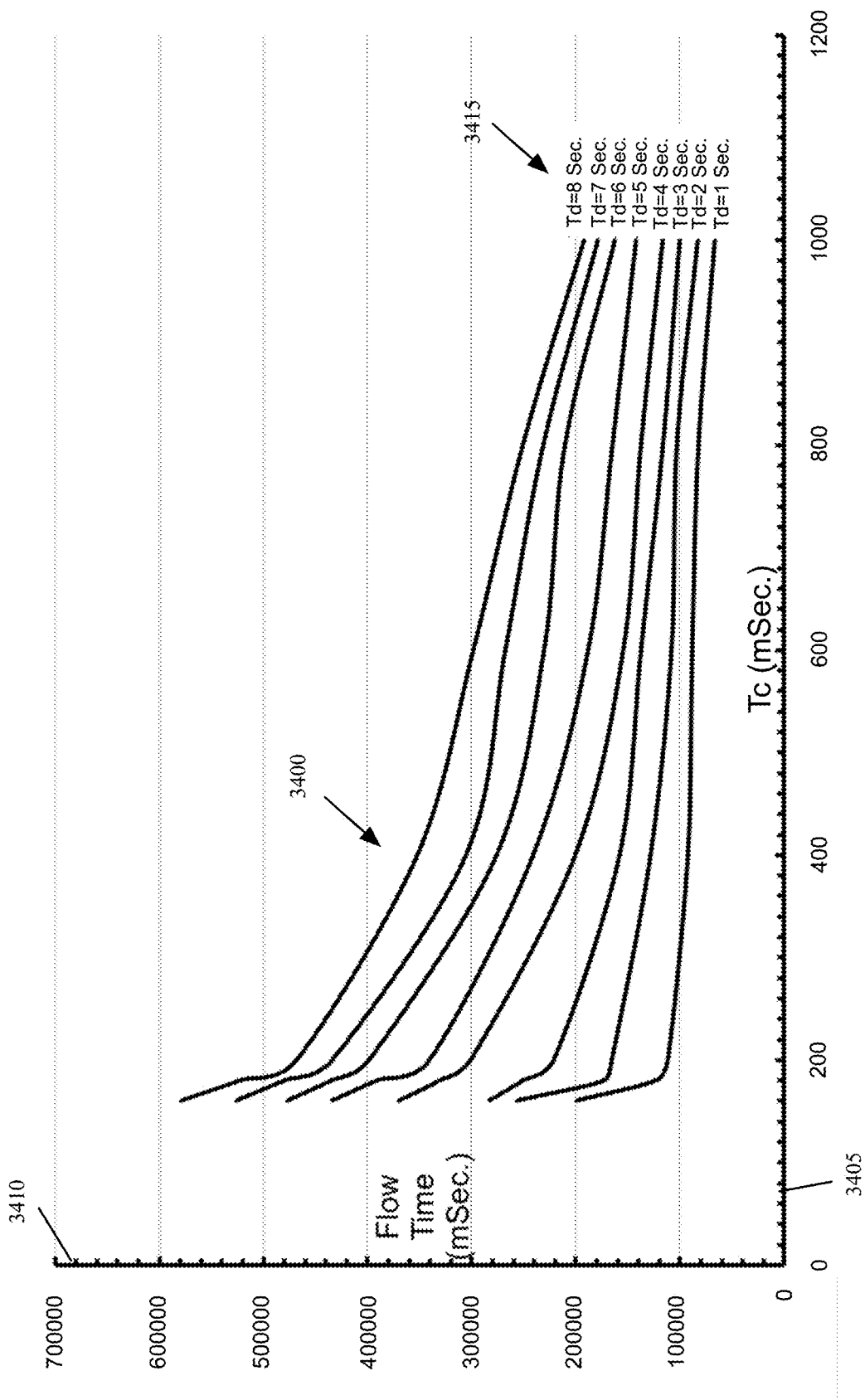
Figure 35:
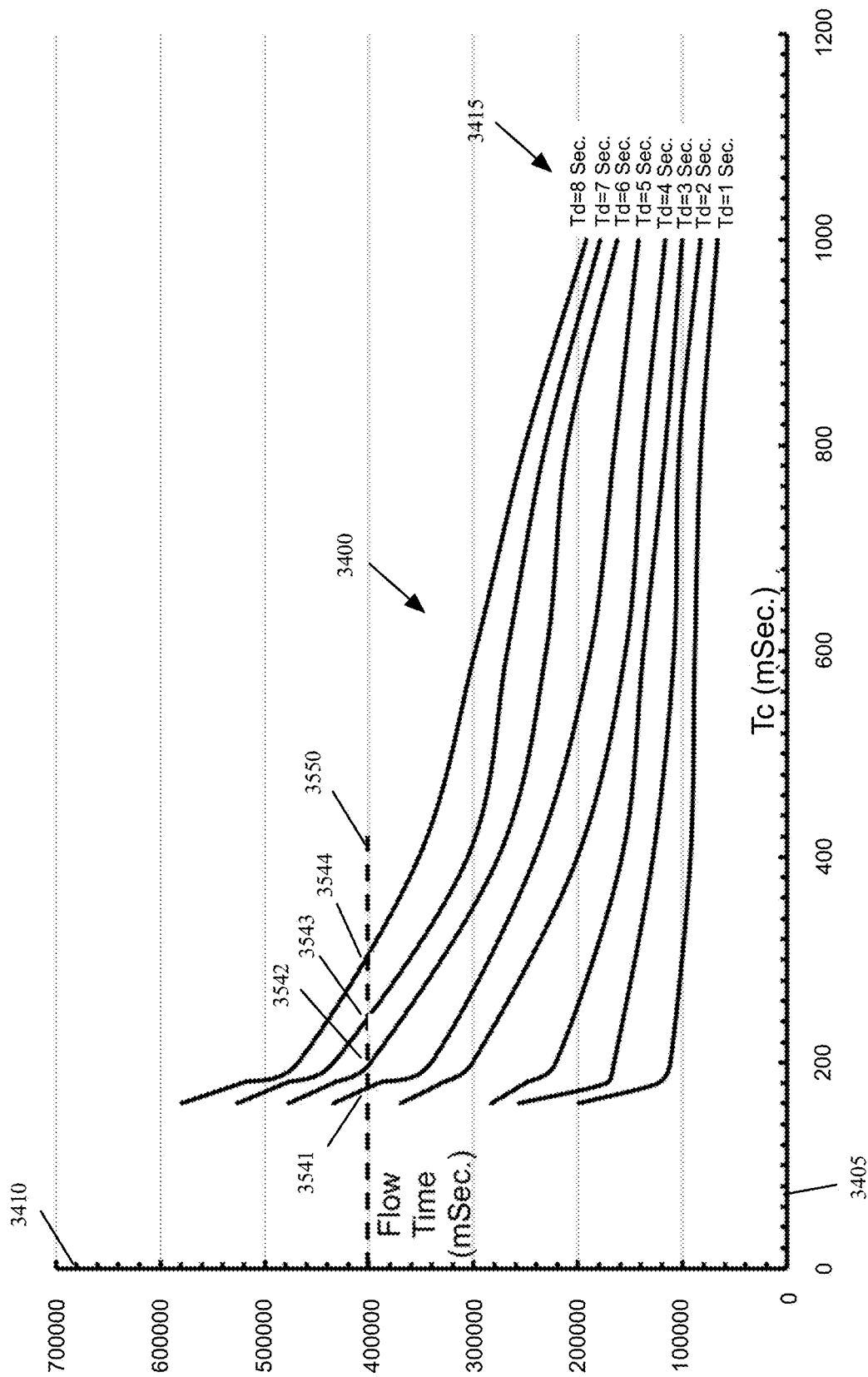
Figure 36:
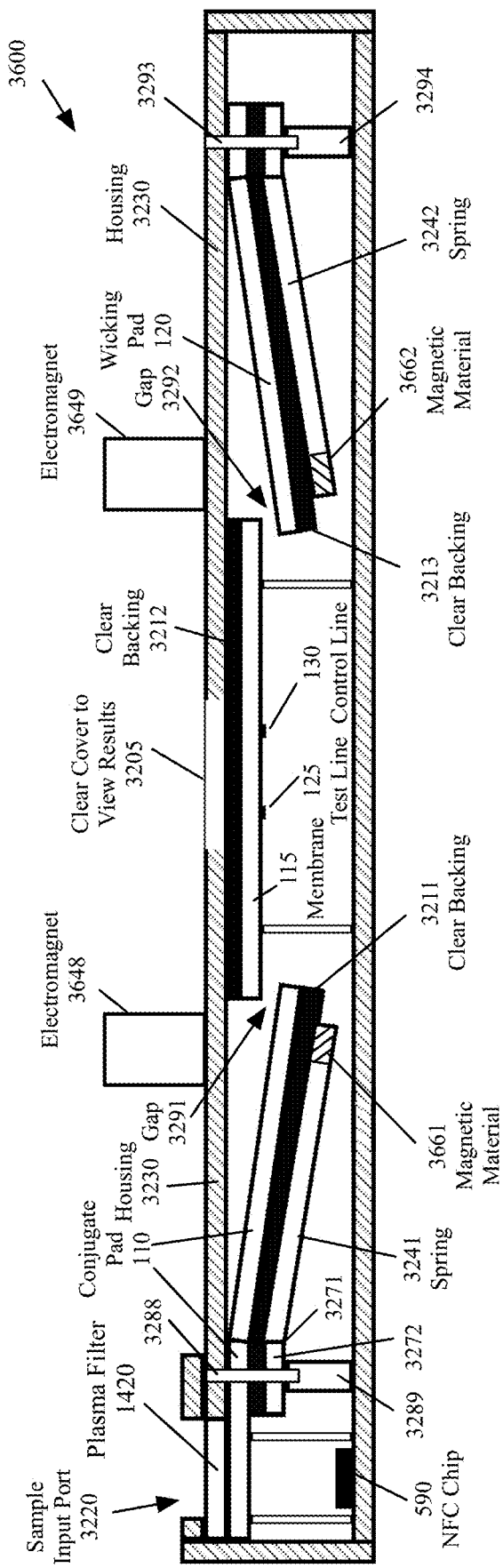
Figure 37:
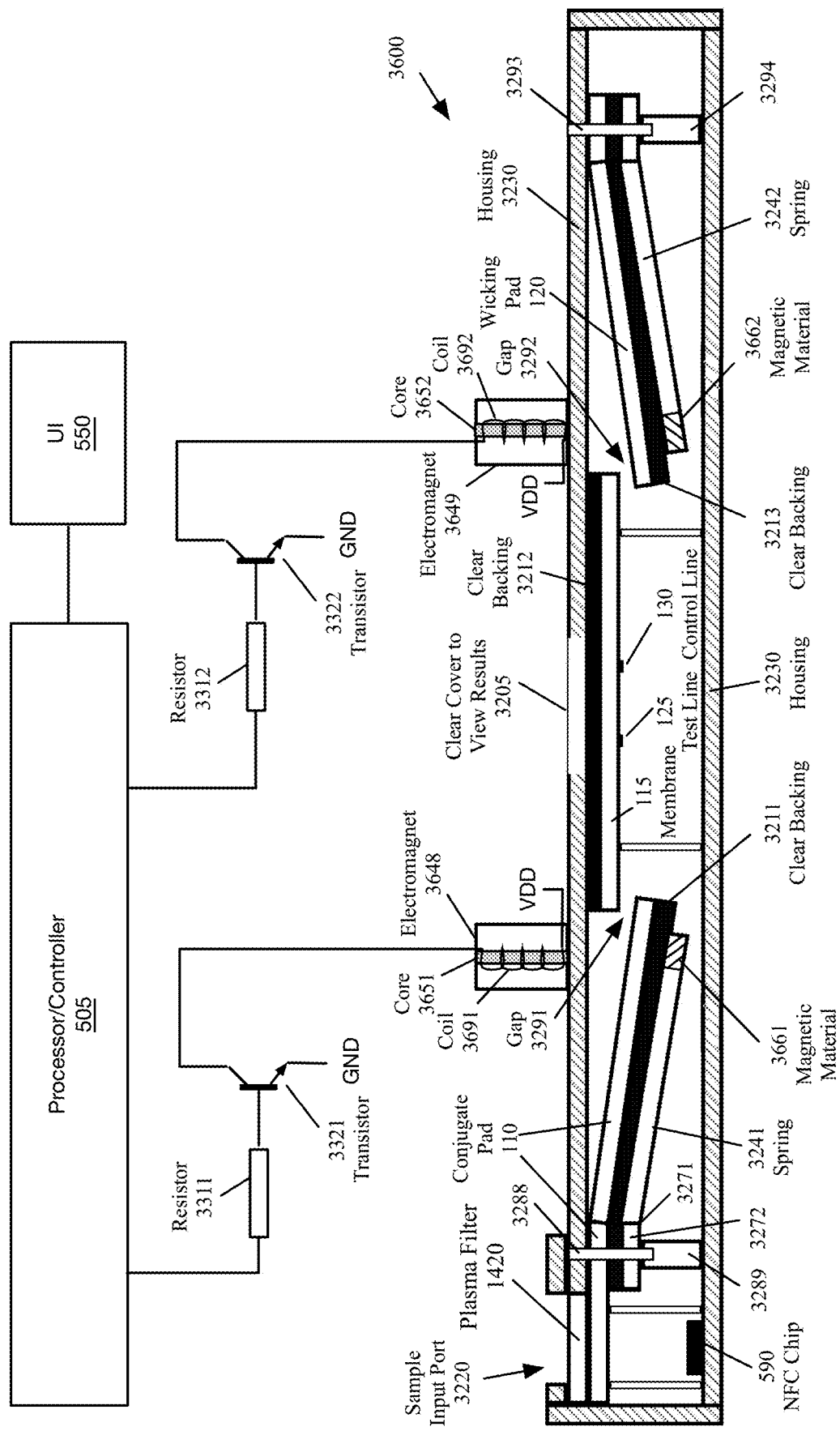
Figure 38:
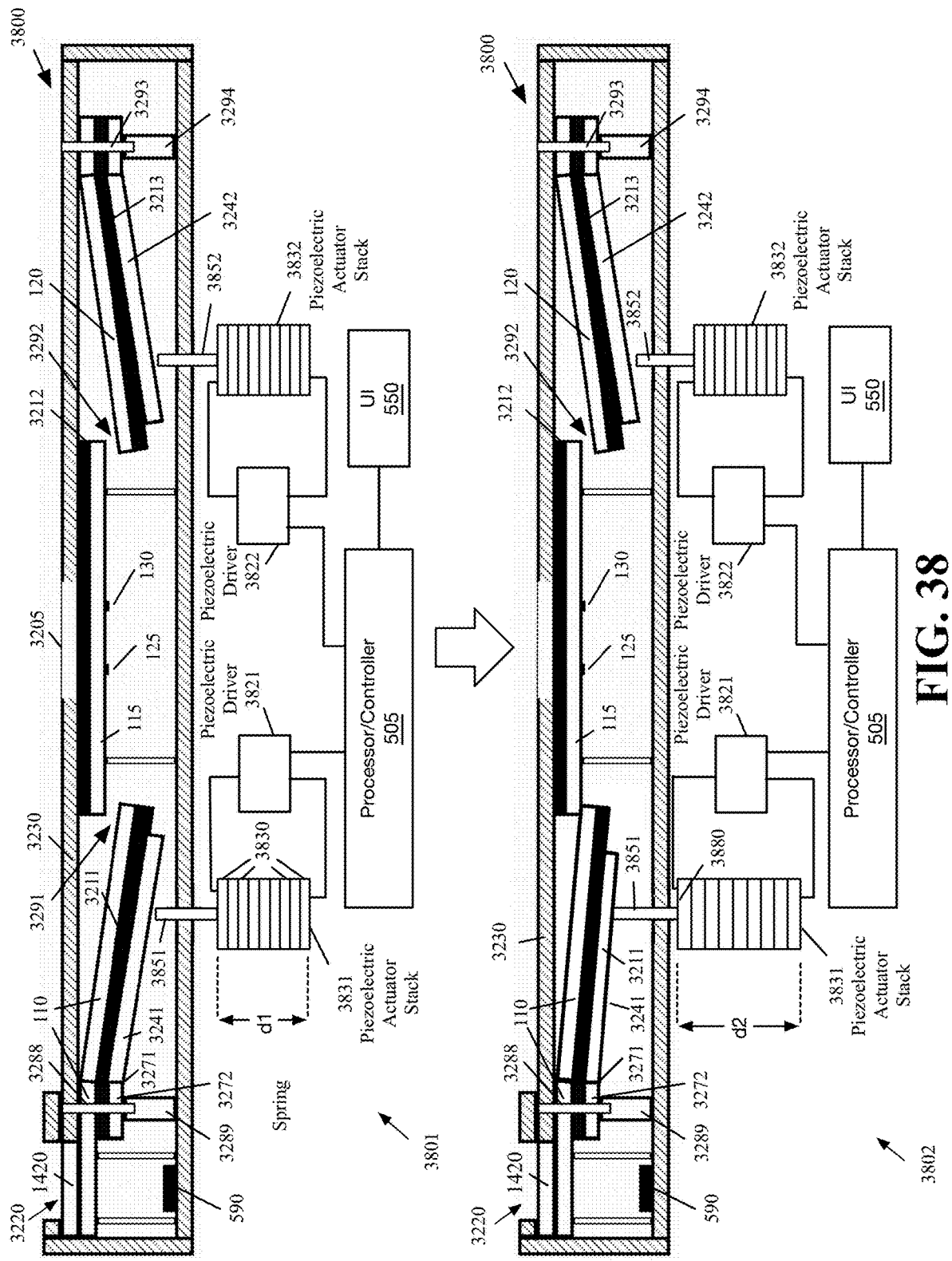
Figure 39:
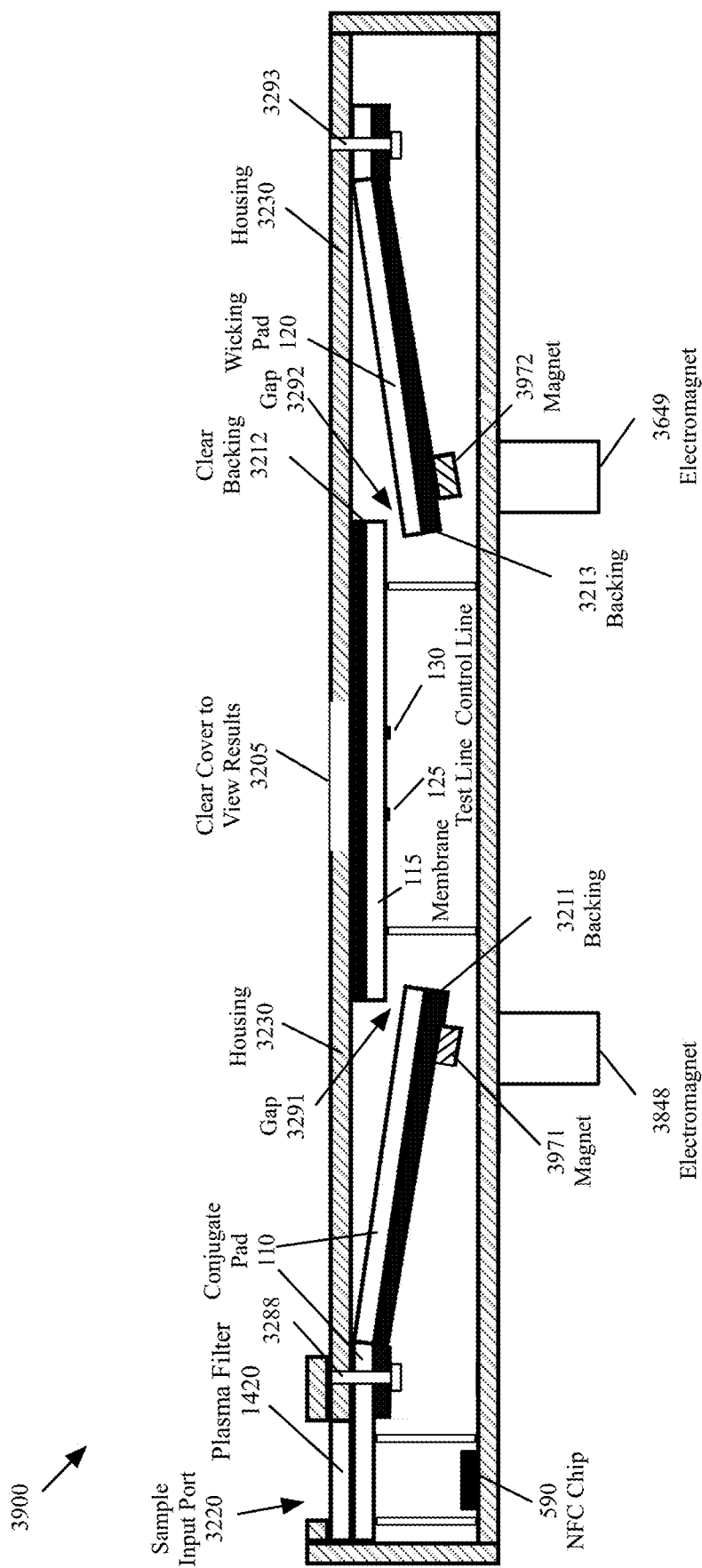
Figure 40:
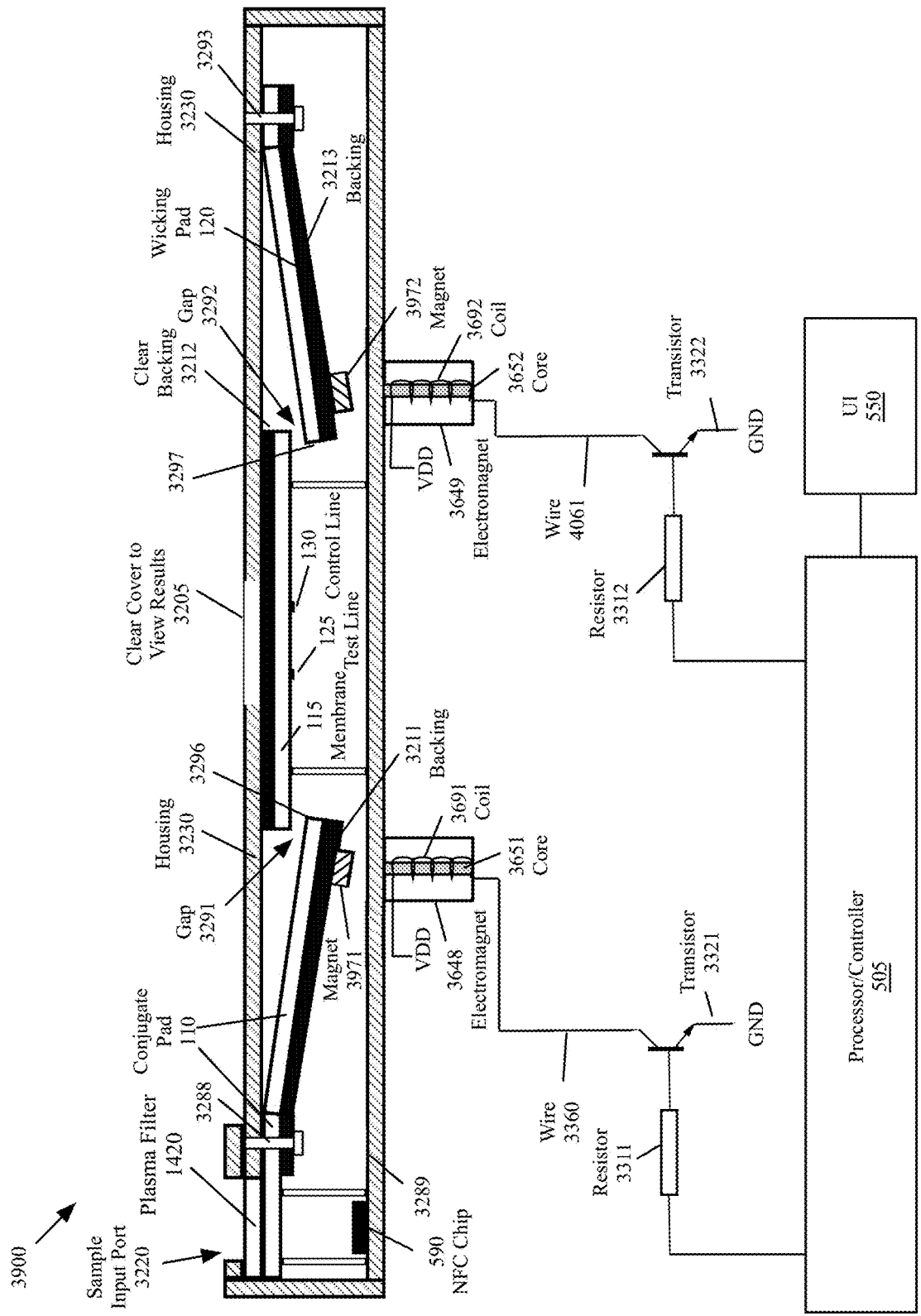
Figure 41:
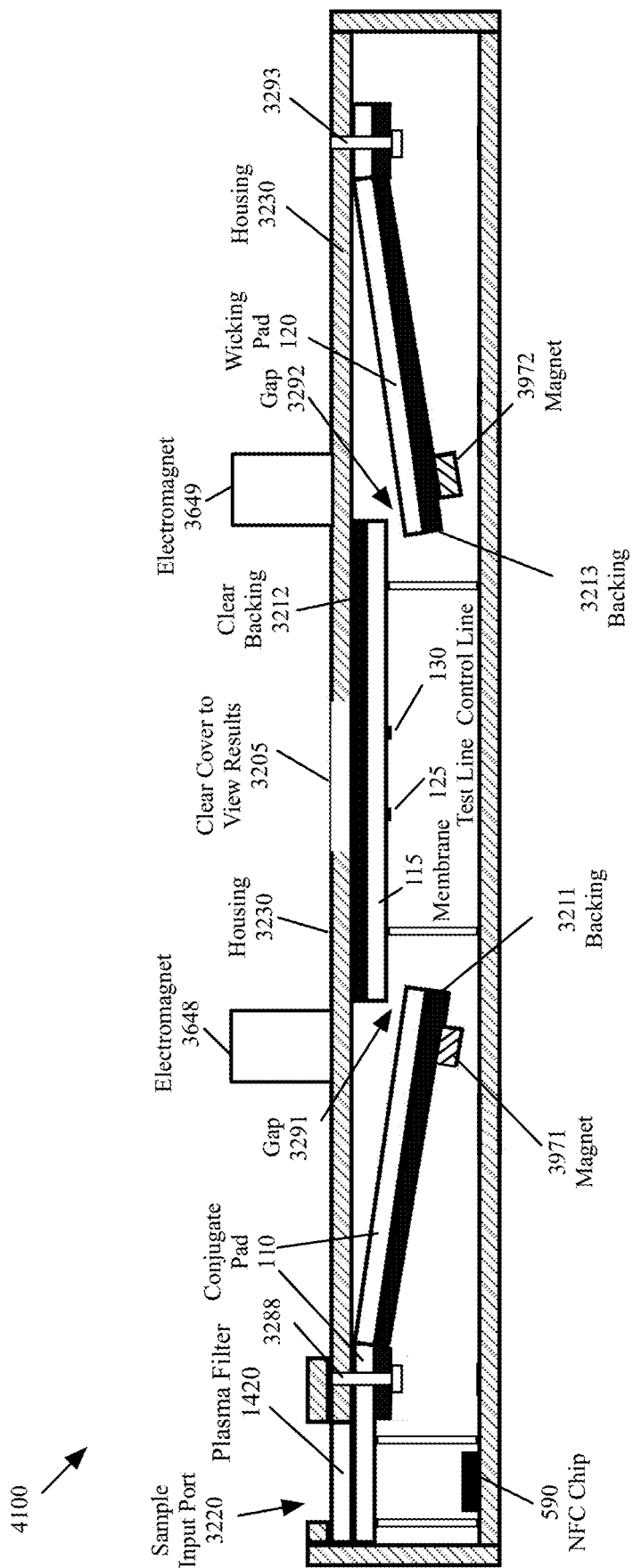
Figure 42:
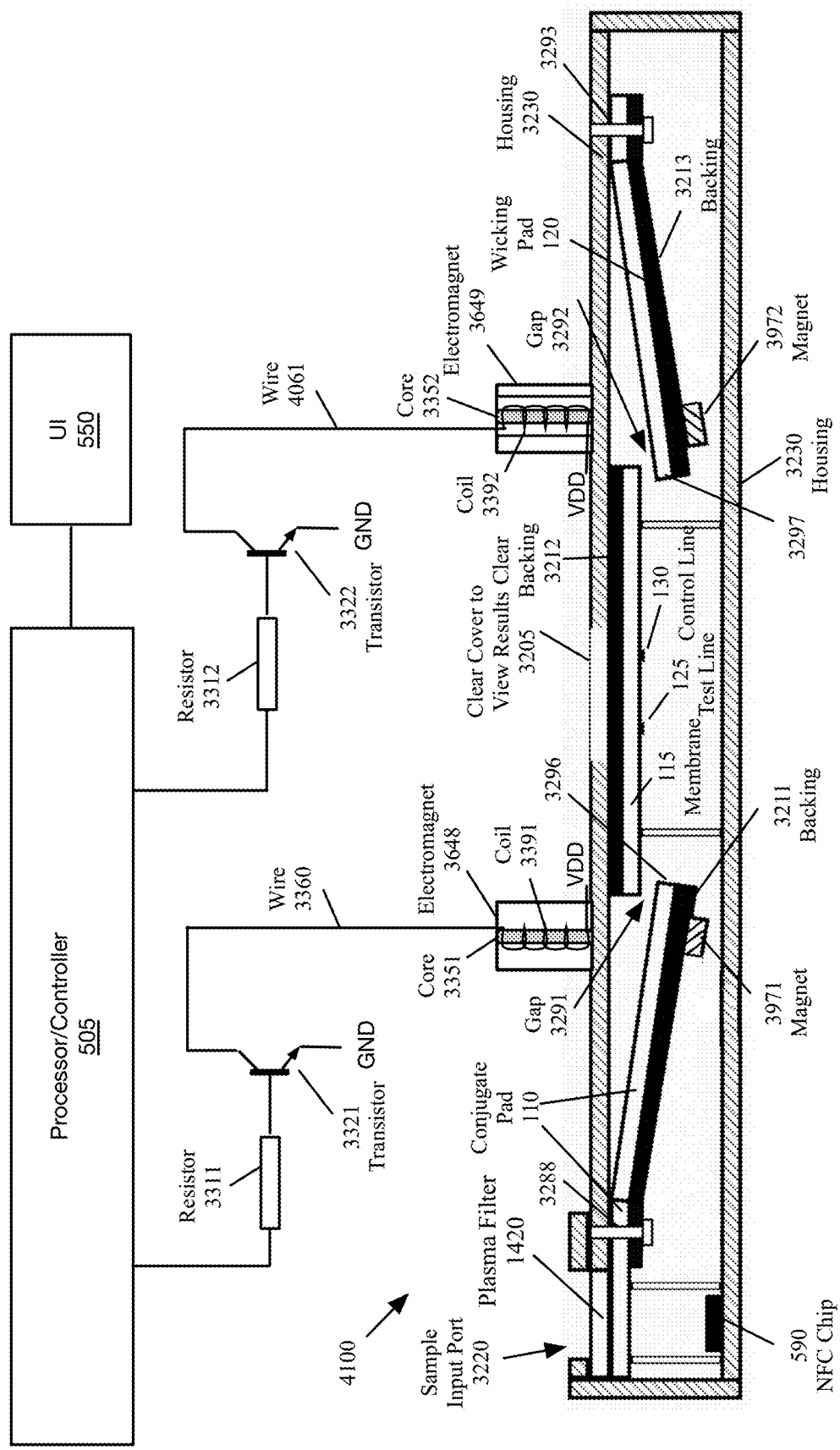
Figure 43:
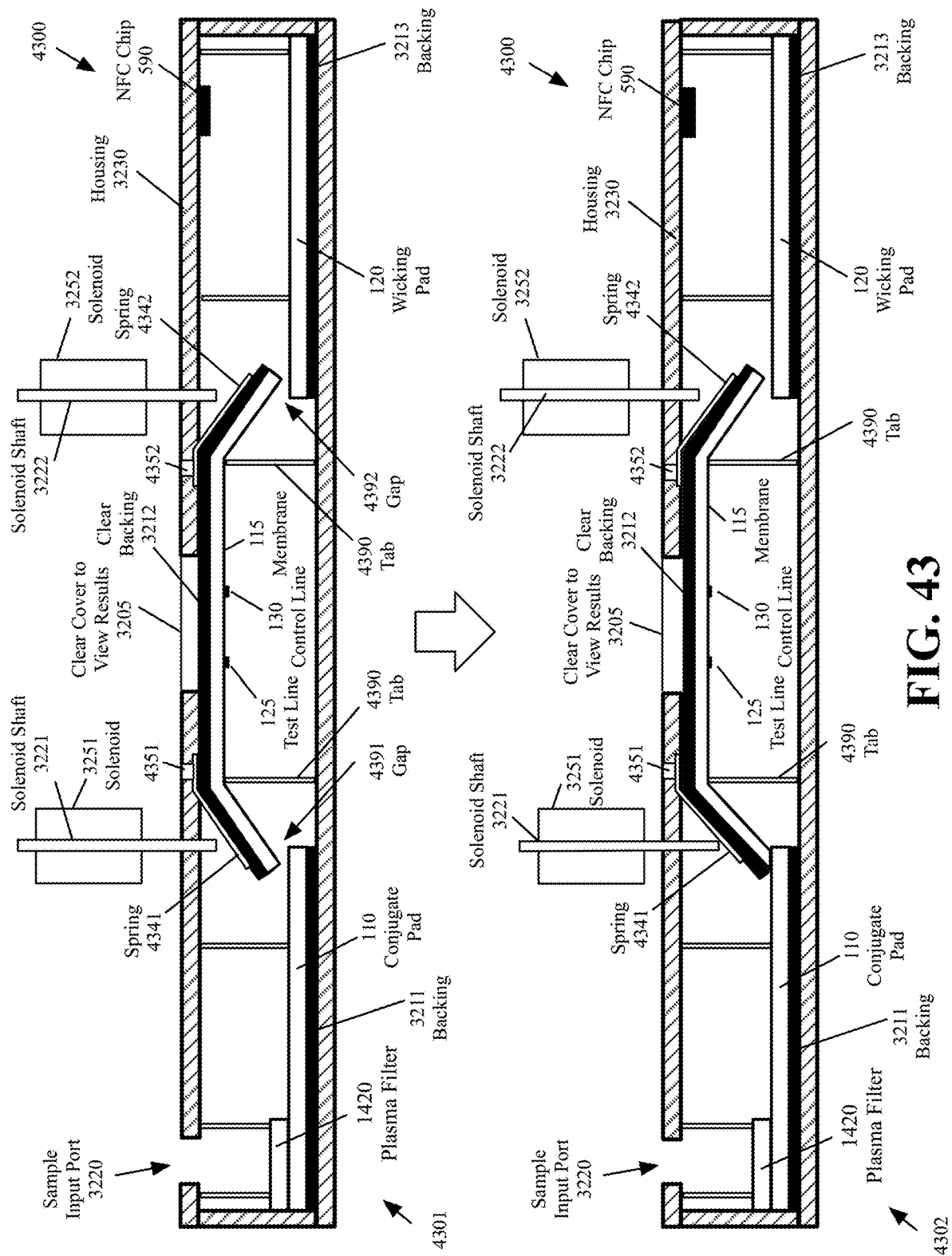
Figure 44:
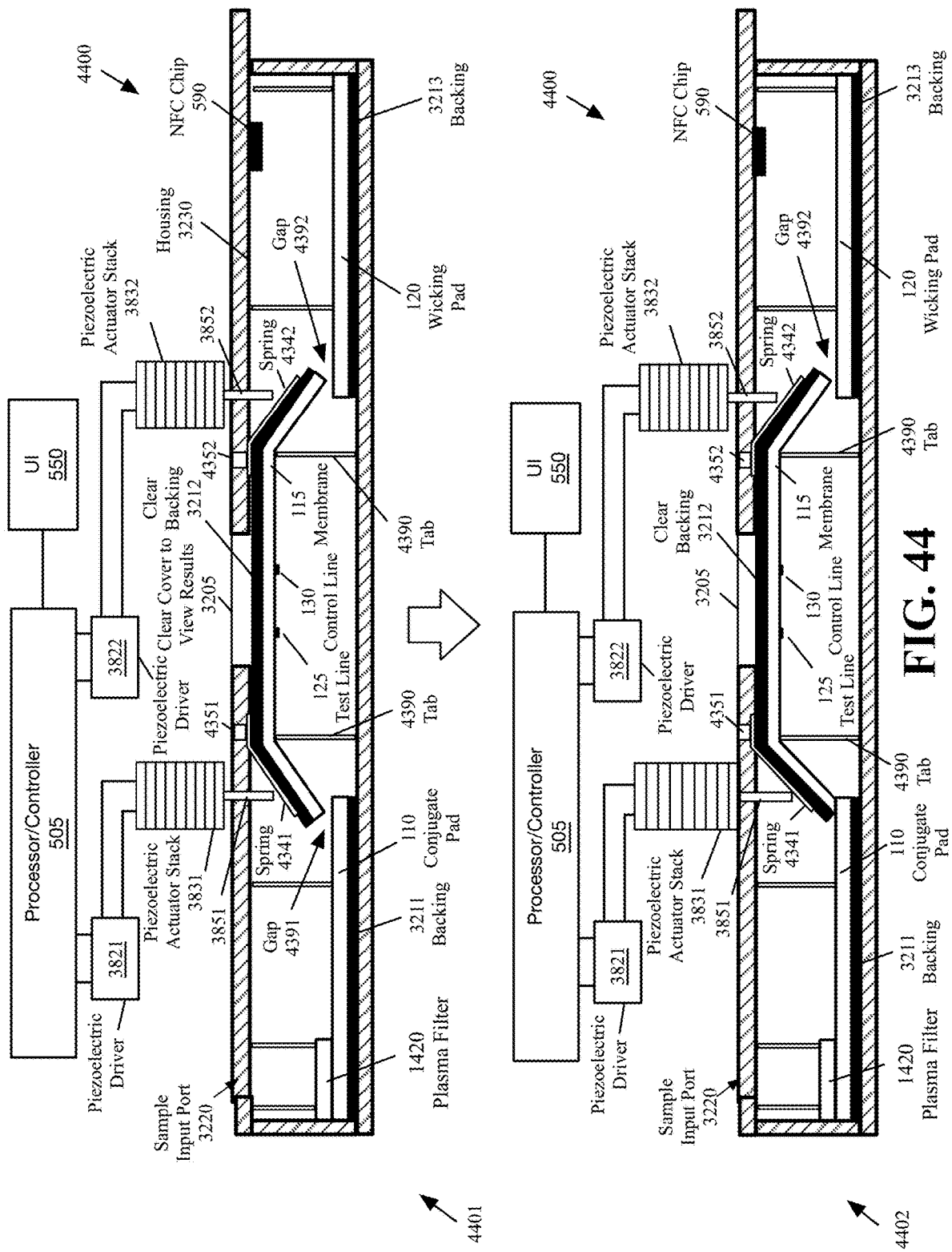
Figure 45:
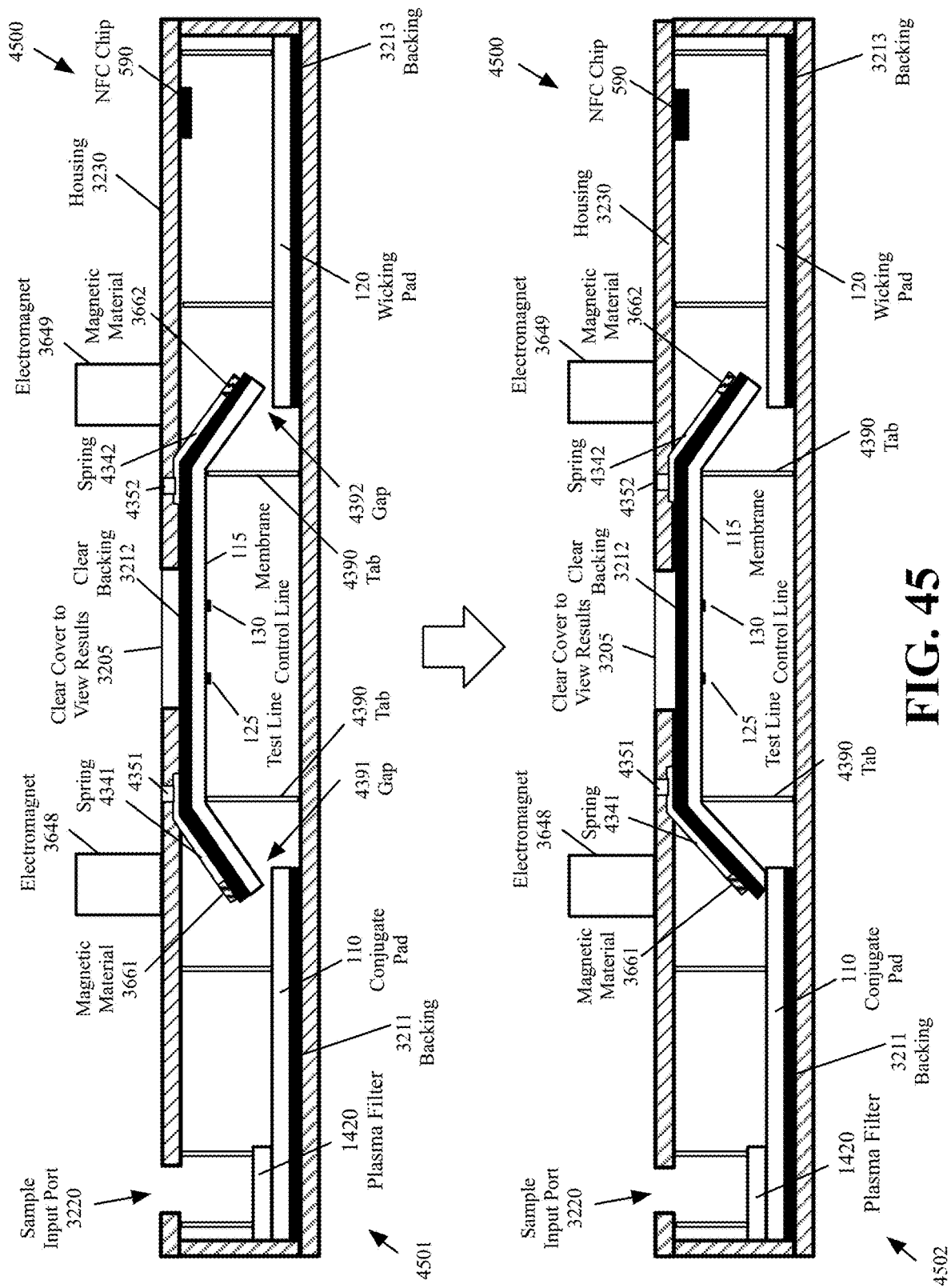
Figure 46:
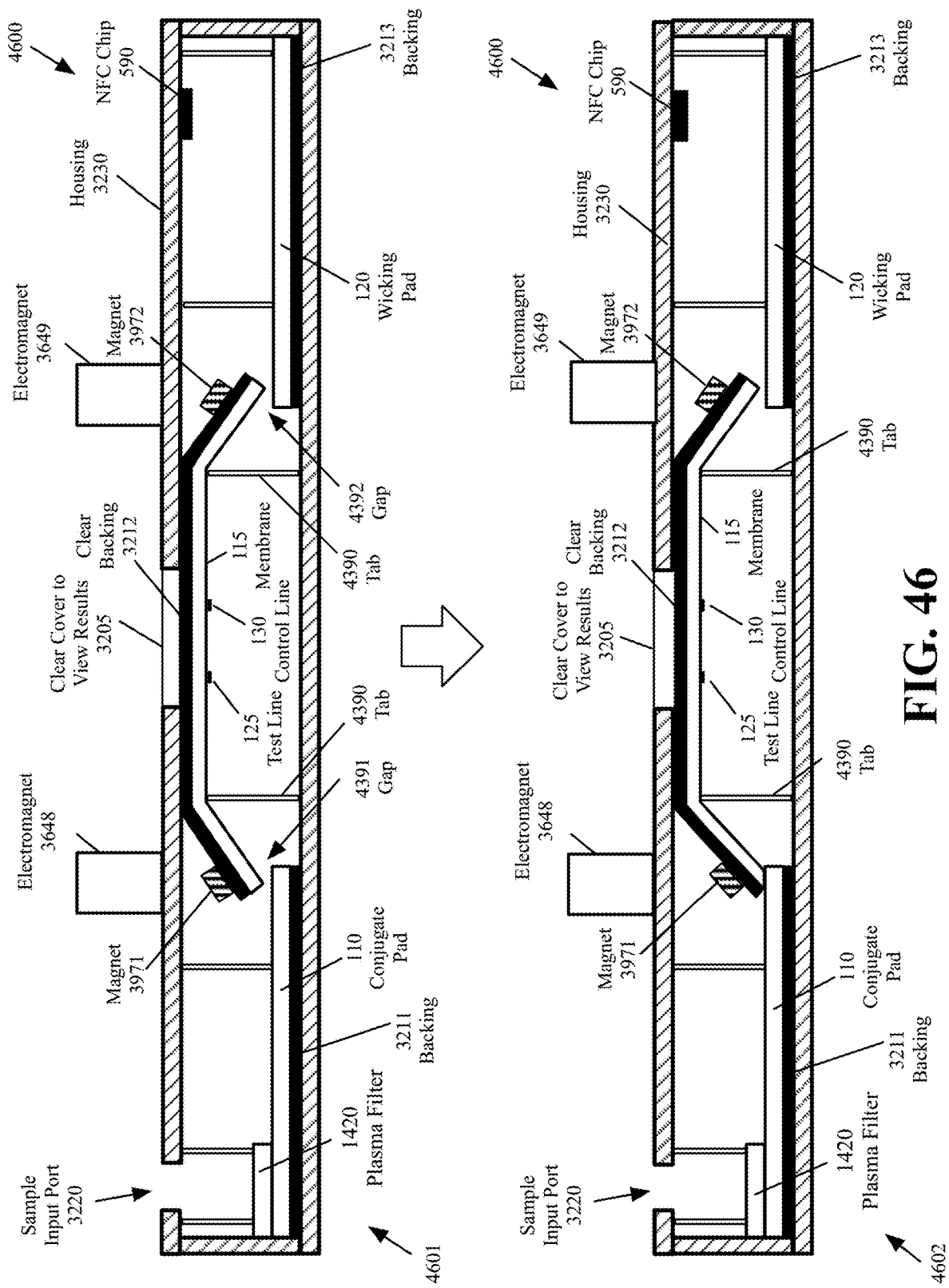
Figure 47:
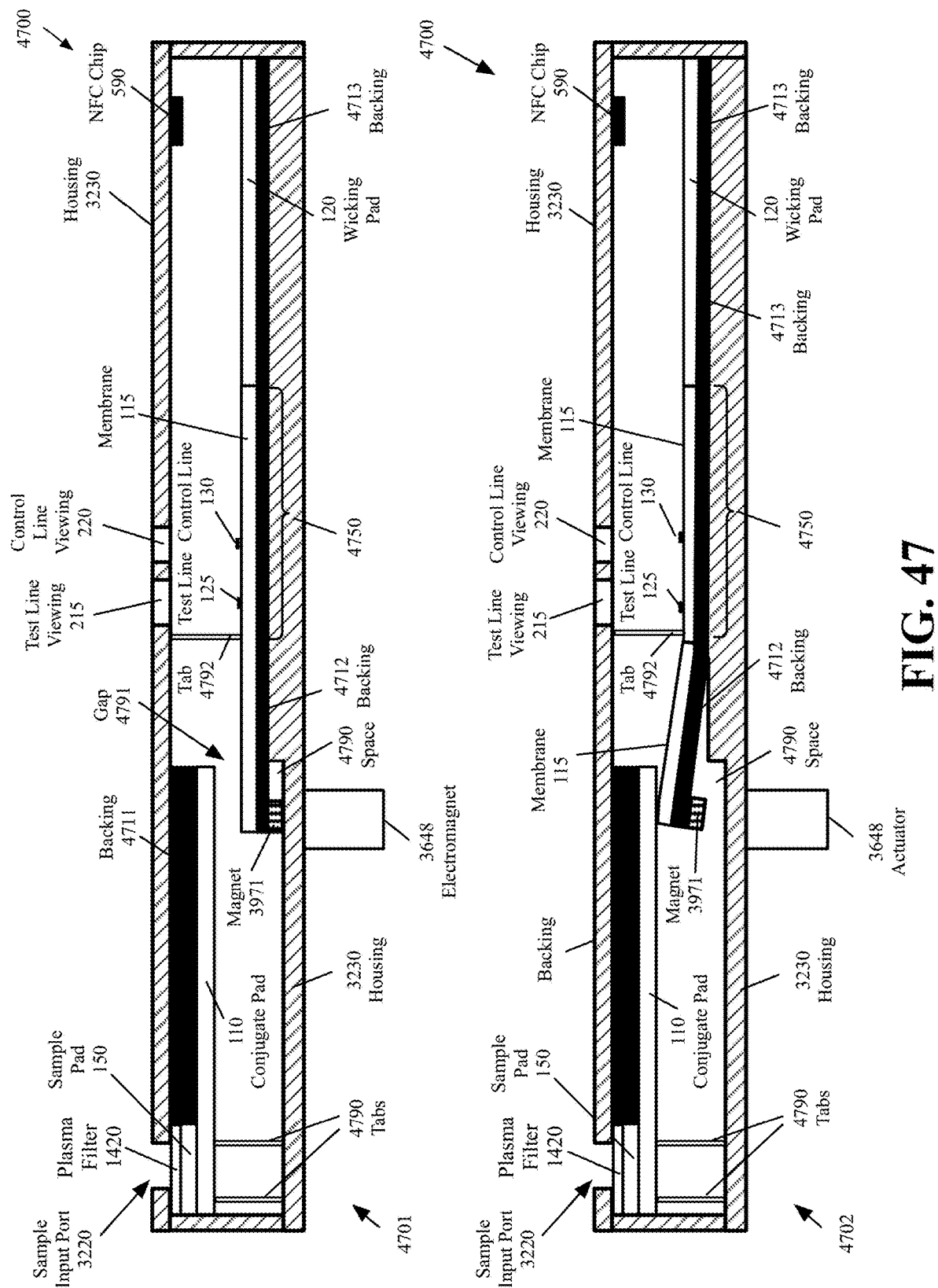
Figure 48:
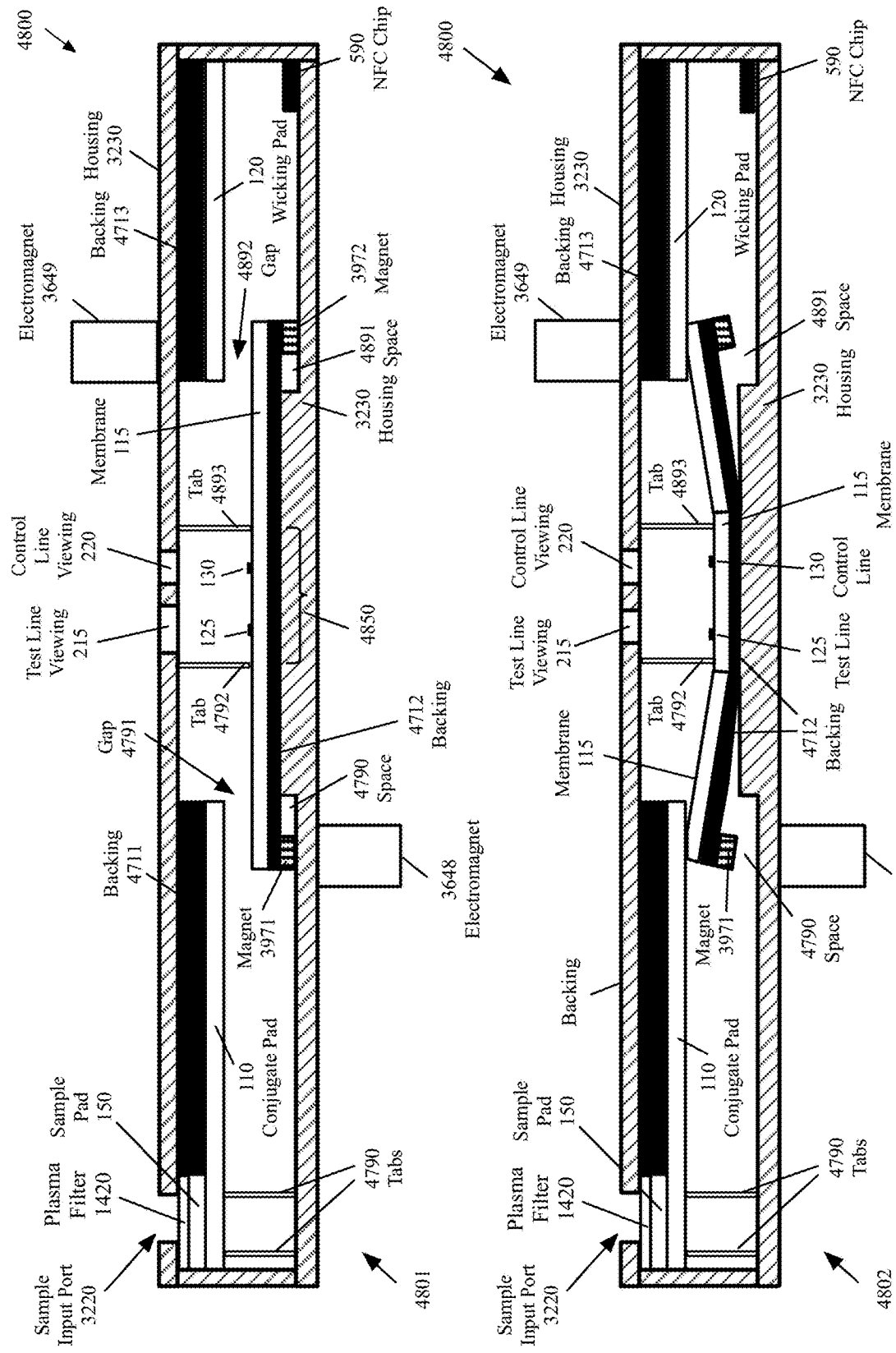
Figure 49A:
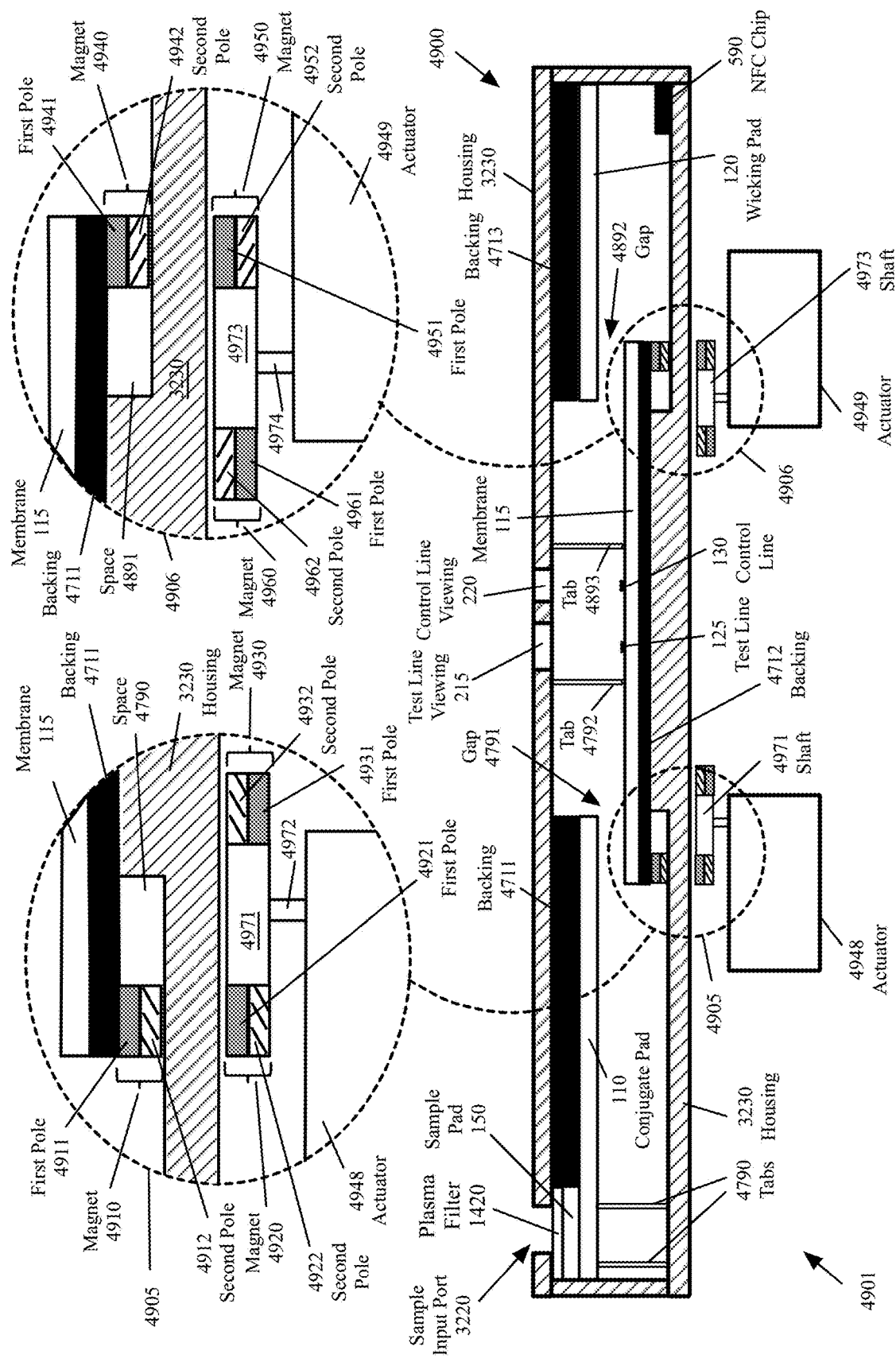
Figure 49B:
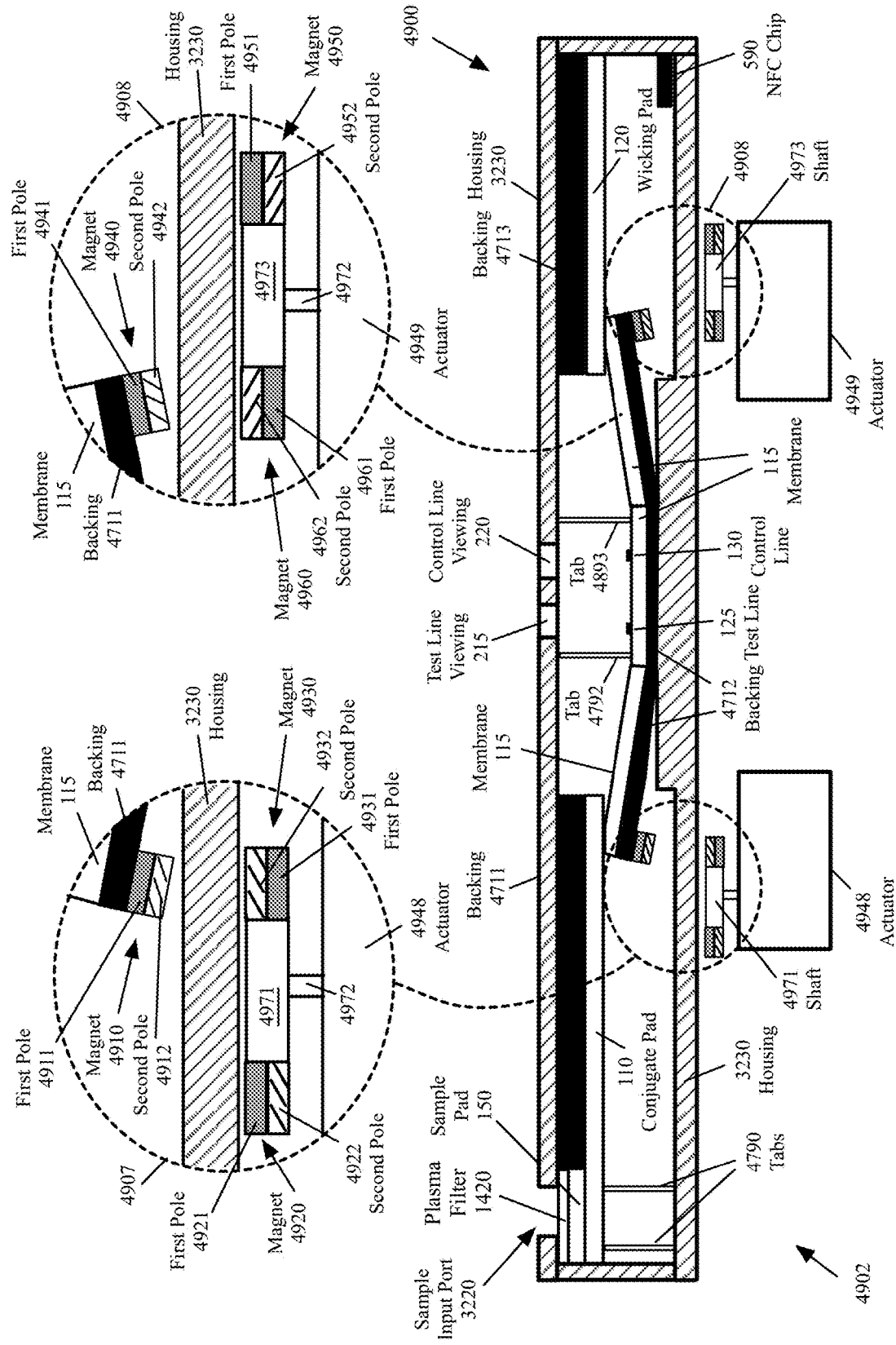
Figure 50A:
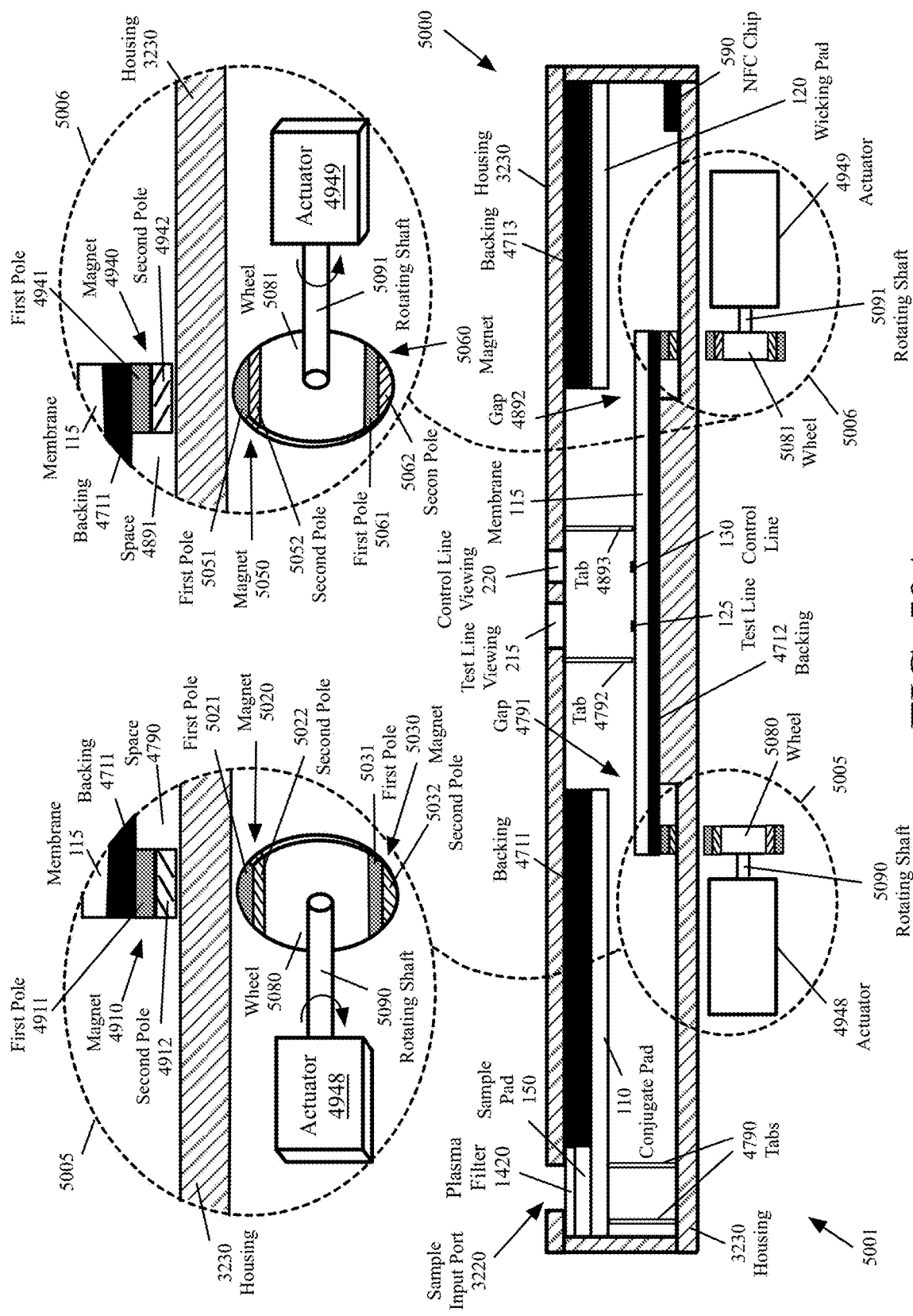
Figure 50B:
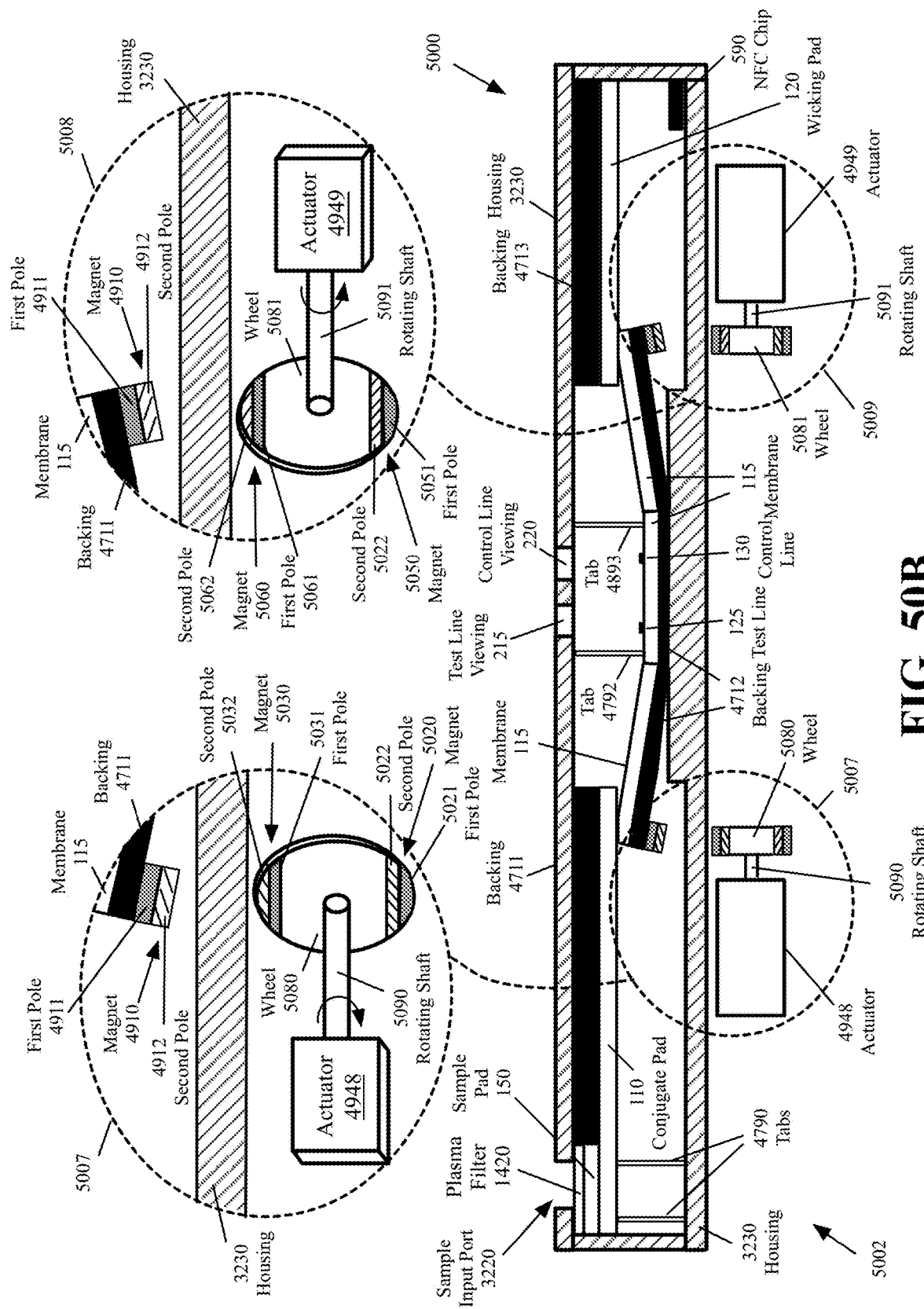
Figure 51:
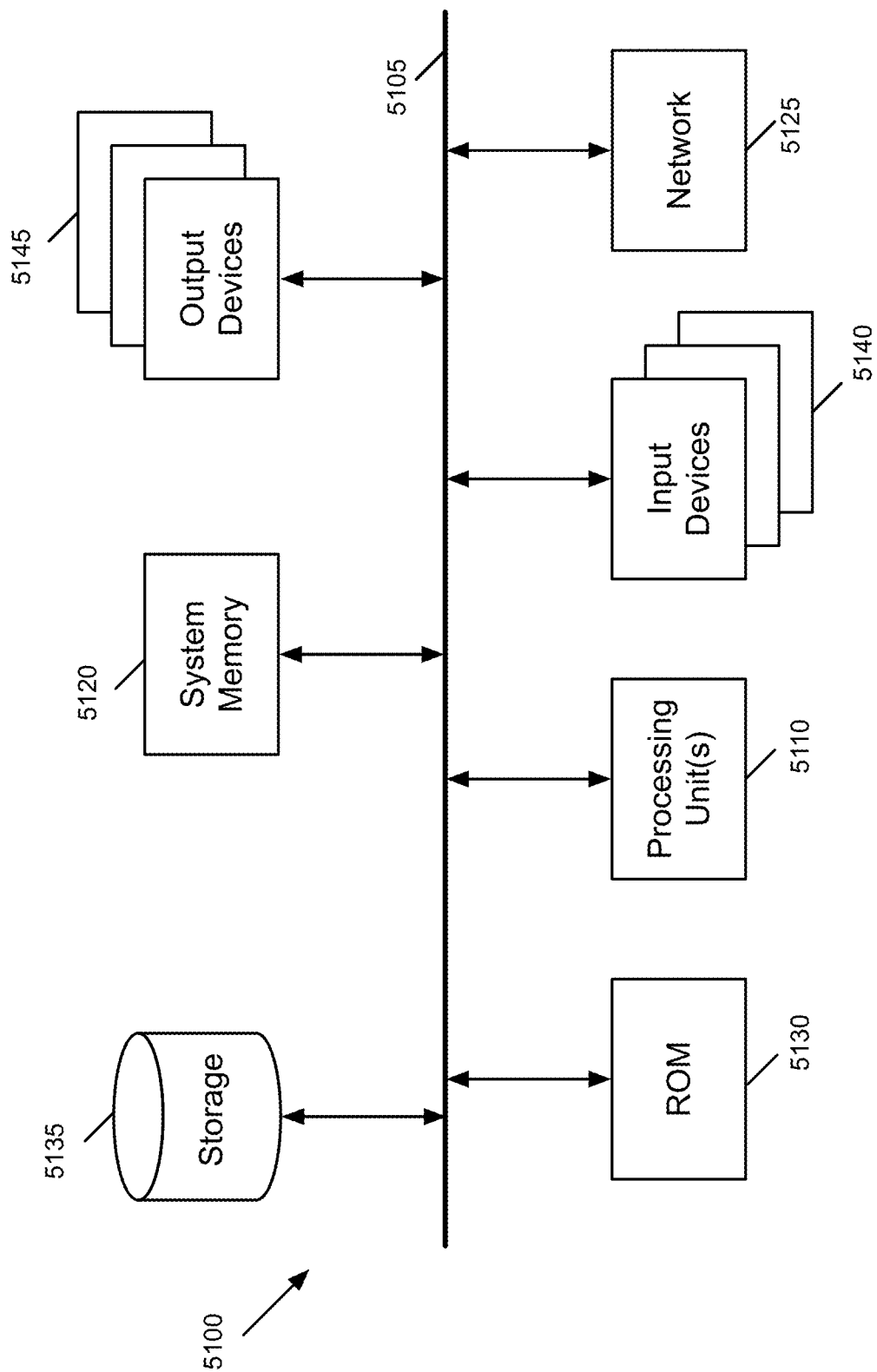

FIG. 10 is an upper front perspective of one example embodiment of a physical barrier that includes a groove for pulling out the physical barrier of a lateral flow assay device, according to various aspects of the present disclosure;

FIG. 11 is a flowchart illustrating an example process for pulling out a barrier that separates the labeling and capture zones of a lateral flow assay device, according to various aspects of the present disclosure;

FIG. 12 is an upper front perspective view of one example embodiment of a portion of a lateral flow assay device that includes a permanent gap in the backing card and/or the cartridge bed to prevent the leaking of the fluid material from under the conjugate pad into the membrane while the barrier is in place, according to various aspects of the present disclosure;

FIG. 13 is an upper front perspective view of one example embodiment of a portion of a lateral flow assay device with a permanent gap in the backing card and/or the cartridge bed, showing the removal of the barrier, according to various aspects of the present disclosure;

FIG. 14 is an upper front perspective view of one example embodiment of a portion of a lateral flow assay device showing a cartridge inside the device's housing, according to various aspects of the present disclosure;

FIG. 15 is a front elevation view of the lateral flow assay device of FIG. 14, according to various aspects of the present disclosure;

FIG. 16 is an upper front perspective view of one example embodiment of a portion of a lateral flow assay device with multiple barrier zones, according to various aspects of the present disclosure;

FIG. 17 is an upper front perspective view of one example embodiment of a portion of a lateral flow assay device showing a cross section of the lateral flow assay device's housing, according to various aspects of the present disclosure;

FIG. 18 is an upper front perspective view of one example embodiment of a portion of a lateral flow assay device showing the removal of multiple barriers, according to various aspects of the present disclosure;

FIG. 19 is an upper front perspective view of one example embodiment of a portion of a lateral flow assay device that includes one or more permanent gaps in the backing card and/or the cartridge bed to prevent the leaking of the fluid material while the corresponding barrier(s) is/are in place, according to various aspects of the present disclosure;

FIG. 20 is an upper front perspective view of one example embodiment of a portion of a lateral flow assay device that has a gap separating the labelling zone and the capture zone, according to various aspects of the present disclosure;

FIG. 21 is an upper front perspective view of one example embodiment of a portion of a lateral flow assay device showing a cross section of the lateral flow assay device's housing before and after removing a gap between the labeling zone and the capture zone, according to various aspects of the present disclosure;

FIG. 22 is a top elevational view of the housing of the lateral flow assay device of FIG. 21, according to various aspects of the present disclosure;

FIG. 23 is a front elevational view of one example embodiment of a portion of a lateral flow assay device that may use one or more posts or pillars to create a removable gap between the conjugate pad and the membrane, according to various aspects of the present disclosure;

FIG. 24 is a top elevational view of one example embodiment of the lateral flow assay device of FIG. 23, according to various aspects of the present disclosure;

FIG. 25 is a front elevational view of one example embodiment of a portion of a lateral flow assay device after a gap between the conjugate pad and the membrane is removed, according to various aspects of the present disclosure;

FIG. 26 is a flowchart illustrating an example process for removing a gap that separates the labeling and capture zones of a lateral flow assay device, according to various aspects of the present disclosure;

FIG. 27 is an upper front perspective view of one example embodiment of a portion of a lateral flow assay device with multiple gaps separating different components of the lateral flow assay device, according to various aspects of the present disclosure;

FIG. 28 is an upper front perspective view of one example embodiment of a portion of a lateral flow assay device showing a cross section of the lateral flow assay device's housing before and after removing multiple gaps, according to various aspects of the present disclosure;

FIG. 29 is a front elevational view of one example embodiment of a portion of a lateral flow assay device that may use multiple posts or pillars to create removable gaps between different components of the lateral flow assay device, according to various aspects of the present disclosure;

FIG. 30 is a top elevational view of one example embodiment of the lateral flow assay device of FIG. 29, according to various aspects of the present disclosure;

FIG. 31 is a front elevational view of one example embodiment of a portion of a lateral flow assay device after several gaps are removed between different components of the lateral flow assay device, according to various aspects of the present disclosure;

FIG. 32 is a front elevation view of one example embodiment of a portion of a lateral flow assay device that removes gaps by a spring mechanism, according to various aspects of the present disclosure;

FIG. 33 is a functional block diagram illustrating one example embodiment of the lateral flow assay device of FIG. 32, according to various aspects of the present disclosure;

FIG. 34 illustrates an example of a number of curves generated for a particular membrane paper material for a range of connection time and disconnection time of the conjugate pad and the membrane, according to various aspects of the present disclosure;

FIG. 35 illustrates an example of selecting the connection and disconnection times of the conjugate and membrane pads for a specified flow time, according to various aspects of the present disclosure;

FIG. 36 is a front elevation view of one example embodiment of a portion of a lateral flow assay device that controls the gap between the conjugate pad and the membrane and/or the gap between the wicking pad and the membrane by a spring mechanism and an electromagnet, according to various aspects of the present disclosure;

FIG. 37 is a functional block diagram illustrating one example embodiment of the lateral flow assay device of FIG. 36, according to various aspects of the present disclosure;

FIG. 38 is a front elevation view of one example embodiment of a portion of a lateral flow assay device that controls the gap between the conjugate pad and the membrane and/or the gap between the wicking pad and the membrane by a piezoelectric actuator, according to various aspects of the present disclosure;

FIG. 39 is a front elevation view of one example embodiment of a portion of a lateral flow assay device that controls the gap between the conjugate pad and the membrane and/or the gap between the wicking pad and the membrane by magnets and electromagnets, according to various aspects of the present disclosure;

FIG. 40 is a functional block diagram illustrating one example embodiment of the lateral flow assay device of FIG. 39, according to various aspects of the present disclosure;

FIG. 41 is a front elevation view of one example embodiment of a portion of a lateral flow assay device that controls the gap between the conjugate pad and the membrane and/or the gap between the wicking pad and the membrane by magnets and electromagnets that are positioned over the lateral flow assay device's housing, according to various aspects of the present disclosure;

FIG. 42 is a functional block diagram illustrating one example embodiment of the lateral flow assay device of FIG. 41, according to various aspects of the present disclosure;

FIG. 43 is a front elevation view of one example embodiment of a portion of a lateral flow assay device that controls the gap between the conjugate pad and the membrane and/or the gap between the wicking pad and the membrane by moving a portion of the membrane with a spring mechanism, according to various aspects of the present disclosure;

FIG. 44 is a front elevation view of one example embodiment of a portion of a lateral flow assay device that controls the gap between the conjugate pad and the membrane and/or the gap between the wicking pad and the membrane by a piezoelectric actuator that moves a portion of the membrane, according to various aspects of the present disclosure;

FIG. 45 is a front elevation view of one example embodiment of a portion of a lateral flow assay device that controls the gap between the conjugate pad and the membrane and/or the gap between the wicking pad and the membrane by a spring mechanism and an electromagnet that moves a portion of the membrane, according to various aspects of the present disclosure;

FIG. 46 is a front elevation view of one example embodiment of a portion of a lateral flow assay device that controls the gap between the conjugate pad and the membrane and/or the gap between the wicking pad and the membrane by a magnet and an electromagnet that moves a portion of the membrane, according to various aspects of the present disclosure;

FIG. 47 is a front elevation view of one example embodiment of a portion of a lateral flow assay device that controls the gap between the conjugate pad and the membrane by a magnet and an electromagnet that move a portion of the membrane, according to various aspects of the present disclosure;

FIG. 48 is a front elevation view of one example embodiment of a portion of a lateral flow assay device that controls the gap between the conjugate pad and the membrane, and the gap between the membrane and the wicking pad by two pairs of magnet and electromagnet that move portions of the membrane, according to various aspects of the present disclosure;

FIGS. 49A and 49B illustrate a front elevation view of one example embodiment of a portion of a lateral flow assay device that controls the gap between the conjugate pad and the membrane, and/or the gap between the membrane and the wicking pad by two magnets that are positioned over a moving shaft, according to various aspects of the present disclosure;

FIGS. 50A and 50B illustrate a front elevation view of one example embodiment of a portion of a lateral flow assay device that controls the gap between the conjugate pad and the membrane, and/or the gap between the membrane and the wicking pad by two magnets that are positioned over a rotating wheel, according to various aspects of the present disclosure; and FIG. 51 conceptually illustrates an electronic system with which some embodiments of the invention are implemented.

DETAILED DESCRIPTION

One aspect of the present embodiments includes the realization that some analytes may require a long binding time, also referred to as conjugate time, in order to bind with the labeled antibody on the conjugate pad to form an immunocomplex. It may also be necessary to have a long binding time for the immunocomplex that flows onto the test/control membrane pad to bind to the test line and control line on the membrane pad. The time it takes for the immunocomplex fluid to flow from one end of the membrane pad to the other end is referred to as flow time.

It may also be desirable to precisely control the conjugate time for certain types of tests. In a lateral flow assay, the fluid flows laterally from the sample pad into the conjugate pad and from the conjugate pad into the membrane through capillary action. The capillary flow rate depends on the material used (e.g., what the material is made of, the porosity of the material, the grade of the material, etc.) to make the sample pad, the conjugate pad, and the membrane. The time allowed for the binding between the analyte and the labeled antibody on the conjugate pad (conjugate time), or the time allowed for the immunocomplex fluid to travel through the membrane pad over the test line and the control line (flow time), therefore, depends on the length and the type of material used for the conjugate pad and the membrane pad respectively.

Controlling the conjugate time and the flow time based on the length and the type of material used for the conjugate pad and the membrane, however, suffers from several drawbacks. Selecting different types of material for the conjugate pad and the membrane would typically provide a capillary flow rate that ranges from approximately 60 seconds per centimeter (cm) to approximately 10 seconds per cm. As the required conjugate time for a test increases, the length of the conjugate pad has to increase. For example, a conjugate time of one hour may require a conjugate pad (even when the materials with the slowest flow rate are used), that is too long to be practical to use in a handheld or portable lateral flow assay due to the length of the conjugate pad, as well as the amount of sample that may be required. In addition, the capillary flow rate may be difficult to estimate and may vary among different specimens of the same type and the same brand of conjugate pad. Accordingly, a precise conjugate time or flow time may not be achievable even when a shorter conjugate time and/or a shorter flow time is required.

Some of the present embodiments solve the aforementioned problems by placing a removable physical barrier between the conjugate pad and the membrane. After the desired conjugate time is achieved, the barrier may be removed to allow the sample fluid to flow from the conjugate pad into the membrane. The barrier may be made of a material (e.g., plastic) which blocks the sample fluid from flowing from conjugate pad into the membrane. The barrier material is selected from material that do not react with the sample fluid.

In some of the present embodiments, a solenoid, an electromagnet, a servo (also referred to as a servo motor or servomotor), or a linear actuator may be used to remove the barrier after a specific amount of time from the start of the test. For example, at the start of the assay test, a timer may be set to provide a desired conjugate time. After the timer is expired, a signal may be generated to cause the solenoid, the electromagnet, the servo, or the linear actuator to remove (e.g., by a pulling action) the barrier from between the conjugate pad and the membrane. In some of the present embodiments, the barrier may be attached to a magnet or may include a hole, a groove, and/or a string to facilitate the barrier removal.

In some of the present embodiments, the solenoid, the electromagnet, the servo, or the linear actuator may be a part of the lateral flow assay device. In other embodiments, the solenoid, the electromagnet, the servo, or the linear actuator may be a part of a separate non-disposable device that couples with the lateral flow assay during the testing. In some of the present embodiments, the lateral flow assay device may include a housing that may apply pressure to the conjugate pad, the membrane pad, or both. The pressure may facilitate the conjugate pad and the membrane touching each other after the barrier is removed.

Some of the present embodiments may include a removable physical barrier to prevent the sample fluid to flow from the test line towards the control line and the wicking pad. After a desired time is achieved for the immobilized molecules at the test line to bind with the fluid material, the barrier may be removed to allow the sample fluid to flow from the test line towards the control line and the wicking pad. Some of the present embodiments may include a removable physical barrier to prevent the sample fluid to flow from the control line towards the wicking pad. After a desired time is achieved for the immobilized molecules at the control line to bind with the fluid material, the barrier may be removed to allow the fluid material to flow from the control line towards the wicking pad. Some of the present embodiments may include more than of the aforementioned three barriers.

The lateral flow assay device may include a replaceable cartridge that may be intended for single use. The lateral flow assay device may include a cartridge bed for holding the cartridge in place. The lateral flow assay device may include a backing card that is used to assemble different portions of the sample receiving zone. In some embodiments, each of the sample, conjugate, membrane, and wicking pads may have a separate backing card. Depending on the type of material used for the pads and the backing card, and/or the way the pads are placed on the cartridge bed, even when a physical barrier is in place, some of fluid material may leak from under the pads that are on either side of the barrier. To prevent such a leak, some embodiments may include a permanent gap in the cartridge bed and/or in the backing card in order to prevent the fluid material to leak from under a pad on one side of a barrier to a pad on the other side of the barrier while the barrier is in place. Once the barrier is removed, the fluid may flow freely in the direction of the flow path.

In some embodiments, the barrier may not be pulled out of the cartridge at once. Instead, the barrier between the conjugate pad and the membrane may be partially pulled out and then pushed back several times in order to repeatedly bring the conjugate pad and the membrane in touch with each other and then separate them from each other. Repeatedly connecting and disconnecting the conjugate pad and the membrane may be used to control the flow of fluid material from the conjugate pad into the membrane, which in turns control the flow time over the membrane.

The number of times the barrier is pulled out and pushed back into the cartridge, the duration that the barrier stays in or out of the cartridge, and the time between the pulling and pushing actions may control the amount of contact between the conjugate pad and the membrane. The amount of contact between the conjugate pad and the membrane may in turn be used to control the flow time (the time it would take for the fluid material to travel the membrane length over the test line and the control line and reach the wicking pad). A similar technique may be used to partially pull out and then push back the barrier that prevents the flow of the fluid material from the test line towards the control line and/or the barrier that controls the flow of the fluid material from the control line towards the wicking pad.

Some of the present embodiments may place a gap (instead of a physical barrier) between the conjugate pad and the membrane. The gap may be substantially occupied by air and may not allow the liquid material to flow from the conjugate pad into the membrane. After the desired conjugate time is achieved (e.g., after a timer expires), the gap may be removed by pressing the conjugate pad and the membrane together. After the gap is removed, the liquid material may flow from the conjugate pad into the membrane by capillary action.

In some of the present embodiments, the gap may be maintained by a movable section of the lateral flow assay device's housing. After a desired time is achieved, the gap may be removed by moving the movable section of the housing towards the membrane until the conjugate pad and the membrane come into contact with each other. In some of the present embodiments, a solenoid, an electromagnet, a servo, or a linear actuator may be used to move the movable section of the housing to remove the gap after a specific amount from the start of the test. For example, at the start of the assay test, a timer may be set to provide a desired conjugate time. After the timer is expired, a signal may be generated to cause the solenoid, the electromagnet, the servo, or the linear actuator to push the movable section of the housing to remove the gap. In some of the present embodiments, the solenoid, the electromagnet, the servo, or the linear actuator may be a part of the lateral flow assay device. In other embodiments, the solenoid, the electromagnet, the servo, or the linear actuator may be a part of a separate non-disposable device that couples with the lateral flow assay during the testing.

In some of the present embodiments, the gap may be maintained by one or more small poles (pillar, rods) and/or springs between the conjugate pad and the membrane. In some of the present embodiments, a solenoid, an electromagnet, a servo, or a linear actuator may be used to pull (or push) the pole(s) or the spring(s) to remove the gap after a specific amount from the start of the test. For example, at the start of the assay test, a timer may be set to provide a desired conjugate time. After the timer is expired, a signal may be generated to cause the solenoid, the electromagnet, the servo, or the linear actuator to pull (or push) the pole(s) or the spring(s) to remove the gap. In some of the present embodiments, the solenoid, the electromagnet, the servo, or the linear actuator may be a part of the lateral flow assay device. In other embodiments, the solenoid, the electromagnet, the servo, or the linear actuator may be a part of a separate non-disposable device that couples with the lateral flow assay during the testing.

Some of the present embodiments may include a gap to prevent the fluid material to flow from the test line towards the control line and the wicking pad. After a desired time is achieved for the immobilized molecules at the test line to bind with the fluid material, the gap may be removed to allow the fluid material to flow from the test line towards the control line and the wicking pad. Some of the present embodiments may include a gap to prevent the fluid material to flow from the control line towards the wicking pad. After a desired time is achieved for the immobilized molecules at the control line to bind with the fluid material, the gap may be removed to allow the fluid material to flow from the control line towards the wicking pad. Some of the present embodiments may include more than of the aforementioned three gaps.

In some embodiments, the gap between the conjugate pad and the membrane may be repeatedly opened and closed to control the flow of fluid material from the conjugate pad into the membrane. The number of times the gap is opened and closed, the duration that the gap remains open or closed, and the time between the opening and the closings of the gap may control the amount of contact between the conjugate pad and the membrane. The amount of contact between the conjugate pad and the membrane may in turn be used to control the flow time. A similar technique may be used to repeatedly open and close the gap that control the flow of the fluid material from the test line towards the control line and/or the gap that controls the flow of the fluid material from the control line towards the wicking pad.

In some embodiments, the backing card of conjugate pad or the backing card of the membrane pad may be curved to initially (e.g., prior to the start of a test and for a time period after the start of the test) prevent the pads from touching each other. A mechanism such as a solenoid, a small linear actuator, or a small servo motor may be used to repeatedly bring the conjugate pad and the membrane in touch with and then separate them from each other. Repeatedly connecting and disconnecting the conjugate pad and the membrane may be used to control the flow of fluid material from the conjugate pad into the membrane.

The connecting and disconnecting of the conjugate pad and the membrane may be done according to an algorithm controlled by a processor of the lateral flow assay device. The processor may use three parameters to generate one or more signals to connect and disconnect the conjugate pad and the membrane pad in order to control the flow time of the fluid from the time the fluid starts at the beginning of the membrane to the time the fluid reaches the wicking pad. The three parameters are the number of times the pads are connected (or disconnected), the duration of each connections, and the duration of each disconnection (or the time between consecutive connection and disconnections).

The longer the duration of each connection, the more fluid is transferred from the conjugate pad to the membrane. These three parameters may be calculated by the processor using an algorithm and a set of calibration tables or calibration curves. The algorithm input may be the desired conjugation time and flow time.

FIG. 1 is an upper front perspective view of one example embodiment of a portion of a lateral flow assay device 100, according to various aspects of the present disclosure. The lateral flow assay (also referred to as lateral flow immunochromatographic assay or lateral flow dipstick immunoassay) device 100 may be a portable device (e.g., a handheld device or benchtop device) that is used to analyze a sample fluid (also referred to as matrix) to determine the presence and/or the amount of one or more analytes (referred to as target analytes). In this specification, the terms lateral flow assay device and lateral flow assay are interchangeably used to refer to a device that performs lateral flow tests.

The lateral flow assay device 100 may include a replaceable cartridge that may be intended for single use. For example, the components shown in FIG. 1 may be part of a disposable cartridge of the lateral flow assay device 100. As described below, the lateral flow assay device 100 may also include components such as actuators, processors, displays, etc., that may or may not be disposable. The non-disposable components of the lateral flow assay device may be used for performing multiple tests for the same or different subjects (e.g., the same person or different persons).

The sample may be human or animal bodily fluid, such as, without limitations, one or more of urine, blood, serum, plasma, saliva, sweat, milk, mucous, semen, vaginal or urethral secretions, etc. The sample may also be a fluid taken from sources other than a human or an animal. For example, the sample may contain plant material, fuel, food, drink, animal feed, drugs, chemical compounds, etc. The sample may naturally be a liquid, may be a liquid diluted with another liquid, such as water, or may have originally been in a solid form (e.g., a tissue sample) and is treated to be in liquid form for the application to the lateral flow assay device 100. The target analytes may be substances such as, without limitations, proteins, haptens, enzymes, hormones, infectious disease agents, immunoglobulins, polynucleotides, steroids, drugs, nucleic acids, markers for gene mutations, etc.

I. Using Removable Physical Barriers in the Flow Path to Control the Flow and Flow Time With reference to FIG. 1, the lateral flow assay device 100 may include a sample receiving zone 101, a labeling zone 102, a barrier zone 103, a capture zone 104, and optionally a wicking zone 105. The sample receiving zone 101, the labeling zone 102, the capture zone 104, and the wicking zone 105 may be made of materials that make a fluid sample applied to the sample receiving zone 101 flow by capillary action downstream (i.e., from the sample receiving zone 101 towards the wicking zone 105) from each zone 101, 102, and 104 into the next adjacent zone 102, 104, and 105, respectively.

The sample receiving zone 101 may include a sample pad (also referred to as sample strip or sample receiving member) 150. The sample pad 150 may be made of natural and/or synthetic porous, microporous, mesoporous, or macroporous materials capable of receiving a sample fluid and laterally conducting the sample fluid towards the labeling zone 102 by capillary action. The sample pad 150 may be made of a material such as, without limitations, cellulose, nitrocellulose, paper, silica, cotton, glass (e.g., glass fiber), or synthetic material (e.g., polyester, polyethylene, polymers, rayon, nylon, etc.). Depending on the type of the sample (e.g., urine, saliva, blood, etc.), the sample pad 150 may be treated by a buffer (e.g., an organic compound such as tris or tris(hydroxymethyl)aminomethane) to mitigate sample variabilities (pH, protein concentration, viscosity, salt concentration, etc.). During the manufacture of the sample pad 150, the buffer compound may be coated, impregnated, or otherwise applied or deposited on the sample pad 150 and then dried.

With further reference to FIG. 1, the labeling zone 102 may include a conjugate pad 110 that is fluidically connected (i.e., capable of receiving fluid, e.g., by capillary action) to the sample pad 150. In the depicted embodiment, the sample pad 150 is in contact with and partially covers the conjugate pad 110. In other embodiments, the sample pad 150 may be in more contact or less contact with the conjugate pad 110 in order to provide slower or faster binding reagent and/or conjugate release respectively. A sample fluid that is applied to the sample pad 150 may be laterally transferred from the sample pad 150 to the conjugate pad 110 by capillary action.

The conjugate pad 110 may be made of natural and/or synthetic porous, microporous, mesoporous, or macroporous materials capable of receiving the sample fluid from the sample pad 150. The conjugate pad 110 may be made of material such as, without limitations, glass (e.g., glass fiber), cellulose, nitrocellulose, paper, silica, cotton, or synthetic material (e.g., polyester, polyethylene, polymers, rayon, nylon, etc.).

The conjugate pad may contain a binding reagent (also referred to as antibody) that is capable of binding to the target analyte in the sample fluid. The binding reagent may be coupled to a label (also referred to as conjugate, detection conjugate, probe, or detector nanoparticle) which, in its natural state, is readily visible either to the naked eye, or with the aid of an optical filter. Depending on the type of the lateral flow assay, the binding reagent may be an antibody, an antigen, a protein, a nucleic acid, etc., that is capable of binding to the target analyte. The label may be made of small particles (e.g., nanoparticles), such as, without limitations, metallic sols (e.g., colloidal gold or gold sol), dye sols, colored latex particles, carbon, etc. During the manufacture of the conjugate pad 110, the labeled binding reagent may be coated, impregnated, or otherwise applied or deposited on the conjugate pad 110 and then dried.

After the sample fluid flows from the sample pad 150 into the conjugate pad 110, the sample fluid may solubilize the labeled binding reagent. If the sample fluid contains the target analyte, the target analyte may bind with the labeled binding reagent and form an immunocomplex. The labeled binding reagents that do not bind with the target analyte (e.g., when the sample fluid does not include the target analyte or there is excess labeled binding reagent) flow downstream towards the capture zone 104 by capillary action. As described below, some of the present embodiments may include a barrier zone 103 that may initially block the sample fluid and any other material in the flow path (e.g., unbound labeled binding reagents, wash fluid, etc.) from flowing from the labeling zone 102 into the capture zone 104. The sample fluid and any other material in the flow path (e.g., unbound labeled binding reagents, wash fluid, etc.) are herein referred to as fluid material.

Depending on the type of test performed by the lateral flow assay device, the device may not include separate sample and conjugate pads in some embodiments and may only include the conjugate pad 110. Although the sample pad 150 is shown to go over the conjugate pad 110, in some embodiments, the conjugate pad 110 may go over the sample pad 150.

The capture zone 104 may include a membrane 115 and a test line (or test zone) 125 that may be embedded in the membrane. The capture zone 104 may optionally include a control line (or control zone) 130 that may be embedded in the membrane 115. The membrane 115 may be made of a material such as, without limitations, cellulose, nitrocellulose, paper, silica, cotton, glass (e.g., glass fiber), or synthetic material (e.g., polyester, polyethylene, polymers, rayon, nylon, etc.) that allow the fluid material to flow downstream from the conjugate pad 101 into the membrane 115 and from the membrane 115 towards the wicking zone 105 by capillary action. Although the conjugate pad 110 is shown to go over the membrane 115, in some embodiments, the membrane 115 may go over the conjugate pad 110.

The test line 125 may be made of a porous material such as, without limitations, cellulose, nitrocellulose, paper, silica, cotton, glass (e.g., glass fiber), or synthetic material (e.g., polyester, polyethylene, polymers, rayon, nylon, etc.). The test line 125, in a sandwich assay format, may contain an unlabeled binding reagent that is immobilized on the test line 125 and does not flow downstream when porous material of the test line is moistened (e.g., by the fluid material). Depending on a particular test made by the lateral flow assay device 100, the binding reagent immobilized on the test line may be the same or different than the binding reagent contained on the conjugate pad 110.

In the sandwich assay format, the binding reagent contained on the test line 125 may be an immobilized antibody that is capable of binding to the immunocomplex that is formed from the binding of the analyte with the labelled binding reagent on the conjugate pad 110. As the immunocomplex moves over the test line 125, the immunocomplex binds with the immobilized antibody on the test line 125, resulting in a second immunocomplex that colors the test line 125. The intensity of the colored test line is correlated with the density of the analyte in the sample fluid. The second immunocomplex includes the analyte that is bound with the labelled binding reagent at one site and is bound with the immobilized binding agent at another site. When the sample fluid does not include the target analyte, no immunocomplex is formed on the conjugate pad 110 and no immunocomplex binds with the immobilized antibody on the test line 125. As a result, the test line 125 does not change color.

In a competitive assay format, the test line 125 may contain the immobilized analyte molecule (or a protein-analyte complex). If the sample liquid does not contain the analyte, the labeled antibody that is solubilized by the sample liquid may flow from the conjugate pad 110 into the test line 125 and may bind to the analyte at the test line 125, resulting in a colored test line 125 that indicates the lack of the target analyte in the sample liquid. If the target analyte is present in the sample liquid, the analyte may bind to the labeled antibodies on the conjugate pad 110 and may prevent the labeled antibody to bind to the analyte at the test line 125. As a result, the test line 125 may not change color, indicating the presence of the analyte in the sample fluid.

The capture zone 104 may optionally include a control line (or control zone) 130 that may be embedded in the membrane 115. The control line 130 may be made of a porous material such as, without limitation, cellulose, nitrocellulose, paper, silica, cotton, glass (e.g., glass fiber), or synthetic material (e.g., polyester, polyethylene, polymers, rayon, nylon, etc.). In a sandwich assay format, the control line 130 may contain an immobilized antibody that binds to the free labeled binding reagents resulting in a colored control line 130, which confirms that the test has operated correctly regardless of whether or not the target analyte has been present in the sample. In a competitive assay format, the control line 130 may contain an immobilized analyte molecule (or a protein-analyte complex) that binds to the free labeled binding reagents resulting in a colored control line 130, which confirms that the test has operated correctly regardless of whether or not the target analyte has been present in the sample.

The fluid material that do not bind to the test line 125 or the control line 130 may continue to flow from the capture zone 104 into the wicking zone 105. The wicking zone 105 may include a wicking pad 120 to absorb the fluid material that are not taken up by the test line 125 and the control line 130 while maintaining the capillary flow from the membrane 125 into the wicking pad 120. The wicking pad 120 may be made of a porous material such as, without limitations, cellulose, nitrocellulose, paper, silica, cotton, glass (e.g., glass fiber), or synthetic material (e.g., polyester, polyethylene, polymers, rayon, nylon, etc.). Depending on the type of test performed by the lateral flow assay device, the device may not include a wicking zone 105 or a wicking pad 120. Although the wicking pad 120 is shown to go over the membrane 115, in some embodiments, the membrane 115 may go over the wicking pad 120.

In some of the present embodiments, the analyte in the sample fluid may require more time to bind with the labeled binding reagent than the time it takes for the sample fluid to flow by capillary action through the conjugate pad 110 into the membrane 115. For example, without limitation, the target analyte may inherently require a long time to bind with the labeled binding reagent. The required binding time may depend on the type and concentration of the target analyte and the labeled binding reagent.

If the analyte is not provided enough time on the conjugate pad 110 to bind with the labeled binding reagent, there may not be enough immunocomplex in fluid that flows to the test line 125 to bind with the immobilized binding reagent on the test line 125 in a sandwich assay format (or with the immobilized analyte/protein-analyte complex in a competitive assay format) to generate a strong color signal at the test line 125 to indicate the presence or absence of the target analyte in the sample fluid. Furthermore, it may be desirable to precisely control the time allowed for the analyte to bind with the labeled binding reagent regardless of the amount of time required for the analyte to bind with the labeled binding reagent on the conjugate pad.

Some of the present embodiments provide a barrier zone 103 between the labeling zone 102 and the capture zone 104. The barrier zone 103 may include a removable barrier 135. In the embodiment depicted in FIG. 1, the removable barrier is a physical barrier made of solid material (e.g., a thin film of material) that prevents the flow of the fluid material from the labeling zone 102 into the capture zone 104. The physical barrier 135 may be made of materials that do not react with the sample fluid and any other material in the flow path (e.g., unbound labeled binding reagents, wash fluid, etc.). In other embodiments (e.g., as shown in FIG. 20 described below) the barrier zone 103 may include a gap that may be substantially occupied by air.

In some of the present embodiments, a timer is programmed to allow time for the analyte in the sample fluid to bind with the labeled binding reagent on the conjugate pad 110. The timer may start at the beginning of the test (e.g., substantially at or around the same time as the sample liquid is applied to the sample pad 150). The timer may be set such that enough time is allowed for the sample fluid to flow from the sample pad 150 into the conjugate pad 110 and for the analyte (if any) in the sample fluid to bind with the labelled binding reagent on the conjugate pad 110.

After the timer expires, the physical barrier 135 may be removed from between the labeling zone 102 and the capture zone 104 in order to fluidically connect the conjugate pad 110 in the labeling zone 102 to the membrane 115 in the capture zone 104. After the conjugate pad 110 and the membrane 115 come to contact to each other, the fluid material may flow from the labeling zone 102 into the capture zone 104 by capillary action.

The lateral flow assay device 100 may include a backing card 140 that is used to assemble different portions of the sample receiving zone 101, the labeling zone 102, the capture zone 104, and the wicking zone 105. The backing card, in some embodiments, may be a continuous piece that may go under the pads 150, 110, 115, and 120. In other embodiments, each pad may have a separate backing card.

For example, during the manufacturing of the device, a roll or sheet of backing material may be used such that the width of the roll or the sheet is the same as (or is cut to be the same as) the length of the lateral flow assay cartridge (i.e., in the pictured orientation, from the left end of the sample pad 150 to the right end of the wicking pad 120). The membrane pad 115, the conjugate pad 110, the sample pad, 150, and the wicking pad 120 are then placed on the backing card with the proper overlaps (e.g., as shown in FIG. 1). The pads may, for example, be connected to the backing card with a two sided tape or a glue. The pads and the attached backing card may then be cut into separate strips and each strip may be used to make a different lateral flow assay device.

Alternatively, each pad may be separately connected to a corresponding backing card. The pads with the corresponding backing cards may then be assembled over each other with the proper overlaps to make a lateral flow assay device. The lateral flow assay device 100 may include a housing. In FIG. 1, only a portion of the housing that includes the cartridge bed 170 is shown for simplicity.

In some of the present embodiments, the lateral flow assay may include a housing that may apply pressure to the conjugate pad 110, the membrane pad 115, or both. The pressure may facilitate the conjugate pad 110 and the membrane 115 touching each other after the barrier 135 is removed. FIG. 2 is an upper front perspective view of one example embodiment of a portion of a lateral flow assay device 100 showing a cross section of the lateral flow assay device's housing, according to various aspects of the present disclosure. With reference to FIG. 2, the perspective shows a cross sectional view of the housing 205 across the surfaces 206.

The housing 205 may include a sample port 210 for applying the sample liquid to the sample pad 150. The housing 205 may also include an opening 215 for viewing the test line 125. The embodiments that include a control line 130, may also include an opening 220 for viewing the control line 130. Some embodiments may include one opening for viewing both the test line 125 and the control line 130. The housing 205 may include a cartridge bed 170 for holding the lateral flow assay device's cartridge.

In some of the present embodiments, the housing applies pressure to the conjugate pad 110 and/or the membrane 115 such that when the barrier 135 is removed, the conjugate pad 110 and the membrane 115 come to contact with each other to allow the fluid material in the flow path to flow from the conjugate pad 110 into the membrane 115 by capillary act.

For example, portions 225-226 of the housing 205 may touch the conjugate pad 110 and apply a force (as shown by the arrows 250) to push the conjugate pad 110 towards the barrier 135 and the membrane 115. In some embodiments, the portions 225-226 of the housing 105 may touch a portion of the conjugate pad 110 across a line that is perpendicular to the flow path (the flow path runs from the left to right across the lateral flow assay device 100 in FIG. 2). In other embodiments, the portions 225-226 of the housing 205 may be in the form of one or more columns that touch the conjugate pad 110 at one or more places. In addition to, or in lieu of, pushing the conjugate pad 110 towards the barrier 135 and the membrane 115, the housing 205 may apply a force (as shown by the arrows 255) to push the cartridge bed 170, backing card 140, and the membrane 115 towards the barrier 135 and the conjugate pad 110.

FIG. 3 is an upper front perspective view of one example embodiment of a portion of a lateral flow assay device 100 showing the removal of the barrier 135, according to various aspects of the present disclosure. The figure as shown, includes two operational steps 301 and 302.

With reference to FIG. 3, step 301 shows an initial state where the barrier 135 is between the conjugate pad 110 and the membrane 115. The barrier may be made of a material (e.g., plastic, latex, metal, etc.) which blocks the fluid material from flowing from conjugate pad 110 into the membrane 115. The barrier's material is selected from materials that do not react with the fluid material in the flow path. As shown in step 301, the barrier 135 is flexible and follows (as shown by the dashed lines 335) the contours of the membrane 115 and the conjugate pad 110.

In some of the present embodiments, the lateral flow assay device 100 at the start of a test may include the barrier 135 between the conjugate pad 110 and the membrane 115. For example, lateral flow assay device 100 may be manufactured in the configuration shown in step 301 of FIG. 3. A test may start by applying a sample fluid to the conjugate pad 110 (e.g., through the sample port 210 of FIG. 2). In some of the present embodiments, a timer is programmed to allow time for the analyte (if any) in the sample fluid to bind with the labeled binding reagent on the conjugate pad 110.

In step 302 of FIG. 3, the barrier 135 is removed (as shown by the arrow 360) from between the conjugate pad 110 and the membrane 115. For example, the barrier 135 may be removed after the expiration of the timer. The force that is applied by the housing 205 of FIG. 2 to the conjugate pad 110 (as shown by the arrows 250) and/or by the force that is applied to the cartridge bed 170, the backing card 140, and the membrane 115 (as shown by the arrows 255) may make the conjugate pad 110 and the membrane 115 to come in contact with each other and allow the fluid material to flow from the conjugate pad 110 into the membrane 115 by capillary act. Since the barrier is made of a flexible and relatively thin film of material, the barrier may take a substantially uniform shape (as shown in step 302) after the barrier 135 is pulled out and is no longer under pressure from the conjugate pad 110 and/or the membrane 115.

Figure 4:
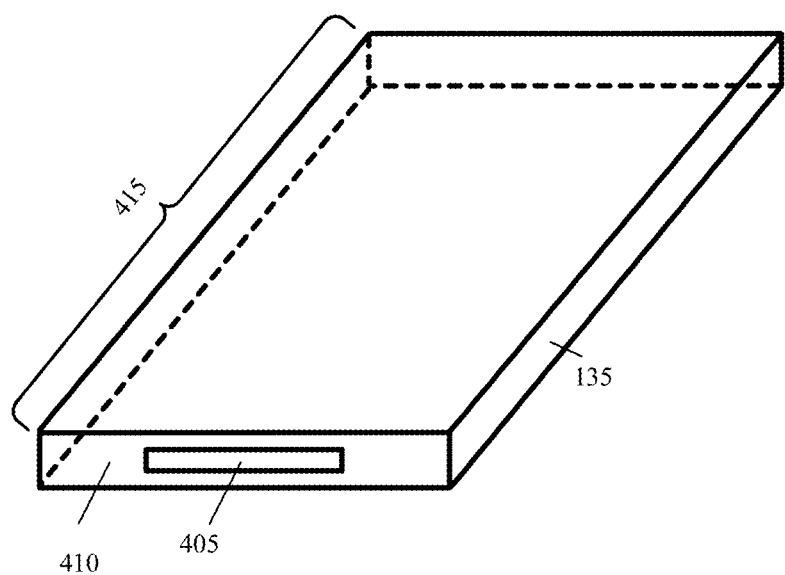
FIG. 4 is an upper front perspective of one example embodiment of a physical barrier with a piece of magnet attached to it, according to various aspects of the present disclosure.

In some of the present embodiments, one or more pieces of magnet may be attached to the barrier 135 to facilitate pulling the barrier 135 out from between the conjugate pad 110 and the membrane 115. FIG. 4 is an upper front perspective of one example embodiment of a physical barrier with a piece of magnet attached to it, according to various aspects of the present disclosure. As shown in FIG. 4, a piece of magnet (e.g., in the shape of a thin strip of magnetic material, in an arbitrary shape, etc.) 405 is attached to one side 410 of the physical barrier 135. The piece of magnet 405 may facilitate pulling the barrier 135 by another magnet attached to a moving shaft. In some of the present embodiments, more than one piece of magnet may be attached to the side 140 of the physical barrier 135.

Figure 5:
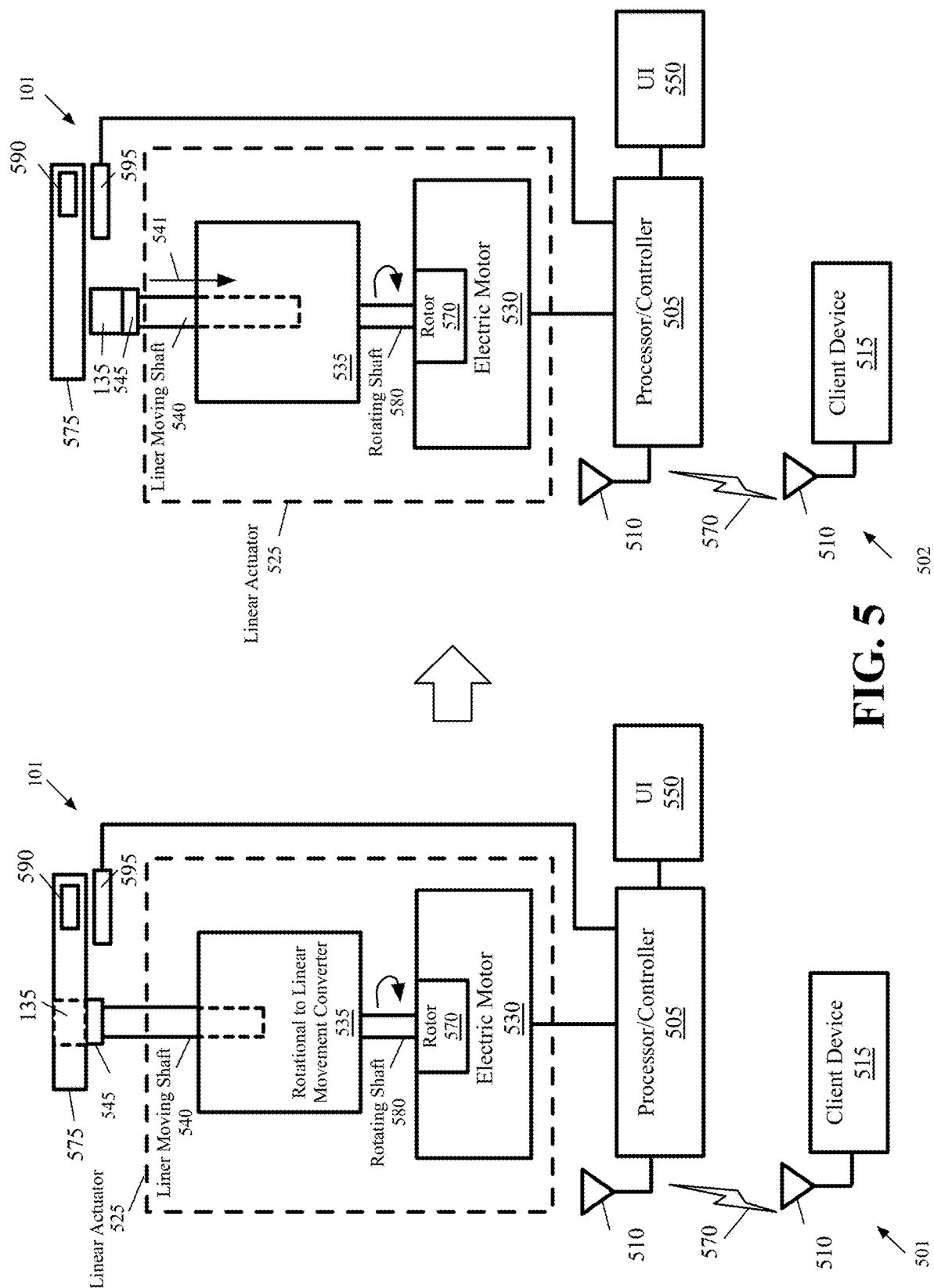
FIG. 5 is a functional block diagram illustrating one example embodiment of a linear actuator that may be used for pulling out the physical barrier of a lateral flow assay device, according to various aspects of the present disclosure.

FIG. 5 is a functional block diagram illustrating one example embodiment of a linear actuator 525 that may be used for pulling out the physical barrier of a lateral flow assay device, according to various aspects of the present disclosure. The linear actuator 525 may include an electric motor 530, a rotating shaft 580, a rotational to linear movement converter 535, and a linear moving shaft 540. The electric motor 530, in some embodiments, may be a miniaturized motor (e.g., a micro motor). The electric motor 530 may include a rotor 570 that may rotate and cause the rotating shaft 580 to rotate.

The rotational movement of the rotating shaft 580 may be converted to linear movement of the linear moving shaft 540 by the rotational to linear movement converter 535. The rotational to linear movement converter 535 may be a set of one or more screws, a wheel and axle, and/or a set of one or more cams that receive a rotational movement from the rotating shaft 580 and move the linear moving shaft 540 in a straight line.

The linear moving shaft 540 may move in and out in a straight line towards or away from the rotating shaft 580. Some of the present embodiments may include one or more magnets 545 (only one magnet is shown) at the end of the linear moving shaft 540. In some of the present embodiments, a processor (or controller) 505 may be used to set a timer to determine the time to pull out the barrier 135. Although the terms processor or controller are used in several examples in this specification, it should be understood that these terms apply to different types processing units, processors, central processing units (CPUs), microprocessors, and/or microcontrollers. The processor (or controller) 505 may include a single-core processor or a multi-core processor in different embodiments.

In some embodiments, the processor 505 may be associated with, and communicatively coupled to, a user interface (UI) 550 that may include a keyboard and/or a display. The display, in some embodiments, may be a touchscreen. In addition to, or in lieu of the UI 550, the processor 505, in some embodiments, may communicate with one or more client devices 515 to send and/or receive signals.

FIG. 5, as shown, includes two operational steps 501 and 502. Step 501 shows that at the beginning of a test, the electric motor 530 may be configured to extend the linear moving shaft 545 away from the rotating shaft 580, and the linear actuator 525 may be placed adjacent to the cartridge 575 of the lateral flow assay device 100 such that the magnet(s) 545 on the shaft 540 may contact the magnet(s) 405 (FIG. 4) on the barrier 135. The cartridge 575 may include the components shown in FIGS. 1 and 3. In FIG. 5, the top view of the lateral flow assay device 100 is shown and the components of the lateral flow assay device 100, other than the barrier 135, are not shown for simplicity.

In some of the present embodiments, the disposable cartridge 575 of the lateral flow assay device 100 may include a near field communication (NFC) chip (or NFC tag) 590. The NFC chip 590 may identify the test and other parameters and information related to the test including the conjugation time on the conjugate pad. The lateral flow assay device 100 may also include an NFC reader 595. Once the cartridge 575 is placed in the lateral flow assay device's 100 housing (e.g., on the cartridge bed 170 of FIGS. 1-3), the NFC reader 595 (which may be located, for example, and without limitations, under the cartridge bed 170 close to where the NFC chip is located) may automatically detect the presence of the NFC tag.

The NFC reader 595 may read the information regarding the test to be performed by the cartridge. The NFC reader 595 may be communicatively coupled with the processor 505. The processor 505 may receive the information from the NFC reader and, for example, and without limitation, may start a timer to control the conjugate times, may send a signal to activate the electric motor to remove the barrier 135, may display some of the information on its display of the UI 550, and/or may send some of the information and parameters to one or more external devices such as the client device 515.

In some embodiments, all components of the lateral flow assay device, including the processor 505, the UI 550, etc., may be used for one test and may be disposable. In these embodiments, in addition to, or in lieu of the NFC, the parameters and information regarding the test may be pre-programmed into the processor. In other embodiments, the processor/controller 505, the UI 550, the linear actuator 525, and/or the NFC reader may be reusable for performing multiple tests for the same or different subjects (e.g., the same person or different persons).

In some embodiments, in addition to, or in lieu of, using the information from the NFC tag 590, the processor 505 may receive a value for setting the timer through a wireless link 570 from one or more client devices 515 (only one client device is shown for simplicity). The client device 515 may be, without limitations, a cellular telephone (e.g., a smartphone), a computing device (e.g., a tablet computer, a laptop computer, a desktop computer), a personal digital assistant (PDA) device, an electronic device capable of communicating the timer value to the processor 505, etc.

In some of the present embodiments, the processor 505 and the client device 515 may each include one or more antennas 510 and may establish the wireless link 570 through the antennas 510. Alternatively, the client device 515 and the processor 505 may be connected by a wired connection (e.g., without limitation, using a cable, using a connection such as USB, thunderbolt, lightning, etc.). The client device 515 may execute an application program that is used to interact with the processor 505 and/or with the lateral flow assay device 100. For example, the client device 515 may receive a value (e.g., from a user entering the value through a user interface of the application program) for setting a timer value in seconds, in milliseconds, in microseconds, or with any other time units. The client device 515 may then send the timer value to the processor 505 through the wired or wireless connection.

In some embodiments, the processor 505 may start the timer after the processor 505 receives a signal indicating the start of a test. In some of the present embodiments, the signal may be received by the processor 505 from the client device 515. For example, the processor 505 may start the timer as soon as (or a period of time after) the processor 505 receives the value of the timer from the client device 515. In some embodiments, the signal may be received after a physical switch (e.g., a push button or a toggle switch on the UI 550) that is communicatively coupled to the processor 505 is activated to generate the signal.

After the time required for the analyte in the sample fluid to bind with the labeled binding agents on the conjugate pad 110 elapses, the electric motor 530 may receive a signal to pull the linear moving shaft 545 back towards the rotating shaft 580 and away from the cartridge 575 of the lateral flow assay device 100. After the timer expires, the processor 505 may send one or more signals to the linear actuator 525 to move the linear moving shaft 540 to pull the barrier 135 from between the conjugate pad 110 (FIG. 3) and the membrane 115 (FIG. 3) of the lateral flow assay device 100.

In step 502, as the linear moving shaft 540 is pulled away from the lateral flow assay device 100 (as shown by the arrow 541, the magnet(s) 545 on the linear moving shaft 540 may pull the magnet(s) 405 (which is/are firmly attached to the barrier 135), causing the barrier 135 to pull out from between the conjugate pad 110 (FIG. 3) and the membrane 115. The magnets 545 and 405 may have enough magnetic force to allow them to connect to each other (e.g., by magnetic force) and to continue connecting to each other while the barrier 135 is being pulled out from between the conjugate pad 103 and the membrane 115.

In some of the present embodiments, the magnet(s) 545 on the shaft 540 is made to contact the magnet(s) 405 on the barrier at the beginning of a test (when the barrier is located between the conjugate pad 110 and the membrane 115 as shown in step 301 of FIG. 3). The one or more signals may cause the electric motor 530 to generate a predetermined amount of rotational movement to the rotating shaft 580, which is in turn is converted by the rotational to linear movement converter 535 into a predetermined amount of linear movement on the linear moving shaft 540.

For example, the linear moving shaft 540 may move in a linear direction away from the lateral flow assay device 100, causing the magnet(s) 545 attached to the magnet 405(*s*) on the barrier 135 to pull the barrier 135 from between the conjugate pad 110 (FIG. 3) and the membrane 115 (FIG. 3). In some embodiments, the linear moving shaft 540 may move (in the direction of the arrow 541) a distance that is the same as or slightly larger than the width 415 (FIG. 4) of the barrier 135 to completely pull the barrier 135 out of the lateral flow assay device 100.

Figure 6:
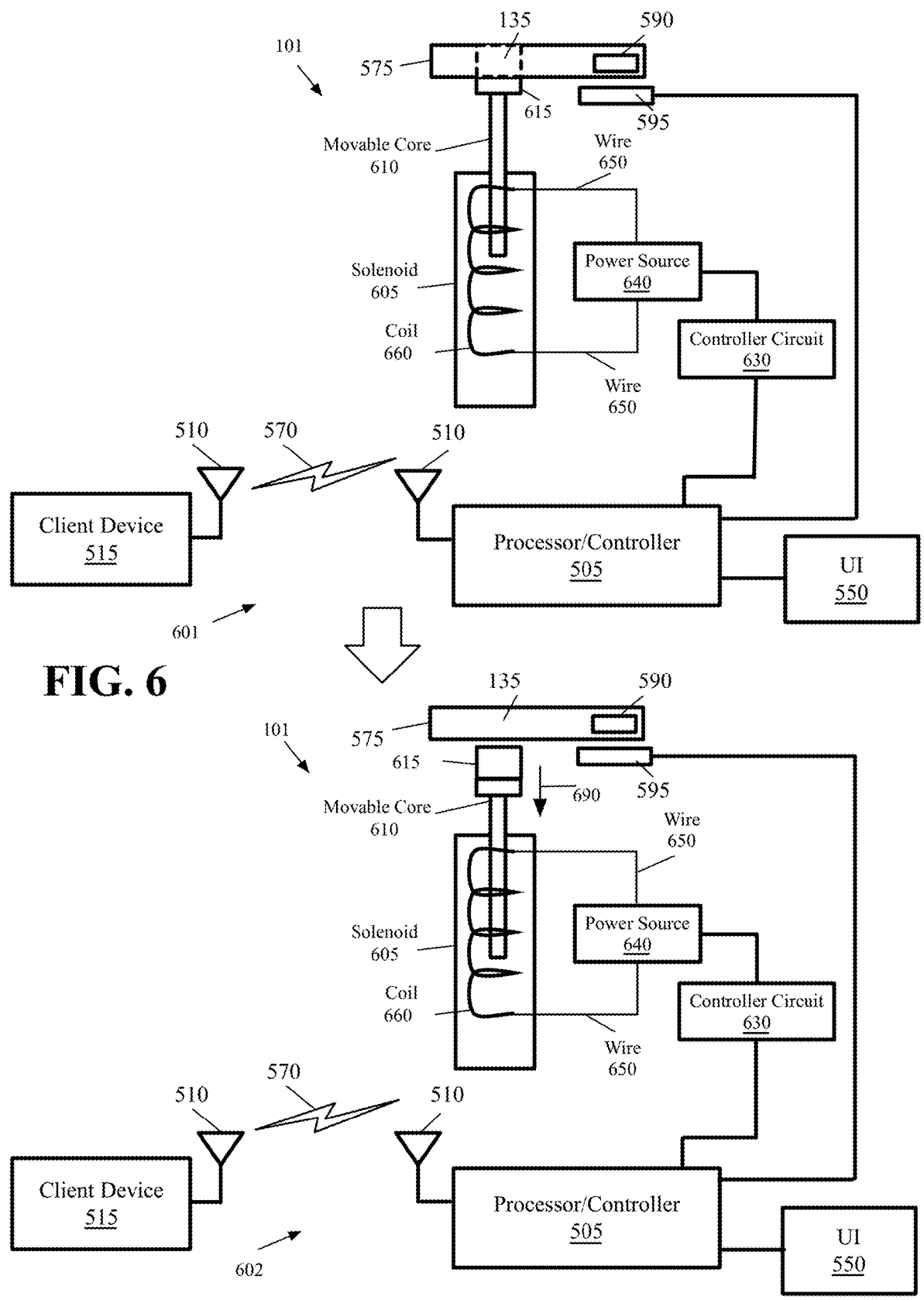
FIG. 6 is a functional block diagram illustrating one example embodiment of a solenoid that may be used for pulling out the physical barrier of a lateral flow assay device, according to various aspects of the present disclosure.

Some of the present embodiments may use a solenoid instead of a linear actuator to pull the barrier 135. FIG. 6 is a functional block diagram illustrating one example embodiment of a solenoid 605 that may be used for pulling out the physical barrier of a lateral flow assay device, according to various aspects of the present disclosure.

A solenoid may function as a transducer that converts energy into linear motion. The solenoid 605 may include an electromagnetically inductive coil 660 that is wrapped around a movable metallic core (or armature) 610. When an electric current passes through the wire 650, a magnetic field is generated by the coil 660 that causes the moveable core 610 to move in a linear line. By changing the direction of the current, the magnetic field is reversed that causes the moveable core 610 to move in the opposite direction. One or more magnets 615 may be attached to one end of the moveable core 610.

The figure as shown, includes two operational steps 601 and 602. As shown in step 601, at the beginning of a test, the solenoid 605 may be configured (e.g., by changing the direction of electric current in the wire 650) to extend the movable core 610 away from the solenoid 605, and the solenoid 605 may be placed adjacent to the lateral flow assay device 100 such that the magnet(s) 615 on the movable core 610 contacts the magnet(s) 405 (FIG. 4) on the barrier 135. In FIG. 6, the top view of the lateral flow assay device 100 is shown and the components of the lateral flow assay device 100, other than the barrier 135, are not shown for simplicity.

The processor 505, the NFC tag 590, the NFC reader 595, and the client device 515 of FIG. 6 may be similar to the corresponding components of FIG. 5. With reference to FIG. 6, the processor 505 may receive a value for setting the timer from the NFC tag 590/NFC reader 595 or from the client device 515. In some embodiments, the processor 505 may start the timer after the processor 505 receives a signal indicating the start of a test. In some of the present embodiments, the signal may be received by the processor 505 from the client device 515. For example, the processor 505 may start the timer as soon as (or a period of time after) the processor 505 receives the value of the timer from the client device 515. In some embodiments, the signal may be received after a physical switch (e.g., a push button or a toggle switch on the UI 550) that is communicatively coupled to the processor 505 is activated to generate the signal.

In some embodiments, all components of the lateral flow assay device, including the processor 505, the UI 550, etc., may be used for one test and may be disposable. In these embodiments, in addition to, or in lieu of the NFC, the parameters and information regarding the test may be pre-programmed into the processor. In other embodiments, the processor/controller 505, the UI 550, the solenoid 605, the power source 640, the controller circuit 630, and/or the NFC reader may be reusable for performing multiple tests for the same or different subjects (e.g., the same person or different persons).

In step 602, after the timer expires, the processor 505 may send one or more signals to the controller circuit 630 to change the direction of current in the wire 650 (e.g., by changing the polarity of the voltage that is applied to the wire 650 by the power source 640). Changing the direction of current in the wire 650 may change the magnetic field generated by the coil 660 that causes the moveable core 610 to move towards the solenoid 605 and away from the lateral flow assay device 100, causing the magnet(s) 615 that is attracting the magnet(s) 405 (FIG. 4) on the barrier 135 to pull the barrier 135 from between the conjugate pad 110 (FIG. 3) and the membrane 115 (FIG. 3). The magnets 615 and 405 may have the polarities (e.g., opposite polarities to attract each other) and enough magnetic force to allow them to connect to each other (e.g., by magnetic force) and to continue connecting to each other while the barrier 135 is being pulled out from between the conjugate pad 103 and the membrane 115. In some embodiments, the movable core 610 may move (in the direction of the arrow 690) a distance that is the same as or slightly larger than the width 415 (FIG. 4) of the barrier 135 to completely pull the barrier 135 out of the lateral flow assay device 100.

Figure 7:
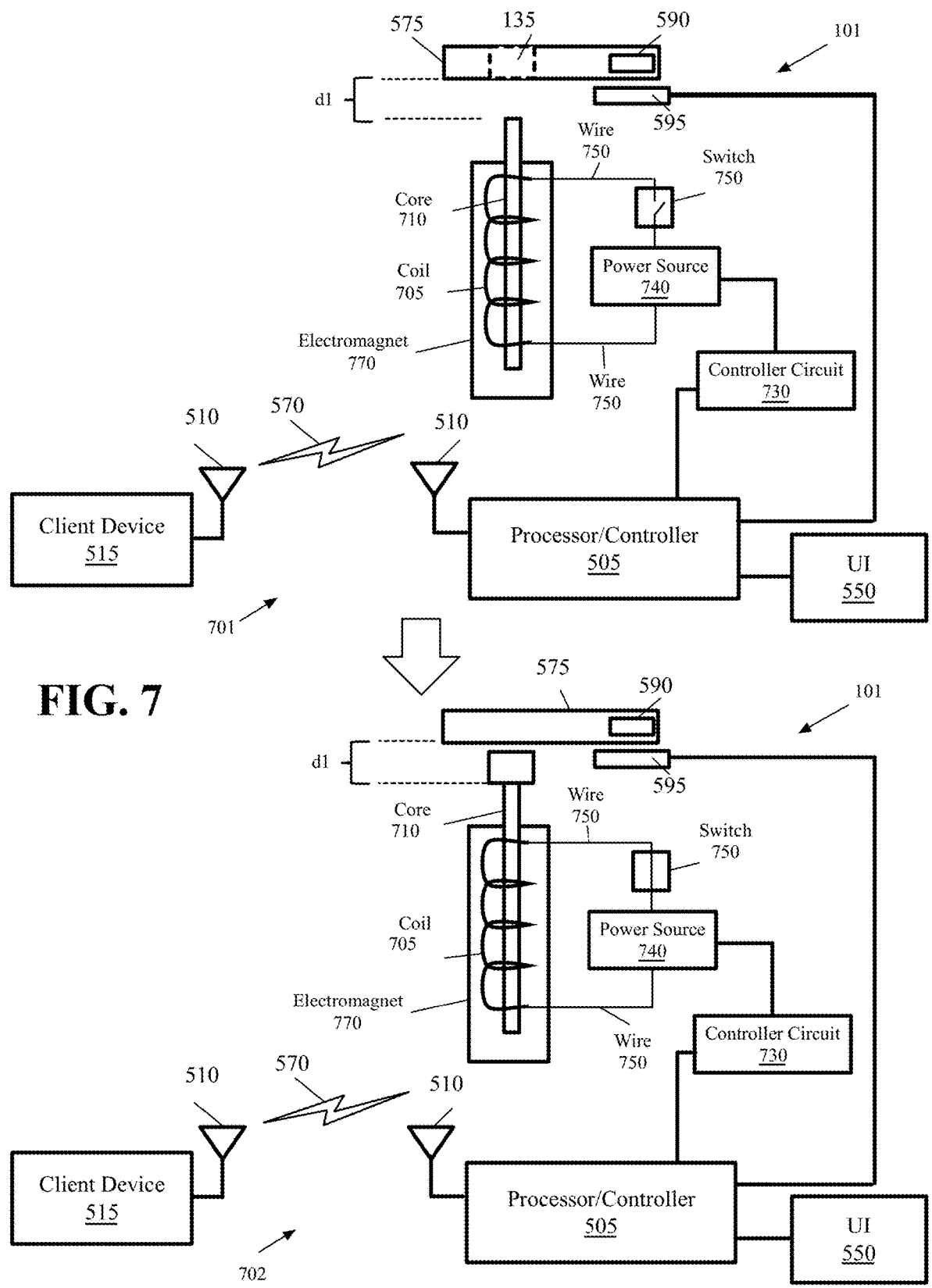
FIG. 7 is a functional block diagram illustrating one example embodiment of an electromagnet that may be used for pulling out the physical barrier of a lateral flow assay device, according to various aspects of the present disclosure.

Some of the present embodiments may use an electromagnet instead of a linear actuator or a solenoid to pull the barrier 135. FIG. 7 is a functional block diagram illustrating one example embodiment of an electromagnet 770 that may be used for pulling out the physical barrier of a lateral flow assay device, according to various aspects of the present disclosure. In FIG. 7, the top view of the lateral flow assay device 100 is shown and the details of the lateral flow assay device 100, other than the barrier 135, are not shown for simplicity.

In an electromagnet, a magnetic field is generated by an electric current. The magnetic field disappears when the electric current is turned off. The electromagnet 770 may include an electromagnetically inductive coil 705 that is wrapped around a metallic core 710. When the electric current is turned off, the coil 705 no longer generates a magnetic field.

The figure as shown, includes two operational steps 701 and 702. As shown in step 701, at the beginning of a test, the switch 750 may be off such that no current is passed through the power source 740, the wire 750, and the core 710. The coil 705 may not generate a magnetic field and the metallic core 710 may not act as a magnet. In step 701, the electromagnet 770 may be placed adjacent to the cartridge 575 of the lateral flow assay device 100 such that the magnet(s) 405 (FIG. 4) on the barrier 135 is/are at a predetermined distance "d1" from the core 710. The distance "d1" may be just enough to allow the removable barrier 135 to be completely pulled out of lateral flow assay device 100 when the electromagnet 770 is turned on.

The processor 505, the NFC tag 590, the NFC reader 595, and the client device 515 of FIG. 7 are similar to the corresponding components of FIG. 5. With reference to FIG. 7, the processor 505 may receive the values of the test parameters from the NFC tag 590/NFC reader 595 or from the client device 515. In some embodiments, the processor 505 may start the timer after the processor 505 receives a signal indicating the start of a test. In some of the present embodiments, the signal may be received by the processor 505 from the client device 515. For example, the processor 505 may start the timer as soon as (or a period of time after) the processor 505 receives the value of the timer from the client device 515. In some embodiments, the signal may be received after a physical switch (e.g., a push button or a toggle switch on the UI 550) that is communicatively coupled to the processor 505 is activated to generate the signal.

In some embodiments, all components of the lateral flow assay device, including the processor 505, the UI 550, etc., may be used for one test and may be disposable. In these embodiments, in addition to, or in lieu of the NFC, the parameters and information regarding the test may be pre-programmed into the processor. In other embodiments, the processor/controller 505, the UI 550, the coil 705, the power source 740, the controller circuit 730, and/or the NFC reader may be reusable for performing multiple tests for the same or different subjects (e.g., the same person or different persons).

In step 702, after the timer expires, the processor 505 may send one or more signals to the controller circuit 730 to close the switch 750 to have a current flow from the power source 740 through the wire 750 and the coil 705. The current in the coil 705 may cause the coil 705 to generate a magnetic field and make the core 710 to become a magnet. The core 710 acting as a magnet may then magnetically attract the magnets(s) 405 (FIG. 4) on the barrier 135 to pull the barrier 135 from between the conjugate pad 110 (FIG. 3) and the membrane 115 (FIG. 3). The magnet generated by the core 710 may have the polarity (e.g., the opposite polarity of the magnet(s) 405) and enough magnetic force to pull the magnet(s) 405 on the barrier 135 and the barrier 135 from between the conjugate pad 103 (FIG. 3) and the membrane 115 (FIG. 3).

As shown in steps 701 and 702 of FIG. 7, the distance "d1" between the core 710 and the cartridge 575 of the lateral flow assay device 100 may not change as the barrier 135 is being pulled out. The distance "d1" in some embodiments is adjusted at the beginning of a test such that when the electromagnet is turn on (e.g., as described with reference to step 702), the barrier 135 is completely pulled out of the lateral flow assay device 100. For example, in some embodiments, the distance "d1" may be the same as, or slightly larger, than the width 415 (FIG. 4) of the barrier 135.

Figure 8:
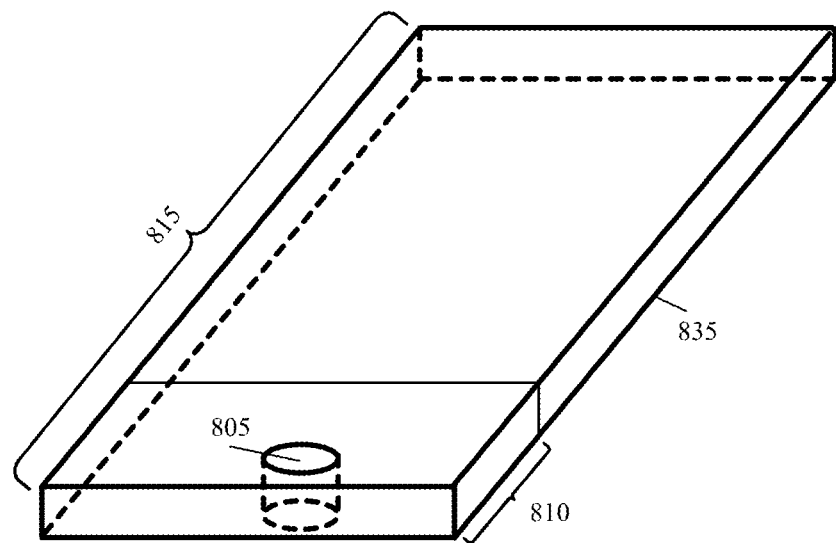
FIG. 8 is an upper front perspective of one example embodiment of a physical barrier that includes a hole, according to various aspects of the present disclosure.

Some of the present embodiments may use a hook instead of a magnet to pull the barrier 135 from between the conjugate pad 110 and the membrane 115. FIG. 8 is an upper front perspective of one example embodiment of a physical barrier that includes a hole, according to various aspects of the present disclosure. The physical barrier 835 may be made of similar materials as the physical barrier 135 (FIGS. 1-4).

With reference to FIG. 8, the physical barrier 835 may have a width 815 that is wider than the width of the conjugate pad 110 and the membrane 115. The barrier 835 may be initially (e.g., at the manufacture time of the lateral flow assay device and/or at the beginning of a test) placed between the conjugate pad 110 and the membrane 115 in such a way that the barrier 835 prevents the flow of the fluid material from the conjugate pad 110 into the membrane 115 and a portion 810 of the barrier comes out of the lateral flow assay device housing 205 of FIG. 2.

As shown in FIG. 8, the portion 810 of the physical barrier 835 that comes out of the lateral flow assay device housing may include one or more holes 805 (only one hole is shown in FIG. 8). The hole 805 may be used to pass a hook through the hole 805 to pull the barrier 835 from between the conjugate pad 110 and the membrane 115 (FIG. 3).

Figure 9:
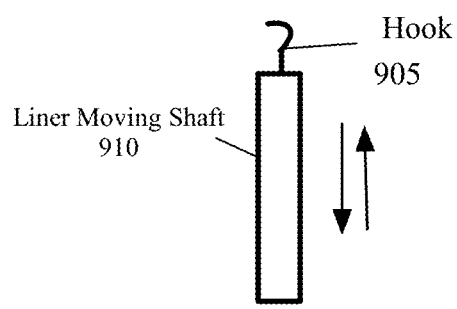
FIG. 9 is a functional block diagram illustrating one example embodiment of the linear moving shaft of FIG. 5 with a hook that is used for pulling out the physical barrier of a lateral flow assay device, according to various aspects of the present disclosure.

FIG. 9 is a functional block diagram illustrating one example embodiment of the linear moving shaft of FIG. 5 with a hook that is used for pulling out the physical barrier of a lateral flow assay device, according to various aspects of the present disclosure. The linear moving shaft 910 in FIG. 9 is similar to the linear moving shaft 540 of FIG. 5 except that the linear moving shaft 910 has a hook 905, instead of a magnet, attached to one end of the linear moving shaft 910.

The linear moving shaft 910 may be part of a linear actuator similar to the linear actuator of FIG. 5. The hook 905 may fit into the hole 805 of FIG. 8. In the embodiments that the barrier 835 includes more than one hole 805, the linear moving shaft may include the same number of hooks 905 as the holes 805. When the linear moving shaft 910 is moved away from the lateral flow assay device (e.g., after the timer described above is expired), the hook pulls out the physical barrier 837 from between the conjugate pad 110 and the membrane 115. When the physical barrier 835 has more than one hole 805, the hook 905 may have more than one head to fit in the holes 805.

A hook similar to the hook 905 may be placed on the movable core 610 of FIG. 6 (instead of a magnet 615) in order to pull out the physical barrier 835 from between the conjugate pad 110 and the membrane 115. In some of the present embodiments, a string may pass through the hole(s) 805 of FIG. 5 and the string may be used to pull the physical barrier 835 from between the conjugate pad 110 and the membrane 115 (e.g., by using a linear actuator or a solenoid as described above).

In some of the present embodiments, the physical barrier may be manually pulled out from between the conjugate pad 110 and the membrane 115. For example, the string described above may be used to manually pull the barrier out (e.g., after the timer described above expires and the processor 505 of FIGS. 5-6 makes a visual and/or audible signal to indicate that the timer has expired). FIG. 10 is an upper front perspective of one example embodiment of a physical barrier that includes a groove for pulling out the physical barrier of a lateral flow assay device, according to various aspects of the present disclosure. The physical barrier 1035 may be made of similar materials as the physical barrier 135 (FIGS. 1-4).

With reference to FIG. 10, the physical barrier 1035 may a have a width 1015 that is wider than the width of the conjugate pad 110 (FIG. 1) and the membrane 115 (FIG. 1). The barrier 1035 may be initially (e.g., at the manufacture time of the lateral flow assay device and/or at the beginning of a test) placed between the conjugate pad 110 and the membrane 115 in such a way that the barrier 1035 prevents the flow of the sample fluid from the conjugate pad 110 into the membrane 115 and a portion 1010 of the barrier comes out of the lateral flow assay device housing 205 of FIG. 2.

The physical barrier 1035 may a have a groove 1005 in the portion 1010 of the physical barrier 1035 that comes out of the lateral flow assay device's housing 205. The groove 1005 may be used to manually pull out the barrier 1035 from between the conjugate pad 110 and the membrane 115 (e.g., after the timer described above expires and the processor 505 of FIG. 5 or 6 makes a visual and/or audible signal to indicate that the timer has expired).

FIG. 11 is a flowchart illustrating an example process 1100 for pulling out a barrier that separates the labeling and capture zones of a lateral flow assay device, according to various aspects of the present disclosure. In some of the present embodiments, the process 1100 may be performed by a processor 505 (FIGS. 5-7).

With reference to FIG. 11, the process 1100 may send (at block 1105) one or more signals to a device to adjust the position of the device with respect to the lateral flow assay device 100 (FIGS. 1-3 and 5-7) and/or to set up the device to pull the barrier 135 out of the lateral flow assay device. As a first example, the processor 505 of FIG. 5 may send one or more signals to the electric motor 530 to rotate the rotating shaft 580 to cause the linear moving shaft 540 to move such that the magnet(s) 545 on the linear moving shaft 540 come(s) in contact with the magnet(s) 405 (FIG. 4) on the barrier 135. Alternatively, the one or more signals may cause one or more hooks 908 (FIG. 9) on the rotating shaft 580 to engage with one or more holes 805 (FIG. 8) on the barrier 135.

As a second example, the processor 505 of FIG. 6 may send one or more signals to the controller circuit 630 to adjust the electric current in the wire 650 and the coil 660 such that the magnet(s) 615 on the movable core 610 come(s) in contact with the magnet(s) 405 (FIG. 4) on the barrier 135. Alternatively, the one or more signals may cause one or more hooks 908 (FIG. 9) on the movable core 610 to engage with one or more holes 805 (FIG. 8) on the barrier 135. As a third example, the processor 505 of FIG. 7 may send one or more signals to the controller circuit 730 to turn off the switch 750 in order for the core 710 not to act as a magnet while the core 710 is kept at a distance "d1" from the barrier 135 as described above by reference to FIG. 7.

With further reference to FIG. 11, the process 1100 may receive (at block 1110) a signal that may include a value to set a timer for removing the barrier. The signal, in some embodiments, may include a value that indicates the amount of time in a predetermined unit of time (e.g., hours, minutes, seconds, milliseconds, microseconds, etc.). The signal, in some embodiments, may include a value and a unit of time (e.g., 2 seconds, 45 milliseconds, etc.).

In some of the present embodiments, the process 1100 may receive, at the processor 505 (FIGS. 5-7), a signal that includes the test parameters values (e.g., and without limitations, the timer value) from the NFC tag 590 and the NFC reader 595. In some of the present embodiments, the process 1100 may receive, at the processor 505 (FIGS. 5-7), a signal that includes test parameters values from the client device 515. In some embodiments, the processor 505 may be associated with, and communicatively coupled to, a user interface including a keyboard and/or a display (e.g., a touchscreen). In these embodiments, the process 1100 may receive, at the processor 505, the signal that includes the test parameter values from the keyboard and/or the touchscreen associated with the processor.

With continued reference to FIG. 11, the process 1100 may then set (at block 1115) a timer to expire after a time period that is identified by the received timer value. For example, the processor 505 may set an internal timer to expire after a time period determined by the received timer value. The process 1100 may then determine (at block 1120) whether to start the timer.

In some of the present embodiments, the process 1100 may receive a signal to start the timer, which is different that the signal that includes the timer value. For example, the client device 515 (FIGS. 5-7) may receive a signal through the application executing on the client device 515 indicating the start of the test. The process 1100 may then receive a signal, at the processor 505, from the client device 515 indicating the start of the test. Alternatively, the process 1100 may receive the signal after a physical switch (e.g., a push button or a toggle switch) that is communicatively coupled to the processor 505 is activated to generate the signal. In some of the present embodiments, the process 1100 may start the timer as soon as the timer value is set (at block 1115). These embodiments may bypass block 1120

When the process 1100 determines (at block 1120) that the timer should not be started, the process 1100 may proceed back to block 1120. Otherwise, the process 1100 may start (at block 1125) the timer. The process 1100 may then determine (at block 1130) whether the timer has expired. When the process 1100 determines (at block 1130) that the timer has not expired, the process 1100 may proceed back to block 1130 to wait for the timer to expire.

Otherwise, the process 1100 may send (at 1135) one or more signals to move a shaft to pull the barrier from between the labeling and capture zones of the lateral flow assay device. The process 1100 may then end. As a first example, with reference to FIG. 5, the processor 505 may send one or more signals to the electric motor 530 to rotate and cause the rotational to linear movement converter 535 to move the shaft 540 a predetermined distance in order to pull the barrier 135 (FIGS. 1-4) from between the conjugate pad 110 and the membrane 115.

In some embodiments, the magnet(s) 545 on the linear moving shaft 540 is/are made to contact the magnet(s) 405 (or the hook(s) 905 of FIG. 9 is/are made to engage the hole(s) 805 of FIG. 8) on the barrier at the beginning of a test (when the barrier is located between the conjugate pad 110 and the membrane 115). The one or more signals (sent at block 1135) may be sent from the processor 505 to the electric motor 530, causing the electric motor 530 to rotate the rotating shaft 580 by a predetermined amount, the rotational to linear movement converter 535 to cause the linear moving shaft 540 to move in a linear direction (e.g., away from the lateral flow assay device), causing the magnet(s) 545 that is/are attached to the magnet(s) 405 (or the hook(s) 905 that is/are engaged in the hole(s) 805) on the barrier 135 to pull the barrier 1135 out from between the conjugate pad 110 and the membrane 115.

As a second example, with reference to FIG. 6, the processor 505 may send one or more signals to the controller circuit 630 to change the direction of the electrical current in the wire 650 and cause the movable core 610 to move a predetermined distance causing the magnet(s) 615 that is/are attached to the magnet(s) 405 (or the hook(s) 905 that is/are engaged in the hole(s) 805) on the barrier 135 to pull the barrier 1135 out from between the conjugate pad 110 and the membrane 115. As a third example, the processor 505 of FIG. 7 may send one or more signals to the controller circuit 730 to turn one the switch 750 in order for the core 710 to act as a magnet and pull the magnet 405 (FIG. 4) that is attached to the barrier 135 out of the lateral flow assay device 100.

With reference to FIGS. 1 and 3, the removable barrier 135 may be used to prevent the flow of the fluid material from the conjugate pad 110 into the membrane 115 until a timer expires and the barrier 135 is removed. However, depending on the type of material used for the conjugate pad 110, the membrane pad 115, and the backing card 140, and/or the way the pads 110 and 115 are placed on the cartridge bed 170, even when the barrier 135 is in place, some of the fluid material may leak from under the conjugate pad 110 (e.g., through the backing card 140 and/or the cartridge bed 170) into the membrane 115.

To prevent such a leak, some embodiments may include a permanent gap in the cartridge bed and/or in the backing card 140 in order to prevent the fluid material to leak from under the conjugate pad 110 into the membrane 115 while the barrier 135 is in place. Once the barrier is removed, the fluid may flow freely from the conjugate pad 110 into the membrane 115.

FIG. 12 is an upper front perspective view of one example embodiment of a portion of a lateral flow assay device that includes a permanent gap in the backing card and/or the cartridge bed to prevent the leaking of the fluid material from under the conjugate pad into the membrane while the barrier is in place, according to various aspects of the present disclosure.

With reference to FIG. 12, the cartridge bed 171 and 172 may have a permanent gap 1205 such that there is no cartridge bed under a portion of the conjugate pad 110 and the membrane 115 where the barrier 135 is located between the conjugate pad 110 and the membrane 115. In some embodiments, the cartridge bed may be made of two separate sections 171 and 172, one section on each side of the cartridge bed gap 1205. The two sections 171 and 172 of the cartridge bed may be secured on the housing (as shown below with reference to FIGS. 14 and 15) of the lateral flow assay device 100.

In addition, there may be a gap 1210 in the backing card 140. In the embodiments that the conjugate pad 110 and the membrane 115 have individual backing cards, each backing card is made such that the backing card of the conjugate pad and the backing card of the membrane do not touch each other.

In the depicted embodiment, a portion of the backing card that is under the membrane has crossed over the cartridge bed gap 1205. However, there is still a gap 1210 between the backing card that is under the membrane 115 and the backing card that is under the conjugate pad 110. In other embodiments, the backing card that is under the membrane 115 may not cross over the cartridge bed gap 1205. In yet other embodiments, the portion of the backing card that is under the conjugate pad 110 may cross over the cartridge bed gap 1205 while maintaining the gap 1210 with the portion of the backing card that is under the membrane 115.

FIG. 13 is an upper front perspective view of one example embodiment of a portion of a lateral flow assay device with a permanent gap in the backing card and/or the cartridge bed, showing the removal of the barrier, according to various aspects of the present disclosure. The figure as shown, includes two operational steps 1301 and 1302.

With reference to FIG. 13, step 1301 shows an initial state where the barrier 135 is between the conjugate pad 110 and the membrane 115. The barrier may be similar to the barrier 135 of FIG. 3. The cartridge bed gap 1205 and/or the backing card gap 1210 prevent the fluid material to leak from underneath the conjugate pad 100 into the membrane 115. As shown by the arrows 1305, as long as the barrier 135 is between the conjugate pad 110 and the membrane 115, fluid material cannot flow from the conjugate pad 110 into the membrane 115. The cartridge bed gap 1205 and/or the backing card gap 1210 provide the technical advantage of preventing the fluid material from leaking from under the conjugate pad 110 into the membrane 115 while the barrier 135 is between the conjugate pad 110 and the membrane 115.

In step 1302 of FIG. 13, the barrier 135 is removed (as shown by the arrow 360) from between the conjugate pad 110 and the membrane 115 (e.g., when a timer expires and the barrier is removed as described above with reference to FIGS. 5-7). As shown by the arrows 1310, once the barrier 135 is removed, the fluid material may flow from the conjugate pad 110 into the membrane 115.

FIG. 14 is an upper front perspective view of one example embodiment of a portion of a lateral flow assay device 100 showing a cartridge inside the device's housing, according to various aspects of the present disclosure. FIG. 15 is a front elevation view of the lateral flow assay device of FIG. 14, according to various aspects of the present disclosure.

With reference to FIGS. 14 and 15, the housing 1405 may include a sample port 1460 for applying the sample liquid to the lateral flow assay device 100. In the example of FIG. 14, the lateral flow assay device 100 does not include a separate sample pad. As shown, the lateral flow assay device 100 may include a conjugate pad 110, a removable barrier 135, a membrane 115, a test line 125, a control line 130, and a wicking pad 120. The conjugate pad 110 may act as both the sample pad to receive a sample fluid and as the conjugate pad to contain a binding reagent that is capable of binding to the target analyte in the sample fluid.

The lateral flow assay device 100 may include an optional plasma filter 1420. When the sample fluid includes blood, the plasma filter 1420 may be used to filter and pass the plasma while stopping the flow of red blood cells onto the conjugate pad 110.

The housing 205 may also include an opening 215 for viewing the test line 125. The embodiments that include a control line 130, may also include an opening 220 for viewing the control line 130. Some embodiments may include one opening for viewing both the test line 125 and the control line 130. The housing 205 may include a cartridge bed 171 and 172 for holding the lateral flow assay device's cartridge.

With further reference to FIGS. 14 and 15, the cartridge bed 171 and 172 may include a permanent cartridge bed gap 1205. As shown, the barrier 135 and a portion of the conjugate pad 110 and the membrane 115 are located over the cartridge bed gap 1205 to prevent the fluid material to leak from under the conjugate pad into the membrane 115. The two sections 171 and 172 of the cartridge bed on either side of the cartridge bed gap 1205 may be fixed to the housing 1405, for example, and without limitations, by one or more support columns/support structures 1430. The housing may include one or more other support columns/support structures 1435 to hold the cartridge of the lateral flow assay device (that includes the components shown in FIGS. 14 and 15). For simplicity, FIGS. 14 and 15 do not show the backing card 140 or the backing card gap 1210 of FIGS. 12 and 13.

In addition to, or in lieu of, a barrier zone between the labelling zone and the capture zone, some of the present embodiments may have one more barrier zones at other locations to provide additional time for the sample fluid and other material in the fluid flow to bind with the immobilized molecules at the test line and/or at the control line. In some of these embodiments, the membrane may be made of several separate pieces (as oppose to one continuous piece of material).

FIG. 16 is an upper front perspective view of one example embodiment of a portion of a lateral flow assay device 1600 with multiple barrier zones, according to various aspects of the present disclosure. The lateral flow assay device 1600 may include a housing, which is not shown in FIG. 16 for simplicity. Similar to the lateral flow assay device 100 of FIG. 1, the lateral flow assay device 1600 may include a sample pad 150 in the capture zone, a conjugate pad 110 in the labeling zone, and a wicking pad 120 in the wicking zone. The capture zone of the lateral flow assay device 1600 may include two separate membranes 1615 and 1616. A test line (or test zone) 125 may be embedded in the membrane 1615. A control line (or control zone) 130 may be embedded in the membrane 1616. The sample pad 150, the conjugate pad 110, the membranes 1615-1616, the test line 125, the control line 130, and the wicking pad 120 of FIG. 16 may be made of similar material as described above for the corresponding components of FIG. 1.

With reference to FIG. 16, the removable physical barrier 135 between the conjugate pad 110 and the membrane 1615 is substantially similar to the removable physical barrier 135 of FIG. 1. The lateral flow assay device 1600 may include a barrier 1630 that may prevent fluid flow from the membrane 1615 and the test line 125 into the membrane 1616. The lateral flow assay device 1600 may include a barrier 1635 that may prevent fluid flow from the membrane 1616 and the control line 130 into the wicking pad 120.

In some of the present embodiments, the lateral flow assay device 1600 may include a housing that may apply pressure to different components of the lateral flow assay device 1600 in order for these components to come into contact with each other after the barrier between them is removed. FIG. 17 is an upper front perspective view of one example embodiment of a portion of a lateral flow assay device 1600 showing a cross section of the lateral flow assay device's housing, according to various aspects of the present disclosure. With reference to FIG. 17, the perspective shows a cross sectional view of the housing 1705 across the surfaces 1706.

Similar to the housing 205 of FIG. 2, the housing 1705 of FIG. 17 may include a sample port 1710 for applying the sample liquid to the sample pad 150, an opening 1715 for viewing the test line 125, and (for the embodiments that include a control line) an opening 1720 for viewing the control line 130. Some embodiments may include one opening for viewing both the test line 125 and the control line 130.

Similar to the housing 205 of FIG. 2, the housing 1705 may apply pressure to the conjugate pad 110 (e.g., as shown by the arrows 250) and/or to the membrane 115 (e.g., as shown by the arrows 255) such that when the barrier 135 is removed, the conjugate pad 110 and the membrane 115 come to contact with each other to allow the fluid material in the flow path to flow from the conjugate pad 110 into the membrane 115 by capillary act.

With continued reference to FIG. 17, the housing 1700 may apply pressure to the membrane 1616 (e.g., as shown by the arrows 1750) and/or to the backing card 140 and the membrane 1615 (e.g., as shown by the arrows 1755) such that when the barrier 1630 is removed, the membrane 1616 and the membrane 2085 come to contact with each other to allow the fluid material in the flow path to flow from the membrane 1615 and the test line 125 (which is embedded in the membrane 1615) into the membrane 1616 by capillary act. The housing 1600 may apply pressure to the wicking pad 120 (e.g., as shown by the arrows 1760) and/or to the backing card 140 and the membrane 1616 (e.g., as shown by the arrows 1765) such that when the barrier 1635 is removed, the wicking pad 120 and the membrane 1616 come to contact with each other to allow the fluid material in the flow path to flow from the membrane 1616 and the control line 130 (which is embedded in the membrane 1616) into the wicking pad 120 by capillary act. With further reference to FIG. 17, the barriers 135, 1630, and 1635 may be removed using any of the mechanisms described above with reference to FIGS. 3-10 for removing the barrier 135 of FIG. 3.

FIG. 18 is an upper front perspective view of one example embodiment of a portion of a lateral flow assay device showing the removal of multiple barriers, according to various aspects of the present disclosure. The figure as shown, includes two operational steps 1801 and 1802. With reference to FIG. 18, step 1801 shows an initial state where the barrier 135 is between the conjugate pad 110 and the membrane 115, the barrier 1630 is between the membrane 1616 and the membrane 1615, and the barrier 1635 is between the wicking pad 120 and the membrane 1616. The barriers 135, 1630, and 1635 may be made of materials (e.g., plastic, latex, metal, etc.) which block the fluid material from flowing downstream on the flow path. The barriers' materials are selected from materials that do not react with the fluid material in the flow path. As shown in step 1801, the barriers 135, 1630, and 1635 are flexible and follow (as shown by the corresponding dashed lines 335, 1631, and 1636) the contours of the components that the barriers 135, 1630, and 1635 are separating.

In some of the present embodiments, the lateral flow assay device 1800 at the start of a test may include the barriers 135, 1630, and 1635. For example, the lateral flow assay device 1800 may be manufactured in the configuration shown in step 1801 of FIG. 18. A test may start by applying a sample fluid to the conjugate pad 110 (e.g., through the sample port 1710 of FIG. 17).

With reference to step 1802 of FIG. 18, some of the present embodiments may use several timers for removing the barriers 135, 1630, and 1635. For example, a first timer may be set to allow the analyte (if any) in the sample fluid to bind with the labeled binding agents on the conjugate pad 110. After the expiration of the first timer, the barrier 135 may be removed (as shown by the arrow 360 of FIG. 18) from between the conjugate pad 110 and the membrane 1615 to allow the fluid material to flow from the conjugate pad 110 into the membrane 1615 by capillary action.

With continued reference to FIG. 18, after the expiration of the first timer, a second timer may be started to determine the time for removing the barrier 1630. In some of the present embodiments, the labelled immunocomplex in a sandwich format assay may require more time to bind with the immobilized binding reagent at the test line than the time it takes for the fluid material to flow by capillary action through the test line 125 into the membrane 1616. The second timer may allow enough time for the binding of the labelled immunocomplex with the immobilized binding reagent at the test line.

Similarly, in a competitive assay format, the labelled binding reagent in the fluid may require more time to bind with the immobilized analyte/protein-analyte complex in the test line. The second timer may allow enough time for the binding of the labelled binding reagent with the immobilized binding reagent at the test line. After the expiration of the second timer, the barrier 1630 may be removed (as shown by the arrow 1831) from between (i) the membrane 1615, the test line 125 and (ii) the membrane 1635 to allow the fluid material to flow from the membrane 1615 and the test line 125 into the membrane 1616 by capillary action.

After the expiration of the second timer, a third timer may be started to determine the time for removing the barrier 1635. In some of the present embodiments, the free labeled binding reagents may require more time to bind with the immobilized antibody in a sandwich format assay at the control line than the time it takes for the fluid material to flow by capillary action through the control line 130 into the wicking pad 120. Similarly, in a competitive assay format, the free labeled binding reagents may require more time to bind with the immobilized analyte molecule (or a protein-analyte complex) at the control line 130 than the time it takes for the fluid material to flow by capillary action through the control line 130 into the wicking pad 120.

The third timer may allow enough time for the free labeled binding reagents to bind with the immobilized antibody (in the sandwich assay format) or with the immobilized analyte molecule/protein-analyte complex (in the competitive assay format) at the control line 130. Similarly, in a competitive assay format, after the expiration of the third timer, the barrier 1635 may be removed (as shown by the arrow 1832) from between the membrane 1616, and the wicking pad 120 to allow the fluid material to flow from the membrane 1616 and the control line 130 into the wicking pad 120 by capillary action.

In some of the present embodiments, a separate linear actuator 525 (FIG. 5), solenoid 605 (FIG. 6), or electromagnet 770 (FIG. 7) may be used to remove each of the barriers 135, 1630, and 1635 of FIG. 16. In some of the present embodiments, a magnet such as the magnet 405 (FIG. 4) may be attached to each barrier 135, 1630, and 1635 of FIG. 18 to pull the barrier using a magnet such as magnet 545 (FIG. 5), magnet 615 (FIG. 6), or the core 710 (FIG. 7).

In some of the present embodiments, each barrier 135, 1630, and 1635 of FIGS. 17-18 may have one or more holes such as the hole 805 (FIG. 8) to pull the barrier using a hook such as the hook 905 (FIG. 9). In some of the present embodiments, each barrier 135, 1630, and 1635 of FIGS. 17-18 may have a groove such as the groove 1005 (FIG. 10) to manually pull the barrier.

Some of the present embodiments may include only one of the barriers 135, 1630, or 1635 of FIGS. 16-18. Other embodiments may include any two of the barriers 135, 1630, or 1635 of FIGS. 16-18. Some embodiments (such as the embodiment of FIGS. 16-18) may include all three barriers 135, 1630, or 1635. In some embodiments, the number of timers may be equal to the number of barriers. Since the fluid flows downstream from the sample pad 150 towards the wicking pad 120, when a lateral flow assay device has two barriers, the barriers are removed starting with the most upstream barrier followed by the next barrier downstream. When the assay device has three barriers, the barrier 135 is removed first, followed by the barrier 1630, followed by the barrier 1635.

As described with reference to FIGS. 12 and 13, depending on the type of the material used for the conjugate pad 110, the membrane 115, and the backing card, and/or the way pads 110 and 115 are placed on the cartridge bed, even when the barrier 135 is in place, some of fluid material may leak from under the conjugate pad 110 (e.g., through the backing card 140 and/or the cartridge bed) into the membrane 115. With reference to FIGS. 17-27, the fluid material may leak from underneath the membrane portion 1615 into the membrane portion 1616 even when the barrier 1630 is in place. The fluid material may also leak from underneath the membrane portion 1616 into the wicking pad 120 even when the barrier 1635 is in place.

To prevent such leaks, some embodiments may include a permanent gap in the cartridge bed and/or the backing card 140 in order to prevent the fluid material to leak from under the membrane portion 1615 into the membrane portion 1616 when the barrier 1630 is in place. Some embodiments may include a permanent gap in the cartridge bed and/or the backing card 140 in order to prevent the fluid material to leak from under the membrane portion 1616 into the wicking pad 120 when the barrier 1635 is in place.

FIG. 19 is an upper front perspective view of one example embodiment of a portion of a lateral flow assay device that includes one or more permanent gaps in the backing card and/or the cartridge bed to prevent the leaking of the fluid material while the corresponding barrier(s) is/are in place, according to various aspects of the present disclosure.

With reference to FIG. 19, the cartridge bed 171, 173, and 174 may have a gap 1205 such that there is no cartridge bed under a portion of the conjugate pad 110 and the membrane 115 where the barrier 135 is between the conjugate pad 110 and the membrane 115. In addition, there is a gap 1210 in the backing card 140.

With further reference to FIG. 19, the cartridge bed 171, 173, and 174 may have a gap 1910 such that there is no cartridge bed under a portion of the membrane 1615 and a portion of the membrane 1616 where the barrier 1630 is located. The cartridge bed 171, 173, and 174 may have a gap 1915 such that there is no cartridge bed under a portion of the membrane 1616 and a portion of the wicking pad 120 where the barrier 1635 is located. As shown, the cartridge bed may be made of three separate sections 171, 173, and 174. The three sections of the cartridge bed may be secured on the housing of the lateral flow assay device 100.

With further reference to FIG. 19, there may be a gap 1920 in the backing card 140 and/or a gap 1915 in the backing card 140. In the embodiments that the pads have individual backing cards, each backing card may be made such that the backing card of the pads on the different sides of a gap do not touch each other.

In the depicted embodiment, the backing cards do not cross over the cartridge bed gaps 1205, 1910, and 1915. In other embodiments, a portion of some or all backing cards may cross over a portion of a cartridge bed gap without touching the backing side of the adjacent pad on the other side of the gap.

With reference to FIG. 19, depending on the type of the test performed by the lateral flow assay device, different embodiments of the lateral flow assay device may include one, two, or all three of the barriers 135, 1630, and 1635. These embodiments may have the cartridge bed gaps 1205, 1910, and 1915 for the corresponding barriers 135, 1630, and 1635. In addition to, or in lieu of the cartridge bed gaps 1205, 1910, and 1915, some of these embodiments may include the backing card gaps 1210, 1915, and 1929 for the corresponding barriers 135, 1630, and 1635.

With reference to FIGS. 1-19, the exemplary embodiments were described with reference to pulling the barrier 135 out of the cartridge 575. In other embodiments, the barrier 135 may not be pulled out of the cartridge 575 at once. Instead, the barrier 135 may be partially pulled out and then pushed back in order to repeatedly bring the conjugate pad 110 and the membrane 115 in touch with each other and then separate from each other. Repeatedly connecting and disconnecting the conjugate pad 110 and the membrane 115 is a technical advantage that may be used to control the flow of fluid material from the conjugate pad 110 into the membrane 115.

The number of times the barrier 135 is pulled out and pushed back into the cartridge 575, the duration that the barrier 135 stays in or out of the cartridge 575, and the time between the pulling and pushing actions may control the amount of contact between the conjugate pad 110 and the membrane 115. The amount of contact between the conjugate pad 110 and the membrane 115 may in turn be used by the processor 505 to control the flow time (the time it would take for the fluid material to travel the length of the membrane 115, over the test line 125, and over the control line 135 to reach the wicking pad 120).

As a first example, the electric motor 530 and the rotor 570 of FIG. 5 may be controlled by the processor/comptroller 505 by repeatedly changing the direction of the current through the electric motor, causing the linear moving shaft 540 to partially pull out the barrier 135 out of the cartridge 575 and push beck the barrier 135 into the cartridge 575.

As a second example, the direction of current into the coil 660 of FIG. 6 may be controlled by the processor/comptroller 505 by repeatedly changing the direction of the current, causing the movable core 610 to partially pull out the barrier 135 out of the cartridge 575 and push beck the barrier 135 into the cartridge 575.

As a third example, the direction of current into the coil 705 of FIG. 7 may be controlled by the processor/comptroller 505 by repeatedly changing the direction of the current, causing the core 710 to partially pull out the barrier 135 out of the cartridge 575 and push beck the barrier 135 into the cartridge 575.

With reference to FIGS. 16-19, a similar technique may be used to repeatedly pull the barrier 1630 and/or the barrier 1635 partially out of the lateral flow assay cartridge (i.e., to partially pull out the barrier from between the two pads that are separated by the barrier) and pushing the barrier back into the cartridge in order to control the time the fluid material comes in contact with the test line 125, the time the fluid material comes in contact with the control line 130, and/or the flow rate across the flow path of the lateral flow assay device. Controlling the flow rate of the fluid as it passes over the test line provides the technical advantage of allowing enough binding time at the test line location resulting in increased sensitivity for the test. Similarly, for the control line, the flow rate control provides the technical advantage of allowing enough binding time resulting in stronger signal (color change) at the control line.

II. Using Removable Gaps in the Flow Path to Control the Flow and Flow Time

Some of the present embodiments may place a gap (instead of a physical barrier) in the barrier zone between the labeling zone and the capture zone. The gap may be placed between the conjugate pad and the membrane to separate the conjugate pad and the membrane until a timer expires. The lateral flow assay may include a housing (e.g., as described below with reference to FIGS. 20-21) that may initially (e.g., prior to the start of a test and for a time period after the start of the test) hold one of the conjugate pad or the membrane pad, preventing the pads from touching each other. In other embodiments, the backing card of conjugate pad or the backing card of the membrane pad may be curved (e.g., as shown in FIGS. 32 and 33) to initially (e.g., prior to the start of a test and for a time period after the start of the test) prevent the pads from touching each other.

FIG. 20 is an upper front perspective view of one example embodiment of a portion of a lateral flow assay device 2000 that has a gap separating the labelling zone and the capture zone, according to various aspects of the present disclosure. The lateral flow assay device 2000 may be similar to the lateral flow assay device 100 of FIG. 1, except that the lateral flow assay device 2000 may include a gap 2050 (instead of the physical barrier 135 of FIG. 1) in the barrier zone 2003. The gap 2050 separates (as shown by the dashed line 2020 and 2025) the conjugate pad 110 and the membrane 115.

With reference to FIG. 20, the gap 2050 may be substantially occupied by air and may not allow the liquid material to flow from the conjugate pad 110 into the membrane 115. Other components of the lateral flow assay device 2000 may be similar to the corresponding components of the lateral flow assay device 100 of FIG. 1. The lateral flow assay device 2000 may include a housing, which is not shown in FIG. 20 for simplicity.

In some of the present embodiments, the lateral flow assay may include a housing (shown in FIG. 21) that may initially (e.g., prior to the start of a test and for a time period after the start of the test) hold the conjugate pad 110, preventing the conjugate pad 110 and the membrane 115 from touching each other. The gap created between the conjugate pad 110 and the membrane 115 may then be removed after a time period from the start of the test.

FIG. 21 is an upper front perspective view of one example embodiment of a portion of a lateral flow assay device 2100 showing a cross section of the lateral flow assay device's housing before and after removing a gap between the labeling zone and the capture zone, according to various aspects of the present disclosure. With reference to FIG. 21, the perspective shows a cross sectional view of the housing 170, 2105, and 2106 across the surfaces 2108-2109. Similar to the housing 205 of FIG. 2, the housing of FIG. 21 may include a sample port 210, an opening 215 for viewing the test line 125, and an opening 220 for viewing the control line 130. The figure as shown, includes two operational steps 2101 and 2102. The housing 2105 may include a cartridge bed 170 for holding the lateral flow assay device's cartridge.

With reference to FIG. 21, step 2101 shows an initial state where there is a gap 2050 (same as the gap 2050 of FIG. 20) between the conjugate pad 110 and the membrane 115. The gap may be maintained by a movable section 2106 of the housing. Since FIG. 21 shows a cross sectional view of the lateral flow assay device's 2100 housing, the figure shows a cross section of the movable section 2106 across the surface 2109. The movable section 2106 may, therefore, substantially extend over the width of the conjugate pad 110 along a surface delimited by line 2175, as shown in FIGS. 21 and 22.

FIG. 22 is a top elevational view of the housing of the lateral flow assay device of FIG. 21, according to various aspects of the present disclosure. With reference to FIG. 22, the top view of the housing 2105-2106 shows the sample port 210, the test line 125 (partially hidden by the housing), the control line 130 (partially hidden by the housing), the opening 215 for viewing the test line 125, the opening 220 for viewing the control line 130, and the movable section 2106 of the housing 2105. FIG. 22 also shows the approximate extents of the sample pad 150, the conjugate pad 110, the membrane 115, and the wicking pad 120.

With reference to FIG. 22, the lower portion of the movable section (shown by the dashed line 2175, which corresponds to the line 2175 of FIG. 21) is attached to the conjugate pad (e.g., by an adhesive substance such as glue, resin, gum, etc.) and holds the conjugate pad 110 separate from the membrane 115 (as shown in step 2101 of FIG. 21). With reference to FIG. 22, the lower portion 2175 of the movable section 2106 may substantially extend over the width of the conjugate pad 110.

With further reference to FIG. 21, in some of the present embodiments, a timer may be programmed to allow time for the analyte (if any) in the sample fluid to bind with the labeled binding reagent on the conjugate pad 110. The timer may be started at the beginning of the test (e.g., substantially at or around the same time as the sample fluid is applied to the sample pad 150). The timer may be set such that enough time is allowed for the sample fluid to flow from the sample pad 150 into the conjugate pad 110 and for the analyte (if any) in the sample fluid to bind with the labelled binding reagent on the conjugate pad 110.

After the timer expires, the gap 2050 may be removed from between the conjugate pad 110 and the membrane in order to fluidically connect the conjugate pad 110 in the labeling zone 102 to the membrane 115 in the capture zone 104. After the conjugate pad 110 and the membrane 115 come to contact with each other, the fluid material in the flow path may flow from the conjugate pad 110 into the membrane 115 by capillary action.

In step 2102 of FIG. 21, the gap 2050 may be removed (e.g., after the expiration of the timer) from between the conjugate pad 110 and the membrane 115 by moving the movable section 2106 towards the membrane 115 until the conjugate pad 110 and the membrane 115 come into contact with each other. As a first example, the movable section 2106 may be moved towards the membrane 115 using a linear actuator similar to the linear actuator 525 of FIG. 5 or a solenoid similar to the solenoid 605 of FIG. 6. The linear moving shaft 540 of FIG. 5 may include a surface (e.g., instead of the magnet 545) with a shape sufficient for pushing down the movable section 2106 (e.g., with a surface that may be smaller than the outside surface 2190 of the movable section 2106 that is facing outside of the lateral flow assay device 2100).

At the beginning of a test, the electric motor 530 of FIG. 5 may be configured to pull the linear moving shaft 545 towards the rotating shaft 580, and the linear actuator 525 may be placed adjacent to the lateral flow assay device 2100 (FIG. 21) such that the surface 545 on the shaft 540 contacts the outside surface 2190 (FIG. 21) of the movable surface 2106.

After the time required for the analyte in the sample fluid to bind with the labeled binding agents on the conjugate pad 110 elapses, the electric motor 530 may receive a signal (e.g., from the processor 505, from a pushbutton, from a toggle switch, etc., as described above with reference to FIG. 5) to extend the linear moving shaft 545 away from the rotating shaft 580 and towards the lateral flow assay device 2100. As the linear moving shaft 540 is extended towards the lateral flow assay device 100, the surface 545 on the linear moving shaft 540 pushes the external surface 2190 of the movable section 2106, causing the gap 2015 to be removed from between the conjugate pad 110 and the membrane 115.

With reference to step 2102 of FIG. 21, the movable section 2106 may move in the direction of the arrow 2195 until the surface of the movable section 2106 that is attached to the conjugate pad 110 (e.g., the surface that is delimited by the line 2175 of FIGS. 21 and 22) makes contact with the membrane 115 and removes (as shown by the arrow 2185) the gap from between the conjugate pad 110 and the membrane 115.

As a second example, the movable section 2106 of the housing 2105 may be pushed towards the membrane 115 using the solenoid 605 of FIG. 6. For example, the movable core 610 may include a surface 615 (e.g., instead of the magnet 615) with a shape sufficient for pushing down the movable section 2106 (e.g., with a surface that may be smaller than the outside surface 2190 of the movable section 2106 that is facing outside of the lateral flow assay device 2100).

At the beginning of a test, the solenoid 605 may be configured (e.g., by changing the direction of electric current in the wire 650) to pull the movable core 610 towards the solenoid 605, and the solenoid 605 may be placed adjacent to the lateral flow assay device 100 (FIG. 21) such that the surface 615 on the movable core 610 contacts the outside surface 2190 (FIG. 21) of the movable surface 2106.

After the time required for the analyte in the sample fluid to bind with the labeled binding agents on the conjugate pad 110 elapses, the controller circuit 630 may receive one or more signals (e.g., from the processor 505, a pushbutton, a toggle switch, etc., as described above with reference to FIG. 6) to extend the movable core 610 away from the solenoid 605 and towards the lateral flow assay device 2100. As the movable core 610 is extended towards the lateral flow assay device 2100, the surface 615 on the movable core 610 may push the external surface 2190 of the movable section 2106, causing the gap 2015 to be removed from between the conjugate pad 110 and the membrane 115.

As a third example, one or more magnets may be attached to the upper surface 2190 of the movable section 2106 of the lateral flow assay device 2100. The core 710 of FIG. 7 may be placed next to the lateral flow assay device 2100 such that the cross section of the core 710 touches the upper surface 2190 of the movable section 2106 while the switch 750 is open. After the time required for the analyte in the sample fluid to bind with the labeled binding agents on the conjugate pad 110 115 elapses, the controller circuit 730 may receive one or more signals (e.g., from the processor 505, a pushbutton, a toggle switch, etc., as described above with reference to FIG. 7) to close the switch 750. The amount and the direction of the current on the wire 750 and the coil 705 may be adjusted such that the magnetic field generated by the core 710 may repel the magnet(s) on the surface 2190 and push the movable section 2106 in the direction of the arrow 2195 until the conjugate pad 110 comes into contact with the membrane 115. For example, the magnetic field generated by the core 710 may be of the same polarity as the magnet(s) on the surface 2190 in order for the magnets to repel each other.

In some of the present embodiments, the lateral flow assay device's housing may include one or more movable poles, pillars, rods, and/or springs to hold the conjugate pad separate from the membrane to create a gap between the conjugate pad and the membrane. FIG. 23 is a front elevational view of one example embodiment of a portion of a lateral flow assay device 2300 that may use one or more posts or pillars to create a removable gap between the conjugate pad and the membrane, according to various aspects of the present disclosure.

With reference to FIG. 23, the lateral flow assay device 2300 may include one or more holes (the cross section of one of the holes is shown as delimited by the lines 2305). The hole(s) may go through the cartridge bed 170, the backing card 140, and the membrane 115.

The lateral flow assay device 2300, in some of the present embodiments, may include one or more movable poles, pillars, rods, and/or springs 2310 (referred to herein as the pole or the poles for simplicity). Each movable pole 2310 may go through a hole 2305 to create a gap 2050 between the conjugate pad 110 and the membrane 115 by keeping the conjugate pad 110 at a distance from the membrane 115, as shown in FIG. 23.

FIG. 24 is a top elevational view of one example embodiment of the lateral flow assay device of FIG. 23, according to various aspects of the present disclosure. With reference to FIG. 24, the lateral flow assay device's 2300 housing is not shown for simplicity. In the example of FIG. 24, the lateral flow assay device 2300 includes five holes 2305. In other embodiments, the lateral flow assay device may include any number of one or more holes 2305.

With reference to FIG. 24, there is a pole 2310 in each of the holes 2305. In the example of FIG. 24, the holes 2305 and the poles 2310 have a circular cross section. In other embodiments, the holes 2305 and the poles 2310 may have a triangular, a rectangular, a polygon, or any arbitrary shape cross sections.

The poles 2310 may be made of any material (e.g., plastic, metal, glass, etc.) that is capable of holding the conjugate pad 110 separate from the membrane 115 and do not react with the fluid material in the fluid flow. In some of the present embodiments, the poles 2310 may be attached to the conjugate pad 110 by an adhesive substance (e.g., glue, resin, gum, etc.). In other embodiments, the poles 2310 may press against the conjugate pad 110 in order to keep the conjugate pad 110 separate from the membrane 115.

In some of the present embodiments, a timer may be programmed to allow time for the analyte (if any) in the sample fluid to bind with the labeled binding reagent on the conjugate pad 110. At the beginning of a test, the poles 2310 may be at the position shown in FIG. 23 to keep the conjugate pad 110 separate from the membrane 115. The gap 2050 may be substantially filled by air and may prevent the fluid material in the fluid flow to move from the conjugate pad 110 into the membrane 115.

After the timer expires, the poles 2310 of FIGS. 23-24 may be pulled to bring the conjugate pad 110 into contact with the membrane 115. FIG. 25 is a front elevational view of one example embodiment of a portion of a lateral flow assay device 2300 after the gap between the conjugate pad and the membrane is removed, according to various aspects of the present disclosure.

With reference to FIG. 25, the pole(s) 2310 are pulled in the direction of the arrow 2540 until the conjugate pad 110 and the membrane 115 come in contact with each other to allow the fluid material in the flow path to flow from the conjugate pad 110 into the membrane 115 by capillary act.

In some of the present embodiments, one or more pieces of magnet 2550 (FIG. 25) may be attached to the poles 2310 of FIGS. 23-25 on the surface of the poles that is facing outside of the housing 2505. The poles 2310 may be pulled down using a linear actuator similar to the linear actuator 525 (as described above with reference to FIG. 5 for pulling the barrier 135), a solenoid similar to the solenoid 606 (as described above with reference to FIG. 6 for pulling the barrier 135), or an electromagnet 770 (as described above with reference to FIG. 7 for pulling out the barrier 135).

For example, with reference to FIG. 5, at the beginning of a test, the electric motor 530 may be configured to extend the linear moving shaft 545 away from the rotating shaft 580, and the linear actuator 525 may be placed adjacent to the lateral flow assay device 2300 (FIG. 25) such that the magnet(s) 545 on the shaft 540 may contact the magnet(s) 2550 (FIG. 25) on the pole 2550. In the embodiments that the lateral flow assay device 2300 includes more than one pole 2310, the magnet 545 on the shaft 540 may be large enough to make contact with the magnet 2550 of all poles 2310. Alternatively, there may be multiple magnets 545 on the shaft 540 to come in contact with the magnets on the poles 2550.

After the time required for the analyte (if any) in the sample fluid to bind with the labeled binding agents on the conjugate pad 110 elapses, the electric motor 530 may receive a signal to pull the linear moving shaft 545 back towards the rotating shaft 580 and away from the lateral flow assay device 2300. As the linear moving shaft 540 is pulled away from the lateral flow assay device 2300, the magnet(s) 545 on the linear moving shaft 540 pull(s) the magnet(s) 2550 (which is firmly attached to the pole(s) 2310), causing the pole(s) 2310 to move in the direction of the arrow 2540 until the conjugate pad 110 comes in contact with the membrane 115. The magnets 545 and 2550 may have the polarities (e.g., opposite polarities to attract each other) and enough magnetic force to allow them to connect to each other (e.g., by magnetic force) and to continue connecting to each other while the pole 2310 is being pulled through the hole 2305. After the conjugate pad 110 comes in contact with the membrane 115, the gap 2050 of FIG. 23 is removed and the fluid may flow from the conjugate pad 110 into the membrane 115 by capillary act.

The pole(s) 2310 may be pulled using the solenoid 605 of FIG. 6. With reference to FIG. 6, at the beginning of a test, the solenoid 605 may be configured to extend the movable core 610 away from the solenoid 605, and the solenoid 605 may be placed adjacent to the lateral flow assay device 2300 (FIG. 25) such that the magnet(s) 615 on the movable core 610 may contact the magnet 2550 (FIG. 25) on the pole 2550. In the embodiments that the lateral flow assay device 2300 includes more than one pole 2310, the magnet 615 on the movable core 610 may be large enough to make contact with the magnet 2550 of all poles 2310. Alternatively, there may be multiple magnets 615 on the movable core 610 to come in contact with the magnets on the poles 2550.

After the time required for the analyte (if any) in the sample fluid to bind with the labeled binding agents on the conjugate pad 110 elapses, the controller circuit 630 may receive a signal to pull the movable core 610 back towards the solenoid 605 and away from the lateral flow assay device 2300. As the movable core 610 is pulled away from the lateral flow assay device 2300, the magnet(s) 615 on the movable core 610 may pull the magnet(s) 2550 (which is/are firmly attached to the pole(s) 2310), causing the pole(s) 2310 to move in the direction of the arrow 2540 until the conjugate pad 110 comes in contact with the membrane 115. The magnets 615 and 2550 may have the polarities (e.g., opposite polarities to attract each other) and enough magnetic force to allow them to connect to each other (e.g., by magnetic force) and to continue connecting to each other while the pole 2310 is being pulled through the hole 2305. After the conjugate pad 110 comes in contact with the membrane 115, the gap 2050 of FIG. 23 is removed and the fluid may flow from the conjugate pad 110 into the membrane 115 by capillary act.

The pole(s) 2310 may be pulled using the electromagnet 770 of FIG. 7. The core 710 of FIG. 7 may be placed next to the lateral flow assay device 2300 (FIG. 25) such that the cross section of the core 710 is a distance "d2" away from the magnet 2550 while the switch 750 is open. The distance "d2" may be substantially the same as the height of the gap between the conjugate pad 110 and the membrane 115 (e.g., the distance required to pull the conjugate pad 110 towards the membrane 115) in order for the conjugate pad 110 and the membrane 115 to contact each other.

After the time required for the analyte (if any) in the sample fluid to bind with the labeled binding agents on the conjugate pad 110 elapses, the controller circuit 730 may receive one or more signals (e.g., from the processor 505, a pushbutton, a toggle switch, etc., as described above with reference to FIG. 7) to close the switch 750. The amount and the direction of the current on the wire 750 and the coil 705 may be adjusted such that the magnet generated by the core 710 may attract the magnet(s) 2550 on the pole(s) 2310 and pull the pole(s) 2310 in the direction of the arrow 2540 until the conjugate pad 110 comes into contact with the membrane 115. For example, the magnet generated by the core 710 may be of the opposite polarity as the magnet(s) 2550 in order for the magnets to attract each other. After the conjugate pad 110 comes in contact with the membrane 115, the gap 2050 of FIG. 23 is removed and the fluid may flow from the conjugate pad 110 into the membrane 115 by capillary act.

FIG. 26 is a flowchart illustrating an example process 2600 for removing a gap that separates the labeling and capture zones of a lateral flow assay device, according to various aspects of the present disclosure. In some of the present embodiments, the process 2600 may be performed by a processor 505 (FIGS. 5-7).

With reference to FIG. 26, the process 2600 may send (at block 2605) one or more signals to a device to adjust the position of the device with respect to the lateral flow assay device 2300 (FIGS. 23-25) and/or to set up the device to remove the gap 2050 of the lateral flow assay device 2300.

As a first example, the processor 505 (as described above with reference to FIGS. 5 and 21-22) may send one or more signals to the electric motor 530 to rotate and cause the rotational to linear movement converter 535 to move the linear moving shaft 540 a predetermined distance in order to make a contact between the linear moving shaft 540 and the upper surface 2190 of the movable section 2106 of the housing 2105.

As a second example, the processor 505 (as described above with reference to FIGS. 6 and 21-22) may send one or more signals to the controller circuit 630 to move the movable core 610 a predetermined distance in order to make a contact between the movable core 610 and the upper surface 2190 of the movable section 2106 of the housing 2105. As a third example, the processor 505 (as described above with reference to FIGS. 7 and 21-22) may send one or more signals to the controller circuit 730 to turn off the switch 750 and prevent the core 710 to act as a magnet while the core 710 is contacting the top surface 2190 of the movable section 2116.

As a fourth example, the processor 505 of FIG. 5 may send one or more signals to the electric motor 530 to rotate the rotating shaft 580 to cause the linear moving shaft 540 to move such that the magnet(s) 545 on the linear moving shaft 540 come(s) in contact with the magnet(s) 2550 (FIG. 25) on pole(s) 2310.

As a fifth example, the processor 505 of FIG. 6 may send one or more signals to the controller circuit 630 to adjust the electric current in the wire 650 and the coil 660 such that the magnet(s) 615 on the movable core 610 come(s) in contact with the magnet(s) 2550 (FIG. 25) on pole(s) 2310. As a third example, the processor 505 of FIG. 7 may send one or more signals to the controller circuit 730 to turn off the switch 750 in order for the core 710 not to act as a magnet.

As a sixth example, the processor 505 (as described above with reference to FIGS. 7 and 23-25) may send one or more signals to the controller circuit 730 to turn off the switch 750 and prevent the core 710 to act as a magnet while the core 710 is kept at a distance "d2" from the magnet(s) 2550 on the pole(s) 2310.

With further reference to FIG. 26, the process 2600 may receive (at block 2610) a signal that includes a value to set a timer for removing the barrier. The signal, in some embodiments, may include a value that indicates the amount of time in a predetermined unit of time (e.g., hours, minutes, seconds, milliseconds, microseconds, etc.). The signal, in some embodiments, may include a value and a unit of time. In some embodiments, the process 2600 may receive, at the processor 505 (FIGS. 5-7), a signal that includes the timer value from the client device 515. In some embodiments, the processor 505 may be associated with and communicatively coupled to a user interface including a keyboard and a display. In these embodiments, the process 2600 may receive, at the processor 505, the signal that includes the timer value from the keyboard associated with the processor.

With continued reference to FIG. 26, the process 2600 may then set (at block 2615) set a timer to expire after a time period that is identified by the received value. For example, the processor 505 may set an internal timer to expire after a time period determined by the received timer value. The process 2600 may then determine (at block 2620) whether to start the timer.

In some of the present embodiments, the process 2600 may receive a signal to start the timer, which is different that the signal that includes the timer value. For example, the client device 515 (FIGS. 5-7) may receive a signal through the application executing on the client device 515 indicating the start of the test. The process 2600 may then receive a signal, at the processor 505, from the client device 515 indicating the start of the test. Alternatively, the process 2600 may receive the signal after a physical switch (e.g., a push button or a toggle switch) that is communicatively coupled to the processor 505 is activated to generate the signal. In some of the present embodiments, the process 2600 may start the timer as soon as the timer value is set (at block 2615). These embodiments may bypass block 2620.

When the process 1100 determines (at block 2620) that the timer should not be started, the process 2600 may proceed back to block 2620. Otherwise, the process 2600 may start (at block 2625) the timer. The process 2600 may then determine (at block 2630) whether the timer has expired. When the process 2600 determines (at block 2630) that the timer has not expired, the process 2600 may proceed back to block 2630 to wait for the timer to expire.

Otherwise, the process 2600 may send (at 2635) one or more signals to remove the gap by bringing together the labeling and capture zones of the lateral flow assay device. The process 2600 may then end. As a first example, as described above with reference to FIGS. 5 and 21-22, the processor 505 may send one or more signals to the electric motor 530 to rotate and cause the rotational to linear movement converter 535 to move the linear moving shaft 540 a predetermined distance in order to move the movable section 2106 of the housing 2105 in the direction of the arrow 2195 in order to make a contact between the conjugate pad 110 and the membrane 115.

As a second example, as described above with reference to FIGS. 6 and 21-22, the processor 505 may send one or more signals to the controller circuit 630 to change the direction of the electric current in the wire 650 and cause the movable core 610 to move a predetermined distance in order to move the movable section 2106 of the housing 2105 in the direction of the arrow 2195 in order to move the movable section 2106 of the housing 2105 in the direction of the arrow 2195 and make a contact between the conjugate pad 110 and the membrane 115.

As a third example, as described above with reference to FIGS. 7 and 21-22, the processor 505 may send one or more signals to the controller circuit 730 to close the switch 750 and cause the core 710 to act as a magnet and repel the magnet(s) on the top surface 2190 of the movable section 2116 in order to move the movable section 2106 of the housing 2105 in the direction of the arrow 2195 and make a contact between the conjugate pad 110 and the membrane 115.

As a fourth example, as described above with reference to FIGS. 5 and 23-25, the processor 505 may send one or more signals to the electric motor 530 to rotate and cause the rotational to linear movement converter 535 to move the linear moving shaft 540 a predetermined distance in order to move the pole(s) 2310 in the direction of the arrow 2540 (FIG. 25) in order to make a contact between the conjugate pad 110 and the membrane 115. As a fifth example, as described above with reference to FIGS. 6 and 23-25, the processor 505 may send one or more signals to the controller circuit 630 to change the direction of the electric current in the wire 650 and cause the movable core 610 to move a predetermined distance in order to move the pole(s) 2310 in the direction of the arrow 2540 (FIG. 25) to make a contact between the conjugate pad 110 and the membrane 115.

As a sixth example, as described above with reference to FIGS. 7 and 23-25, the processor 505 may send one or more signals to the controller circuit 730 to close the switch 750 and cause the core 710 to act as a magnet and attract the magnet(s) 2550 on the pole(s) 2310 in order to move the pole(s) 2310 in the direction of the arrow 2540 (FIG. 25) to make a contact between the conjugate pad 110 and the membrane 115.

Some of the present embodiments may place gaps (instead of a physical barriers) between different components of the lateral flow assay device. In addition to, or in lieu of, a gap between the labelling zone and the capture zone, some of the present embodiments may have one or more gaps at other locations to provide additional time for the fluid material in the fluid flow to have additional time to bind with the immobilized molecules at the test line and/or at the control line. In some of these embodiments, the membrane may be made of several separate pieces (as oppose to one continuous piece of material). The gaps may be substantially filled with air.

FIG. 27 is an upper front perspective view of one example embodiment of a portion of a lateral flow assay device 2700 with multiple gaps separating different components of the lateral flow assay device, according to various aspects of the present disclosure. The lateral flow assay device 2700 may include a housing that is not shown in FIG. 27 for simplicity. The lateral flow assay device 2700 may be similar to the lateral flow assay device 1600 of FIG. 16, except that the lateral flow assay 2700 may include gaps (instead of the physical barriers) to separate different components of the lateral flow assay device 2700.

With reference to FIG. 27, the gap 2015 between the conjugate pad 110 and the membrane 1615 is substantially similar to the gap 2015 of FIG. 20. The lateral flow assay device 2700 may include a gap 2750 separating the membranes 1615 and 1616 (as shown by the dashed lines 2751-2752) that may prevent fluid flow from the membrane 1615 and the test line 125 into the membrane 1616. The lateral flow assay device 2700 may include a gap 2755 separating the membrane 1616 and the wicking pad 120 (as shown by the dashed lines 2756-2757) that may prevent fluid flow from the membrane 1616 and the control line 130 into the wicking pad 120.

In some of the present embodiments, the lateral flow assay may include a housing that may initially (e.g., prior to the start of a test and for a time period after the start of the test) hold different components of the lateral flow assay device separate from each other to maintain the gaps 2050, 2750, and 255. FIG. 28 is an upper front perspective view of one example embodiment of a portion of a lateral flow assay device showing a cross section of the lateral flow assay device's housing before and after removing multiple gaps, according to various aspects of the present disclosure.

With reference to FIG. 28, the perspective shows a cross sectional view of the housing 2805-2308 across the surfaces 2811-2314. Similar to the housing of FIG. 17, the housing 2805-2308 of FIG. 28 may include a sample port 1710, an opening 1715 for viewing the test line 125, and an opening 1720 for viewing the control line 130.

The figure as shown, includes two operational steps 2801 and 2802. With reference to FIG. 28, step 2801 shows an initial state where there may be a gap 2050 (same as the gap 2050 of FIG. 17) between the conjugate pad 110 and the membrane 1615. The gap 2050 may be maintained by a movable section 2806 of the housing. There may be a gap 2750 (same as the gap 2750 of FIG. 17) between the membrane 1615 and the membrane 1616. The gap 2750 may be maintained by a movable section 2807 of the housing. There may be a gap 2755 (same as the gap 2755 of FIG. 17) between the membrane 1616 and the wicking pad 120. The gap 2755 may be maintained by a movable section 2106 of the housing. The gap 2755 may be maintained by a movable section 2808 of the housing.

Since FIG. 28 shows a cross sectional view of the lateral flow assay device's 2700 housing, the figure shows a cross section of the movable sections 2806, 2807, and 2808 across the surfaces 2812, 2813, and 2814, respectively. The movable sections 2806, 2807, and 2808 may substantially extend over the width of the lateral flow assay device 2700 similar to what was described above with reference to FIGS. 21 and 22 for section 2106.

With reference to step 2802 of FIG. 28, some of the present embodiments may use several timers for removing the gaps 2050, 2750, and 2755 of FIG. 28. For example, a first timer may be set to allow the analyte (if any) in the sample fluid to bind with the labeled binding agents on the conjugate pad 110. After the expiration of the first timer, the gap 2050 may be removed by moving (as shown by the arrow 2891) the movable section 2806 towards the membrane 1615 until the conjugate pad 110 and the membrane 1615 come into contact with each other. After the conjugate pad 110 and the membrane 1615 come to contact with each other, the fluid material in the flow path may flow from the conjugate pad 110 into the membrane 1615 by capillary action.

With continued reference to FIG. 28, after the expiration of the first timer, a second timer may be started to determine the time for removing the gap 2750. In some of the present embodiments, the labelled immunocomplex in a sandwich format assay may require more time to bind with the immobilized binding reagent at the test line than the time it takes for the fluid material to flow by capillary action through the test line 125 into the membrane 1616. The second timer may allow enough time for the binding of the labelled immunocomplex with the immobilized binding reagent at the test line. Similarly, in a competitive assay format, the labelled binding reagent in the fluid may require more time to bind with the immobilized analyte/protein-analyte complex in the test line. The second timer may allow enough time for the binding of the labelled binding reagent with the immobilized binding reagent at the test line.

After the expiration of the second timer, the gap 2750 may be removed by moving (as shown by the arrow 2892) the movable section 2807 towards the membrane 1615 until the membrane 1616 and the membrane 1615 come into contact with each other. After the membrane 1616 and the membrane 1615 come to contact with each other, the fluid material in the flow path may flow from the membrane 1615 into the membrane 1616 by capillary action.

After the expiration of the second timer, a third timer may be started to determine the time for removing the gap 2755. In some of the present embodiments, the free labeled binding reagents may require more time to bind with the immobilized antibody in a sandwich format assay at the control line than the time it takes for the fluid material to flow by capillary action through the control line 130 into the wicking pad 120. Similarly, in a competitive assay format, the free labeled binding reagents may require more time to bind with the immobilized analyte molecule (or a protein-analyte complex) at the control line 130 than the time it takes for the fluid material to flow by capillary action through the control line 130 into the wicking pad 120.

The third timer may allow enough time for the free labeled binding reagents to bind with the immobilized antibody (in the sandwich assay format) or with the immobilized analyte molecule/protein-analyte complex (in the competitive assay format) at the control line 130. Similarly, in a competitive assay format. After the expiration of the third timer, the gap 2755 may be removed by moving (as shown by the arrow 2893) the movable section 2808 towards the membrane 1616 until the wicking pad 120 and the membrane 1616 come into contact with each other to allow the fluid material to flow from the membrane 1616 and the control line 130 into the wicking pad 120 by capillary action.

The movable sections 1250, 2750, and 2755 of the housing may be moved by mechanisms such as a linear actuator 525 (FIG. 5), a solenoid 615 (FIG. 6), or an electromagnet 770 (FIG. 7) as described above with reference to the lateral flow assay 2100 of FIG. 21.

Some of embodiments may include a housing with a one or more sets of holes. Each hole may include a pole for maintaining one of the gaps in the barrier zone of the lateral flow assay device. FIG. 29 is a front elevational view of one example embodiment of a portion of a lateral flow assay device 2900 that may use multiple posts or pillars to create removable gaps between different components of the lateral flow assay device, according to various aspects of the present disclosure.

As shown, the lateral flow assay device 2900 may include one or more set of holes (the cross section of one of the holes is shown as delimited by the lines 2305, 2906, and 2907). The lateral flow assay device 2900, in some of the present embodiments, may include one or more sets of movable poles (or pillars) 2310, 2911, and 2912. Each movable pole 2310 may go through a hole 2305 to create the gap 2050 between the conjugate pad 110 and the membrane 1615 by keeping the conjugate pad 110 at a distance from the membrane 1615, as shown in FIG. 29.

Each movable pole 2911 may go through a hole 2906 to create the gap 2750 between the membrane 1615 and the membrane 1616 by keeping the membrane 1616 at a distance from the membrane 1615, as shown in FIG. 29. Each movable pole 2912 may go through a hole 2907 to create the gap 2755 between the membrane 1616 and the wicking pad 120 by keeping the wicking pad 120 at a distance from the membrane 1616, as shown in FIG. 29.

FIG. 30 is a top elevational view of one example embodiment of the lateral flow assay device of FIG. 29, according to various aspects of the present disclosure. With reference to FIG. 30, the lateral flow assay device's 2700 housing is not shown for simplicity. In the example of FIG. 30, the lateral flow assay device 2700 includes three sets of three holes 2305, 2911, and 2912. In other embodiments, the lateral flow assay device may include any number of holes in each set of holes 2305, 2906, and 2907. In the example of FIG. 29, the holes 2305, 2906, and 2907 and the poles 2310, 2911, and 2912 have a circular cross section. In other embodiments, the holes 2305, 2906, and 2907 and the poles 2310, 2911, and 2912 may have a triangular, a rectangular, a polygon, or any arbitrary shape cross sections. The poles 2310, 2911, and 2912 may be made of any material (e.g., plastic, metal, glass, etc.) that is capable of holding the components of the lateral flow assay device separate from each other (as described below) and do not react with the fluid material in the fluid flow.

With reference to FIG. 30, the holes 2305 and the poles 2310 are substantially similar to the holes 2305 and the poles 2310 of FIG. 24. In some of the present embodiments, the poles 2310 may be attached to the conjugate pad 110 by an adhesive substance (e.g., glue, resin, gum, etc.) to keep the conjugate pad 110 separate from the membrane 1615. In other embodiments, the poles 2310 may press against the conjugate pad 110 in order to keep the conjugate pad 110 separate from the membrane 1615.

With further reference to FIG. 29, each pole 2911 may go through a hole 2906. Each pole 2911 may be attached to the membrane 1616 by an adhesive substance (e.g., glue, resin, gum, etc.) to keep the membrane 1616 separate from the membrane 1615. In other embodiments, the poles 2911 may press against the membrane 1616 in order to keep the membrane 1616 separate from the membrane 1615.

With continued reference to FIG. 29, each pole 2912 may go through a hole 2907. Each pole 2912 may be attached to the wicking pad 120 by an adhesive substance (e.g., glue, resin, gum, etc.) to keep the wicking pad 120 separate from the membrane 1616. In other embodiments, the poles 2912 may press against the wicking pad 120 in order to keep the wicking pad 120 separate from the membrane 1616.

FIG. 31 is a front elevational view of one example embodiment of a portion of a lateral flow assay device 2900 after several gaps are removed between different components of the lateral flow assay device, according to various aspects of the present disclosure. With reference to FIG. 31, some of the present embodiments may use several timers for removing the gaps 2050, 2750, and 2755. For example, a first timer may be set to allow the analyte (if any) in the sample fluid to bind with the labeled binding agents on the conjugate pad 110. After the expiration of the first timer, the gap 2050 may be removed by pulling down the pole(s) 2310 (as shown by the arrow 3131) until the conjugate pad 110 and the membrane 1615 come into contact with each other. After the conjugate pad 110 and the membrane 1615 come to contact with each other, the fluid material in the flow path may flow from the conjugate pad 110 into the membrane 1615 by capillary action.

With continued reference to FIG. 31, after the expiration of the first timer, a second timer may be started to determine the time for removing the gap 2750. In some of the present embodiments, the labelled immunocomplex in a sandwich format assay may require more time to bind with the immobilized binding reagent at the test line than the time it takes for the fluid material to flow by capillary action through the test line 125 into the membrane 1616. The second timer may allow enough time for the binding of the labelled immunocomplex with the immobilized binding reagent at the test line. Similarly, in a competitive assay format, the labelled binding reagent in the fluid may require more time to bind with the immobilized analyte/protein-analyte complex in the test line. The second timer may allow enough time for the binding of the labelled binding reagent with the immobilized binding reagent at the test line.

After the expiration of the second timer, the gap 2750 may be removed by pulling down the pole(s) 2911 (as shown by the arrow 3132) until the membrane 1616 and the membrane 1615 come into contact with each other. After the membrane 1616 and the membrane 1615 come to contact with each other, the fluid material in the flow path may flow from the membrane 1615 into the membrane 1616 by capillary action.

After the expiration of the second timer, a third timer may be started to determine the time for removing the gap 2755. In some of the present embodiments, the free labeled binding reagents may require more time to bind with the immobilized antibody in a sandwich format assay at the control line than the time it takes for the fluid material to flow by capillary action through the control line 130 into the wicking pad 120. Similarly, in a competitive assay format, the free labeled binding reagents may require more time to bind with the immobilized analyte molecule (or a protein-analyte complex) at the control line 130 than the time it takes for the fluid material to flow by capillary action through the control line 130 into the wicking pad 120.

The third timer may allow enough time for the free labeled binding reagents to bind with the immobilized antibody (in the sandwich assay format) or with the immobilized analyte molecule/protein-analyte complex (in the competitive assay format) at the control line 130. Similarly, in a competitive assay format. After the expiration of the third timer, the gap 2755 may be removed by pulling down the pole(s) 2912 (as shown by the arrow 3133) until the wicking pad and the membrane 1616 come into contact with each other to allow the fluid material to flow from the membrane 1616 and the control line 130 into the wicking pad 120 by capillary action.

The poles 2310, 2911, and 2912 may be moved by mechanisms such as a linear actuator 525 (FIG. 5), a solenoid 615 (FIG. 6), or an electromagnet 770 (FIG. 7) as described above with reference to the lateral flow assay 2300 of FIGS. 23-24. Some of the present embodiments may include only one of the gaps 2015, 2750, or 2755 of FIG. 27. Other embodiments may include any two of the gaps 2015, 2750, or 2755 of FIG. 27. Some embodiments (such as the embodiment of FIG. 27) may include all three gaps 2015, 2750, or 2755. In some embodiments, the number of timers to remove the gaps may be equal to the number of gaps. Since the fluid flows downstream from the sample pad 150 towards the wicking pad 120, when a lateral flow assay device has two gaps, the gaps are removed starting with the most upstream gap followed by the next gap downstream. When the assay device has two or three gaps, the existing gaps are removed in the following order: gap 2015 is removed first, followed by the gap 2750, followed by the gap 2755.

In some embodiments, the backing card of conjugate pad or the backing card of the membrane pad may be curved to initially (e.g., prior to the start of a test and for a time period after the start of the test) prevent the pads from touching each other. FIG. 32 is a front elevation view of one example embodiment of a portion of a lateral flow assay device 3200 that removes gaps by a spring mechanism, according to various aspects of the present disclosure. FIG. 33 is a functional block diagram illustrating one example embodiment of the lateral flow assay device of FIG. 32, according to various aspects of the present disclosure.

With reference to FIGS. 32 and 33, the lateral flow assay device 3200 may include a housing 3230, a sample input port 3220, and a clear cover 3205 to view the results on the test line 125 and the control line 130. The disposable cartridge of the lateral flow assay device 3200 may include an NFC chip 590. The NFC chip 590 may identify the test and other parameters and information related to the test, including but not limited to, the conjugation time on the conjugate pad and the flow time, which is the time it should take for the sample fluid to flow from the point the sample is applied through the sample input port 3220 to the wicking pad 120.

The lateral flow assay device 3200 may include an NFC reader (not shown), such as the NFC reader 595 of FIGS. 5-7. When the cartridge is placed in the lateral flow assay device, the NFC reader automatically detects the presence of the NFC tag 590, reads the information and parameters of the test, and sends the information and parameters to a processor or controller (e.g., the processor/controller 505 of FIG. 33) of the lateral flow device 3200. The processor/controller may use the information and the parameters to perform the test. The processor/controller may display a portion of the information or parameters on a display of the lateral flow assay device (e.g., on a display of the UI 550 of FIG. 33). The processor/controller may send a portion of the information or parameters to an electronic device external to the lateral flow assay device.

When the sample is blood and the test needs plasma separation, the disposable cartridge may include the optional plasma separator filter 1420. The plasma separator filter 1420 may be located over the conjugate pad 110 between the sample input port 3220 and the conjugate pad 110. Once the sample is added, a start button either on the device's UI (e.g., on a keyboard or a touch screen) or a button on the device's housing may be pushed to start the test. This may also start a timer for the conjugation time. Alternatively, a signal to start the test may be received by the processor of the lateral flow assay device 3200 from an electronic device (e.g., a client device) external to the lateral flow assay device 3200.

After the sample is applied, the sample flows on the conjugate pad 110 and starts mixing and interacting with the conjugate chemicals on the conjugate pad 110. As shown in FIGS. 32 and 33, a gap 3291 may initially be maintained between the conjugate pad 110 and the membrane 115. Similarly, a gap 3292 may initially be maintained between the membrane 115 and the wicking pad. The gaps 3291 and 3292 may be substantially filled by air. Accordingly, unlike the conventional flow lateral assay cartridges and systems, the conjugate pad 110 is not touching the membrane 115. The conjugate pad 110 is held away from the membrane 115 by the spring 3241 (e.g., a thin flat metal, such as steel, with a bend 3271 at the base 3272) that is attached to the clear backing 3211 of the conjugation pad 110. Although a clear backing may be used, especially for the membrane, so the colored test and control lines may be seen from both side, it should be understood that at least a portion of the backing, in some embodiments, may be opaque. The conjugate pad 110, the backing 3211, and the spring 3241 may be connected to the housing 3230 by a pin or screw 3288. The spring 3241 may be anchored to the housing 3230 by a pin or screw 3289.

Once the specified conjugation time is lapsed (e.g., specified by the NFC chip 590, received from the UI of the lateral flow assay device, received from an external device, etc.), the solenoid 3251 may be activated by a command from the processor/controller 505 (FIG. 33), which may cause the solenoid shaft 3221 to push on the spring 3241 and make the conjugate pad 110 touch the membrane 115 to allow the flow of the fluid material from the conjugate pad 110 to the membrane 115.

The solenoid 3251 may function as a transducer that converts energy into linear motion. The solenoid 3251 may include an electromagnetically inductive coil 3365 (FIG. 33) that is wrapped around the movable solenoid shaft (or armature) 3221. When an electric current passes through the wire 3360 of FIG. 33, a magnetic field is generated by the coil 3365 that causes the moveable shaft 3221 to move in a linear line. By changing the direction of the current, the magnetic field is reversed that causes the solenoid shaft (or armature) 3221 to move in the opposite direction. If a spring loaded solenoid is used, there may be no need to reverse the direction of the current as removing the current (zero current) causes the solenoid to return to its original position via the spring on its shaft. The use of the spring loaded solenoid provides the advantage that the spring loaded solenoid does not draw any current and does not consume any energy in the off position, resulting in much longer battery life for battery-operated lateral flow assay devices.

The solenoid 3251 may be repeatedly activated and deactivated to push the solenoid shaft 3221 against the spring 3241 to bring the conjugate pad 110 and the membrane 115 in touch with each other, followed by pulling the solenoid shaft 3221 away from the spring 3241 to cause the spring 3241 to separate the conjugate pad 110 from the membrane 115. Repeatedly connecting and disconnecting the conjugate pad 110 and the membrane 115 may be used to control the flow of fluid material from the conjugate pad 110 into the membrane 115.

The processor/controller 505 may generate signals (e.g., and without limitations, a set of pulses) to activate the solenoid 3251 according to an algorithm. The processor may use three parameters to control the flow time of the fluid from the time the sample fluid starts flowing at the beginning of the membrane 115 (i.e., the intersection of the conjugate pad 110 and the membrane 115) to the time the fluid reaches the wicking pad 120. The three parameters are the number of times the conjugate pad and the membrane pad are connected (or disconnected), the duration of each connections, and the duration of each disconnection (or the time between consecutive connection and disconnections).

The longer the duration of each connection, the more fluid is transferred from the conjugate pad 110 to the membrane 115. These three parameters may be calculated by the processor 505 using an algorithm and a set of calibration tables or calibration curves. The algorithm input may be the desired conjugation time and flow time, which may be, for example, programmed into the NFC tag 590 at manufacturing. The algorithm input may also include one or more parameters related to the paper material used in the cartridge pads, as described below.

The conjugation time may be controlled by a timer. The conjugate time may be received by the processor (e.g., and without limitations, from the NFC chip 950, from a client device, from the UI 550, etc.). The processor 505 may also receive a signal (e.g., and without limitations, from a client device, from the UI 550, from a switch or button on the lateral flow device's housing, etc.) indicating the start of the test. The processor 505 may measure the elapsed time since the start of the test. After the elapse of the specified conjugation time from the start of the test, the processor 505 may activate the solenoid (or an electromagnet, a servo, a linear actuator, or other mechanism used for bringing the conjugate pad and the membrane pad together).

Unlike the membrane 115, the test line 125, and the control line 130, the conjugate pad 110, in some embodiments, may not need any flow rate control. The flow rate for the membrane pad and the flow time (which is the time it takes for the solution to travel from one end of the membrane to the other) may be controlled by on-off cycling (pulsing) of the mechanism (e.g., and without limitations, the solenoid, the electromagnet, the servo, the linear actuator) that brings the conjugate pad and the membrane pad together. The flow time may be controlled with the time that the pads are connected (Tc) and the time that the pads are disconnected (Td). The value of these parameters and the number of times the pads are connected and disconnected may be determined via an algorithm that uses calibration tables or calibration curves as described below.

The calibration curves or tables may be generated by a number of controlled experiments for the type of membrane paper material used by the desired test to be performed by the lateral flow assay cartridge and the lateral flow assay device. FIG. 34 illustrates an example of a number of curves generated for a particular membrane paper material for a range of connection time (Tc) and disconnection time (Td) of the conjugate pad and the membrane, according to various aspects of the present disclosure. In order to generate the curves 3400, Tc and Td are varied and the time it takes for the solution to travel from one end of the membrane pad 115 to the other is measured and recorded. This process may be repeated for a large number (e.g., and without limitations, tens, hundreds, thousands, etc.) of Tc and Td values in a specified range.

The example of FIG. 34 shows curves that are generated for the values of Tc ranging from 160 milliseconds (mSec) to 1000 mSec, and Td ranging from 1 Sec. to 8 Sec. The exemplary curves 3400 were generated for a total of 56 points. The horizontal axis 3405 shows the values of Tc. The vertical axis 3410 shows the flow time (in mSec) as a function of the Tc time for each of eight different values 3415 of Td used for this particular calibration operation (one curve is generated for each Td).

When a desired flow time is specified for a test that a cartridge is made for, the algorithm uses the flow time value to calculate the proper Tc and Td from the calibration curves 3400. FIG. 35 illustrates an example of selecting the connection and disconnection times of the conjugate and membrane pads for a specified flow time, according to various aspects of the present disclosure. In the example of FIG. 35, the specified flow time is 400 Seconds.

With reference to FIG. 35, the intersection points 3541-3544 of the horizontal line 3550 representing the 400 Sec. time on the vertical axis 3410 with the curves 3500 are calculated. For example, one or more calibration tables may store the values corresponding to the curves 3400 and the values in the table may be searched and/or interpolated/extrapolated to identify the intersection points 3541-3544.

In the example of FIG. 35, points 3541-3544 correspond to the different combinations of (Tc, Td) pairs that may achieve the specified flow time. The algorithm may consider the slope of each curve at the intersection points 3541-3544 and pick the one with the smallest slope as that results in the smallest variation around the selected Tc value. In this example, point 3544 may be picked that corresponds to Tc of approximately 308 mSec, and Td of 8 Sec. Once these values are selected, the number of times the connection and disconnection of the conjugate and membrane pads are to be repeated is calculated by dividing the flow time by Tc+Td. It should be understood that the algorithm described above for selecting the point on the curves 3400 is an example. Other methods and algorithms may be devised to select the desired parameters. As another two-step procedure, once the points on the curves 3400 (e.g., the points 3541-3544 in FIG. 35) are calculated, another set of calibration experiments with more timing resolution may be performed in a region of the interest around the points 3541-3544 to refine the parameters.

The more points are chosen for generating the calibration curves 3400, the more accurate the results of choosing the appropriate Tc and Td may be. In the example of FIGS. 34-35, 56 points were used to demonstrate the process. For a better calibration, more points (e.g., and without limitations, hundreds, thousands, etc.) may be used. The calibration curves 3400 may be generated once for each membrane type for each manufacturer of the membrane. Generating the curves 3400 and the corresponding table(s), may not be a time consuming process given that the result are applicable to a very large number of cartridges.

The calibration process may be done by either the manufacturer of the membrane paper or the developer of the test cartridge. Once the appropriate parameters are determined for the particular test the cartridge is supposed to be made for, the parameters may be programmed into the NFC chip on the cartridge. In the case of the stand-alone disposable cartridges, these parameters may be programmed into the firmware of the processor/controller embedded in the cartridge. Alternatively, the parameters may be stored on a network device that may be downloaded to a client device. The client device may then transfer the parameters to the processor/controller of the lateral flow assay device prior to the start of a test.

If the lateral flow assay device cartridge also includes a flow control mechanism between the wicking pad and the membrane pad (e.g., as shown in FIGS. 32 and 33), the flow control mechanism between the wicking pad and the membrane pad may also have its Tc and Td parameters that may either use the same values as the Tc and Td for the mechanism between the conjugate pad and the membrane or it may use its own independent Tc and Td values. In either case, the calibration curves may be generated in a similar manner as described above where for the case of independent set of Tc, Td for the wicking pad the experiments may be more extensive in that there may be multiple curve sets to generate.

In membrane papers used in conventional lateral flow assay strips and cartridges not employing the flow control techniques described herein, the flow rate of the solution on the membrane paper varies with time and gets slower as the solution front moves away from the beginning strip with time. Another technical advantage provided by the lateral flow assay device and cartridges of the embodiments disclosed herein, is that the values of Tc and Td may change for every cycle of connection and disconnection of the pads and not necessarily be the same every cycle. It, therefore, is possible to control the shape of the flow rate curve and, if desired, even equalize it to become close to linear across the length of the membrane.

Some of the present embodiments provide a cycle by cycle control of the flow rate of the fluid. A slower flow rate of the fluid over the membrane results in higher sensitivity for the test as a slower flow rate gives the solution fluid more time to bind to, and interact with, the reagents on the test and control lines as the solution fluid passes over the test and control lines which are on a narrow region on the membrane.

Since the present embodiments provide cycle by cycle control over connecting and disconnecting of the conjugate pad and the membrane and provide control over setting the values of Tc and Td, the lateral flow assay device may be configured to keep the flow rate at a higher speed until the fluid front reaches close to the test line and then change the Tc and Td values to slow down the flow rate. This results in a faster overall test time without losing sensitivity. The values of Tc and Td to be used for both the beginning of the flow and for slowing the flow rate down when the fluid reaches near the test line may be determined from calibration curves similar to the calibration curves shown in FIGS. 34-35 once those curves are generated for the particular membrane material used in the test as was explained above. Since the distance of the test line from the beginning of the membrane and the rate set for the beginning phase of the flow is known, the time it takes for the fluid front to get to a predetermined distance from the test line may be calculated. The processor/controller 505 controlling the lateral flow assay device may keep track of the time and may switch the flow to the slower rate at the right time (e.g., after a time period required for the fluid to reach the predetermined distance from the test line). The cycle by cycle control over connecting and disconnecting of the conjugate pad and the membrane may be applied to any of the embodiments described herein with reference to FIGS. 32-33 and 36-50B.

Some of the present embodiments may compensate for the membrane manufacturing variabilities. One of the factors in manufacturing the membranes is the variability of the flow rate of the membrane from lot to lot. Using the flow control technology of the present embodiments, the flow rate may be set at a point slightly beyond where increase in the sensitivity (e.g., making the flow rate of the fluid over the membrane slower to give the solution fluid more time to bind) is saturated and the material variability may have very minimal to no effect if the flow rate is made slower. In this way, the test cartridge product may have a smaller percent coefficient of variability (CV %). Where to set the optimum flow rate depends on the membrane material selected and the test itself. For each test type and for a given membrane material, some embodiments generate the set of calibration curves and/or tables similar to what was described above with reference to FIGS. 34-35. Using these curves and/or tables, a set of experiments are conducted where the flow rate for each experiment is set from the calibration curves, the test is performed, and the sensitivity of the test is measured (e.g. by repeating the test for sequentially diluted concentration levels).

The flow rate is then set at a lower value and the tests are repeated to measure the sensitivity again. This process is continued until a point is reached where there is no improvements in the sensitivity. The flow rate and the Tc and Td values corresponding to this saturation point are recorded. The final flow rate set for the test is picked from the calibration curves at a point slightly lower than this flow rate. This ensures that any variations in manufacturing the selected membrane material does not affect the sensitivity of the test as the selected flow rate is always above the point where maximum gain in sensitivity is achieved. The process above may be done once during the manufacturing of a given test type and the Tc and Td parameters are then fixed for volume production for this particular test type and the membrane material selected. The technique of compensating for the membrane manufacturing variabilities may be applied to any of the embodiments described herein with reference to FIGS. 32-33 and 36-50B.

Some embodiments compensate for the viscosity variations of the sample fluid. The flow rate of the membrane is also dependent on the viscosity of the sample fluid. Instead of changing the membrane material for different sample fluids, some embodiments keep the material the same and use the flow control technology described herein to determine parameters for on-off cycling (pulsing) of the conjugate pad and/or the wicking pad to compensate for the viscosity dependence. The optimum values of Tc and Td for a given viscosity are determined by a similar approach described above in generating the calibration curves for a given membrane and experimentally finding the optimum sensitivity for the test type. These parameters may be loaded into the NFC tag of the cartridge and when the processor/controller 505 reads the NFC, the processor/controller 505 sets up the correct parameters automatically. The technique of compensating for the viscosity variations may be applied to any of the embodiments described herein with reference to FIGS. 32-33 and 36-50B.

With further reference to FIGS. 32 and 33, the processor 505 may activate and deactivate the solenoid 3251 as described above until the number of connection and disconnection of the pads required to achieve the flow time is achieved. The processor may then stop pulsing the solenoid 3251 and may leave the solenoid 3251 at either engaged or disengaged position depending on what the test specifies.

With continued reference to FIGS. 32 and 33, a gap 3292 may be initially maintained between the membrane 115 and the wicking pad 120. Unlike the conventional flow lateral assay cartridges and systems, the membrane 115 is not touching the wicking pad 120. The membrane 115 may be held away from the wicking pad 120 by the spring 3242 that is attached to the backing 3213 of the wicking pad 120. The wicking pad 120, the backing 3213, and the spring 3242 may be connected to the housing 3230 by a pin or screw 3293. The spring 3242 may be anchored to the housing 3230 by a pin or screw 3294.

The solenoid 3252 may be used to attach and detach the wicking pad 120 to the membrane 115 by a similar technique as described above with reference to the solenoid 3251. The processor 505 may start pulsing the solenoid 3252 either at the same time as the solenoid 3251 or once the pulsing of the solenoid 3251 is completed. The latter approach may use less power.

The attaching and detaching of the wicking pad 120 and the membrane 115 by the solenoid 3252 and the solenoid shaft 3222 may continue for a certain number of connection and disconnection (which may be determined based on the desired flow rate as described above) after the pulsing of solenoid 3251 is completed at which time the result of the test may be ready for viewing through the clear cover 3205 and/or for reading via sensors such as, for example and without limitations, optical sensors.

Some lateral flow assay based tests may not need a wicking pad. The embodiments of the lateral flow assay device 3200 that are used for these test may not include the wicking pad 120 and the solenoid 3252. For some other tests, the wicking pad 120 may always be left connected to the membrane. The embodiments of the lateral flow assay device 3200 that are used for these tests may not include the solenoid 3252. In cartridges where both the conjugation pad 110 and the wicking pad 120 have the spring mechanism as discussed above, the solenoid 3252 may always be activated and kept in a position to always attach the wicking pad 120 to the membrane 115 for the entire duration of the test if that is what is desired and specified for the test (e.g., specified by the NFC chip 590, received from the UI of the lateral flow assay device, received from an external device, etc.).

As shown in FIGS. 32 and 33, the springs 3241 and 3242 do not continue all the way to the tip 3296 of the conjugation pad and the tip 3297 of the wicking pad. There is a small portion of the pads 110 and 120 at the tips 3296 or 3297 that comes in contact with the membrane 115 when the spring 3241 or 3242 is pushed by the corresponding solenoid shaft 3251 or 3252. With further reference to FIGS. 32 and 33, the position of the solenoid shafts 3221 and 3222 on the springs 3241 and 3242 is at a point away from the tips 3296 and 3297. This is to avoid putting direct pressure on the contact area between the pads from the solenoid shaft and spring which may possibly affect the fluid flow and restrict the flow to some extent.

The transistors 3321 and 3322 may perform current amplification to drive the solenoids 3251 and 3252, respectively. The transistors 3321 and 3322 may be included in the lateral flow assay devices 3200 with a processor 505 that cannot supply enough current on the output pins to drive the solenoids 3251 and 3252. The embodiments with a processor 505 that provides sufficient current on its output pins to drive the solenoid 3251 and 3252, may not include the transistors 3321 and 3322. The resistors 3311 and 3312 that are connected between an output pin of the microcontroller and the base connection of the corresponding transistor 3321 and 3322 are for setting the desired current and may be variable resistors that are adjusted at the manufacturing, depending on the current needed to drive the solenoid.

The amount of pressure the conjugate pad 110 may apply on the membrane 115 may be controlled by configuring the amount of pressure that the solenoid shaft 3221 may apply on the spring 3241 and the strength of the spring 3241. The amount of pressure the wicking pad 120 may apply on the membrane 115 may be controlled by configuring the amount of pressure that the solenoid shaft 3222 may apply on the spring 3242 and the strength of the spring 3242.

Instead of the solenoids 3351 and 3352, some embodiments may use other actuation mechanisms such as, for example and without limitation, servo motors to push (and pull) the springs 3241 and 3242. The servo motor may operate in a similar way as described above with reference to the electric motor 530 FIG. 5. For example, the servo motor may include a rotor (such as the rotor 570 of FIG. 5) that may rotate and cause a rotating shaft (such as the rotating shaft 580 of FIG. 5) to rotate. The rotational movement of the rotating shaft may be converted to linear movement of a linear moving shaft (such as the linear moving shaft 540 of FIG. 5) by a rotational to linear movement converter (such as the rotational to linear movement converter 535 of FIG. 5 or the shafts 3221/3222 of FIGS. 32-33). The rotational to linear movement converter may be a set of one or more screws, a wheel and axle, and/or a set of one or more cams that receive a rotational movement from the rotating shaft and move the linear moving shaft in a straight line.

The use of servo motors may eliminate the need for the driver transistors 3321 and 3322 as the servo motors inputs may be directly connected to the processor 505 and may not need high currents. The use of servo motors may lead to a more power efficient design. One advantage of using the servo motor is that, unlike the solenoid, the position of the spring, and hence the proximity of the overlap area of the conjugate pad 110 and membrane 115, may be accurately controlled, which in turn may result in having more control in the flow time and flow rate.

The cartridge shown in FIGS. 32-33 is for use with a lateral flow assay device that integrates components such as the solenoids, processor, drive transistors, UI (e.g., a keyboard, a display, and/or a touch display), NFC reader, battery, and other switches, connectors, and components.

In another embodiment, all the actuation mechanisms and electronics plus a battery may be integrated inside the cartridge providing a completely standalone and disposable cartridge. Small servo motors may be used to actuate the springs. Since the cartridge is standalone and for one-time use, the battery may be small and does not have to be rechargeable. The use of standalone cartridge provides the convenience of not having an external device, but it adds to the cost of the cartridge. In another embodiment of the standalone cartridge, entirely mechanical timers may be used to eliminate the need for the battery, servo motor, and processor/controller (or other electronic circuits) in the disposable cartridge.

FIGS. 32-33 illustrate an example of a specific arrangement of the pads 110, 115, 120 as well as the mechanisms to connection and disconnect the pads. It should be understood that other arrangements may be used for connecting and disconnecting the pads. For example, the entire system shown in FIG. 32-33 may designed to be flipped vertically, in which case the actuators working on the springs may operate from the top. Examples of this type of arrangements are described below with reference to FIGS. 43-50B.

As another example, electromagnets may be used instead of the solenoids 3251 and/or 3252 and the springs 3241 and 3242 may be made from magnetic material. It should be noted that substances that are attracted by a magnet are called magnetic material or magnetic substances. Examples of the magnetic material include, for example, and without limitations, iron, cobalt, nickel, etc. Substances that are not attracted by a magnet are called non-magnetic materials. Magnetic materials do not have magnetic fields around them, but they are attracted by magnetic fields. Magnets, on the other hand, have magnetic fields around them and can attract and repel other magnets. A magnet can attract magnetic materials but cannot repel them.

The electromagnet may be located adjacent to the cartridge's housing 3230 (e.g., as close as possible to the housing or touching it). When the electromagnet is activated, the magnetic field generated by the electromagnet may pull the corresponding spring towards the electromagnet. When the electromagnet is deactivated, the corresponding spring is released. In order not to consume power when the gap between the pads is open, the preferred direction would be for the conjugate pad 110 to be on top of the membrane 115 (either moving the membrane of FIG. 32 to the floor of the cartridge housing or vertically flipping the entire system in FIG. 32) such that when the electromagnet is activated and the spring is pulled towards the electromagnet, the conjugate pad 110 may come in contact with the membrane 115. In the standalone disposable version of the cartridge, the electromagnet may be included inside the cartridge.

In another embodiment of the electromagnet-based implementation, the spring may have a post made from a magnetic material that is permanently attached to it and goes through the cartridge housing via a hole on the housing wall and sits flush with the surface of the housing. The electromagnet then interacts with this post. As another example, the spring may have a built-in hook attached to it (e.g., as shown in FIG. 9) that is pulled with a shaft that is controlled and moved via a servo, an electromagnet, a solenoid, or linear actuator. The examples described above with reference to FIG. 5-7 may be used to move the pads to connect to and disconnect from each other.

As described above with reference to FIGS. 32 and 33, electromagnets may be used instead of the solenoids 3251 and/or 3252, and the springs 3241 and 3242 may be made from magnetic material. In some of these embodiments, only a portion (e.g., the tip) of the springs 3241 and 3242 may be made of magnetic material and the rest of the springs 3241 and 3242 may be made of non-magnetic material. In other embodiments, small pieces of magnetic material may be attached to the tips of the springs 3241 and 3242.

FIG. 36 is a front elevation view of one example embodiment of a portion of a lateral flow assay device 3600 that controls the gap between the conjugate pad and the membrane and/or the gap between the wicking pad and the membrane by a spring mechanism and an electromagnet, according to various aspects of the present disclosure. FIG. 37 is a functional block diagram illustrating one example embodiment of the lateral flow assay device of FIG. 36, according to various aspects of the present disclosure. With reference to the lateral flow assay device 3600 of FIGS. 36 and 37, the tip of the spring 3241 may be made of magnetic material 3661 and the tip of the spring 3242 may be made of magnetic material 3662. The rest of the springs 3241 and 3242 may be made of non-magnetic material. Alternatively, a piece of magnetic material 3661 may be attached (e.g., by glue or other appropriate material) to the tip of the spring 3241 and a piece of magnetic material 3662 may be attached to the tip of the spring 3242.

With further reference to FIG. 36, the lateral flow assay device 3600 may include the electromagnets 3648 and 3649 instead of the solenoids 3251-3252 and the solenoid shafts 3221-3222 of FIG. 32. Other components of FIG. 36 may be similar to the corresponding components of FIG. 32, which were described above. The electromagnets 3648-3649 may be located adjacent to the cartridge's housing 3230 (e.g., as close as possible to the housing or touching it) without a need to make a hole in the housing (as was needed for the solenoid shafts 3221-3222 of FIG. 32).

Similar to the lateral flow assay device 3200 of FIGS. 32 and 33, in the lateral flow assay device 3600, the flow rate for the membrane pad 115 and the flow time (which is the time it takes for the solution to travel from one end of the membrane to the other) may be controlled by on-off cycling (pulsing) of the mechanism that brings the conjugate pad 110 and the membrane pad 115 together. The flow time may be controlled with the time that the conjugate 110 and the membrane 115 pads are connected (Tc) and the time that the pads are disconnected (Td). The value of these parameters and the number of times the pads are connected and disconnected may be determined via an algorithm that uses calibration tables or calibration curves as described above with reference to FIGS. 34 and 35.

If the lateral flow assay device cartridge also includes a flow control mechanism between the wicking pad and the membrane pad (e.g., as shown in FIGS. 36 and 37), the flow control mechanism between the wicking pad and the membrane pad may also have its Tc and Td parameters that may either use the same values as the Tc and Td for the mechanism between the conjugate pad and the membrane or it may use its own independent Tc and Td values, as described above.

As shown in FIGS. 36 and 37, the electromagnet 3648 may initially (e.g., before the start of a test) be deactivated and a gap 3291 may be maintained between the conjugate pad 110 and the membrane 115. Similarly, a gap 3292 may initially be maintained between the membrane 115 and the wicking pad 120 in some embodiments. The gaps 3291 and 3292 may be substantially filled by air. The conjugate pad 110 may be held away from the membrane 115 by the spring 3241 (and by the weight of the magnetic material 3661) that is attached to the clear backing 3211 of the conjugation pad 110. When the electromagnet 3648 is activated, the magnetic field generated by the electromagnet 3648 may pull the magnetic material 3661 and the spring 3241 towards the electromagnet 3648 resulting in closing the gap 3291 between the conjugate pad 110 and the membrane 115 and causing the conjugate pad 110 to touch the membrane 115.

For the embodiments that include a wicking pad (such as the embodiment of FIGS. 36-37), when the electromagnet 3649 is deactivated, the wicking pad 120 may be held away from the membrane 115 by the spring 3242 (and by the weight of the magnetic material 3662) that is attached to the clear backing 3213 of the wicking pad 120 to maintain the gap 3292. When the electromagnet 3649 is activated, the magnetic field generated by the electromagnet 3649 may pull the magnetic material 3662 and the spring 3242 towards the electromagnet 3649 resulting in the gap 3292 between the wicking pad 120 and the membrane 115 to be removed and the wicking pad 120 and the membrane 115 to make contact.

With further reference to FIGS. 36 and 37, the activation and deactivation of the electromagnets 3648 and 3649 may be controlled in order to control the flow the fluid material from the conjugate pad 110 to the membrane 115 and from the membrane 115 to the wicking pad 120, respectively. Once the specified conjugation time is lapsed (e.g., specified by the NFC chip 590, received from the UI of the lateral flow assay device, received from an external device, etc.), the electromagnet 3648 may be activated by a command from the processor/controller 505 (FIG. 37), which may cause the electromagnet 3648 to pull the magnetic material 3661 and the spring 3241 such that the conjugate pad 110 to make contact with the membrane 115 to allow the flow of the fluid material from the conjugate pad 110 to the membrane 115. The electromagnet 3648 may be deactivated by a command from the processor/controller 505, which may cause the magnetic material 3661 and the spring 3241 to be released, resulting in the gap 3291 to be maintained between the conjugate pad 110 and the membrane 115. The electromagnet 3648 may include an electromagnetically inductive coil 3691 that is wrapped around a metallic core (or ferrite core) 3651. The direction of the magnetic field of the coil 3691 may change by the direction of the current through the coil 3691. Furthermore, when the electric current is turned off, the coil 3691 may no longer generate a magnetic field.

Similarly, when the electromagnet 3649 is activated by a command from the processor/controller 505 (FIG. 37), the electromagnet 3649 may pull the magnetic material 3662 and the spring 3242 which may cause the wicking pad 120 to make contact with the membrane 115 to allow the flow of the fluid material from the membrane 115 to the wicking pad 120. The electromagnet 3649 may be deactivated by a command from the processor/controller 505 that causes the magnetic material 3662 and the spring 3242 to be released, resulting in the gap 3292 to be maintained between the conjugate pad 110 and the membrane 115. The electromagnet 3649 may include an electromagnetically inductive coil 3692 that is wrapped around a metallic core (or ferrite core) 3652. The direction of the magnetic field of the coil 3692 may change by the direction of the current through the coil 3692. Furthermore, when the electric current is turned off, the coil 3692 no longer generates a magnetic field.

The transistors 3321 and 3322 may perform current amplification to drive the electromagnets 3648 and 3649, respectively. The transistors 3321 and 3322 may be included in the lateral flow assay devices 3600 with a processor 505 that cannot supply enough current on the output pins to drive the electromagnets 3648 and 3649. The embodiments with a processor 505 that provides sufficient current on its output pins to drive the electromagnets 3648 and 3649, may not include the transistors 3321 and 3322. The resistors 3311 and 3312 that are connected between an output pin of the processor/controller 505 and the base connection of the corresponding transistor 3321 and 3322 are for setting the desired current and may be variable resistors that are adjusted at the manufacturing, depending on the current needed to drive the solenoid.

The amount of pressure the conjugate pad 110 may apply on the membrane 115 may be controlled by configuring the strength of the magnetic field that the electromagnet 3648 may generate, the strength of the magnetic material 3661, and the strength of the spring 3241. The amount of pressure the wicking pad 120 may apply on the membrane 115 may be controlled by configuring the strength of the magnetic field that the electromagnet 3649 may generate, the strength of the magnetic material 3662, and the strength of the spring 3242.

Some embodiments may use a piezoelectric actuator instead of the solenoids 3251-3252 of FIGS. 32-33 or the electromagnets 3648-3649 of FIGS. 36-37 to control the gaps 3291-3292. A piezoelectric actuator converts an electrical signal into a controlled displacement, referred to as stroke. A piezoelectric stack actuator is made by stacking piezoelectric ceramic discs and metal electrode foils. Applying a voltage to the piezoelectric stack, may result in a controlled displacement of the stack. If the displacement is prevented, a force, referred to as blocking force, may develop.

A piezoelectric stack, depending on the type, may require a voltage of between 100 volts to 1000 volts to operate. The precise displacement control of the piezoelectric stack actuators may be used in some of the present embodiments to move a shaft to control the gap between the conjugate pad and membrane and to move another shaft to control the gap between the wicking pad and the membrane.

FIG. 38 is a front elevation view of one example embodiment of a portion of a lateral flow assay device 3800 that controls the gap between the conjugate pad and the membrane and/or the gap between the wicking pad and the membrane by a piezoelectric actuator, according to various aspects of the present disclosure. With reference to FIG. 38, the lateral flow assay device 3800 may include the piezoelectric actuator stack 3831 to control the gap 3291 between the conjugate pad 110 and the membrane 115.

The piezoelectric actuator, in the example of FIG. 38 is a piezoelectric stack actuator 3831 that may be made of several individual piezoelectric actuators 3830 that are factory made to be connected to each other. Other embodiments may use other types of piezoelectric actuators. The piezoelectric actuator stack 3831 may be connected to the shaft 3851.

The piezoelectric stack actuator 3831 may be controlled by the processor/controller 505 through the piezoelectric driver 3821. The piezoelectric driver 3821 may receive one or more signals from the processor/controller 505 and may generate the voltages required for activating and deactivating the piezoelectric stack actuator 3831.

If the lateral flow assay device cartridge also includes a flow control mechanism between the wicking pad and the membrane pad (e.g., as shown in FIG. 38), the lateral flow assay device 3800 may include the piezoelectric actuator stack 3832 to control the gap 3292 between the wicking pad 120 and the membrane 115. The piezoelectric actuator stack 3832 may be connected to the shaft 3852. The piezoelectric stack actuator 3832 may be controlled by the processor/controller 505 through the piezoelectric driver 3822. The piezoelectric driver 3822 may receive one or more signals from the processor/controller 505 and may generate the voltages required for activating and deactivating the piezoelectric stack actuator 3832. Other components of the lateral flow assay device of FIG. 38 may be similar to the corresponding components of the lateral flow assay device 3200 of FIGS. 32-33.

FIG. 38, as shown, includes two operational steps 3801 and 3802. As shown in step 3801, a gap 3291 may initially (e.g., at the start of a test) be maintained between the conjugate pad 110 and the membrane 115 by the spring 3241. A gap 3292 may also initially be maintained between the membrane 115 and the wicking pad by the spring 3242. The gaps 3291 and 3292 may be substantially filled by air.

The processor/controller 505, in some embodiments, may send one or more signals prior to, or at the start of a test, to the piezoelectric driver 3821 to deactivate the piezoelectric stack actuator 3831. For example, the piezoelectric driver 3821 may turn off the voltage to the piezoelectric stack actuator 3831. As shown, the length of the piezoelectric stack actuator 3831 in step 3801 is d1 and the shaft 3851 is not in contact with the spring 3241.

The processor/controller 505, in some embodiments, may also send one or more signals to the piezoelectric driver 3822 to deactivate the piezoelectric stack actuator 3832. For example, the piezoelectric driver 3822 may turn off the voltage to the piezoelectric stack actuator 3832. As shown, the shaft 3852 is not in contact with the spring 3242.

Once the specified conjugation time is lapsed (e.g., specified by the NFC chip 590, received from the UI of the lateral flow assay device, received from an external device, etc.), the processor/controller 505 may send one or more signals, in step 3802, to the piezoelectric driver 3821 to activate the piezoelectric stack actuator 3831. The piezoelectric driver 3821 may turn on the voltage to the piezoelectric stack actuator 3831.

As shown in step 3802, the length of the piezoelectric stack actuator 3831 may expand to d2, generating a stroke of d2−d1. Assuming that the piezoelectric stack actuator 3831 may equally expand in two opposite directions, the edge 3880, which is closer to the housing 3230 may move at a distance of (d2−d1)/2 towards the housing 3230, causing the shaft 3851 to move by the same distance of (d2−d1)/2. The lateral flow assay device 3800 may be configured such that the movement of the shaft 3851 by the distance (d2−d1)/2 may cause the gap 3291 to be removed and the conjugate pad 110 may come in contact with the membrane 115. Once the conjugate pad 110 and the membrane 115 come in full contact, any further displacement of the piezoelectric stack actuator 3831 may be prevented and may be automatically converted to a blocking force.

The piezoelectric stack actuator 3831 may be repeatedly activated and deactivated to push the shaft 3851 against the spring 3241 to bring the conjugate pad 110 and the membrane 115 in touch with each other, followed by pulling the shaft 3851 away from the spring 3241 to cause the spring 3241 to separate the conjugate pad 110 from the membrane 115. Repeatedly connecting and disconnecting the conjugate pad 110 and the membrane 115 may be used to control the flow of fluid material from the conjugate pad 110 into the membrane 115, as described above with reference to FIGS. 32-33. The piezoelectric stack actuator 3832 may be similarly controlled to open and close the gap 3292 between the wicking pad 120 and the membrane 115.

Some embodiments do not use springs in order to open and close the gaps between the conjugate pad and the membrane or between the wicking pad and membrane. Some of these embodiments may connect a magnet to the backing of the conjugate pad and/or to the backing of the wicking pad. FIG. 39 is a front elevation view of one example embodiment of a portion of a lateral flow assay device 3900 that controls the gap between the conjugate pad and the membrane and/or the gap between the wicking pad and the membrane by magnets and electromagnets, according to various aspects of the present disclosure. FIG. 40 is a functional block diagram illustrating one example embodiment of the lateral flow assay device of FIG. 39, according to various aspects of the present disclosure.

With reference to FIGS. 39 and 40, the conjugate pad 110 may be connected to the backing 3211 and the wicking pad 120 may be connected to the backing 3213. Unlike the lateral flow assay devices of FIGS. 32-33 and 36-38, the lateral flow assay device 3900 of FIGS. 39 and 40 do not include the springs 3241 and 3242 to pull down the conjugate pad 110 and the wicking pad 120, respectively.

The lateral flow assay device 3900 may include a magnet 3971 connected to the backing 3211 and/or a magnet 3972 connected to the backing 3213. The electromagnets 3648-3649, the coils 3691-36392, and the cores 3651-3652, may be similar to the corresponding components of FIG. 37.

Similar to the lateral flow assay device 3200 of FIGS. 32 and 33, in the lateral flow assay device 3900, the flow rate for the membrane pad 115 and the flow time (which is the time it takes for the solution to travel from one end of the membrane to the other) may be controlled by on-off cycling (pulsing) of the mechanism that brings the conjugate pad and the membrane pad together. The flow time may be controlled with the time that the conjugate 110 and the membrane 115 pads are connected (Tc) and the time that the pads are disconnected (Td). The value of these parameters and the number of times the pads are connected and disconnected may be determined via an algorithm that uses calibration tables or calibration curves as described above with reference to FIGS. 34 and 35.

If the lateral flow assay device cartridge also includes a flow control mechanism between the wicking pad and the membrane pad (e.g., as shown in FIGS. 39 and 40), the flow control mechanism between the wicking pad and the membrane pad may also have its Tc and Td parameters that may either use the same values as the Tc and Td for the mechanism between the conjugate pad and the membrane or it may use its own independent Tc and Td values, as described above.

The activation and deactivation of the electromagnets 3648 and 3649 may be controlled in order to control the flow of the fluid material from the conjugate pad 110 to the membrane 115 and from the membrane 115 to the wicking pad 120, respectively. Initially (e.g., before the start of a test), the direction of current in the wire 3360 (FIG. 40) may be set by the processor/controller 505 such that the electromagnet 3648 may pull on the magnet 3971 to maintain the gap 3291 between the conjugate pad 110 and the membrane 115.

Once the specified conjugation time is lapsed (e.g., specified by the NFC chip 590, received from the UI of the lateral flow assay device, received from an external device, etc.), the processor/controller 505 may change the direction of current in the wire 3360, such that the electromagnet 3648 may repel the magnet 3971 to make the conjugate pad 110 contact the membrane 115 to allow the flow of the fluid material from the conjugate pad 110 to the membrane 115.

Similarly, the direction of current in the wire 4061 (FIG. 40) may be set by the processor/controller 505 such that the electromagnet 3649 may pull on the magnet 3972 to maintain the gap 3292 between the wicking pad 120 and the membrane 115. In order to close the gap 3292, the processor/controller 505 may change the direction of current in the wire 4061, such that the electromagnet 3649 may repel the magnet 3972 to make the wicking pad 120 contact the membrane 115 to allow the flow of the fluid material from the membrane 115 to the wicking pad 120.

The amount of pressure the conjugate pad 110 may apply on the membrane 115 may be controlled by configuring the strength of the magnetic field that the electromagnet 3648 may generate and the strength of the magnet 3971. The amount of pressure the wicking pad 120 may apply on the membrane 115 may be controlled by configuring the strength of the magnetic field that the electromagnet 3649 may generates and the strength of the magnet 3972.

In alternative embodiments, the lateral flow assay device may be configured such that the weight of the magnets 3971 and 3972 may pull down the conjugate pad under the force of gravity to maintain the gaps 3291 and 3292, respectively. In these embodiments, the polarities of the electromagnet 3648 and the magnet 3971 may be configured such that processor/controller may activate the electromagnet 3648 to repel the magnet 3971 in order to close the gap 3291 and bring the conjugate pad 110 in contact with the membrane 115. Similarly, the polarities of the electromagnet 3649 and the magnet 3972 may be configured such that processor/controller may activate the electromagnet 3649 to repel the magnet 3972 in order to close the gap 3292 and bring the wicking pad 120 in contact with the membrane 115.

FIG. 41 is a front elevation view of one example embodiment of a portion of a lateral flow assay device 4100 that controls the gap between the conjugate pad and the membrane and/or the gap between the wicking pad and the membrane by magnets and electromagnets that are positioned over the lateral flow assay device's housing, according to various aspects of the present disclosure. FIG. 42 is a functional block diagram illustrating one example embodiment of the lateral flow assay device of FIG. 41, according to various aspects of the present disclosure.

With reference to FIGS. 41-42, the electromagnets 3648 and 3649 are positioned over the housing 3230. Other components of FIGS. 41-42 are similar to the corresponding components of FIGS. 39-40. With further reference to FIG. 41-42, initially (e.g., before the start of a test), the direction of current in the wire 3360 (FIG. 42) may be set by the processor/controller 505 such that the electromagnet 3648 may repel (i.e., push on) the magnet 3971 to maintain the gap 3291 between the conjugate pad 110 and the membrane 115.

Once the specified conjugation time is lapsed (e.g., specified by the NFC chip 590, received from the UI of the lateral flow assay device, received from an external device, etc.), the processor/controller 505 may change the direction of current in the wire 3360, such that the electromagnet 3648 may attract the magnet 3971 to make the conjugate pad 110 contact the membrane 115 to allow the flow of the fluid material from the conjugate pad 110 to the membrane 115.

Similarly, the direction of current in the wire 4061 (FIG. 42) may be set by the processor/controller 505 such that the electromagnet 3649 may repel the magnet 3972 to maintain the gap 3292 between the wicking pad 120 and the membrane 115. In order to close the gap 3292, the processor/controller 505 may change the direction of current in the wire 4061, such that the electromagnet 3649 may attract the magnet 3972 to make the wicking pad 120 contact the membrane 115 to allow the flow of the fluid material from the membrane 115 to the wicking pad 120.

In alternative embodiments, the lateral flow assay device 4100 may be configured such that the weight of the magnets 3971 and 3972 may pull down the conjugate pad under the force of gravity to maintain the gaps 3291 and 3292, respectively. In these embodiments, the polarities of the electromagnet 3648 and the magnet 3971 may be configured such that processor/controller may activate the electromagnet 3648 to attract the magnet 3971 in order to close the gap 3291 and bring the conjugate pad 110 in contact with the membrane 115. Similarly, the polarities of the electromagnet 3649 and the magnet 3972 may be configured such that processor/controller may activate the electromagnet 3649 to attract the magnet 3972 in order to close the gap 3292 and bring the wicking pad 120 in contact with the membrane 115.

The amount of pressure the conjugate pad 110 may apply on the membrane 115 may be controlled by configuring the strength of the magnetic field that the electromagnet 3648 may generate and the strength of the magnet 3971. The amount of pressure the wicking pad 120 may apply on the membrane 115 may be controlled by configuring the strength of the magnetic field that the electromagnet 3649 may generates and the strength of the magnet 3972.

In all embodiments of FIGS. 32-33 and 36-42, the role of the conjugate pad and the membrane in controlling the gap between the two may be switched. The spring mechanisms, the magnets, or the combination of both may be placed on the membrane instead of the conjugate pad. In these embodiments, the conjugate pad is stationary and the membrane may move up and down to control the opening and closing of the gap between the two.

Similarly, In all embodiments of FIGS. 32-33 and 36-42, the role of the wicking pad and the membrane in controlling the gap between the two may be switched. The spring mechanisms, the magnets, or the combination of both may be placed on the membrane instead of the wicking pad. In this case, the wicking pad is stationary and the membrane may move up and down to control the opening and closing of the gap between the two.

Alternatively, a mix of both approaches may be used where one side may have a stationary conjugate pad and a moving membrane while the other side may have a moving wicking pad and a stationary membrane. And yet in another alternative, a mix of both approaches may be used where one side may have a moving conjugate pad and a stationary membrane while the other side may have a stationary wicking pad and a moving membrane.

FIG. 43 is a front elevation view of one example embodiment of a portion of a lateral flow assay device 4300 that controls the gap between the conjugate pad and the membrane and/or the gap between the wicking pad and the membrane by moving a portion of the membrane with a spring mechanism, according to various aspects of the present disclosure. With reference to FIG. 43, the lateral flow assay device 4300 is configured such that the conjugate pad 110 and the wicking pad 120 are positioned on the floor (or the bottom side) of the cartridge housing and the membrane 155 is positioned on the side opposite to the floor, facing towards the conjugate pad 110 and the wicking pad 120. As shown, a portion of the membrane 115 may be held in place by several tabs (or poles) 4390. The tabs 4390 may be narrow poles configured to hold the membrane 115 in place with minimal contact with the surface of the membrane in order not to impede the flow of the liquid over the membrane 115. The springs 4341 and 4342 may be secured to the housing 3205 by the pins or screws 4351-4352.

With further reference to FIG. 43, the solenoids 3251 and 3252 may include the solenoid shafts 3221 and 3222, respectively. The solenoids 3251 and 3252 may be positioned on the top of the housing 3230. Other components of the lateral flow assay device 4300 may provide similar functionalities as the corresponding components of FIG. 32.

FIG. 43, as shown, includes two operational steps 4301 and 4302. As shown in step 4301, a gap 4391 may initially (e.g., at the start of a test) be maintained between the conjugate pad 110 and the membrane 115 by the spring 4341. The spring 4341 may be configured such that the spring 4341 holds a portion of the membrane 115 and the clear backing 3212 down towards the conjugate pad 110 without the membrane 115 and the conjugate pad 110 touching each other. As shown in step 4301, a gap 4391 is maintained between the conjugate pad 110 and the membrane 115.

A gap 4392 may also initially be maintained between the membrane 115 and the wicking pad by the spring 4342. The spring 4342 may be configured such that the spring 4342 holds a portion of the membrane 115 and the clear backing 3212 down towards the wicking pad 120 without the membrane 115 and the wicking pad 120 touching each other. As shown in step 4301, a gap 4392 is maintained between the wicking pad 120 and the membrane 115. The gaps 4391 and 4392 may be substantially filled by air.

The lateral flow assay device 4300 may be configured such that in step 4301 the solenoid shaft 3221 of the solenoid 3251 is kept away from the spring 4311. For example, the power to the solenoid 3251 may be turned off and/or the lateral flow assay device's processor/controller (not shown for simplicity) may send one or more signals prior to, or at the start of a test, to the solenoid 3251 to keep the shaft 3221 away from the spring 4341.

The lateral flow assay device 4300 may be configured such that in step 4301 the solenoid shaft 3222 of the solenoid 3252 is kept away from the spring 4312. For example, the power to the solenoid 3252 may be turned off and/or the lateral flow assay device's processor/controller may send one or more signals prior to, or at the start of a test, to the solenoid 3252 to keep the shaft 3222 away from the spring 4342.

Once the specified conjugation time is lapsed (e.g., specified by the NFC chip 590, received from the UI of the lateral flow assay device, received from an external device, etc.), the processor/controller may send one or more signals, in step 4302, to the solenoid 3251 to move the shaft 3221 to push the spring 4341 towards the conjugate pad 110. As shown in step 4302, the solenoid shaft 3221 may cause the gap 4391 to be removed and the membrane 115 may come in contact with the conjugate pad 110.

The solenoid shaft 3221 may be repeatedly moved down to push against the spring 4341 to bring the membrane 115 and the conjugate pad 110 in touch with each other, followed by pulling the shaft 3221 away from the spring 4341 to cause the spring 4341 to separate the membrane 115 from the conjugate pad 110. Repeatedly connecting and disconnecting the membrane 115 and the conjugate pad 110 may be used to control the flow of fluid material from the conjugate pad 110 into the membrane 115, as described above with reference to FIGS. 32-33. A similar process may be used to control the gap 4392 between the membrane 115 and the wicking pad 120 by repeatedly moving the shaft 3222 up and down.

The amount of pressure the membrane 115 may apply on the conjugate pad 110 may be controlled by configuring the amount of pressure that the shaft 3221 may apply on the spring 4341 and the strength of the spring 4341. The amount of pressure the membrane 115 may apply on the wicking pad 120 may be controlled by configuring the amount of pressure that the shaft 3222 may apply on the spring 4342 and the strength of the spring 4342.

FIG. 44 is a front elevation view of one example embodiment of a portion of a lateral flow assay device 4400 that controls the gap between the conjugate pad and the membrane and/or the gap between the wicking pad and the membrane by a piezoelectric actuator that moves a portion of the membrane, according to various aspects of the present disclosure.

With reference to FIG. 44, the lateral flow assay device 4400 is configured such that the conjugate pad 110 and the wicking pad 120 are positioned on the floor (or the bottom side) of the cartridge housing and the membrane 155 is positioned on the opposite side of the floor facing towards the conjugate pad 110 and the wicking pad 120. As shown, the membrane 115 may be held in place by several tabs (or poles) 4390, which may be similar to the tabs 4390 of FIG. 43.

With reference to FIG. 44, the lateral flow assay device 4400 may include the piezoelectric actuator stack 3831 to control the gap 4391 between the conjugate pad 110 and the membrane 115. The piezoelectric actuator may be similar to the piezoelectric stack actuator 3831 of FIG. 38 and may be controlled by the processor/controller 505 through the piezoelectric driver 3821, as described above with reference to FIG. 38.

If the lateral flow assay device cartridge also includes a flow control mechanism between the wicking pad 120 and the membrane pad 115 (e.g., as shown in FIG. 44), the lateral flow assay device 4400 may include the piezoelectric actuator stack 3832 to control the gap 4392 between the wicking pad 120 and the membrane 115. The piezoelectric actuator stack 3832 may be connected to the shaft 3852. The piezoelectric stack actuator 3832 may be controlled by the processor/controller 505 through the piezoelectric driver 3822, as described above with reference to FIG. 38. The piezoelectric stack actuators 4332-3832 may be positioned on the top of the housing 3230. Other components of the lateral flow assay device 4400 of FIG. 44 may be similar to the corresponding components of the lateral flow assay device of FIGS. 32-33 and 38.

FIG. 44, as shown, includes two operational steps 4401 and 4402. As shown in step 4401, a gap 4391 may initially (e.g., at the start of a test) be maintained between the conjugate pad 110 and the membrane 115 by the spring 4341. The spring 4341 may be configured such that the spring 4341 holds a portion of the membrane 115 and the clear backing 3212 down towards the conjugate pad 110 without the membrane 115 and the conjugate pad 110 touching each other. As shown in step 4401, a gap 4391 is maintained between the conjugate pad 110 and the membrane 115.

A gap 4392 may also initially be maintained between the membrane 115 and the wicking pad by the spring 4342. The spring 4342 may be configured such that the spring 4342 holds a portion of the membrane 115 and the clear backing 3212 down towards the wicking pad 120 without the membrane 115 and the wicking pad 120 touching each other. As shown in step 4401, a gap 4392 is maintained between the wicking pad 120 and the membrane 115. The gaps 4391 and 4392 may be substantially filled by air.

Once the specified conjugation time is lapsed (e.g., specified by the NFC chip 590, received from the UI of the lateral flow assay device, received from an external device, etc.), the processor/controller 505 may send one or more signals, in step 4402, to the piezoelectric driver 3821 to activate the piezoelectric stack actuator 3831. The piezoelectric driver 3821 may turn on the voltage to the piezoelectric stack actuator 3831.

As shown in step 4402, the length of the piezoelectric stack actuator 3831 may expand and may move the shaft 3851 to push the spring 4341 down, as described above with reference to step 3802 of FIG. 38. The lateral flow assay device 4400 may be configured such that the movement of the shaft 3851 may cause the gap 4391 to be removed and the membrane 115 may come in contact with the conjugate pad 110. Once the membrane 115 and the conjugate pad 110 come to full contact, any further displacement of the piezoelectric stack actuator 3831 may be prevented and may be automatically converted to a blocking force.

The piezoelectric stack actuator 3831 may be repeatedly activated and deactivated to push the shaft 3851 against the spring 4341 to bring the membrane 115 and the conjugate pad 110 in touch with each other, followed by pulling the shaft 3851 away from the spring 4341 to cause the spring 4341 to separate the membrane 115 from the conjugate pad 110. Repeatedly connecting and disconnecting the membrane 115 and the conjugate pad 110 may be used to control the flow of fluid material from the conjugate pad 110 into the membrane 115, as described above with reference to FIGS. 32-33. A similar process may be used to control the gap 4392 between the membrane 115 and the wicking pad 120 by repeatedly activating and deactivating the piezoelectric actuator stack 3832.

The amount of pressure the membrane 115 may apply on the conjugate pad 110 may be controlled by configuring the stroke and the blocking force of the piezoelectric stack 3831, and by configuring the strength of the spring 4341. The amount of pressure the membrane 115 may apply on the wicking pad 120 may be controlled by configuring the stroke and the blocking force of the piezoelectric stack 3832, and by configuring the strength of the spring 4342.

FIG. 45 is a front elevation view of one example embodiment of a portion of a lateral flow assay device 4500 that controls the gap between the conjugate pad and the membrane and/or the gap between the wicking pad and the membrane by a spring mechanism and an electromagnet that moves a portion of the membrane, according to various aspects of the present disclosure. With reference to FIG. 45, the lateral flow assay device 4500 is configured such that the conjugate pad 110 and the wicking pad 120 are positioned on the floor (or the bottom side) of the cartridge housing and the membrane 155 is positioned on the opposite side of the floor facing towards the conjugate pad 110 and the wicking pad 120. As shown, the membrane 115 may be held in place by several tabs (or poles) 4390, which may be similar to the tabs 4390 of FIG. 43.

With reference to the lateral flow assay device 4500 of FIG. 45, the tip of the spring 4341 may be made of magnetic material 3661 and the tip of the spring 4342 may be made of magnetic material 3662. The rest of the springs 4341 and 4342 may be made of non-magnetic material. Alternatively, a piece of magnetic material 3661 may be attached (e.g., by glue or other appropriate material) to the tip of the spring 4341 and a piece of magnetic material 3662 may be attached to the tip of the spring 4342.

With further reference to FIG. 45, the lateral flow assay device 4500 may include the electromagnets 3648 and 3649, which may be similar to the electromagnets 3648 and 3649 of FIG. 36. Other components of FIG. 45 may be similar to the corresponding components of FIGS. 36 and 43, which were described above.

FIG. 45, as shown, includes two operational steps 4501 and 4502. As shown in step 4501, a gap 4391 may initially (e.g., at the start of a test) be maintained between the conjugate pad 110 and the membrane 115 by the spring 4341. The spring 4341 may be configured such that the spring 4341 holds a portion of the membrane 115 and the clear backing 3212 down towards the conjugate pad 110 without the membrane 115 and the conjugate pad 110 touching each other. As shown in step 4501, a gap 4391 is maintained between the conjugate pad 110 and the membrane 115.

A gap 4392 may also initially be maintained between the membrane 115 and the wicking pad by the spring 4342. The spring 4342 may be configured such that the spring 4342 holds a portion of the membrane 115 and the clear backing 3212 down towards the wicking pad 120 without the membrane 115 and the wicking pad 120 touching each other. As shown in step 4501, a gap 4392 is maintained between the wicking pad 120 and the membrane 115. The gaps 4391 and 4392 may be substantially filled by air.

The lateral flow assay device 4500, in some embodiments, may be configured such that in step 4501 the power to the electromagnet 3648 is turned off and the spring 4341 may be configured such that the spring pushes a portion of the membrane 115 and a portion of the clear backing 3212 such that the gap 4391 is still maintained between the membrane 115 and the conjugate pad 110. In other embodiments, the direction of current to the electromagnet 3648, the strength of the magnetic field generated by the electromagnet 3698, and the strength of the spring 4341 may be configured such that, in step 4501, the gap 4391 is still maintained between the membrane 115 and the conjugate pad 110.

In the embodiments that control a gap between the wicking pad and the membrane (e.g., the embodiment shown in FIG. 45), the lateral flow assay device 4500 may be configured such that, in step 4501, the power to the electromagnet 3649 is turned off and the spring 4342 may be configured such that the spring pushes a portion of the membrane 115 and a portion of the clear backing 3212 such that the gap 4392 is still maintained between the membrane 115 and the wicking pad 120. In other embodiments, the direction of current to the electromagnet 3649, the strength of the magnetic field generated by the electromagnet 3699, and the strength of the spring 4342 may be configured such that, in step 4501, the gap 4392 is still maintained between the membrane 115 and the wicking pad 120.

Once the specified conjugation time is lapsed (e.g., specified by the NFC chip 590, received from the UI of the lateral flow assay device, received from an external device, etc.), the processor/controller (not shown) of the lateral flow device 4500 may send one or more signals, in step 4502, to the electromagnet 3648 to push the spring 4341 towards the conjugate pad 110.

As shown in step 4502, the gap 4391 may be removed and the membrane 115 may come in contact with the conjugate pad 110. The electromagnet 3648 may be repeatedly turned on and off (or the direction of the current in the electromagnet 3648 may repeatedly be changed) to push the spring 4341 to bring the membrane 115 and the conjugate pad 110 in touch with each other, followed by releasing the spring 4341 (or by pulling spring 4341 towards the electromagnet) to cause the spring 4341 to separate the membrane 115 from the conjugate pad 110. Repeatedly connecting and disconnecting the membrane 115 and the conjugate pad 110 may be used to control the flow of fluid material from the conjugate pad 110 into the membrane 115, as described above with reference to FIGS. 32-33. A similar process may be used to control the gap 4392 between the membrane 115 and the wicking pad 120 by repeatedly turning electromagnet 3649 on and off or by repeatedly changing the direction of the current in the electromagnet 3649.

The amount of pressure the membrane 115 may apply on the conjugate pad 110 may be controlled by configuring the strength of the magnetic field that the electromagnet 3648 may generate, the strength of the magnetic material 3661, and the strength of the spring 4341. The amount of pressure the membrane 115 may apply on the wicking pad 120 may be controlled by configuring the strength of the magnetic field that the electromagnet 3649 may generate, the strength of the magnetic material 3662, and the strength of the spring 4342.

FIG. 46 is a front elevation view of one example embodiment of a portion of a lateral flow assay device 4600 that controls the gap between the conjugate pad and the membrane and/or between the wicking pad and the membrane by a magnet and an electromagnet that moves a portion of the membrane, according to various aspects of the present disclosure. With reference to FIG. 46, the lateral flow assay device 4600 may have a similar configuration as the lateral flow assay device 4500 of FIG. 45, except that the lateral flow assay device 4600 does not include the springs 4341-4342 and instead has the magnets 3971 and 3972 that are connected to the two sides of the clear backing 3212.

FIG. 46, as shown, includes two operational steps 4601 and 4602. As illustrated in step 4601, a gap 4391 may initially (e.g., at the start of a test) be maintained between the conjugate pad 110 and the membrane 115. Initially, the direction of current to the electromagnet 3648 may be set by the processor/controller (not shown) of the lateral flow assay device 4600 such that the electromagnet 3648 may attract (i.e., pull on) the magnet 3971 to maintain the gap 4391 between the conjugate pad 110 and the membrane 115.

As illustrated in step 4602, once the specified conjugation time is lapsed (e.g., specified by the NFC chip 590, received from the UI of the lateral flow assay device, received from an external device, etc.), the processor/controller may change the direction of current to the electromagnet 3648, such that the electromagnet 3648 may repel (i.e., push) the magnet 3971 to make the membrane 115 to contact the conjugate pad 110 to allow the flow of the fluid material from the conjugate pad 110 to the membrane 115.

In the embodiments that control a gap between the wicking pad 120 and the membrane 115 (e.g., the embodiment shown in FIG. 46), the direction of current to the electromagnet 3649 may be set by the processor/controller such that the electromagnet 3649 may attract the magnet 3972 to maintain the gap 4392 between the wicking pad 120 and the membrane 115. In order to close the gap 4392, the processor/controller may change the direction of current to the electromagnet 3649, such that the electromagnet 3649 may repel the magnet 3972 to make the membrane 115 to contact the wicking pad 120 to allow the flow of the fluid material from the membrane 115 to the wicking pad 120.

Repeatedly connecting and disconnecting the membrane 115 and the conjugate pad 110 may be used to control the flow of fluid material from the conjugate pad 110 into the membrane 115, as described above with reference to FIGS. 32-33. A similar process may be used to control the gap 4392 between the membrane 115 and the wicking pad 120 by repeatedly turning electromagnet 3649 on and off or by repeatedly changing the direction of the current in the electromagnet 3649.

The amount of pressure the membrane 115 may apply on the conjugate pad 110 may be controlled by configuring the strength of the magnetic field that the electromagnet 3648 may generate and the strength of the magnet 3971. The amount of pressure the membrane 115 may apply on the wicking pad 120 may be controlled by configuring the strength of the magnetic field that the electromagnet 3649 may generate and the strength of the magnet 3972.

In alternative embodiments, the lateral flow assay device 4600 may be configured such that the weight of the magnets 3971 and 3972 may pull down the membrane 115 under the force of gravity to maintain the gaps 4391 and 4392, respectively. In these embodiments, the polarities of the electromagnet 3648 and the magnet 3971 may be configured such that processor/controller may activate the electromagnet 3648 to attract the magnet 3971 in order to open the gap 4391. Similarly, the polarities of the electromagnet 3649 and the magnet 3972 may be configured such that processor/controller may activate the electromagnet 3649 to attract the magnet 3972 in order to open the gap 4392.

As an alternative to the configuration of the conjugate pad 110, the membrane 115, and the wicking pad 120 of FIGS. 43-46, the lateral flow assay in some embodiments may be configured such that the conjugate pad 110 and the wicking pad to be on top of the membrane 115, either by moving the membrane to the floor of the cartridge housing or vertically flipping the entire system. For example, in such an alternative configuration for FIG. 36, when the electromagnet 3648 is deactivated, the spring 3241 may push down the conjugate pad 110 away from the membrane to maintain the gap 4391. In these alternative embodiments, the electromagnet 3648 may be placed under the housing 3230, such that, when the electromagnet 3648 is activated, the magnetic material 3261 and the spring 3241 are pulled down towards the electromagnet 3248 to make the conjugate pad 110 to come in contact with the membrane 115.

Furthermore, in this configuration, the electromagnet 3649 may be placed under the housing 3230. When the electromagnet 3649 is deactivated, the spring 3242 may push down the wicking pad 120 away from the membrane to maintain the gap 4392. When the electromagnet 3649 is activated, the magnetic material 3262 and the spring 3242 are pulled down towards the electromagnet 3649 to make the wicking pad 120 to come in contact with the membrane 115.

As another alternative to the embodiments of FIGS. 43-46, a mix of two approaches may be used where one side may have a stationary conjugate pad and a moving membrane while the other side may have a moving wicking pad and a stationary membrane. And yet in another alternative, a mix of two approaches may be used where one side may have a moving conjugate pad and a stationary membrane while the other side may have a stationary wicking pad and a moving membrane.

FIG. 47 is a front elevation view of one example embodiment of a portion of a lateral flow assay device that controls the gap between the conjugate pad and the membrane by a magnet and an electromagnet that move a portion of the membrane, according to various aspects of the present disclosure. With reference to FIG. 47, the lateral flow assay device 4700 may be configured such that the conjugate pad 110 to be on top of the membrane 115 by moving the membrane to the floor of the cartridge housing 3230. The housing 3230 of the lateral flow assay device 4700 may be configured with a space 4790 to facilitate moving the magnet 3971 down (in the depicted orientation).

In the embodiment of FIG. 47, the wicking pad 120 is also moved the floor of the cartridge housing 3230 and the electromagnet 3648 is positioned below the cartridge housing 3230. The backing 4711 of the conjugate pad 110 may be connected to the housing 3230. As shown, a portion of the membrane 115 may be held in place by the tab (or pole) 4792. The tab 4792 may be a narrow pole configured to hold the membrane 115 in place with minimal contact with the surface of the membrane in order not to impede the flow of the liquid over the membrane 115. In alternative embodiments, a portion 4712 of the backing 4712 of the membrane 115 may be attached to the housing 3230 by an adhesive, such as, for example, and without limitations, by glue. Other components of the lateral flow assay device 4700 may be similar to the corresponding components of the lateral flow assay device 4600 of FIG. 46.

FIG. 47, as shown, includes two operational steps 4701 and 4702. As illustrated in step 4701, a gap 4791 may initially (e.g., at the start of a test) be maintained between the conjugate pad 110 and the membrane 115. The gap 4791 may be substantially filled by air. Initially, the direction of current to the electromagnet 3648 may be set by the processor/controller (not shown) of the lateral flow assay device 4700 such that the electromagnet 3648 may attract (i.e., pull on) the magnet 3971 to maintain the gap 4791 between the conjugate pad 110 and the membrane 115.

As illustrated in step 4702, once the specified conjugation time is lapsed (e.g., specified by the NFC chip 590, received from the UI of the lateral flow assay device, received from an external device, etc.), the processor/controller may change the direction of current to the electromagnet 3648, such that the electromagnet 3648 may repel (i.e., push) the magnet 3971 to make the membrane 115 to contact the conjugate pad 110 to allow the flow of the fluid material from the conjugate pad 110 to the membrane 115. Repeatedly connecting and disconnecting the membrane 115 and the conjugate pad 110 may be used to control the flow of fluid material from the conjugate pad 110 into the membrane 115, as described above with reference to FIGS. 32-33. The amount of pressure the membrane 115 may apply on the conjugate pad 110 may be controlled by configuring the strength of the magnetic field that the electromagnet 3648 may generate and the strength of the magnet 3971.

In the embodiment of FIG. 47, no gap is maintained between the membrane 115 and the wicking pad 120. The backing 4713 of the wicking pad 120 may be connected to the housing 3230, and the membrane 115 and the wicking pad 120 may always be in contact with each other during a test.

In alternative embodiments, the lateral flow assay device 4700 may be configured such that the weight of the magnet 3971 may pull down the membrane 115 under the force of gravity to maintain the gap 4391. In these embodiments, the polarities of the electromagnet 3648 and the magnet 3971 may be configured such that processor/controller may activate the electromagnet 3648 to attract the magnet 3971 in order to open the gap 3291.

In alternative embodiments, the electromagnet 3648 may be positioned over the cartridge housing 3230. In some of these embodiments, the current through the electromagnet may be configured by the processor/controller to repel the magnet 3971 in order to maintain the gap 4791, and the current through the electromagnet may be configured by the processor/controller to attract the magnet 3971 in order to remove the gap 4791 and bring the membrane 115 in contact with the conjugate pad 110.

In some embodiments where the electromagnet 3648 is positioned over the cartridge housing 3230, the lateral flow assay device 4700 may be configured such that the weight of the magnet 3971 may pull down the membrane 115 under the force of gravity to maintain the gap 4391. In these embodiments, the polarities of the electromagnet 3648 and the magnet 3971 may be configured such that processor/controller may activate the electromagnet 3648 to attract the magnet 3971 in order to remove the gap 4791 and bring the membrane 115 in contact with the conjugate pad 110.

FIG. 48 is a front elevation view of one example embodiment of a portion of a lateral flow assay device that controls the gap between the conjugate pad and the membrane, and the gap between the membrane and the wicking pad by two pairs of magnet and electromagnet that move portions of the membrane, according to various aspects of the present disclosure. With reference to FIG. 48, the lateral flow assay device 4800 may be configured such that the conjugate pad 110 and the wicking pad 120 to be on top of the membrane 115 by moving the membrane 115 to the floor of the cartridge housing 3230. The housing 3230 of the lateral flow assay device 4800 may be configured with the spaces 4790 and 4891 to facilitate moving the magnets 3971 and 3972 down (in the depicted orientation).

As shown, a portion of the membrane 115 may be held in place by the tabs (or poles) 4792 and 4893. The tabs 4792 and 4893 may be narrow poles configured to hold the membrane 115 in place with minimal contact with the surface of the membrane in order not to impede the flow of the liquid over the membrane 115. In alternative embodiments, a portion 4812 of the backing 4712 of the membrane 115 may be attached to the housing 3230 by an adhesive, such as, for example, and without limitations, by glue. The magnet 3972 is connected to the backing 4713 of the wicking pad 120 and the electromagnet 3649 is positioned above the housing 3230. Other components of the lateral flow assay device 4800 may be similar to the corresponding components of the lateral flow assay device 4700 of FIG. 47.

FIG. 48, as shown, includes two operational steps 4801 and 4802. As illustrated in step 4801, a gap 4791 may initially (e.g., at the start of a test) be maintained between the conjugate pad 110 and the membrane 115. The gap 4791 in the lateral flow assay device 4800 may be controlled similar to the gap 4791 in the lateral flow assay device 4700.

With further reference to FIG. 48, the gap 4892 between the wicking pad 120 and the membrane 115 may be controlled. The gaps 4791 and 4892 may be substantially filled by air. The direction of current to the electromagnet 3649 may be set by the processor/controller of the lateral flow assay device 4800 such that the electromagnet 3649 may repel the magnet 3972 to maintain the gap 4892 between the wicking pad 120 and the membrane 115. In order to close the gap 4892, the processor/controller may change the direction of current to the electromagnet 3649, such that the electromagnet 3649 may attract the magnet 3972 to make the membrane 115 to contact the wicking pad 120 to allow the flow of the fluid material from the membrane 115 to the wicking pad 120.

Repeatedly connecting and disconnecting the membrane 115 and the wicking pad 110 may be used to control the flow of fluid material from the membrane 115 into the wicking pad. The amount of pressure the membrane 115 may apply on the conjugate pad 110 may be controlled by configuring the strength of the magnetic field that the electromagnet 3648 may generate and the strength of the magnet 3971. The amount of pressure the membrane 115 may apply on the wicking pad 120 may be controlled by configuring the strength of the magnetic field that the electromagnet 3649 may generate and the strength of the magnet 3972.

In alternative embodiments, the lateral flow assay device 4800 may be configured such that the weight of the magnets 3971 and 3972 may pull down the membrane 115 under the force of gravity to maintain the gaps 4791 and 4892, respectively. In these embodiments, the polarities of the electromagnet 3648 and the magnet 3971 may be configured such that processor/controller may activate the electromagnet 3648 to repel the magnet 3971 in order to close the gap 4791. The polarities of the electromagnet 3649 and the magnet 3972 may be configured such that processor/controller may activate the electromagnet 3649 to attract the magnet 3972 in order to open the gap 4392.

In alternative embodiments, the positions of the electromagnet 3648 and/or the electromagnet 3649 may be changed with respect to the cartridge housing 3230. For example, the electromagnet 3648 may be positioned over the housing 3230 and/or the electromagnet 3649 may be positioned under the housing 3230. In these embodiments, the current through the electromagnet 3648 may be configured by the processor/controller to repel the magnet 3971 in order to maintain the gap 4791, and the current through the electromagnet 3648 may be configured by the processor/controller to attract the magnet 3971 in order to remove the gap 4791 and bring the membrane 115 in contact with the conjugate pad 110. In these embodiments, the current through the electromagnet 3649 may be configured by the processor/controller to attract the magnet 3971 in order to maintain the gap 4892, and the current through the electromagnet 3649 may be configured by the processor/controller to repel the magnet 3971 in order to remove the gap 4892 and bring the membrane 115 in contact with the conjugate pad 110.

In some embodiments where the electromagnet 3648 is positioned over the cartridge housing 3230 and the electromagnet 3649 is positioned under the housing 3230, the lateral flow assay device 4800 may be configured such that the weight of the magnets 3971 and 3972 may pull down the membrane 115 under the force of gravity to maintain the gaps 4791 and 4892, respectively. In these embodiments, the polarities of the electromagnet 3648 and the magnet 3971 may be configured such that processor/controller may activate the electromagnet 3648 to attract the magnet 3971 in order to remove the gap 4791 and bring the membrane 115 in contact with the conjugate pad 110. In these embodiments, the polarities of the electromagnet 3649 and the magnet 3972 may be configured such that processor/controller may activate the electromagnet 3649 to repel the magnet 3972 in order to remove the gap 4892 and bring the membrane 115 in contact with the wicking pad 120.

Some embodiments may use a moving element, such as, a shaft or a wheel with two magnets in order to move the magnets that are attached to the conjugate pad 110, the membrane 115, and/or the wicking pad 120. Some embodiments may use a shaft or a wheel with two magnets in order to move the tip of the spring (such as the tip 3661 of the spring 3241 and/or the tip 3662 of the spring 3242 of FIG. 37) which are made of magnetic material. As described below, these embodiments may provide the technical advantage of saving power for the battery (or batteries) of the lateral flow assay device.

FIGS. 49A and 49B illustrate a front elevation view of one example embodiment of a portion of a lateral flow assay device that controls the gap between the conjugate pad and the membrane, and/or the gap between the membrane and the wicking pad by two magnets that are positioned over a moving shaft, according to various aspects of the present disclosure. With reference to FIGS. 49A-49B, the configuration of the conjugate pad 110, the membrane 115, the wicking pad 120, and/or the location of the actuator 4948 may be similar to the corresponding components of any of the embodiments described above with reference to FIGS. 32-33 and 36-48. The location of the actuator 4949 may be similar to the corresponding actuator in any of the above-mentioned embodiments that control the gap between the membrane 115 and the wicking pad 120.

In the example of FIGS. 49A-49B, the configuration of the conjugate pad 110, the membrane 115, the wicking pad 120, and the locations of the actuators 4948 and 4949 are similar to the corresponding components of FIG. 48. With reference to FIGS. 49A-49B, each of the actuators 4948 and 4949 may be an electromagnet, such as, the electromagnets 3648 and 3649 of FIG. 48, a piezoelectric/piezoelectric stack actuator, such as the actuators 3831 and 3832 of FIG. 44, an electric motor, such as, the electric motor 530 of FIG. 5, etc., that may be configured to move the shaft 4971 or the shaft 4972 between two different positions, etc.

As shown in the expanded view 4905, the magnet 4910 may include a first pole 4911 and a second pole 4912. The first and second poles may be north and south (or south and north) poles, respectively. As is known in the art, when the similar poles of two magnets (e.g., the north poles of the two magnets or the south poles of the two magnets) are brought in proximity of each other, the two magnets repel each other, and when the dissimilar poles of two magnets (e.g., the north pole of one magnet and the south pole of the other magnet) are brought in proximity of each other, the two magnets attract each other.

With continued reference to the expanded view 4905, the actuator 4948 may be connected (e.g., and without limitations, by a moving arm 4972) to the shaft 4971. The shaft 4971 may include two ends. The magnet 4920 may be positioned on one end of the shaft 4971 and the magnet 4930 may be positioned on the other end of the shaft 4971. Each of the magnets 4920 and 4930 may, respectively, include first and second poles 4921-4922 and 4931-4932.

As shown in the expanded view 4906, the magnet 4910 may include a first pole 4941 and a second pole 4942. The first and second poles may be north and south (or south and north) poles, respectively. The actuator 4949 may be connected (e.g., and without limitations, by a moving arm 4974) to the shaft 4973. The shaft 4973 may include two ends. The magnet 4940 may be positioned on one end of the shaft 4973 and the magnet 4950 may be positioned on the other end of the shaft 4973. Each of the magnets 4940 and 4950 may, respectively, include first and second poles 4941-4942 and 4951-4952.

FIGS. 49A-49B, as shown, include two operational steps 4901 and 4902. As illustrated in step 4901, a gap 4791 may initially (e.g., at the start of a test) be maintained between the conjugate pad 110 and the membrane 115. As shown in the expanded view 4905, the actuator 4948 may be configured to initially keep the shaft 4971 in a first position, such that the first pole 4921 of the magnet 4920 is in proximity of the second pole 4912 of the magnet 4910. When the shaft 4971 is in the first position (as shown in step 4901), the magnets 4920 and 4910 may attract each other and the gap 4791 between the membrane 115 and the conjugate pad 110 may be maintained.

As illustrated in in the expanded view 4907 in step 4902 (FIG. 49B), once the specified conjugation time is lapsed (e.g., specified by the NFC chip 590, received from the UI of the lateral flow assay device, received from an external device, etc.), the processor/controller (not shown) of the lateral flow assay device 4900 may send one or more signals to the actuator 4948 to move the shaft 4971 to a second position, such that the second pole 4932 of the magnet 4930 is in proximity of the second pole 4912 of the magnet 4910. When the shaft 4971 is in the second position (as shown in the expanded view 4907 in step 4902), the magnets 4920 and 4910 may repel each other and the gap 4791 between the membrane 115 and the conjugate pad 110 may be closed and may make the membrane 115 to contact the conjugate pad 110 to allow the flow of the fluid material from the conjugate pad 110 to the membrane 115.

The processor/controller of the lateral flow assay device 4900 may send one or more signals to the actuator 4948 to move the shaft 4971 to the first position in order to open the gap 4791 between the membrane 115 and the conjugate pad 110. Repeatedly connecting and disconnecting the membrane 115 and the conjugate pad 110 may be used to control the flow of fluid material from the conjugate pad 110 into the membrane 115, as described above with reference to FIGS. 32-33.

In the embodiments that control a gap between the wicking pad 120 and the membrane 115 (e.g., the embodiment shown in FIGS. 49A-49B), the processor/controller of the lateral flow assay device 4900 may send one or more signals to the actuator 4949 to move the shaft 4973 between a first position and a second position in order to open or close the gap 4892 between the membrane 115 and the wicking pad 120. The gap 4892 may initially (e.g., at the start of a test) be either open or closed, depending on a particular test's requirement. For example, in the configuration of FIG. 49A, the gap 4892 may be initially open. The actuator 4949 may be configured to initially keep the shaft 4973 in the first position, such that the first pole 4951 of the magnet 4950 is in proximity of the second pole 4942 of the magnet 4940. When the shaft 4973 is in its first position (as shown in the expanded view 4906 step 4901), the magnets 4940 and 4950 may attract each other and the gap 4892 between the membrane 115 and the wicking pad 120 may be open.

The processor/controller of the lateral flow assay device 4900 may send one or more signals to the actuator 4949 to move the shaft 4973 to the second position, such that the second pole 4962 of the magnet 4960 is in proximity of the second pole 4942 of the magnet 4940. When the shaft 4973 is in its second position (as shown in the expanded view 4908 in step 4902), the magnets 4960 and 4940 may repel each other and the gap 4892 between the membrane 115 and the wicking pad 120 may be closed and may make the membrane 115 to contact the wicking pad 120 to allow the flow of the fluid material from the membrane 115 to the wicking pad 120. Repeatedly connecting and disconnecting the membrane 115 and the wicking pad 120 may be used to control the flow of fluid material from the membrane 115 into the wicking pad 120.

It should be noted that the actuator 4948 may only require power when the shaft 4971 is to move from the first position to the second position or vice versa. When the shaft 4971 is stationary to either maintain the gap 4791 or to close the gap 4791, the actuator 4948 does not require power. Also, the actuator 4949 may only require power when the shaft 4973 is to move from the first position to the second position or vice versa. When the shaft 4973 is stationary to either maintain the gap 4892 or to close the gap 4892, the actuator 4949 does not require power.

The embodiment of FIGS. 49A-49B provides the technical advantage of saving the power of the lateral flow assay device's battery (or batteries). In some embodiments of the lateral flow assay devices of FIGS. 32-33 and 36-49B, the processor/controller, the UI, the power source, the processor/controller circuit, and/or the NFC reader of the lateral flow assay device may be reusable for performing multiple tests for the same or different subjects (e.g., the same person or different persons). Using the actuators 4948-4949, the magnets 4910, 4920, 4930, 4940, 4950, and 4960, the shafts 4971-4972 to open and close the gaps between the membrane 115 and the conjugate pad 110 and/or to open and close the gaps between the membrane 115 and the wicking pad 120 in these configurations prolongs the age of the battery/batteries of the corresponding lateral flow assay devices and make the reusable portion of the these lateral flow assay devices to last for a longer periods of time and/or for performing more tests.

FIGS. 50A and 50B illustrate a front elevation view of one example embodiment of a portion of a lateral flow assay device that controls the gap between the conjugate pad and the membrane, and/or the gap between the membrane and the wicking pad by two magnets that are positioned over a rotating wheel, according to various aspects of the present disclosure. With reference to FIGS. 50A and 50B, the configuration of the conjugate pad 110, the membrane 115, the wicking pad 120, and/or the location of the actuator 4948 may be similar to the corresponding components of any of the embodiments described above with reference to FIGS. 32-33 and 36-48. The location of the actuator 4949 may be similar to the corresponding actuator in any of the above-mentioned embodiments that control the gap between the membrane 115 and the wicking pad 120.

In the example of FIGS. 50A and 50B, the configuration of the conjugate pad 110, the membrane 115, the wicking pad 120, and the locations of the actuators 4948 and 4949 are similar to the corresponding components of FIG. 48. With reference to 50A and 50B, each of the actuators 4948 and 4949 may be an electromagnet, such as, the electromagnets 3648 and 3649 of FIG. 48, a piezoelectric/piezoelectric stack actuator, such as the actuators 3831 and 3832 of FIG. 44, an electric motor, such as, the electric motor 530 of FIG. 5, etc., that may be configured to rotate the wheel 5080 or the wheel 5081.

As shown in the expanded view 5005, the magnet 4910 may include a first pole 4911 and a second pole 4912. The first and second poles may be north and south (or south and north) poles, respectively. The actuator 4948 may be connected (e.g., and without limitations, by a rotating shaft 5090) to the wheel 5080. The magnet 5020 may be positioned on one tip of the wheel 5080 and the magnet 5030 may be positioned another tip of the wheel 5080. For example, and without limitations, the magnets 5020 and 5030 may be located substantially on the opposite sides of a diagonal line that passes through the center of the wheel 5080. Each of the magnets 5020 and 5030 may, respectively, include first and second poles 5021-5022 and 5031-5032.

As shown in the expanded view 5006, the magnet 4940 may include a first pole 4941 and a second pole 4942. The first and second poles may be north and south (or south and north) poles, respectively. The actuator 4949 may be connected (e.g., and without limitations, by a rotating shaft 5091) to the wheel 5081. The magnet 5050 may be positioned on one tip of the wheel 5081 and the magnet 5060 may be positioned another tip of the wheel 5081. For example, and without limitations, the magnets 5050 and 5060 may be located substantially on the opposite sides of a diagonal line that passes through the center of the wheel 5081. Each of the magnets 5050 and 5060 may, respectively, include first and second poles 5051-5052 and 5061-5062.

FIGS. 50A-50B, as shown, include two operational steps S001 and S002. As illustrated in step S001, a gap 4791 may initially (e.g., at the start of a test) be maintained between the conjugate pad 110 and the membrane 115. As shown in the expanded view 5005, the actuator 4948 may be configured to initially keep the wheel 5080 in a first position, such that the first pole 5021 of the magnet 5020 is in proximity of the second pole 4912 of the magnet 4910. When the wheel 5080 is in the first position (as shown in step S001), the magnets 5020 and 4910 may attract each other and the gap 4791 between the membrane 115 and the conjugate pad 110 may be maintained.

As illustrated in the expanded view 5007 in step S002 (FIG. 50B), once the specified conjugation time is lapsed (e.g., specified by the NFC chip 590, received from the UI of the lateral flow assay device, received from an external device, etc.), the processor/controller (not shown) of the lateral flow assay device 5000 may send one or more signals to the actuator 4948 to rotate the wheel 5080 to a second position, such that the second pole 5032 of the magnet 5030 is in proximity of the second pole 4912 of the magnet 4910. When the wheel 5080 is in the second position (as shown in the expanded view 5007 in step S002), the magnets 5020 and 4910 may repel each other and the gap 4791 between the membrane 115 and the conjugate pad 110 may be closed and may make the membrane 115 to contact the conjugate pad 110 to allow the flow of the fluid material from the conjugate pad 110 to the membrane 115.

The processor/controller of the lateral flow assay device 5000 may send one or more signals to the actuator 4948 to move the wheel 5080 to the first position in order to open the gap 4791 between the membrane 115 and the conjugate pad 110. Repeatedly connecting and disconnecting the membrane 115 and the conjugate pad 110 may be used to control the flow of fluid material from the conjugate pad 110 into the membrane 115, as described above with reference to FIGS. 32-33.

In the embodiments that control a gap between the wicking pad 120 and the membrane 115 (e.g., the embodiment shown in FIGS. 50A-50B), the processor/controller of the lateral flow assay device 5000 may send one or more signals to the actuator 4949 to rotate the wheel 5081 between a first position and a second position in order to open or close the gap 4892 between the membrane 115 and the wicking pad 120. The gap 4892 may initially (e.g., at the start of a test) be either open or closed, depending on a particular test's requirement. For example, in the configuration of FIG. 50A, the gap 4892 may be initially open. The actuator 4949 may be configured to initially keep the wheel 5081 in the first position, such that the first pole 5051 of the magnet 5050 is in proximity of the second pole 4942 of the magnet 4940. When the wheel 5081 is in its first position (as shown in the expanded view 5006 in step S001), the magnets 4940 and 5050 may attract each other and the gap 4892 between the membrane 115 and the wicking pad 120 may be open.

The processor/controller of the lateral flow assay device 5000 may send one or more signals to the actuator 4949 to rotate the wheel 5081 to the second position, such that the second pole 5062 of the magnet 5060 is in proximity of the second pole 4942 of the magnet 4940. When the wheel 5081 is in its second position (as shown in the expanded view 5008 in step S002), the magnets 5060 and 4940 may repel each other and the gap 4892 between the membrane 115 and the wicking pad 120 may be closed and may make the membrane 115 to contact the wicking pad 120 to allow the flow of the fluid material from the membrane 115 to the wicking pad 120. Repeatedly connecting and disconnecting the membrane 115 and the wicking pad 120 may be used to control the flow of fluid material from the membrane 115 into the wicking pad 120.

It should be noted that the actuator 4948 of FIGS. 50A-50B may only require power when the wheel 5080 is to rotated from the first position to the second position or vice versa. When the wheel 5080 is stationary to either maintain the gap 4791 or to close the gap 4791, the actuator 4948 does not require power. Also, the actuator 4949 may only require power when the wheel 5081 is to rotated from the first position to the second position or vice versa. When the wheel 5081 is stationary to either maintain the gap 4892 or to close the gap 4892, the actuator 4949 does not require power.

The embodiment of FIGS. 50A-50B provides the technical advantage of saving the power of the lateral flow assay device's battery (or batteries). In some embodiments of the lateral flow assay devices of FIGS. 32-33 and 36-48 and 50A-50B, the processor/controller, the UI, the power source, the processor/controller circuit, and/or the NFC reader of the lateral flow assay device may be reusable for performing multiple tests for the same or different subjects (e.g., the same person or different persons). Using the actuators 4948-4949, the magnets 4910, 5020, 5030, 4940, 5050, and 5060, the wheels 5080-5081 to open and close the gaps between the membrane 115 and the conjugate pad 110 and/or to open and close the gaps between the membrane 115 and the wicking pad 120 in these configurations prolongs the age of the battery/batteries of the corresponding lateral flow assay devices and make the reusable portion of the these lateral flow assay devices to last for a longer periods of time and/or for performing more tests.

With reference to FIGS. 49A-49B and 50A-50B, two magnets, such as the magnets 4020 and 4030 or 5020 and 5030 may be installed on any moving element, such as the shaft 4971 of FIGS. 49A-49B or the wheel 5080 of FIGS. 50A-50B. An actuator may be configured to move the moving element from a first position to a second position. The actuator may be configured to linearly move a shaft or rotationally move a wheel. A magnet, such as the magnet 4910 may be installed on a pad such as the conjugate pad 110 or the membrane 115. The polarity and orientation of the magnet installed on a pad and the two corresponding magnets installed on a moving element that is located in the proximity of magnet on the pad may be configured such that at a first position of the moving element, one of the magnets on the moving element may attract the magnet on the pad, and at a second position of the moving element, the other magnet on the moving element may repel the magnet on the pad.

Depending on the position of the pad, the position of an actuator that moves the moving element, the polarity of the three magnets, and/or the orientation of the of the three magnets may be configured such that attracting the magnet on the pad may open the gap between the conjugate pad 110 and the membrane 115 and repelling the magnet on the pad may close the gap between the conjugate pad 110 and the membrane 115. Examples of this type of configuration are shown in FIGS. 49A-49B and 50A-50B.

Alternatively, the position of the actuator that moves the moving element, the polarity of the three magnets, and/or the orientation of the of the three magnets may be configured such that repelling the magnet on the pad may open the gap between the conjugate pad 110 and the membrane 115 and attracting the magnet on the pad may close the gap between the conjugate pad 110 and the membrane 115. Such a configuration may be achieved, for example, and without limitations, by changing the polarity of the magnet 4910 of FIGS. 49A-49B and 50A-50B, by changing the polarity of the magnets 4920 and 4930 of FIGS. 49A-49B, by changing the polarity of the magnets 5020 and 5030 of FIGS. 50A-50B, by moving the actuator 4948 of FIGS. 49A-49B and 50A-50B to the top of cartridge housing 3230, etc.

With further reference to FIGS. 49A-49B and 50A-50B, two magnets, such as the magnets 4050 and 4060 or 5050 and 5060 may be installed on any moving element, such as the shaft 4972 of FIGS. 49A-49B or the wheel 5081 of FIGS. 50A-50B. An actuator may be configured to move the moving element from a first position to a second position. The actuator may be configured to linearly move a shaft or rotationally move a wheel. A magnet, such as the magnet 4940 may be installed on a pad such as the membrane 115 or the wicking pad 120. The polarity and orientation of the magnet installed on a pad and the two corresponding magnets installed on a moving element that is located in the proximity of magnet on the pad may be configured such that at a first position of the moving element, one of the magnets on the moving element may attract the magnet on the pad, and at a second position of the moving element, the other magnet on the moving element may repel the magnet on the pad.

Depending on the position of the pad, the position of an actuator that moves the moving element, the polarity of the three magnets, and/or the orientation of the of the three magnets may be configured such that attracting the magnet on the pad may open the gap between the membrane 115 and the wicking pad 120, and repelling the magnet on the pad may close the gap between the membrane 115 and the wicking pad 120. Examples of this type of configuration are shown in FIGS. 49A-49B and 50A-50B.

Alternatively, the position of the actuator that moves the moving element, the polarity of the three magnets, and/or the orientation of the of the three magnets may be configured such that repelling the magnet on the pad may open the gap between the membrane 115 and the wicking pad 120, and attracting the magnet on the pad may close the gap between the membrane 115 and the wicking pad 120. Such a configuration may be achieved, for example, and without limitations, by changing the polarity of the magnet 4940 of FIGS. 49A-49B and 50A-50B, by changing the polarity of the magnets 4950 and 4960 of FIGS. 49A-49B, by changing the polarity of the magnets 5050 and 5060 of FIGS. 50A-50B, by moving the actuator 4949 of FIGS. 49A-49B and 50A-50B to the top of cartridge housing 3230, etc.

Several examples of a lateral flow assay device have been provided above with reference to FIGS. 32-33, 36-48, 49A-49B, and 50A-50B. It should be noted that the present embodiments are not limited to specific configuration and specific position of different components. For example, in the example of FIG. 32, the lateral flow assay device is configured such that the conjugate pad 110, the membrane 115, and the wicking pad 120 are positioned at the same level (e.g., positioned against the upper wall of the cartridge housing 3320). Alternatively, the lateral flow assay device may be configured with a mirror image configuration, where the conjugate pad 110, the membrane 115, and the wicking pad 120 are positioned at the same level on the floor of the cartridge housing 3320.

As another alternative, one or more of the conjugate pad 110, the membrane 115, and the wicking pad 120 may be positioned against the upper wall of the cartridge housing 3320 and the other of the conjugate pad 110, the membrane 115, and the wicking pad 120 may be positioned on the floor of the cartridge housing 3320. For example, in the configuration of FIG. 43, the membrane 115 is positioned against the upper wall of the cartridge housing 3320 and the conjugate pad 110 and the wicking pad 120 are positioned on the floor of the cartridge housing 3320. As another example, in the configuration of FIG. 48, the conjugate pad 110 and the wicking pad 120 are positioned against the upper wall of the cartridge housing 3320 and the membrane 115 is positioned on the floor of the cartridge housing 3320. As another example, in the configuration of FIG. 47, the conjugate pad 110 is positioned against the upper wall of the cartridge housing 3320, and the membrane 115 and the wicking pad 120 are positioned on the floor of the cartridge housing 3320. In this embodiment, there is no gap between the membrane 115 and the wicking pad 120.

In order to open and remove the gap between the conjugate pad 110 and the membrane 115 either one of the conjugate pad 110 or the membrane 115 may be moved against each other. In order to open and remove the gap between the membrane 115 and the wicking pad 120, either one of the membrane 115 or the wicking pad 120 may be moved against each other. For example, in the example of FIG. 42, the conjugate pad 110 and the wicking pad 120 are moved against the membrane 115, while in the example of FIG. 46, the membrane 115 is moved against the conjugate pad 110 and the wicking pad 120. Any of these moving configurations may be used for the lateral flow assay of the present embodiments.

Different embodiments may use different mechanisms for moving the conjugate pad 110, the membrane 115, and/or the wicking pad 120. For example, some embodiments may have a hole in the cartridge housing, as discussed above with reference to FIG. 32, to apply a force to push a shaft against either the conjugate pad 110 or the wicking pad 120 to move them against the membrane 115. The same technique may be used to move the membrane 115 against the conjugate pad 110 or the wicking pad 120. In some of the embodiments that use a shaft to move the conjugate pad 110, the membrane 115, and/or the wicking pad 120, a spring may be used to pull against the conjugate pad 110, the membrane 115, and/or the wicking pad 120 once the shaft is no longer applies the force. In some of the embodiments that use a shaft to move the conjugate pad 110, the membrane 115, and/or the wicking pad 120, the force of gravity may be used to pull against the conjugate pad 110, the membrane 115, and/or the wicking pad 120 once the shaft is no longer applies the force.

Some embodiments may include magnetic material on the backing of the conjugate pad 110, the membrane 115, and/or the wicking pad 120 and may use an actuator that generates a magnetic field to apply a force to pull either the conjugate pad 110 or the wicking pad 120 to move them against the membrane 115. The same technique may be used to move the membrane 115 against the conjugate pad 110 or the wicking pad 120. An example of the use of the magnetic material was described above with reference to FIG. 36. In some of the embodiments that magnetic material and a magnetic field to move the conjugate pad 110, the membrane 115, and/or the wicking pad 120, a spring may be used to pull against the conjugate pad 110, the membrane 115, and/or the wicking pad 120 once the shaft is no longer applies the force. An example of the use of the magnetic material was described above with reference to FIG. 36. In some of the embodiments that use a shaft to move the conjugate pad 110, the membrane 115, and/or the wicking pad 120, the force of gravity may be used to pull against the conjugate pad 110, the membrane 115, and/or the wicking pad 120 once the shaft is no longer applies the force.

Some embodiments may include a magnet on the backing of the conjugate pad 110, the membrane 115, and/or the wicking pad 120 and may use an actuator that generates a magnetic field to attract or repel the magnet. The lateral flow assay device may be configured (e.g., by positioning the conjugate pad 110 and the membrane 115, by positioning the magnet, by positioning the actuator, and/or by configuring the polarity of the magnet and the actuator's magnetic field) such that attracting/repelling the magnet may either respectively open/close or close/open the gap between the conjugate pad 110 and the membrane 115. The lateral flow assay device may be configured (e.g., by positioning the membrane 115 and the wicking pad 120, by positioning the magnet, by positioning the actuator, and/or by configuring the polarity of the magnet and the actuator's magnetic field) such that attracting/repelling the magnet may either respectively open/close or close/open the gap between the membrane 115 and the wicking pad 120. Examples of such configurations are provided above with reference to FIGS. 39-42 and 46-48, which may be applied to different configurations of the lateral flow assays of the present embodiments.

In some embodiments, instead of an actuator that generates a magnetic field for moving a first magnet installed on the conjugate pad 110, the membrane 115, or the wicking pad 120, a shaft may be moved, between two positions, in the proximity of the magnet. A second and a third magnet may be installed on each end of the shaft. The polarity of the first, second, and the third magnets may be configured such that in the first position of the shaft, one of the magnets on the shaft may attract the first magnet, and in the second position of the shaft, the other magnet on the shaft may repel the first magnet. An example of this mechanism is provided above with reference to FIGS. 49A-49B. This mechanism may be applied to any of the configurations of the lateral flow assays of the present embodiments.

In some embodiments, instead of an actuator that generates a magnetic field for moving a first magnet installed on the conjugate pad 110, the membrane 115, or the wicking pad 120, a wheel may be rotated, between two positions, in the proximity of the magnet. A second and a third magnet may be installed on the wheel (e.g., and without limitations, in substantially opposite sides of the center of the wheel). The polarity of the first, second, and the third magnets may be configured such that in the first position of the wheel, one of the magnets on the wheel may attract the first magnet, and in the second position of the wheel, the other magnet on the wheel may repel the first magnet. An example of this mechanism is provided above with reference to FIGS. 50A-50B. This mechanism may be applied to any of the configurations of the lateral flow assays of the present embodiments.

The lateral flow assays of the present embodiments may use different types of actuators. The actuators that are used to move a shaft or a wheel may be, for example, and without limitations, a solenoid (as described above with reference to FIGS. 32-33), a piezoelectric actuator or a piezoelectric actuator stack (as described above with reference to FIG. 32-33), an electric motor (e.g., a servo motor, etc.) as described above with reference to FIG. 5. These actuators may be used in any of the configurations of the lateral flow assays of the present embodiments that may require to move a moving element, such as, shaft or a wheel. These actuators may be configured to receive one or more signals from the processor/controller of the lateral flow assay device to move the moving elements from one position to another position.

The actuators that are used to generate a magnetic field may be, for example, and without limitations, an electromagnet, as described above with reference to FIGS. 36-37 and 39-40. These actuators may be used in any of the configurations of the lateral flow assays of the present embodiments that may require an actuator to generate a magnetic field. These actuators may be configured to receive one or more signals from the processor/controller of the lateral flow assay device to generate and/or to change the polarity of the magnetic field.

With reference to FIGS. 20-31, the exemplary embodiments were described with reference to removing the gap between the pads at once. For example, FIG. 21 was described by moving down the section 2106 of the lateral flow device's housing to remove the gap 2050. In other embodiments, the gap 2050 may be repeatedly opened and closed by moving the section 2106 of the housing up and down in order to repeatedly bring the conjugate pad 110 and the membrane 115 in touch with each other and then separate them from each other. Repeatedly connecting and disconnecting the conjugate pad 110 and the membrane 115 provides the technical advantage of controlling the flow of fluid material from the conjugate pad 110 into the membrane 115.

The number of times the moving section 2106 is moved up or down, the duration that the moving section 2106 stays up or down, and the time between the moving up and down actions may control the amount of contact between the conjugate pad 110 and the membrane 115. The amount of contact between the conjugate pad 110 and the membrane 115 may in turn be used by the processor of the lateral flow assay device to control the flow time (the time would take for the fluid material to travel the length of the membrane 115, going over the test line 125 and the control line 135 to reach the wicking pad 120).

With reference to FIG. 28, a similar technique may be used to repeatedly move the sections 2806, 2807, and/or 2808 up or down to control the time the fluid material comes in contact with the test line 125, the time the fluid material comes in contact with the control line 130, and/or the flow rate across the flow path of the lateral flow assay device.

With reference to FIG. 23, the pole 2310 was described to moving down to remove the gap 2050. In other embodiments, the gap 2050 may be repeatedly opened and closed by moving the pole 2310 up and down in order to repeatedly bring the conjugate pad 110 and the membrane 115 in touch with each other and then separate them from each other. Repeatedly connecting and disconnecting the conjugate pad 110 and the membrane 115 may be used to control the flow of fluid material from the conjugate pad 110 into the membrane 115.

With reference to FIG. 29, a similar technique may be used to repeatedly move the poles 2310, 2911, and/or 2912 up or down, which provides the technical advantage of controlling the time the fluid material comes in contact with the test line 125, the time the fluid material comes in contact with the control line 130, and/or the flow rate across the flow path of the lateral flow assay device.

One advantage of using a servo or a linear actuator for moving the shaft that pushes the spring 3241 (and/or 3242) is that the position of the shaft 3221 (and/or 3222) may be accurately controlled, which in turn results in the technical advantage of being able to control the proximity of the overlap area of the conjugate pad 110 and the membrane 115 (and/or, similarly, the overlap area of the membrane 115 and the wicking pad 120).

The accurate control over the proximity, which also controls the amount of pressure between the two pads at the overlap area, is another independent parameter in controlling the flow rate and flow time. For the embodiments of the lateral flow assays that use this feature, the set of the calibration tables or calibration curves may be generated for each distinct position of the servo. Without limitations, the distinct positions of the servo shaft may usually be few in practical cases. If a servo or linear actuator is used on both the conjugate pad side as well of the wicking pad side of the device, then there may be two sets of positions for which the calibration tables or curves need to be generated. For example, if the distinct positions of the servo are limited to three positions for each side, there will be nine different combination of the two positions resulting in nine different sets of calibration tables or curves.

In some applications of the lateral flow assay testing, there might be a need for a preparation step before the solution may be applied to the strip. These preparation steps often require time and cannot be integrated into conventional lateral flow assay test devices. Using the controlled conjugate and controlled flow time techniques of the present embodiments, the preparation step may be included and integrated in the first stage of the device either at the conjugate pad or by inserting another step prior to the conjugate pad controlled by a similar pulsing flow control mechanism as is used in the conjugate pad.

As an example, a test for a virus may require a lysing step where the sample is mixed with a lysing solution and incubated for a certain period of time. Such a lysing step may be integrated in the lateral flow assay devices of some embodiments. For example, in any of the lateral flow assay device described above with reference to FIGS. 1-3, 12-21, 23, 25, 27-29, 31-33, and 36-50B, both the sample solution and the lysing solution may be applied to the sample pad (or to the conjugate pad, when the lateral flow assay device does not include a sample pad). The time from the beginning of the test to the time that the conjugate pad is connected to the membrane may be programmed to allow enough time for both lysing and binding to conjugated antibodies to take place.

In alternate embodiments, the lysing step may take place on a separate pad, referred herein as the preparation pad, that is located before the conjugate pad in the flow path. The preparation pad may be initially separated from the conjugate pad and the time from the beginning of the test to the time that the preparation pad is connected to the conjugate pad may be programmed to allow enough time for both lysing to take place. The preparation pad may be connected to the conjugate pad with similar mechanisms described above with reference to FIGS. 1-3, 12-21, 23, 25, 27-29, 31-33, and 36-50B that control the connection of the conjugate pad to the membrane.

The flow control mechanism of the present embodiments is conceptually a programmable valve and a programmable pump combined embedded in a paper-based and/or membrane-based capillary flow system. As an alternative non-electronic, mechanical and battery-less approach to control the valve mechanism of the present embodiments, a wound up clock mechanism may be used to control the timing of the opening and closing of the gap between the conjugate pad and the membrane, to control the timing of the opening and closing of the gap between the membrane and the wicking pad, and/or to control the timing of the opening and closing of the gap between the preparation pad and the conjugate pad.

A spiral spring similar to what is used in wound up clock mechanisms (and many wound up toys) may be compressed, wound up, and locked in position. Once the lock is released (e.g., with a start button on the test cartridge), the spring transfers its energy to a rotating wheel through a set of gears whose ratios determine the rotation speed of the wheel. A set of pegs distributed around the periphery of the wheel activate a spring-loaded push rod that may close and open the gap similar to the actuators described above. The timing of the activation may be determined by the speed of the wheel, the number of pegs on the wheel, and the width of each peg. For each particular lateral flow assay test type, these timing parameters may be fixed once the parameters are optimized for that test. The fixed timing parameters may be used to determine the physical parameters of the mechanical wound up structure which may be built into the cassette housing of the lateral flow assay device. Among the advantages of this mechanical approach integrated on the lateral flow assay device's cassette housing are low cost, battery-less operation, and no need for any electronic components.

In addition to, or in lieu of the opening 215 (FIG. 2) for viewing the test line 125 and/or the opening 220 for viewing the control line 130, the lateral flow assay device of the present embodiments (e.g., as described above with reference to FIGS. 1-3, 12-21, 23, 25, 27-29, 31-33, and 36-50B) may include a sensor to read the test results. For example, in the embodiments that the label includes gold particles, the sensor may be a light sensor (or photo sensor) that may read the intensity of light reflected from the test line 125, and/or the light reflected from the control line 130. The reading may be a quantitative reading. The light sensor, in some embodiments, may be included in a miniaturized camera. The reading, in some embodiments, may be converted to a positive or negative result by the microcontroller.

The sensor, in some embodiments, may be integrated with the lateral flow assay device. For example, the sensor may be installed on the cartridge of the lateral flow assay device over the test line and/or the control line. The sensor, in some embodiments, may be part of an external device. For example, and without limitations, the sensor may be a photo sensor integrated in an external electronic device, such as a smartphone.

The processor/controller of the lateral flow assay device may receive the test results from the sensor and may receive location of the lateral flow assay device from a global positioning system (GPS) receiver of the lateral flow assay device. The processor/controller may transmit, through the transceiver(s), the location of the lateral flow assay device where a test is performed and test results to one or more external electronic devices.

III. Computer System

Some of the above-described features and applications are implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

FIG. 51 conceptually illustrates an electronic system 5100 with which some embodiments of the invention (e.g., the microprocessors, the microcontrollers, the controller, the client devices described above) are implemented. The electronic system 5100 can be used to execute any of the control, virtualization, or operating system applications described above. The electronic system 5100 may be a computer (e.g., desktop computer, personal computer, tablet computer, server computer, mainframe, blade computer etc.), phone, PDA, or any other sort of electronic device. Such an electronic system includes various types of computer readable media and interfaces for various other types of computer readable media. Electronic system 5100 includes a bus 5105, processing unit(s) 5110, a system memory 5120, a read-only memory (ROM) 5130, a permanent storage device 5135, input devices 5140, and output devices 5145.

The bus 5105 collectively represents all system, peripheral, and chipset buses that communicatively connect the numerous internal devices of the electronic system 5100. For instance, the bus 5105 communicatively connects the processing unit(s) 5110 with the read-only memory 5130, the system memory 5120, and the permanent storage device 5135.

From these various memory units, the processing unit(s) 5110 retrieve instructions to execute and data to process in order to execute the processes of the invention. The processing unit(s) may be a single processor or a multi-core processor in different embodiments.

The read-only-memory 5130 stores static data and instructions that are needed by the processing unit(s) 5110 and other modules of the electronic system. The permanent storage device 5135, on the other hand, is a read-and-write memory device. This device is a non-volatile memory unit that stores instructions and data even when the electronic system 5100 is off. Some embodiments of the invention use a mass-storage device (such as a magnetic or optical disk and its corresponding disk drive) as the permanent storage device 5135.

Other embodiments use a removable storage device (such as a flash drive, Universal Serial Bus (USB) drive etc.) as the permanent storage device. Like the permanent storage device 5135, the system memory 5120 is a read-and-write memory device. However, unlike storage device 5135, the system memory is a volatile read-and-write memory, such as random access memory. The system memory stores some of the instructions and data that the processor needs at runtime. In some embodiments, the invention's processes are stored in the system memory 5120, the permanent storage device 5135, and/or the read-only memory 5130. From these various memory units, the processing unit(s) 5110 retrieve instructions to execute and data to process in order to execute the processes of some embodiments.

The bus 5105 also connects to the input and output devices 5140 and 5145. The input devices enable the user to communicate information and select commands to the electronic system. The input devices 5140 include alphanumeric keyboards and pointing devices (also called "cursor control devices"). The output devices 5145 display images generated by the electronic system. The output devices include printers and display devices, such as cathode ray tubes (CRT) or liquid crystal displays (LCD). Some embodiments include devices, such as a touchscreen, that function as both input and output devices.

Finally, as shown in FIG. 51, bus 5105 also couples electronic system 5100 to a network 5125 through a network adapter (not shown). In this manner, the computer can be a part of a network of computers (such as a local area network ("LAN"), a wide area network ("WAN"), an Intranet, or a network of networks, such as the Internet. Any or all components of electronic system 5100 may be used in conjunction with the invention.

Some embodiments include electronic components, such as microprocessors, storage, and memory, that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some embodiments are performed by one or more integrated circuits, such as application specific integrated circuits (ASICs) or field programmable gate arrays (FPGAs). In some embodiments, such integrated circuits execute instructions that are stored on the circuit itself.

As used in this specification, the terms "computer," "server," "processor," "processing unit," "controller," and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to tangible, physical objects that store information in a form that is readable by a computer. These terms exclude any wireless signals, wired download signals, and any other ephemeral or transitory signals.

While the invention has been described with reference to numerous specific details, one of ordinary skill in the art will recognize that the invention can be embodied in other specific forms without departing from the spirit of the invention. In addition, a number of the figures (including FIGS. 11 and 26) conceptually illustrate processes. The specific operations of these processes may not be performed in the exact order shown and described. The specific operations may not be performed in one continuous series of operations, and different specific operations may be performed in different embodiments. Furthermore, the process could be implemented using several sub-processes, or as part of a larger macro process.

In a first aspect, a lateral flow assay device, comprises: a conjugate pad configured to receive a quantity of fluid; a membrane comprising a test line for determining whether the fluid comprises a target analyte; and a removable physical barrier, wherein, in a first state of the lateral flow assay device, the removable physical barrier is between the conjugate pad and the membrane and prevents the fluid from flowing from the conjugate pad into the membrane, and wherein, in a second state of the lateral flow assay device, the removable physical barrier is removed from between the conjugate pad and the membrane causing the conjugate pad to be connected to the membrane and allowing the fluid to flow from the conjugate pad into the membrane and the test line by capillary action.

In an embodiment of the first aspect, the lateral flow assay device further comprises at least a first magnet connected to the removable physical barrier for pulling out the removable physical barrier from between the conjugate pad and the membrane by a second magnet external to the lateral flow assay device.

In another embodiment of the first aspect, the conjugate pad contains an antibody for binding to the target analyte, wherein the target analyte and the antibody require a first time period to bind, the lateral flow assay device further comprises at least a first magnet connected to the removable physical barrier; an electromagnet comprising a coil and a core, wherein the core acts as a magnet when a current is passed through the coil, wherein the core does not act as a magnet when no current is passed through the coil, wherein the core is configured to stay at a specific distance from the first magnet at a beginning of an assay test, and wherein the core is configured to attract the first magnet and pull the removable physical barrier from between the conjugate pad and the membrane when the core acts as a magnet and the core is at the specific distance from the first magnet; and a processing unit configured to: disconnect the current from the coil prior to the beginning of the assay test; and after the first time period from the beginning of the assay test, connecting the current to the coil to cause the core to act as a magnet and pull the first magnet and the movable physical barrier from between the conjugate pad and the membrane.

In another embodiment of the first aspect, the fluid is transported from the conjugate pad to the membrane by capillary action, and the first time period is greater than a time that takes for the fluid to be transported by capillary action from the sample pad to the conjugate pad and from the conjugate pad to the membrane.

In another embodiment of the first aspect, the lateral flow assay device further comprises at least one hole on the removable physical barrier for pulling out the removable physical barrier from between the conjugate pad and the membrane by at least one hook engaged into the at least one hole.

In another embodiment of the first aspect, the lateral flow assay device further comprises at least one hole on the removable physical barrier; and at least one string going through the at least one pole for pulling out the removable physical barrier from between the conjugate pad and the membrane by at least one hook engaged into the at least one string.

In another embodiment of the first aspect, the lateral flow assay device further comprises at least one grove on the removable physical barrier for pulling out the removable physical barrier from between the conjugate pad and the membrane.

In another embodiment of the first aspect, wherein the removable physical barrier is a first removable physical barrier, and wherein the membrane is a first membrane, the lateral flow assay device further comprises: a second membrane comprising a control line for determining whether the lateral flow assay device has successfully analyzed the fluid; and a second removable physical barrier, wherein, in a third state of the lateral flow assay device, the second removable physical barrier is between the first and second membranes and preventing the fluid from flowing from the first membrane and the test line into the second membrane, and wherein, in a fourth state of the lateral flow assay device, the second removable physical barrier is removed from between the first and the second membranes causing the first membrane to be connected to the second membrane and allowing the fluid to flow from the first membrane and the test line into the second membrane and the control line by capillary action.

In another embodiment of the first aspect, the lateral flow assay device further comprises: a wicking pad; and a third removable physical barrier, wherein, in a fifth state of the lateral flow assay device, the third removable physical barrier is between the second membrane and the wicking pad and preventing the fluid from flowing from the second membrane and the control line into the wicking pad, and wherein, in a sixth state of the lateral flow assay device, the third removable physical barrier is removed from between the second membrane and the wicking pad causing the second membrane to be connected to the wicking pad and allowing the fluid to flow from the second membrane and the control line into the wicking pad by capillary action.

In another embodiment of the first aspect, the lateral flow assay device further comprises a sample pad fluidically connected to the conjugate pad, wherein the sample is configured to receive said quantity of fluid and transport the fluid to the conjugate pad by capillary action.

In another embodiment of the first aspect, the lateral flow assay device further comprises a housing comprising a housing bed, where a portion of the conjugate pad and a portion of the membrane are located on the housing bed, wherein the housing bed has a permanent gap, wherein in said first state of the lateral flow assay device, the permanent gap in the housing bed prevents the fluid from leaking from the conjugate pad into the membrane.

In a second aspect, a lateral flow assay device, comprises: a sample pad for receiving a quantity of fluid; a conjugate pad fluidically connected to the sample pad, wherein the sample pad is configured to transport the fluid to the conjugate pad by capillary action; and a membrane comprising a test line for determining whether the fluid comprises a target analyte, wherein, in a first state of the lateral flow assay device, the lateral flow assay device is configured with a removable gap between the conjugate pad and the membrane, the removable gap substantially filled with air and preventing the fluid from flowing from the conjugate pad into the membrane, and wherein, in a second state of the lateral flow assay device, the removable gap is removed from between the conjugate pad and the membrane causing the conjugate pad to come in contact with the membrane and allowing the fluid to flow from the conjugate pad into the membrane and the test line by capillary action.

In an embodiment of the second aspect, the lateral flow assay device further comprises: a housing covering at least a portion of the conjugate pad and the membrane, wherein the housing comprises a movable section comprising a side attached to at least a portion of the conjugate pad, wherein, in the first state of the lateral flow assay device, the movable section creates the removable gap by keeping the conjugate pad and the membrane separate, and wherein, in the second state of the lateral flow assay device, the movable section pushes the conjugate pad towards the membrane causing the conjugate pad and the membrane to come in contact with each other.

In another embodiment of the second aspect, the side of the movable part is attached to the conjugate pad by an adhesive substance.

In another embodiment of the second aspect, the lateral flow assay device further comprises: a set of one or more holes going through the conjugate pad and the membrane; and a set of one or more movable poles, each movable pole going through a hole in the set of holes, wherein, in the first state of the lateral flow assay device, the set of movable poles is connected to the conjugate pad and creates the removable gap by keeping the conjugate pad and the membrane separate, and wherein, in the second state of the lateral flow assay device, the set of one or more movable poles is moved to remove the removable gap and connect the conjugate pad and the membrane.

In another embodiment of the second aspect, the set of movable poles is connected to the conjugate pad by an adhesive substance.

In another embodiment of the second aspect, wherein the removable gap is a first removable gap, and wherein the membrane is a first membrane, the lateral flow assay device further comprises: a second membrane comprising a control line for determining whether the lateral flow assay device has successfully analyzed the fluid, wherein, in a third state of the lateral flow assay device, the lateral flow assay device is configured with a second removable gap between the first membrane and the second membrane, the second removable gap substantially filled with air and preventing the fluid from flowing from the first membrane and the test line into the second membrane and the control line, and wherein in a fourth state of the lateral flow assay device, the second removable gap is removed from between the first membrane and the second membrane causing the first membrane to be connected to the second membrane and allowing the fluid to flow from the first membrane and the test line into the second membrane and the control line by capillary action.

In another embodiment of the second aspect, the lateral flow assay device further comprises: a housing covering at least a portion of the conjugate pad and the first and second membranes, wherein the housing comprises a movable section comprising a side attached to at least a portion of the second membrane, wherein, in the third state of the lateral flow assay device, the movable section creates the second removable gap by keeping the second membrane and the first membrane separate, and wherein, in the fourth state of the lateral flow assay device, the movable section pushes the second membrane towards the first membrane causing the second membrane and the first membrane to connect to each other.

In another embodiment of the second aspect, the lateral flow assay device further comprises: a set of one or more holes going through the first and second membranes; and a set of one or more movable poles, each movable pole going through a hole in the set of holes, wherein, in the third state of the lateral flow assay device, the set of movable poles is connected to the second membrane and creates the second removable gap by keeping the first and second membranes separate, and wherein, in the fourth state of the lateral flow assay device, the set of one or more movable poles is moved to remove the second removable gap and connect the first and second membranes.

In another embodiment of the second aspect, the lateral flow assay device further comprises: a wicking pad, wherein, in a fifth state of the lateral flow assay device, the lateral flow assay device is configured with a third removable gap between the wicking pad and the second membrane, the third removable gap substantially filled with air and preventing the fluid from flowing from the second membrane and the control line into the wicking pad, and wherein, in a sixth state of the lateral flow assay device, the third gap is removed from between the second membrane and the wicking pad causing the second membrane to be connected to the wicking pad and allowing the fluid to flow from the second membrane and the control line into the wicking pad by capillary action.

In another embodiment of the second aspect, the lateral flow assay device further comprises: a housing covering at least a portion of the second membrane and the wicking pad, wherein the housing comprises a movable section comprising a side attached to at least a portion of the wicking pad, wherein, in the fifth state of the lateral flow assay device, the movable section creates the third removable gap by keeping the wicking pad separate from the second membrane, and wherein, in the sixth state of the lateral flow assay device, the movable section pushes the wicking pad towards the second membrane causing the wicking pad and the second membrane to connect to each other.

In another embodiment of the second aspect, the lateral flow assay device further comprises: a set of one or more holes going through the second membrane and the wicking pad; and a set of one or more movable poles, each removable pole going through a hole in the set of holes, wherein, in the fifth state of the lateral flow assay device, the set of movable poles is connected to the wicking pad and creating the third removable gap by keeping the wicking pad and the second membrane separate, and wherein, in the sixth state of the lateral flow assay device, the set of one or more movable poles is moved to remove the third removable gap and connect the wicking pad and the second membrane.

In a third aspect, a lateral flow assay device, comprises: a sample pad for receiving a quantity of fluid; a conjugate pad fluidically connected to the sample pad, wherein the sample pad is configured to transport the fluid to the conjugate pad by capillary action, wherein the conjugate pad contains an antibody for binding to the target analyte, and wherein the target analyte and the antibody require a first time period to bind; a membrane comprising a test line for determining whether the fluid comprises a target analyte; a removable physical barrier; at least a first magnet connected to the removable physical barrier; a processing unit; and an electromagnet comprising a coil and a core, wherein the core acts as a magnet when a current is passed through the coil, wherein the core does not act as a magnet when no current is passed through the coil, wherein the core is configured to stay at a specific distance from the first magnet at a beginning of an assay test, and wherein the core is configured to attract the first magnet and pull the removable physical barrier from between the conjugate pad and the membrane when the core acts as a magnet and the core is at the specific distance from the first magnet, wherein the removable physical barrier is configured to stay between the conjugate pad and the membrane at the beginning of the assay test, preventing the fluid from flowing from the conjugate pad into the membrane, wherein the processing unit is configured to: disconnect the current from the coil prior to the beginning of the assay test; and after the first time period from the beginning of the assay test, connecting the current to the coil to cause the core to act as a magnet and pull the first magnet and the movable physical barrier from between the conjugate pad and the membrane, wherein, when the removable physical barrier is pulled from between the conjugate pad and the membrane, the conjugate pad is connected to the membrane, allowing the fluid to flow from the conjugate pad into the membrane and the test line by capillary action.

In an embodiment of the third aspect, the first time period is greater than a time that takes for the fluid to be transported by capillary action from the sample pad to the conjugate pad and from the conjugate pad to the membrane.

In a fourth aspect, a system for performing an assay test comprises: a lateral flow assay device; an electromagnet; and a processing unit, wherein the lateral flow assay device comprises: a sample pad for receiving a quantity of fluid; a conjugate pad fluidically connected to the sample pad, wherein the sample pad is configured to transport the fluid to the conjugate pad by capillary action, wherein the conjugate pad contains an antibody for binding to the target analyte, and wherein the target analyte and the antibody require a first time period to bind; a membrane comprising a test line for determining whether the fluid comprises a target analyte; a removable physical barrier; and at least a first magnet connected to the removable physical barrier; wherein the electromagnet comprises a coil and a core, wherein the core acts as a magnet when a current is passed through the coil, wherein the core does not act as a magnet when no current is passed through the coil, wherein the core is configured to stay at a specific distance from the first magnet at a beginning of the assay test, and wherein the core is configured to attract the first magnet and pull the removable physical barrier from between the conjugate pad and the membrane when the core acts as a magnet and the core is at the specific distance from the first magnet; wherein the removable physical barrier is configured to stay between the conjugate pad and the membrane at the beginning of the assay test, preventing the fluid from flowing from the conjugate pad into the membrane, wherein the processing unit is configured to: disconnect the current from the coil prior to the beginning of the assay test; and after the first time period from the beginning of the assay test, connecting the current to the coil and causing the core to act as a magnet and pull the first magnet and the movable physical barrier from between the conjugate pad and the membrane, and wherein, when the removable physical barrier is pulled from between the conjugate pad and the membrane, the conjugate pad is connected to the membrane, allowing the fluid to flow from the conjugate pad into the membrane and the test line by capillary action.

In an embodiment of the fourth aspect, the first time period is greater than a time that takes for the fluid to be transported by capillary action from the sample pad to the conjugate pad and from the conjugate pad to the membrane.

In a fifth aspect, a lateral flow assay device, comprises: a conjugate pad configured to receive a quantity of fluid after a start of a test, the conjugate pad configured to move the fluid by capillary action; a membrane comprising a test line for determining whether the fluid comprises a target analyte, the membrane configured to move the fluid by capillary action; a backing connected to the membrane; a first magnet attached to the backing of the membrane, the first magnet comprising a first pole and a second pole; a moving element; a second magnet connected to the moving element, the second magnet comprising a first pole and a second pole; a third magnet connected to the moving element, the third magnet comprising a first pole and a second pole; an actuator connected to the connected to the moving element; and a processor. The actuator is configured to receive one or more signals to move the moving element to a first position such that the first pole of the second magnet attracts the second pole of the first magnet to open a gap between the membrane and the conjugate pad. The actuator and the moving element are configured to keep the moving element at the first position prior to the start of the test. The actuator is configured to receive one or more signals to move the moving element to a second position such that the second pole of the third magnet repels the second pole of the first magnet to close the gap between the membrane and the conjugate pad.

The processor is configured to: receive a signal indicating the start of the test; and send one or more signals after the start of the test to the actuator to move the moving element between the first and second positions to open and close the gap between the membrane and the conjugate pad a plurality of times to control an amount of time that the fluid travels across the membrane.

In an embodiment of the fifth aspect, the moving element is a shaft and the actuator is configured to move the shaft in a linear direction between the first and second positions.

In another embodiment of the fifth aspect, the moving element is a wheel, wherein the actuator is configured to move the wheel between the first and second positions by applying a rotational movement to the wheel.

In another embodiment of the fifth aspect, the actuator is a first actuator, and the moving element is a first moving element. The lateral flow assay device further comprises: a wicking pad; a backing connected to the wicking pad; a fourth magnet attached to the backing of the membrane, the fourth magnet comprising a first pole and a second pole; a second moving element; a fifth magnet connected to the second moving element, the fifth magnet comprising a first pole and a second pole; a sixth magnet connected to the second moving element, the sixth magnet comprising a first pole and a second pole; and a second actuator connected to the second moving element. The second actuator is configured to receive one or more signals to move the second moving element to a first position of the second moving element such that the first pole of the fifth magnet attracts the second pole of the second magnet to open a gap between the membrane and the wicking pad. The second actuator is configured to receive one or more signals to move the second moving element to a second position of the second moving element such that the second pole of the sixth magnet repels the second pole of the second magnet to close the gap between the membrane and the wicking pad. The processor is configured to: send one or more signals after the start of the test to the second actuator to move the second moving element between the first and second positions of the second moving element to open and close the gap between the membrane and the wicking pad a plurality of times to control an amount of time that the fluid travels from the membrane into the wicking pad.

In a sixth aspect, a lateral flow assay device, comprises: a conjugate pad configured to receive a quantity of fluid after a start of a test, the conjugate pad configured to move the fluid by capillary action; a membrane comprising a test line for determining whether the fluid comprises a target analyte, the membrane configured to move the fluid by capillary action; a backing connected to the membrane; a first magnet attached to the backing of the membrane, the first magnet comprising a first pole and a second pole; a moving element; a second magnet connected to the moving element, the second magnet comprising a first pole and a second pole; a third magnet connected to the moving element, the third magnet comprising a first pole and a second pole; an actuator connected to the connected to the moving element; and a processor. The actuator is configured to receive one or more signals to move the moving element to a first position such that the second pole of the second magnet repels the second pole of the first magnet to open a gap between the membrane and the conjugate pad. The actuator and the moving element are configured to keep the moving element at the first position prior to the start of the test. The actuator is configured to receive one or more signals to move the moving element to a second position such that the first pole of the third magnet attracts the second pole of the first magnet to close the gap between the membrane and the conjugate pad. The processor is configured to: receive a signal indicating the start of the test; and send one or more signals after the start of the test to the actuator to move the moving element between the first and second positions to open and close the gap between the membrane and the conjugate pad a plurality of times to control an amount of time that the fluid travels across the membrane.

In an embodiment of the sixth aspect, the moving element is a shaft and the actuator is configured to move the shaft in a linear direction between the first and second positions.

In another embodiment of the sixth aspect, the moving element is a wheel, wherein the actuator is configured to move the wheel between the first and second positions by applying a rotational movement to the wheel.

In another embodiment of the sixth aspect, the actuator is a first actuator, and the moving element is a first moving element. The lateral flow assay device further comprises: a wicking pad; a backing connected to the wicking pad; a fourth magnet attached to the backing of the membrane, the fourth magnet comprising a first pole and a second pole; a second moving element; a fifth magnet connected to the second moving element, the fifth magnet comprising a first pole and a second pole; a sixth magnet connected to the second moving element, the sixth magnet comprising a first pole and a second pole; and a second actuator connected to the second moving element. The second actuator is configured to receive one or more signals to move the second moving element to a first position of the second moving element such that the first pole of the fifth magnet attracts the second pole of the second magnet to open a gap between the membrane and the wicking pad. The second actuator is configured to receive one or more signals to move the second moving element to a second position of the second moving element such that the second pole of the sixth magnet repels the second pole of the second magnet to close the gap between the membrane and the wicking pad. The processor is configured to: send one or more signals after the start of the test to the second actuator to move the second moving element between the first and second positions of the second moving element to open and close the gap between the membrane and the wicking pad a plurality of times to control an amount of time that the fluid travels from the membrane into the wicking pad.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A lateral flow assay device, comprising:
a conjugate pad configured to receive a quantity of fluid after a start of a test, the conjugate pad configured to move the fluid by capillary action;
a membrane comprising a test line for determining whether the fluid comprises a target analyte, the membrane configured to move the fluid by capillary action;
a backing connected to the membrane;
a first magnet fixedly attached to the backing of the membrane, the first magnet comprising a first north pole and a second south pole;
a shaft connected to a second magnet and a third magnet, the second magnet comprising a north pole and a south pole, and positioned on the shaft such that the north pole of the second magnet is closer to the first magnet than the south pole of the second magnet, the third magnet comprising a north pole and a south pole, and positioned on the shaft such that the south pole of the third magnet is closer to the first magnet than the north pole of the third magnet;
an actuator connected to the shaft;
  wherein the actuator is configured to receive one or more signals to move the shaft to a first position such that the north pole of the second magnet attracts the south pole of the first magnet to open a gap between the membrane and the conjugate pad, wherein the actuator is configured to keep the shaft at the first position prior to the start of the test; and
  wherein the actuator is configured to receive one or more signals to move the shaft to a second position such that the south pole of the third magnet repels the south pole of the first magnet to close the gap between the membrane and the conjugate pad; and
a processor configured to:
  receive a signal indicating the start of the test; and
  send one or more signals after the start of the test to the actuator to move the shaft between the first and second positions to open and close the gap between the membrane and the conjugate pad a plurality of times to control an amount of time that the fluid travels across the membrane.

2. The lateral flow assay device of claim 1, wherein the actuator is configured to move the shaft in a linear direction between the first and second positions.

3. The lateral flow assay device of claim 1,
wherein the processor is configured to receive a conjugate time indicating an amount of time required for the fluid to remain on the conjugate pad prior to the membrane making contact with the conjugate pad; and
wherein the processor is configured to generate the one or more signals to change a direction of a current received by the actuator after determining that the conjugate time has elapsed since the start of the test.

4. The lateral flow assay device of claim 1, wherein the actuator is a first actuator, and wherein the shaft is a first shaft, the lateral flow assay device further comprising:
a wicking pad;
a backing connected to the wicking pad;
a fourth magnet attached to the backing of the membrane, the fourth magnet comprising a north pole and a south pole;
a second shaft connected to a fifth magnet and a sixth magnet, the fifth magnet comprising a north pole and a south pole, and positioned on the second shaft such that the north pole of the fifth magnet is closer to the fourth magnet than the south pole of the fifth magnet, the sixth magnet comprising a north pole and a south pole, and positioned on the second shaft such that the south pole of the sixth magnet is closer to the fourth magnet than the north pole of the sixth magnet; and
a second actuator connected to the second shaft;
  wherein the second actuator is configured to receive one or more signals to move the second shaft to a first position of the second shaft such that the north pole of the fifth magnet attracts the south pole of the fourth magnet to open a gap between the membrane and the wicking pad;
  wherein the second actuator is configured to receive one or more signals to move the second shaft to a second position of the second shaft such that the south pole of the sixth magnet repels the south pole of the fourth magnet to close the gap between the membrane and the wicking pad;
wherein the processor is configured to:
  send one or more signals after the start of the test to the second actuator to move the second shaft between the first and second positions of the second shaft to open and close the gap between the membrane and the wicking pad a plurality of times to control an amount of time that the fluid travels from the membrane into the wicking pad.

5. The lateral flow assay device of claim 1, wherein the processor is configured to:
receive a value for a flow time indicating the amount of time that the fluid travels across the membrane;
determine, based on the value of the flow time, a duration for the conjugate pad and the membrane to have contact with each other, a duration for the conjugate pad and the membrane to have no contact with each other, and a number of times to connect and disconnect the conjugate pad and the membrane; and
generate said one or more signals to change the direction of an electric current received by the actuator by using the duration for the conjugate pad and the membrane to have contact with each other, the duration for the conjugate pad and the membrane to have no contact with each other, and the number of times to connect and disconnect the conjugate pad and the membrane.

6. The lateral flow assay device of claim 5, wherein the processor is configured to control a flow rate of the fluid across the membrane by changing the duration for the conjugate pad and the membrane to have contact with each other a plurality of times.

7. The lateral flow assay device of claim 5, wherein the processor is configured to control a flow rate of the fluid across the membrane by changing the duration for the conjugate pad and the membrane to have no contact with each other a plurality of times.

8. The lateral flow assay device of claim 5, wherein the processor is configured to determine the duration for the conjugate pad and the membrane to have contact with each other, and the duration for the conjugate pad and the membrane to have no contact with each other by using experimental values stored in a one or more tables that map the duration for the conjugate pad and the membrane to have contact with each other, and the duration for the conjugate pad and the membrane to have no contact with each other to a set of flow times.

9. The lateral flow assay device of claim 1, wherein the actuator is one of:
an electromagnet comprising an electromagnetically inductive coil wrapped around a metallic core, wherein the coil is configured to generate a magnetic field in a first direction when the actuator receives the current in the first direction, and wherein the coil is configured to generate a magnetic field in a second direction when the actuator receives the current in the second direction;

a piezoelectric actuator configured to convert an electrical current into a displacement;

a piezoelectric stack actuator comprising a stack of piezoelectric ceramic discs and metal electrode foils, the actuator configured to convert an electrical current into a displacement; and an electric motor configured to convert the rotational movement of a rotating shaft to linear movement.

10. A lateral flow assay device, comprising:

a conjugate pad configured to receive a quantity of fluid after a start of a test, the conjugate pad configured to move the fluid by capillary action;

a membrane comprising a test line for determining whether the fluid comprises a target analyte, the membrane configured to move the fluid by capillary action;

a backing connected to the membrane;

a first magnet fixedly attached to the backing of the membrane, the first magnet comprising a north pole and a south pole;

a shaft connected to a second magnet and a third magnet, the second magnet comprising a north pole and a south pole, and positioned on the shaft such that the north pole of the second magnet is closer to the first magnet than the south pole of the second magnet, the third magnet comprising a north pole and a south pole, and positioned on the shaft such that the south pole of the third magnet is closer to the first magnet than the north pole of the third magnet;

an actuator connected to the shaft; and wherein the actuator is configured to receive one or more signals to move the shaft to a first position such that the north pole of the second magnet repels the north pole of the first magnet to open a gap between the membrane and the conjugate pad, wherein the actuator is configured to keep the shaft at the first position prior to the start of the test; and wherein the actuator is configured to receive one or more signals to move the shaft to a second position such that the south pole of the third magnet attracts the north pole of the first magnet to close the gap between the membrane and the conjugate pad; and a processor configured to:

receive a signal indicating the start of the test; and send one or more signals after the start of the test to the actuator to move the shaft between the first and second positions to open and close the gap between the membrane and the conjugate pad a plurality of times to control an amount of time that the fluid travels across the membrane.

11. The lateral flow assay device of claim 10, wherein the actuator is configured to move the shaft in a linear direction between the first and second positions.

12. The lateral flow assay device of claim 10, wherein the processor is configured to receive a conjugate time indicating an amount of time required for the fluid to remain on the conjugate pad prior to the membrane making contact with the conjugate pad; and wherein the processor is configured to generate the one or more signals to change a direction of a current received by the actuator after determining that the conjugate time has elapsed since the start of the test.

13. The lateral flow assay device of claim 10, wherein the actuator is a first actuator, and wherein the shaft is a first shaft, the lateral flow assay device further comprising:

a wicking pad;

a backing connected to the wicking pad;

a fourth magnet attached to the backing of the membrane, the fourth magnet comprising a north pole and a south pole;

a second shaft connected to a fifth magnet and a sixth magnet, the fifth magnet comprising a north pole and a south pole, and positioned on the second shaft such that the north pole of the fifth magnet is closer to the fourth magnet than the south pole of the fifth magnet, the sixth magnet comprising a north pole and a south pole, and positioned on the second shaft such that the south pole of the sixth magnet is closer to the fourth magnet than the north pole of the sixth magnet; and a second actuator connected to the second shaft;

wherein the second actuator is configured to receive one or more signals to move the second shaft to a first position of the second shaft such that the north pole of the fifth magnet repels the north pole of the fourth magnet to open a gap between the membrane and the wicking pad;

wherein the second actuator is configured to receive one or more signals to move the second shaft to a second position of the second shaft such that the south pole of the sixth magnet attracts the north pole of the fourth magnet to close the gap between the membrane and the wicking pad;

wherein the processor is configured to:

send one or more signals after the start of the test to the second actuator to move the second shaft between the first and second positions of the second shaft to open and close the gap between the membrane and the wicking pad a plurality of times to control an amount of time that the fluid travels from the membrane into the wicking pad.

14. The lateral flow assay device of claim 10, wherein the processor is configured to:

receive a value for a flow time indicating the amount of time that the fluid travels across the membrane;

determine, based on the value of the flow time, a duration for the conjugate pad and the membrane to have contact with each other, a duration for the conjugate pad and the membrane to have no contact with each other, and a number of times to connect and disconnect the conjugate pad and the membrane; and generate said one or more signals to change the direction of an electric current received by the actuator by using the duration for the conjugate pad and the membrane to have contact with each other, the duration for the conjugate pad and the membrane to have no contact with each other, and the number of times to connect and disconnect the conjugate pad and the membrane.

15. The lateral flow assay device of claim 14, wherein the processor is configured to control a flow rate of the fluid across the membrane by changing the duration for the conjugate pad and the membrane to have contact with each other a plurality of times.

16. The lateral flow assay device of claim 14, wherein the processor is configured to control a flow rate of the fluid across the membrane by changing the duration for the conjugate pad and the membrane to have no contact with each other a plurality of times.

17. The lateral flow assay device of claim 14, wherein the processor is configured to determine the duration for the conjugate pad and the membrane to have contact with each other, and the duration for the conjugate pad and the membrane to have no contact with each other by using experimental values stored in a one or more tables that map the duration for the conjugate pad and the membrane to have contact with each other, and the duration for the conjugate pad and the membrane to have no contact with each other to a set of flow times.

18. The lateral flow assay device of claim 10, wherein the actuator is one of:
   an electromagnet comprising an electromagnetically inductive coil wrapped around a metallic core, wherein the coil is configured to generate a magnetic field in a first direction when the actuator receives the current in the first direction, and wherein the coil is configured to generate a magnetic field in a second direction when the actuator receives the current in the second direction;
   a piezoelectric actuator configured to convert an electrical current into a displacement;
   a piezoelectric stack actuator comprising a stack of piezoelectric ceramic discs and metal electrode foils, the actuator configured to convert an electrical current into a displacement; and
   an electric motor configured to convert the rotational movement of a rotating shaft to linear movement.

19. A lateral flow assay device, comprising:
   a conjugate pad configured to receive a quantity of fluid after a start of a test, the conjugate pad configured to move the fluid by capillary action;
   a membrane comprising a test line for determining whether the fluid comprises a target analyte, the membrane configured to move the fluid by capillary action;
   a backing connected to the membrane;
   a first magnet fixedly attached to the backing of the membrane, the first magnet comprising a north pole and a south pole;
   a shaft connected to a second magnet and a third magnet, the second magnet comprising a north pole and a south pole, and positioned on the shaft such that the south pole of the second magnet is closer to the first magnet than the north pole of the second magnet, the third magnet comprising a north pole and a south pole, and positioned on the shaft such that the north pole of the third magnet is closer to the first magnet than the south pole of the third magnet;
   an actuator connected to the shaft;
      wherein the actuator is configured to receive one or more signals to move the shaft to a first position such that the south pole of the second magnet attracts the north pole of the first magnet to open a gap between the membrane and the conjugate pad, wherein the actuator is configured to keep the shaft at the first position prior to the start of the test; and
      wherein the actuator is configured to receive one or more signals to move the shaft to a second position such that the north pole of the third magnet repels the north pole of the first magnet to close the gap between the membrane and the conjugate pad; and
   a processor configured to:
      receive a signal indicating the start of the test; and
      send one or more signals after the start of the test to the actuator to move the shaft between the first and second positions to open and close the gap between the membrane and the conjugate pad a plurality of times to control an amount of time that the fluid travels across the membrane.

20. The lateral flow assay device of claim 19, wherein the actuator is configured to move the shaft in a linear direction between the first and second positions.

21. The lateral flow assay device of claim 19,
   wherein the processor is configured to receive a conjugate time indicating an amount of time required for the fluid to remain on the conjugate pad prior to the membrane making contact with the conjugate pad; and
   wherein the processor is configured to generate the one or more signals to change a direction of a current received by the actuator after determining that the conjugate time has elapsed since the start of the test.

22. The lateral flow assay device of claim 19, wherein the actuator is a first actuator, and wherein the shaft is a first shaft, the lateral flow assay device further comprising:
   a wicking pad;
   a backing connected to the wicking pad;
   a fourth magnet attached to the backing of the membrane, the fourth magnet comprising a north pole and a south pole;
   a second shaft connected to a fifth magnet and a sixth magnet, the fifth magnet comprising a north pole and a south pole, and positioned on the second shaft such that the south pole of the fifth magnet is closer to the fourth magnet than the north pole of the fifth magnet, the sixth magnet comprising a north pole and a south pole, and positioned on the second shaft such that the north pole of the sixth magnet is closer to the fourth magnet than the south pole of the sixth magnet; and
   a second actuator connected to the second shaft;
      wherein the second actuator is configured to receive one or more signals to move the second shaft to a first position of the second shaft such that the south pole of the fifth magnet attracts the north pole of the fourth magnet to open a gap between the membrane and the wicking pad;
      wherein the second actuator is configured to receive one or more signals to move the second shaft to a second position of the second shaft such that the north pole of the sixth magnet repels the north pole of the fourth magnet to close the gap between the membrane and the wicking pad;
   wherein the processor is configured to:
      send one or more signals after the start of the test to the second actuator to move the second shaft between the first and second positions of the second shaft to open and close the gap between the membrane and the wicking pad a plurality of times to control an amount of time that the fluid travels from the membrane into the wicking pad.

23. The lateral flow assay device of claim 19, wherein the processor is configured to:
   receive a value for a flow time indicating the amount of time that the fluid travels across the membrane;
   determine, based on the value of the flow time, a duration for the conjugate pad and the membrane to have contact with each other, a duration for the conjugate pad and the membrane to have no contact with each other, and a number of times to connect and disconnect the conjugate pad and the membrane; and
   generate said one or more signals to change the direction of an electric current received by the actuator by using the duration for the conjugate pad and the membrane to have contact with each other, the duration for the conjugate pad and the membrane to have no contact with each other, and the number of times to connect and disconnect the conjugate pad and the membrane.

24. The lateral flow assay device of claim 23, wherein the processor is configured to control a flow rate of the fluid across the membrane by changing the duration for the conjugate pad and the membrane to have contact with each other a plurality of times.

25. The lateral flow assay device of claim 23, wherein the processor is configured to control a flow rate of the fluid across the membrane by changing the duration for the conjugate pad and the membrane to have no contact with each other a plurality of times.

26. The lateral flow assay device of claim 23, wherein the processor is configured to determine the duration for the conjugate pad and the membrane to have contact with each other, and the duration for the conjugate pad and the membrane to have no contact with each other by using experimental values stored in a one or more tables that map the duration for the conjugate pad and the membrane to have contact with each other, and the duration for the conjugate pad and the membrane to have no contact with each other to a set of flow times.

27. The lateral flow assay device of claim 19, wherein the actuator is one of:
an electromagnet comprising an electromagnetically inductive coil wrapped around a metallic core, wherein the coil is configured to generate a magnetic field in a first direction when the actuator receives the current in the first direction, and wherein the coil is configured to generate a magnetic field in a second direction when the actuator receives the current in the second direction;
a piezoelectric actuator configured to convert an electrical current into a displacement;
a piezoelectric stack actuator comprising a stack of piezoelectric ceramic discs and metal electrode foils, the actuator configured to convert an electrical current into a displacement; and
an electric motor configured to convert the rotational movement of a rotating shaft to linear movement.

28. A lateral flow assay device, comprising:
a conjugate pad configured to receive a quantity of fluid after a start of a test, the conjugate pad configured to move the fluid by capillary action;
a membrane comprising a test line for determining whether the fluid comprises a target analyte, the membrane configured to move the fluid by capillary action;
a backing connected to the membrane;
a first magnet fixedly attached to the backing of the membrane, the first magnet comprising a north pole and a south pole;
a shaft connected to a second magnet and a third magnet, the second magnet comprising a north pole and a south pole, and positioned on the shaft such that the south pole of the second magnet is closer to the first magnet than the north pole of the second magnet, the third magnet comprising a north pole and a south pole, and positioned on the shaft such that the north pole of the third magnet is closer to the first magnet than the south pole of the third magnet;
an actuator connected to the shaft; and
wherein the actuator is configured to receive one or more signals to move the shaft to a first position such that the south pole of the second magnet repels the south pole of the first magnet to open a gap between the membrane and the conjugate pad, wherein the actuator is configured to keep the shaft at the first position prior to the start of the test; and
wherein the actuator is configured to receive one or more signals to move the shaft to a second position such that the north pole of the third magnet attracts the south pole of the first magnet to close the gap between the membrane and the conjugate pad; and
a processor configured to:
receive a signal indicating the start of the test; and
send one or more signals after the start of the test to the actuator to move the shaft between the first and second positions to open and close the gap between the membrane and the conjugate pad a plurality of times to control an amount of time that the fluid travels across the membrane.

29. The lateral flow assay device of claim 28, wherein the actuator is configured to move the shaft in a linear direction between the first and second positions.

30. The lateral flow assay device of claim 28,
wherein the processor is configured to receive a conjugate time indicating an amount of time required for the fluid to remain on the conjugate pad prior to the membrane making contact with the conjugate pad; and
wherein the processor is configured to generate the one or more signals to change a direction of a current received by the actuator after determining that the conjugate time has elapsed since the start of the test.

31. The lateral flow assay device of claim 28, wherein the actuator is a first actuator, and wherein the shaft is a first shaft, the lateral flow assay device further comprising:
a wicking pad;
a backing connected to the wicking pad;
a fourth magnet attached to the backing of the membrane, the fourth magnet comprising a north pole and a south pole;
a second shaft connected to a fifth magnet and a sixth magnet, the fifth magnet comprising a north pole and a south pole, and positioned on the second shaft such that the south pole of the fifth magnet is closer to the fourth magnet than the north pole of the fifth magnet, the sixth magnet comprising a north pole and a south pole, and positioned on the second shaft such that the north pole of the sixth magnet is closer to the fourth magnet than the south pole of the sixth magnet; and
a second actuator connected to the second shaft;
wherein the second actuator is configured to receive one or more signals to move the second shaft to a first position of the second shaft such that the south pole of the fifth magnet repels the south pole of the fourth magnet to open a gap between the membrane and the wicking pad;
wherein the second actuator is configured to receive one or more signals to move the second shaft to a second position of the second shaft such that the north pole of the sixth magnet attracts the south pole of the fourth magnet to close the gap between the membrane and the wicking pad;
wherein the processor is configured to:
send one or more signals after the start of the test to the second actuator to move the second shaft between the first and second positions of the second shaft to open and close the gap between the membrane and the wicking pad a plurality of times to control an amount of time that the fluid travels from the membrane into the wicking pad.

32. The lateral flow assay device of claim 28, wherein the processor is configured to:
receive a value for a flow time indicating the amount of time that the fluid travels across the membrane;
determine, based on the value of the flow time, a duration for the conjugate pad and the membrane to have contact with each other, a duration for the conjugate pad and the membrane to have no contact with each other, and a number of times to connect and disconnect the conjugate pad and the membrane; and generate said one or more signals to change the direction of an electric current received by the actuator by using the duration for the conjugate pad and the membrane to have contact with each other, the duration for the conjugate pad and the membrane to have no contact with each other, and the number of times to connect and disconnect the conjugate pad and the membrane.

33. The lateral flow assay device of claim 32, wherein the processor is configured to control a flow rate of the fluid across the membrane by changing the duration for the conjugate pad and the membrane to have contact with each other a plurality of times.

34. The lateral flow assay device of claim 32, wherein the processor is configured to control a flow rate of the fluid across the membrane by changing the duration for the conjugate pad and the membrane to have no contact with each other a plurality of times.

35. The lateral flow assay device of claim 32, wherein the processor is configured to determine the duration for the conjugate pad and the membrane to have contact with each other, and the duration for the conjugate pad and the membrane to have no contact with each other by using experimental values stored in a one or more tables that map the duration for the conjugate pad and the membrane to have contact with each other, and the duration for the conjugate pad and the membrane to have no contact with each other to a set of flow times.

36. The lateral flow assay device of claim 28, wherein the actuator is one of:

an electromagnet comprising an electromagnetically inductive coil wrapped around a metallic core, wherein the coil is configured to generate a magnetic field in a first direction when the actuator receives the current in the first direction, and wherein the coil is configured to generate a magnetic field in a second direction when the actuator receives the current in the second direction;

a piezoelectric actuator configured to convert an electrical current into a displacement;

a piezoelectric stack actuator comprising a stack of piezoelectric ceramic discs and metal electrode foils, the actuator configured to convert an electrical current into a displacement; and an electric motor configured to convert the rotational movement of a rotating shaft to linear movement.

* * * * *